US008476197B2

(12) United States Patent
Dubost et al.

(10) Patent No.: US 8,476,197 B2
(45) Date of Patent: Jul. 2, 2013

(54) AMINOPROPENOATES AS FUNGICIDES

(75) Inventors: Christophe Dubost, Lyons (FR); Jacky Vidal, Lozanne (FR); Philippe Rinolfi, Chatillon d'Azergues (FR); Marie-Claire Grosjean-Cournoyer, Curis au Mont d'Or (FR); Mazen Es-Sayed, Lyons (FR); Jürgen Benting, Leichlingen (DE); Ulrike Wachendorff-Neumann, Neuwied (DE); Shinichi Narabu, Ibaraki (JP); Koichi Ishikawa, Oyama (JP); Hiroyuki Hadano, Tochigi (JP); Pierre Genix, Lyons (FR); Jean-Pierre Vors, Sainte Foy les Lyon (FR); Angela Becker, Düsseldorf (DE); Ulrich Görgens, Ratingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 12/906,491

(22) Filed: Oct. 18, 2010

(65) Prior Publication Data
US 2011/0152322 A1    Jun. 23, 2011

Related U.S. Application Data

(60) Provisional application No. 61/253,091, filed on Oct. 20, 2009.

(30) Foreign Application Priority Data

Oct. 16, 2009    (EP) ..................................... 09173304

(51) Int. Cl.
*A01N 43/40*    (2006.01)
*A61K 31/44*    (2006.01)
*C07D 213/04*    (2006.01)

(52) U.S. Cl.
USPC ........................... 504/250; 514/332; 546/255

(58) Field of Classification Search
USPC ........................... 546/255; 504/250; 514/332
See application file for complete search history.

(56) References Cited

U.S. PATENT DOCUMENTS

| 4,245,432 | A | 1/1981 | Dannelly |
| 4,272,417 | A | 6/1981 | Barke et al. |
| 4,808,430 | A | 2/1989 | Kouno |
| 5,876,739 | A | 3/1999 | Turnblad et al. |
| 2003/0176428 | A1 | 9/2003 | Schneidersmann et al. |

FOREIGN PATENT DOCUMENTS

| DE | 26 40 965 | 3/1978 |
| EP | 0 088 545 A1 | 9/1983 |
| WO | WO 02/28186 A2 | 4/2002 |
| WO | WO 02/080675 A1 | 10/2002 |
| WO | WO 2005/058829 A1 | 6/2005 |
| WO | WO 2007/024782 A2 | 3/2007 |
| WO | WO 2007/027777 A2 | 3/2007 |

OTHER PUBLICATIONS

Brana, M.F., et al., "Reaction of N-(4-pyridylmethyl)benzamide N-Oxides with Ethyl Cyanoacetate in the Presence of Acetic Anhydride," *J. Heterocyclic Chem.* 23:1019-1022, Journal of Heterocyclic Chemistry, United States (1986).
Draber, W. & Wegler, R., "Phytohormone: 2. Gibberelline", Chemie der Pflanzenschutz und Schädlingbekämpfungsmittel vol. 2:401-412, Springer, Berlin (1970).
English language translation of Draber, W. & Wegler, R., "Phytohormone: 2. Gibberelline", Chemie der Pflanzenschutz und Schädlingbekämpfungsmittel vol. 2:401-412, Springer, Berlin (1970).
Gavar, R.A., et al., "Free-radical Intermediates in the Electrochemical Reduction of α,β Derivatives of β-(5-nitro-2-furyl)-α-cyanoethylene," *Khimiya Geterotsiklicheskikh Soedinenii* (12):1636-1639, Plenum Publishing Company, Germany (1992).
Jähnisch, K., et al., "Reaktionen von β-Fur-2-yl-β-chlorcyanacrylsäureestern mit Aminen," *Journal f. prackt. Chemie* 3(330):361-366, VEB J.A. Barth, Germany (1988).
Liu, Y., et al., "Synthesis, Crystal Structure, and Biological Activities of 2-Cyanoacrylates Containing Furan of Tetrahydrofuran Moieties," *J. Agrc. Food Chem.* 55:3011-3017, American Chemical Society, United States (2007).
Mohareb, R.M. and Sherif, S.M., "Heterocyclic Syntheses With Isothiocyantes: A Novel Synthetic Approach to Polyfunctionally Substituted Pyrazoles and Their Fused Derivatives," *Sulfur Letters* 15(1):91-101, Harwood Academic Publishers, England (1992).
Perez, M.A. and Soto, J.L., "Synthesis of 2-Alkoxy-6-aryl-5-cyano-4(3H)-pyrimidinones," *J. Heterocyclic Chem.* 19:177-179, Journal of Heterocyclic Chemistry, United States (1982).
Abdel Sayed, N.I., "Uses of 4-Phenyl-Thiosemicarbazide in Heterocyclic Synthesis: Synthesis of Pyrazole, Pyrazolo [3,.2c] 1,2,4 Triazole and Pyrimidine Derivatives," *Egypt. J. Chem.* 42(2):175-187, National Information and Documentation Centre (NIDOC), Egypt (1999).
Trofimov, B.A., et al., "Facile Coupling of 2-(1-Ethylthioethenyl)pyrroles with Amines: A Route to 2-(1-Aminoethenyl)pyrroles and 1-Amino-3-iminopyrrolizines," *J. Heterocyclic Chem.* 44:505-513, Journal of Heterocyclic Chemistry, United States (2007).
Wang, L-G., et al., "Synthesis and Fungicidal Activity of Ethyl 2-Cyano-3-substituted Amino-3-(2-methylphenyl)propenoate," *Chin. J. Org. Chem.* 25(10):1254-1258, Shanghai Institute of Organic Chemistry, China (2005).

(Continued)

*Primary Examiner* — Paul V. Ward
(74) *Attorney, Agent, or Firm* — Sterne, Kessler, Goldstein, Fox P.L.L.C.

(57) ABSTRACT

The present invention relates to aminopropenoate derivatives, the process of their preparation, intermediate compounds, their use as fungicide active agents, particularly in the form of fungicide compositions, and methods for the control of phytopathogenic fungi, notably of plants and in material protection, using these compounds or compositions.

20 Claims, No Drawings

OTHER PUBLICATIONS

Caplus Database Accession No. 1982:198888, "Radical reactions of N-Heterocycles 2. Thermolysis of a 1-vinylazopyrazole," Schulz, M., *Zeitschrift fuer Chemie* 22(2)56 (1982).

Caplus Database Accession No. 1968:29522, "Indole Derivatives V. Reaction of 3-methylthio-3-(3-indolyl)acrylic acid derivatives with some amines," Kobayashi, G., *Yakugaku Zasshi* 87(7): 857-860 (1967).

Caplus Database Accession No. 1968:49390, "Indole Derivatives VI. Synthesis of 2-oxo-4-methylthio-2H-pyrano[2,3-b]indole derivatives and their reaction," Fukura, G., *Yakugaku Zasshi* 87(9):1044-1051 (1967).

Caplus Database Accession No. 1971:76324, "Cyanoindolylacrylic acid derivatives," JP45031283B Oct. 9, 1970.

Caplus Database Accession No. 1971:76326, "Oxyindolylacrylic acid derivatives," JP450314284B, Oct. 10, 1970.

Caplus Database Accession No. 1973:97425, "Indole Derivatives XIV. Synthesis of 3-(2-cyano-1-methylthiovinyl)indole derivatives and Reactions of these derivatives with some nucleophilic reagents," *Yakugaku Zasshi* 97(12):1468-1472 (1972).

Caplus Database Accession No. 1992:570618, "Free-radical Intermediates of Electrochemical Reduction of $\alpha,\beta$ Derivatives of $\beta$-(5-nitro-2-furyl)-$\alpha$-cyanoethylene $\alpha,\beta$ derivatives," *Khimiya Geterotsiklicheskikh Soedinenii* (12):1636-1639 (1991).

Caplus Database Accession No. 2005:1151061, "Synthesis and Fungicidal Activity of Ethyl 2-Cyano-3-substituted Amino-3-(2-methylphenyl)propenoate," *Chin. J. Org. Chem.* 25(10):1254-1258 (2005).

Caplus Database Accession No. 2009:314715, "Preparation of 3-amido-2-cyano-3-phenylacrylate derivatives as antifungal agents," CN101381326A, Mar. 11, 2009.

Caplus Database Accession No. 1968:29522, Abstract,"Indole Derivatives V. Reaction of 3-methylthio-3-(3-indolyl)acrylic acid derivaties with some amines," Kobayashi, G., *Yakugaku Zasshi* 87(7): 857-860 (1967).

Bielstein Database Registry No. 8570394, Abdel Sayed, N.I., "Uses of 4-Phenyl-Thiosemicarbazide in Heterocyclic Synthesis: Synthesis of Pyrazole, Pyrazolo [3.2-c] 1,2,4 Triazole and Pyrimidine Derivatives," *Egypt. J. Chem.* 42(2):175-187 (1999).

European Search Report with English language Written Opinion for European Application No. 09173304.8, European Patent Office, Germany, date of issuance Mar. 9, 2010.

AMINOPROPENOATES AS FUNGICIDES

This application claims priority to European Patent Application No. 09173304.8, filed Oct. 16, 2009, and the benefit of U.S. Provisional Application No. 61/253,091, filed Oct. 20, 2009, the disclosure of each of which is incorporated by reference herein in its entirety.

The present invention relates to aminopropenoate derivatives, the process of their preparation, intermediate compounds, their use as fungicide active agents, particularly in the form of fungicide compositions, and methods for the control of phytopathogenic fungi, notably of plants and in material protection, using these compounds or compositions.

Certain aminopropenoate derivatives are already known as synthesis intermediates (cf. *Journal fuer Praktische Chemie* (Leipzig), 1988, 330(3), 361-6; *Khimiya Geterotsiklicheskikh Soedinenii*, 1991, (12), 1636-9; *Egyptian Journal of Chemistry*, 1999, 42(2), 175-187; *Sulfur Letters*, 1992, 15(2), 91-101; and *Zeitschrift fuer Chemie*, 1982, 22(2), 56. Others were prepared during the development of new chemical methodologies towards acrylates derivatives: *Yakugaku Zasshi*, 1967, 87(7), 857-60; *Yakugaku Zasshi*, 1967, 87(9), 1044-51; *Jpn. Tokkyo Koho*, 1970, JP45031283; *Jpn. Tokkyo Koho*, 1970, JP45031284; *Yakugaku Zasshi*, 1972, 92(12), 1468-72; *J. Heterocyclic Chem.*; 2007, 44, 505-513. Certain substituted 3-amino-2-cyano-3-phenylacrylate derivatives are known to exhibit fungicidal activities [cf. CN13171483A, CN101381326A and *Youji Huaxue*, 2005, 25(10), 1254-1258]. Other substituted 3-alkylamino-2-cyano-3-(het)arylacrylate derivatives are known to have the potency to inhibit growth and survival of cancerous cell lines (cf. WO 2005/058829). The compounds disclosed in these documents do not prove to provide a comparable utility than the compounds according to the invention.

Since the ecological and economical demands made on modern active compounds, for example fungicides, are increasing constantly, for example with respect to activity spectrum, toxicity, selectivity, application rate, formation of residues and favorable manufacture, and there can furthermore be problems, for example, with resistance, there is a constant need to develop novel fungicides which, at least in some areas, have advantages over those of the prior art. Surprisingly, it has now been found that aminopropenoates of the formula (I) (see below) are suitable as fungicides and, at least in some aspects, have improved properties compared to known fungicidally active compounds.

It has now been found that aminopropenoate derivatives of the general formula (I):

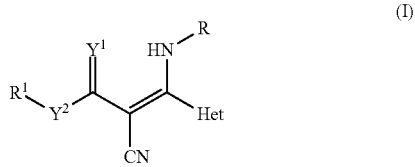

in which

R represents one of the following groups $R^A$, $R^B$ or $R^C$

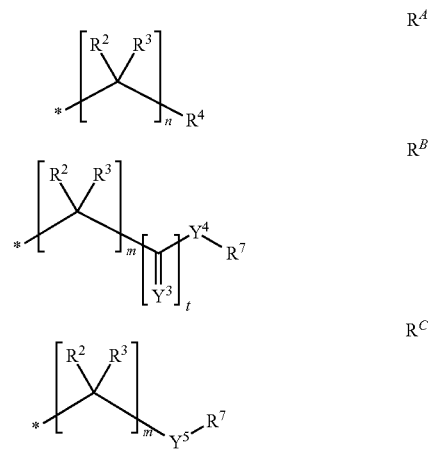

n represents 0, 1, 2, 3 or 4, m represents 1, 2, 3 or 4, t represents 0 or 1, $Y^1$ represents S, O or $NR^5$, $Y^2$ represents O, S or $NR^6$, $Y^3$ represents S, O or $NR^8$, $Y^4$ represents a bond or O, S or $NR^9$, $Y^5$ represents SO or $SO_2$, in case that $Y^2$ represents $NR^6$, then $R^6$ and $R^1$ together with the nitrogen atom to which they are linked may form a 5- to 7-membered, saturated or unsaturated, carbo- or heterocycle comprising up to 3 heteroatoms, which cycle may also include one of the groups C(=O) and C(=S), in case that $Y^4$ represents $NR^9$, then $R^9$ and $R^7$ together with the nitrogen atom to which they are linked may form a 5- to 7-membered, saturated or unsaturated, carbo- or heterocycle comprising up to 3 heteroatoms, which cycle may also include one of the groups C(=O) and C(=S), $R^1$ represents a hydrogen, $C_1$-$C_8$-alkyl, $C_3$-$C_8$-cycloalkyl, $C_1$-$C_8$-halogenoalkyl comprising up to 9 halogen atoms which can be the same or different, $C_2$-$C_8$-alkenyl, $C_2$-$C_8$-alkynyl, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl, $C_1$-$C_8$-trialkylsilyl-$C_1$-$C_8$-alkyl, a benzotriazolyl, an aryl-$C_3$-$C_8$-cycloalkyl which can be substituted by up to 5 groups Q;

and, provided that $Y^2$ does not represent NH, $R^1$ can also represent an aryl which can be substituted by up to 5 groups Q, an aryl-$C_1$-$C_8$-alkyl which can be substituted by up to 5 groups Q;

Het represents one of the heterocycles Het 1 to Het 61:
Het 1
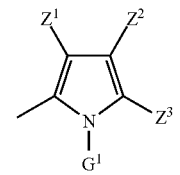
Het 2
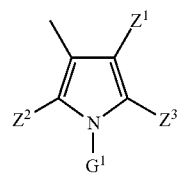
Het 3
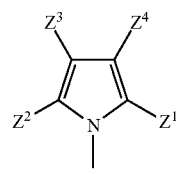
Het 4
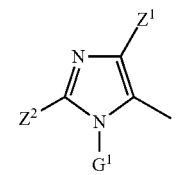
Het 5
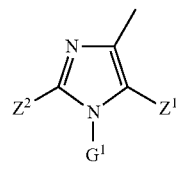
Het 6
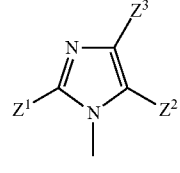
Het 7
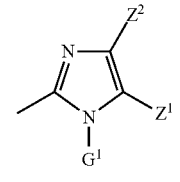
Het 8
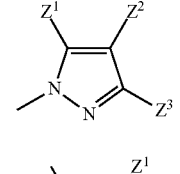
Het 9
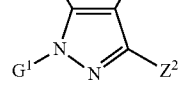
Het 10
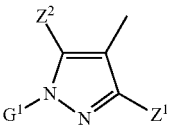
Het 11
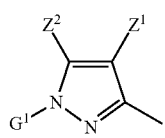
Het 12
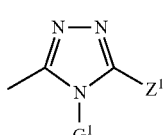
Het 13
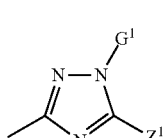
Het 14
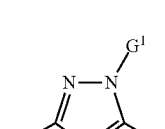
Het 15
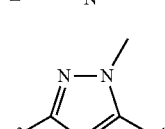
Het 16
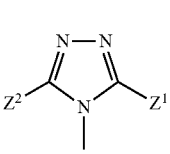
Het 17
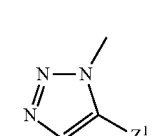
Het 18
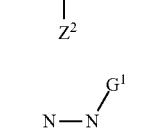
Het 19
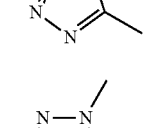
Het 20
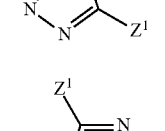

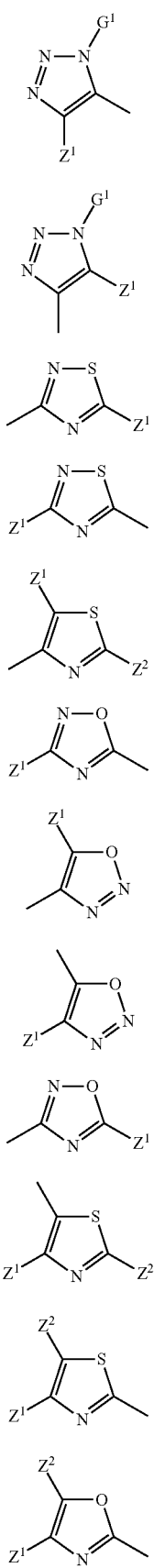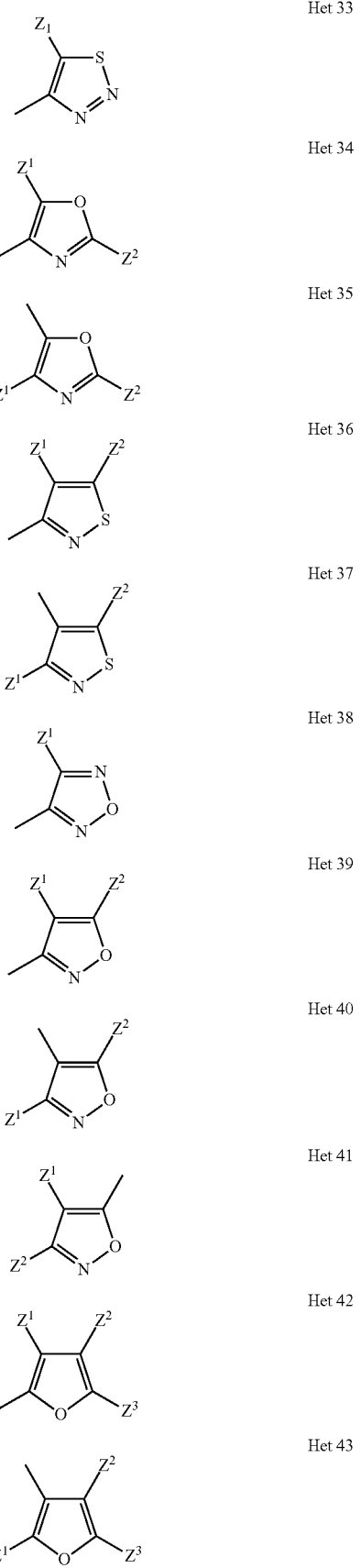

-continued

Het 44 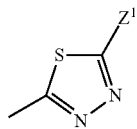

Het 45 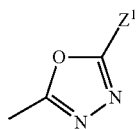

Het 46 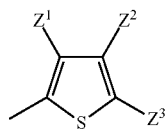

Het 47 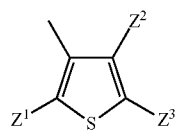

Het 48 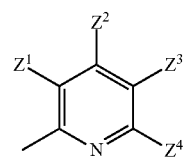

Het 49 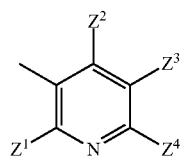

Het 50 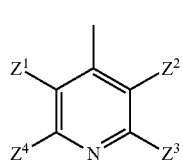

Het 51 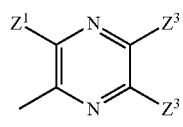

Het 52 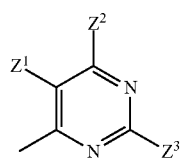

Het 53 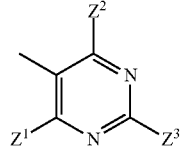

-continued

Het 54 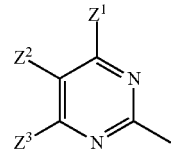

Het 55 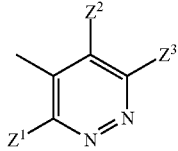

Het 56 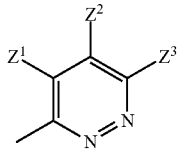

Het 57 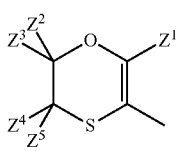

Het 58 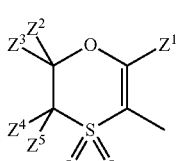

Het 59 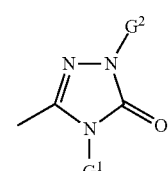

Het 60 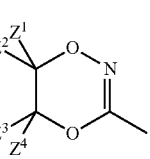

Het 61 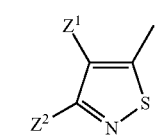

$R^2$ and $R^3$, which can be the same or different, independently of one another represent hydrogen, halogen, CN, $NH_2$, $NO_2$, $C_1$-$C_8$-alkyl, $C_1$-$C_8$-hydroxyalkyl, $C_3$-$C_8$-cycloalkyl, $C_3$-$C_8$-halogenocycloalkyl comprising up to 9 halogen atoms which can be the same or different, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl, $C_2$-$C_8$-halogenoalkenyl comprising up to 9 halogen atoms which can be the same or different, $C_2$-$C_8$-alkynyl, $C_2$-$C_8$-alkenyl-$C_1$-$C_8$-alkyl, $C_2$-$C_8$-alkynyl-$C_1$-$C_8$-alkyl, $C_3$-$C_8$-halogenocycloalkyl comprising up to 9 halogen atoms which can be the same or different, $C_3$-$C_8$-cycloalkenyl, $C_1$-$C_8$-alkoxy-$C_1$-$C_8$- alkoxy-$C_2$-$C_8$-alkenyl, $C_1$-$C_8$-alkoxy-$C_1$-$C_8$-alkynyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylsulfinyl-$C_1$-$C_8$-alkyl, $C_1$-$C_8$-alkylsulfonyl-$C_1$-$C_8$-alkyl, amino-$C_1$-$C_8$-alkyl, $C_1$-$C_8$-alkylamino-$C_1$-$C_8$-alkyl, di-($C_1$-$C_8$-alkyl)amino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, $C_1$-$C_8$-trialkylsilyl, phenyl which can be substituted by up to 5 groups Q, phenyl-$C_2$-$C_4$-alkynyl, which can be substituted in the phenyl moiety by up to 5 groups Q, $R^2$ and $R^3$ also together with the carbon atom to which they are linked can form a $C_3$-$C_7$-cycloalkyl, which may be substituted by 1 to 4 identical or different substituents selected from by halogen, OH, $C_1$-$C_4$-alkyl, $C_1$-$C_4$-halogenoalkyl, $C_1$-$C_4$-alkoxy, $C_1$-$C_4$-alkylthio or phenyl, or can form a $C_5$-$C_{10}$-bicycloalkyl, a 2,3-dihydro-1H-indene-1-yl or a decahydronaphthalenyl, $R^4$ represents an aryl or a heterocycle E 1 to E 144:

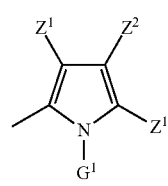

E 1

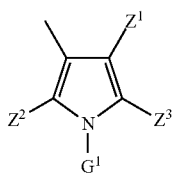

E 2

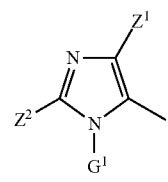

E 3

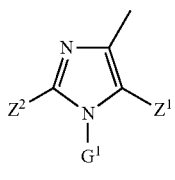

E 4

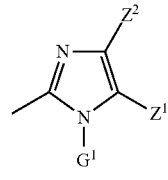

E 5

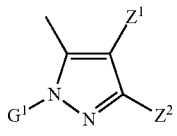

E 6

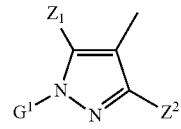

E 7

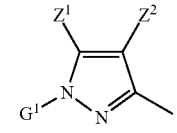

E 8

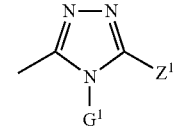

E 9

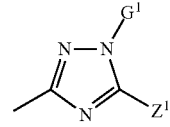

E 10

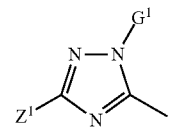

E 11

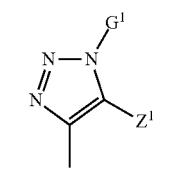

E 12

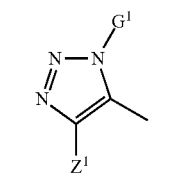

E 13

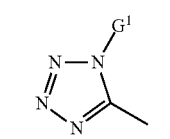

E 14

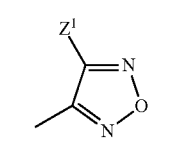

E 15

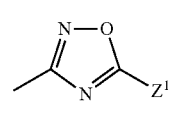

E 16

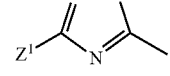

E 17

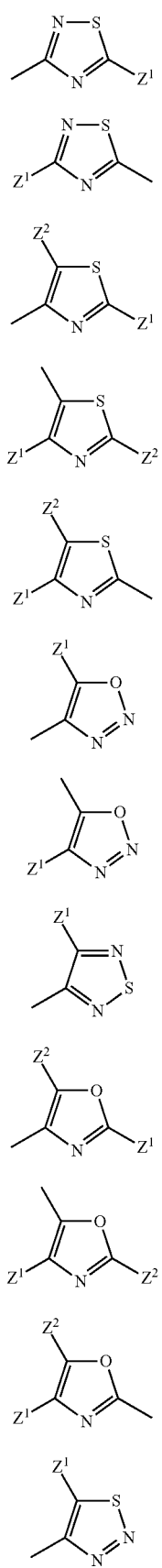
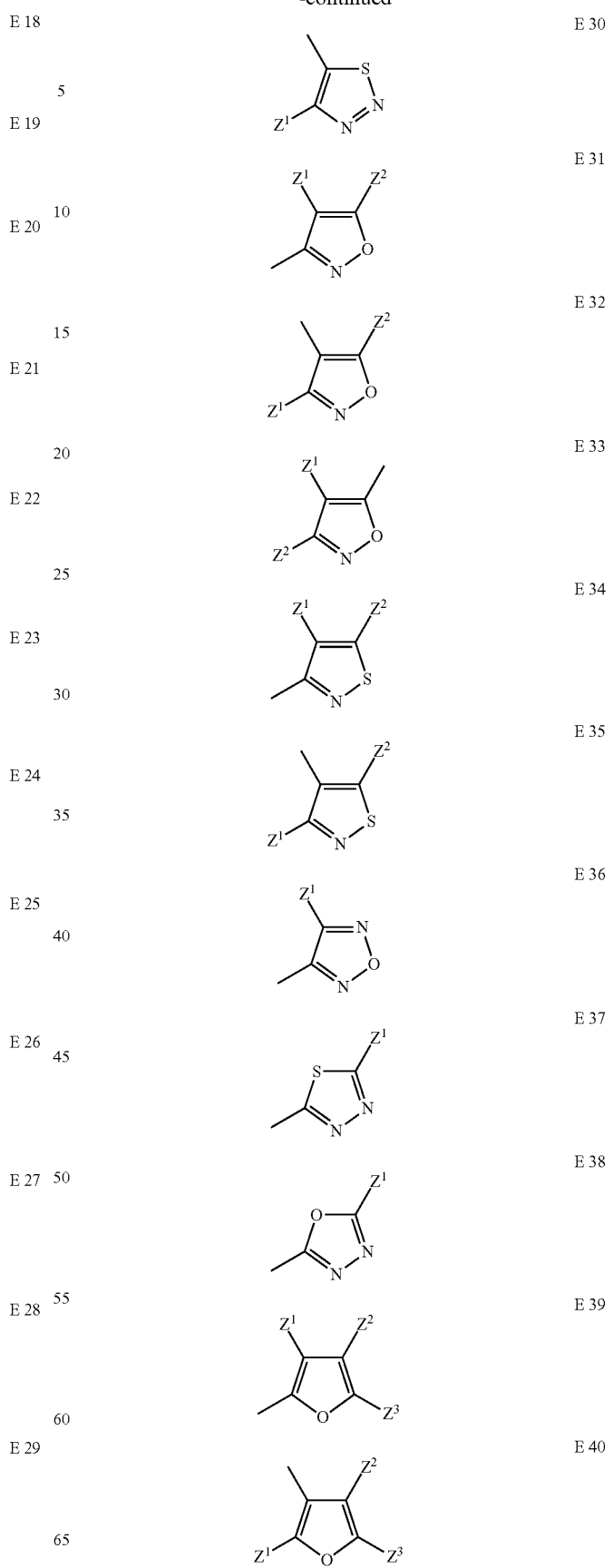

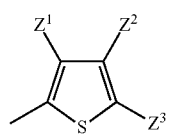 E 41
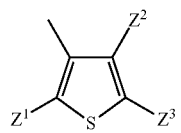 E 42
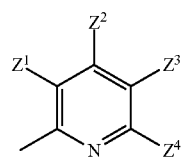 E 43
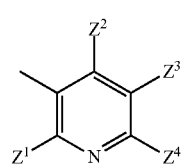 E 44
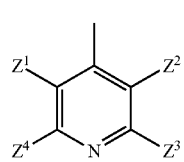 E 45
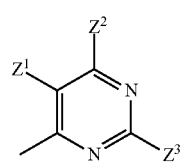 E 46
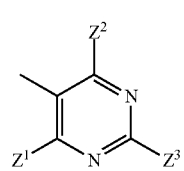 E 47
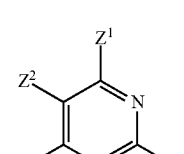 E 48
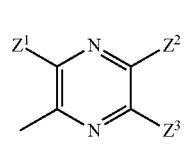 E 49
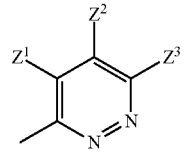 E 50
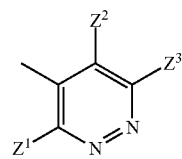 E 51
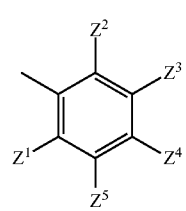 E 52
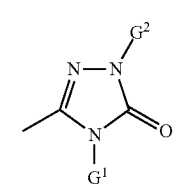 E 53
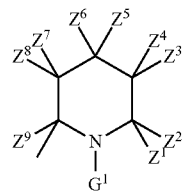 E 54
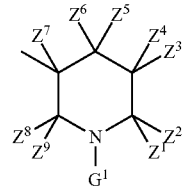 E 55
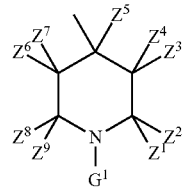 E 56
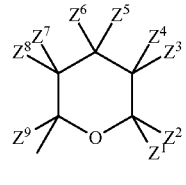 E 57
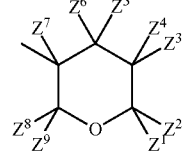 E 58

-continued
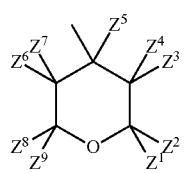 E 59
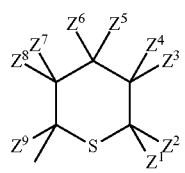 E 60
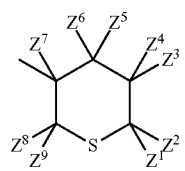 E 61
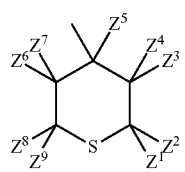 E 62
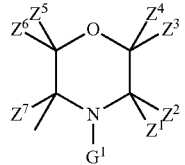 E 63
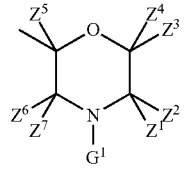 E 64
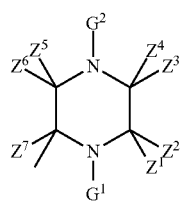 E 65
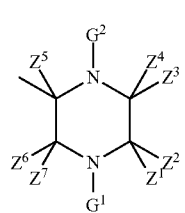 E 66
-continued
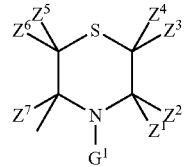 E 67
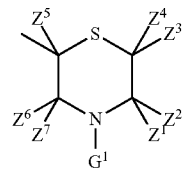 E 68
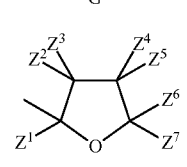 E 69
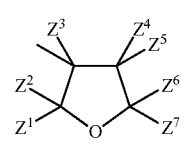 E 70
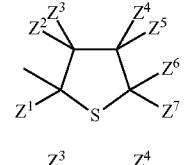 E 71
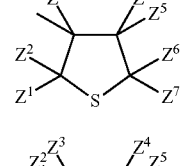 E 72
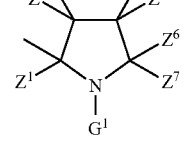 E 73
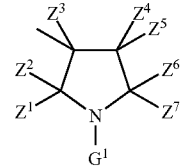 E 74
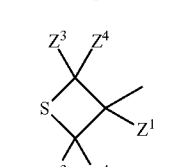 E 75
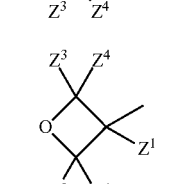 E 76

-continued
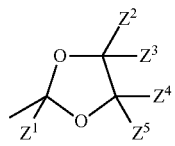 E 77
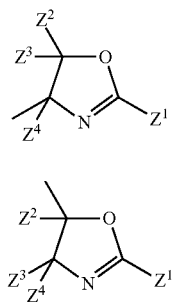 E 78
E 79
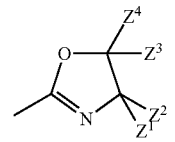 E 80
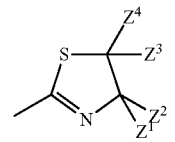 E 81
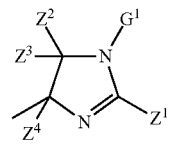 E 82
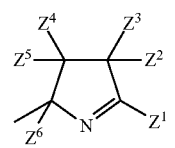 E 83
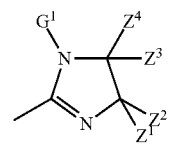 E 84
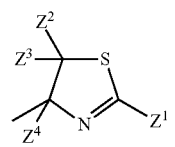 E 85
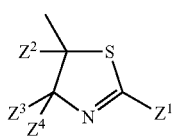 E 86
-continued
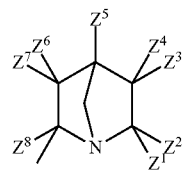 E 87
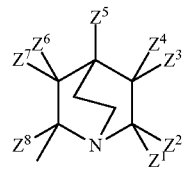 E 88
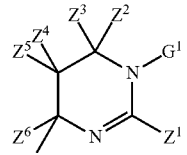 E 89
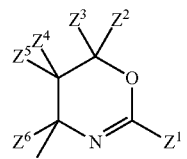 E 90
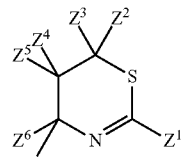 E 91
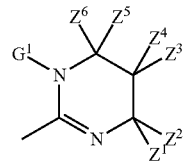 E 92
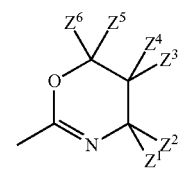 E 93
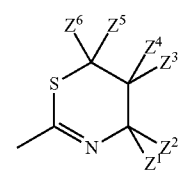 E 94
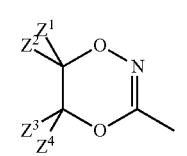 E 95

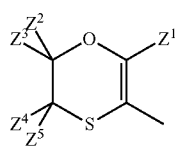 E96
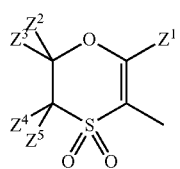 E97
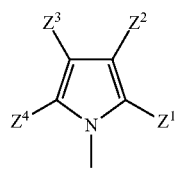 E98
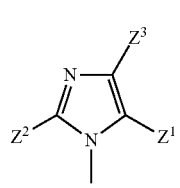 E99
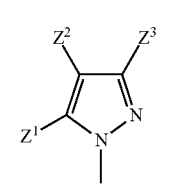 E100
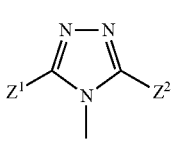 E101
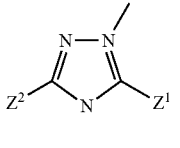 E102
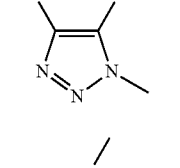 E103
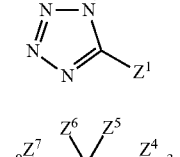 E104
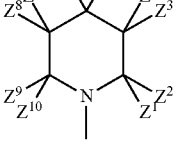 E105
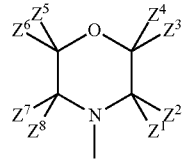 E106
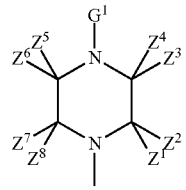 E107
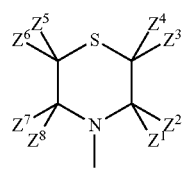 E108
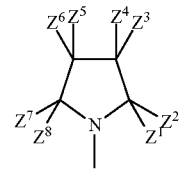 E109
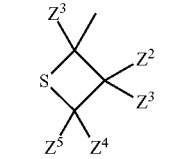 E110
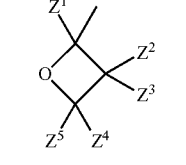 E111
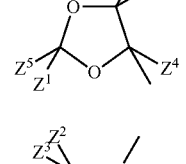 E112
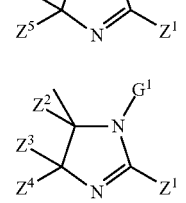 E113
E114

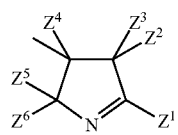 E 115
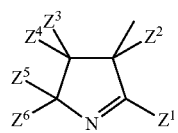 E 116
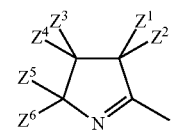 E 117
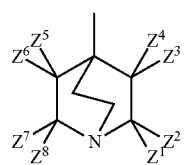 E 118
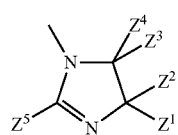 E 119
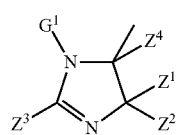 E 120
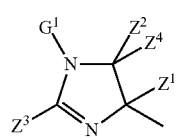 E 121
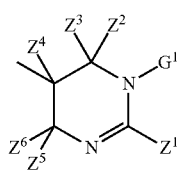 E 122
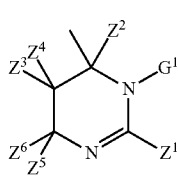 E 123
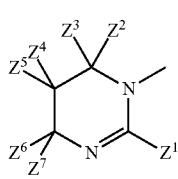 E 124
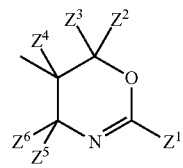 E 125
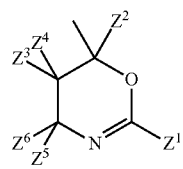 E 126
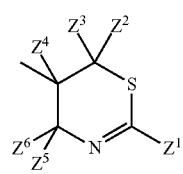 E 127
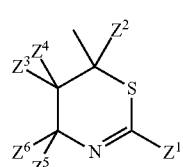 E 128
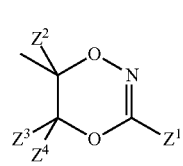 E 129
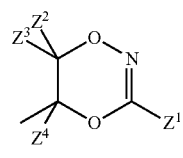 E 130
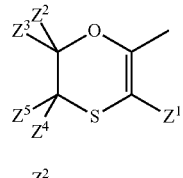 E 131
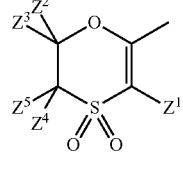 E 132
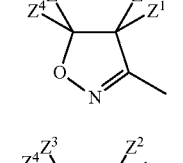 E 133
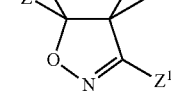 E 134

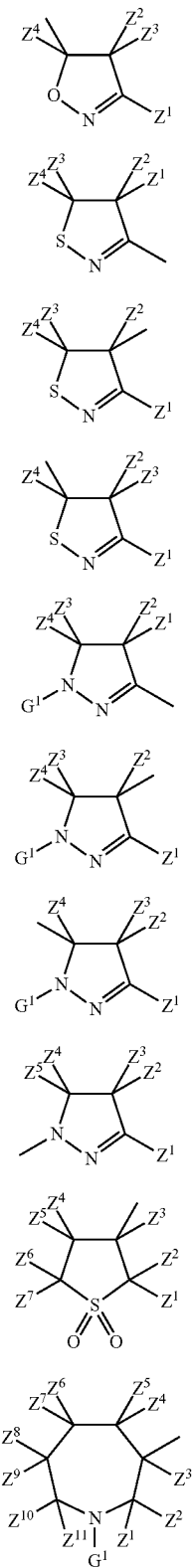

R⁴ also represents hydrogen or halogen when n represents 1, 2, 3 or 4,

R⁵ represents hydrogen, OH, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, an aryl which can be substituted by up to 5 groups Q, an aryl-$C_1$-$C_8$-alkyl which can be substituted by up to 5 groups Q, an aryl-$C_3$-$C_8$-cycloalkyl which can be substituted by up to 5 groups Q;

R⁶ represents hydrogen, OH, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, $C_1$-$C_8$-alkoxy, $C_3$-$C_8$-cycloalkoxy, $C_1$-$C_8$-halogenoalkoxy comprising up to 9 halogen atoms which can be the same or different, $C_3$-$C_8$-cycloalkyl-$C_1$-$C_8$-alkoxy, $C_2$-$C_8$-alkenyl-$C_1$-$C_8$-alkoxy, $C_2$-$C_8$-alkynyl-$C_1$-$C_8$-alkoxy, $C_1$-$C_8$-halogen-$C_3$-$C_8$-cycloalkoxy comprising up to 9 halogen atoms which can be the same or different, $C_3$-$C_8$-cycloalkenyloxy, $C_1$-$C_8$-alkoxy-$C_1$-$C_8$-alkoxy, $C_3$-$C_8$-cycloalkoxy-$C_1$-$C_8$-alkoxy, $C_1$-$C_8$-halogenoalkoxy-$C_1$-$C_8$-alkoxy comprising up to 9 halogen atoms which can be the same or different, $C_1$-$C_8$-alkylsulfanyl-$C_1$-$C_8$-alkoxy, $C_1$-$C_8$-alkylamino-$C_1$-$C_8$-alkoxy, $C_1$-$C_8$-halogenoalkylamino-$C_1$-$C_8$-alkoxy comprising up to 9 halogen atoms which can be the same or different, $C_3$-$C_8$-cycloalkylamino-$C_1$-$C_8$-alkoxy, $C_1$-$C_8$-trialkylsilyl-$C_1$-$C_8$-alkoxy, aryloxy which can be substituted by up to 5 groups Q, benzyloxy which can be substituted by up to 5 groups Q; $C_1$-$C_8$-alkylamino, ($C_1$-$C_8$-alkyl)carbonylamino, $C_3$-$C_8$-cycloalkylamino, $C_1$-$C_8$-halogenoalkylamino comprising up to 9 halogen atoms which can be the same or different, $C_3$-$C_8$-cycloalkyl-$C_1$-$C_8$-alkylamino, $C_2$-$C_8$-alkenyl-$C_1$-$C_8$-alkylamino, $C_2$-$C_8$-alkynyl-$C_1$-$C_8$-alkylamino, halogeno-$C_3$-$C_8$-cycloalkylamino comprising up to 9 halogen atoms which can be the same or different, arylamino which can be substituted by up to 5 groups Q, benzylamino which can be substituted by up to 5 groups Q, an aryl-$C_3$-$C_8$-cycloalkyl which can be substituted by up to 5 groups Q;

R⁷ represents hydrogen, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl, $C_2$-$C_8$-alkynyl, $C_2$-$C_8$-alkenyl-$C_1$-$C_8$-alkyl, $C_2$-$C_8$-alkynyl-$C_1$-$C_8$-alkyl, halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$- alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl or naphthyl, each of which can be substituted by up to 5 groups Q, benzyl which can be substituted by up to 5 groups Q, phenyl-$C_1$-$C_2$-alkylimino, $R^7$ also represents CN, if R is $R^B$, t is 0 and $Y^4$ is a bond, $R^8$ represents hydrogen, OH, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_3$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl which can be substituted by up to 5 groups Q, benzyl which can be substituted by up to 5 groups Q; $C_1$-$C_8$-alkoxy, $C_3$-$C_8$-cycloalkoxy, $C_1$-$C_8$-halogenoalkoxy comprising up to 9 halogen atoms which can be the same or different, $C_3$-$C_8$-cycloalkyl-$C_1$-$C_8$-alkoxy, $C_2$-$C_8$-alkenyl-$C_1$-$C_8$-alkoxy, $C_1$-$C_8$-alkynyl-$C_1$-$C_8$-alkoxy, $C_1$-$C_8$-halogeno-$C_3$-$C_8$-cycloalkoxy comprising up to 9 halogen atoms which can be the same or different, $C_3$-$C_8$-cycloalkenyloxy, $C_1$-$C_8$-alkoxy-$C_1$-$C_8$-alkoxy, $C_3$-$C_8$-cycloalkoxy-$C_1$-$C_8$-alkoxy, $C_1$-$C_8$-halogenoalkoxy-$C_1$-$C_8$-alkoxy comprising up to 9 halogen atoms which can be the same or different, $C_1$-$C_8$-alkylsulfanyl-$C_1$-$C_8$-alkoxy, $C_1$-$C_8$-alkylamino-$C_1$-$C_8$-alkoxy, $C_1$-$C_8$-halogenoalkylamino-$C_1$-$C_8$-alkoxy comprising up to 9 halogen atoms which can be the same or different, $C_3$-$C_8$-cycloalkylamino-$C_1$-$C_8$-alkoxy, $C_1$-$C_8$-trialkylsilyl-$C_1$-$C_8$-alkoxy, aryloxy which can be substituted by up to 5 groups Q, benzyloxy which can be substituted by up to 5 groups Q, $R^9$ represents hydrogen, OH, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_3$-$C_8$-halogenocycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl which can be substituted by up to 5 groups Q, benzyl which can be substituted by up to 5 groups Q; $C_1$-$C_8$-alkoxy, $C_3$-$C_8$-cycloalkoxy, $C_1$-$C_8$-halogenoalkoxy comprising up to 9 halogen atoms which can be the same or different, $C_3$-$C_8$-cycloalkyl-$C_1$-$C_8$-alkoxy, $C_2$-$C_8$-alkenyl-$C_1$-$C_8$-alkoxy, $C_2$-$C_8$-alkynyl-$C_1$-$C_8$-alkoxy, halogeno-$C_3$-$C_8$-cycloalkoxy comprising up to 9 halogen atoms which can be the same or different, $C_3$-$C_8$-cycloalkenyloxy, $C_1$-$C_8$-alkoxy-$C_1$-$C_8$-alkoxy, $C_3$-$C_8$-cycloalkoxy-$C_1$-$C_8$-alkoxy, $C_1$-$C_8$-halogenoalkoxy-$C_1$-$C_8$-alkoxy comprising up to 9 halogen atoms which can be the same or different, $C_1$-$C_8$-alkylsulfanyl-$C_1$-$C_8$-alkoxy, $C_1$-$C_8$-alkylamino-$C_1$-$C_8$-alkoxy, $C_1$-$C_8$-halogenoalkylamino-$C_1$-$C_8$-alkoxy comprising up to 9 halogen atoms which can be the same or different, $C_3$-$C_8$-cycloalkylamino-$C_1$-$C_8$-alkoxy, $C_1$-$C_8$-trialkylsilyl-$C_1$-$C_8$-alkoxy, phenyloxy which can be substituted by up to 5 groups Q, benzyloxy which can be substituted by up to 5 groups Q, Q which can be the same or different, independently represents halogen, CN, $NO_2$, $C_1$-$C_8$-alkyl, $C_1$-$C_8$-alkoxy, $C_1$-$C_8$-alkylsulfanyl, $C_1$-$C_8$-halogenoalkyl comprising up to 9 halogen atoms which can be the same or, $C_1$-$C_8$-halogenoalkoxy comprising up to 9 halogen atoms which can be the same or different, tri($C_1$-$C_8$)alkylsilyl or tri($C_1$-$C_8$)alkylsilyl-$C_1$-$C_8$-alkyl, or two vicinal substituents Q may be —$OCH_2O$—, —$OCF_2O$—, —$O(CH_2)_2O$—, —$O(CF_2)_2O$— or —N—CH—S—, $Z^1, Z^2, Z^3, Z^4, Z^5, Z^6, Z^7, Z^8, Z^9, Z^{10}$ and $Z^{11}$ which can be the same or different, independently of one another represent hydrogen, halogen, $NO_2$, CN, OH, SH, $NH_2$, $SF_5$, $C_1$-$C_8$-alkyl, $C_1$-$C_8$-halogenoalkyl comprising up to 9 halogen atoms which can be the same or different and optionally in addition one hydroxy group, $C_1$-$C_8$-alkylamino, di-$C_1$-$C_8$-alkylamino, $C_1$-$C_8$-alkoxy, $C_1$-$C_8$-halogenoalkoxy comprising up to 9 halogen atoms which can be the same or different, $C_1$-$C_8$-alkoxy-$C_1$-$C_8$-alkyl, $C_1$-$C_8$-alkylsulfanyl, $C_1$-$C_8$-halogenoalkylsulfanyl comprising up to 9 halogen atoms which can be the same or different, $C_2$-$C_8$-alkenyl, $C_2$-$C_8$-halogenoalkenyl comprising up to 9 halogen atoms which can be the same or different, $C_2$-$C_8$-alkynyl, $C_2$-$C_8$-halogenoalkynyl comprising up to 9 halogen atoms which can be the same or different, $C_2$-$C_8$-alkenyloxy, $C_2$-$C_8$-halogenoalkenyloxy comprising up to 9 halogen atoms which can be the same or different, $C_2$-$C_8$-alkynyloxy, $C_2$-$C_8$-halogenoalkynyloxy comprising up to 9 halogen atoms which can be the same or different, $C_2$-$C_8$-alkenylsulfanyl, $C_2$-$C_8$-alkynylsulfanyl, $C_3$-$C_7$-cycloalkyl, $C_3$-$C_7$-cycloalkyl-$C_1$-$C_8$-alkyl, $C_3$-$C_7$-halogenocycloalkyl comprising up to 9 halogen atoms which can be the same or different, formyl, formyloxy, formylamino, carbamoyl, N-hydroxycarbamoyl, (hydroxyimino)-$C_1$-$C_8$-alkyl, $C_1$-$C_8$-alkylcarbonyl, $C_1$-$C_8$-halogenoalkylcarbonyl comprising up to 9 halogen atoms which can be the same or different, ($C_3$-$C_7$-cycloalkyl)carbonyl, $C_1$-$C_8$-alkylcarbamoyl, di-$C_1$-$C_8$-alkylcarbamoyl, N—$C_1$-$C_8$-alkoxycarbamoyl, $C_1$-$C_8$-alkoxycarbamoyl, N—$C_1$-$C_8$-alkyl-$C_1$-$C_8$-alkoxycarbamoyl, $C_1$-$C_8$-alkoxycarbonyl, $C_1$-$C_8$-halogenoalkoxycarbonyl comprising up to 9 halogen atoms which can be the same or different, $C_1$-$C_8$-alkylaminocarbonyl, di-($C_1$-$C_8$-alkyl)aminocarbonyl, $C_1$-$C_8$-alkylcarbonyloxy, $C_1$-$C_8$-halogenoalkylcarbonyloxy comprising up to 9 halogen atoms which can be the same or different, $C_1$-$C_3$-alkylcarbonylamino, $C_1$-$C_8$-halogenoalkylcarbonylamino comprising up to 9 halogen atoms which can be the same or different, $C_1$-$C_8$-alkylaminocarbonyloxy, di-($C_1$-$C_8$-alkyl)-aminocarbonyloxy, $C_1$-$C_8$-alkoxycarbonyloxy, $C_1$-$C_8$-alkylsulphinyl, $C_1$-$C_8$-halogenoalkylsulphinyl comprising up to 9 halogen atoms which can be the same or different, $C_1$-$C_8$-alkylsulphonyl, $C_1$-$C_8$-halogenoalkylsulphonyl comprising up to 9 halogen atoms which can be the same or different, $C_1$-$C_8$-alkoxyimino, ($C_1$-$C_8$-alkylimino)-$C_1$-$C_8$-alkyl, ($C_1$-$C_8$-alkoxyimino)-$C_1$-$C_8$-alkyl, ($C_1$-$C_8$-alkenyloxyimino)-$C_1$-$C_8$-alkyl, ($C_2$-$C_8$-alkynyloxyimino)-$C_1$-$C_8$-alkyl, a (benzyloxyimino)-$C_1$-$C_8$-alkyl, tri-($C_1$-$C_8$-alkyl)silyl, tri ($C_1$-$C_8$-alkyl)silyl-$C_1$-$C_8$-alkyl, benzyloxy which can be substituted by up to 5 groups Q, benzylsulfanyl which can be substituted by up to 5 groups Q, benzylamino which can be substituted by up to 5 groups Q, phenyl which can be substituted by up to 5 groups Q, naphthyl which can be substituted by up to 6 groups Q, phenoxy which can be substituted by up to 5 groups Q, phenylamino which can be substituted by up to 5 groups Q, phenylsulfanyl which can be substituted by up to 5 groups Q, phenylmethylene which can be substituted by up to 5 groups Q.

or two vicinal substituents Z together with the consecutive carbon atoms to which they are linked form a 5- or 6-membered, saturated or unsaturated, carbo- or heterocycle comprising up to 3 heteroatoms, which can be substituted by up to four groups Q which can be the same or different and the other substituents Z are as herein-described, or two geminal substituents Z together with the carbon atom to which they are linked could also be fused to represent C(=O); C(=S), $C_3$-$C_9$-cycloalkyl;

$G^1$ and $G^2$ which can be the same or different, independently of one another represent hydrogen, CN, OH, $NH_2$, $C_1$-$C_8$-alkyl, $C_1$-$C_8$-halogenoalkyl comprising up to 9 halogen atoms which can be the same or different, $C_1$-$C_8$-alkylamino, di-$C_1$-$C_8$-alkylamino, $C_1$-$C_8$-alkoxy, $C_1$-$C_8$-halogenoalkoxy comprising up to 9 halogen atoms which can be the same or different, $C_1$-$C_8$-alkoxy-$C_1$-$C_8$-alkyl, $C_2$-$C_8$-alkenyl, $C_2$-$C_8$-halogenoalkenyl comprising up to 9 halogen atoms which can be the same or different, $C_2$-$C_8$-alkynyl, $C_2$-$C_8$-halogenoalkynyl comprising up to 9 halogen atoms which can be the same or different $C_2$-$C_8$-alkenyloxy, $C_2$-$C_8$-halogenoalkenyloxy comprising up to 9 halogen atoms which can be the same or different, $C_2$-$C_8$-alkynyloxy, $C_2$-$C_8$-halogenoalkynyloxy comprising up to 9 halogen atoms which can be the same or different, $C_3$-$C_7$-cycloalkyl, $C_3$-$C_7$-cycloalkyl-$C_1$-$C_8$-alkyl, $C_3$-$C_7$-halogenocycloalkyl comprising up to 9 halogen atoms which can be the same or different, formyl, carbamoyl, (hydroxyimino)-$C_1$-$C_8$-alkyl, $C_1$-$C_8$-alkylcarbonyl, $C_1$-$C_8$-halogenoalkylcarbonyl comprising up to 9 halogen atoms which can be the same or different, $C_1$-$C_8$-alkylcarbamoyl, $C_1$-$C_8$-alkoxycarbonyl, $C_1$-$C_8$-halogenoalkoxycarbonyl comprising up to 9 halogen atoms which can be the same or different, $C_1$-$C_8$-alkylaminocarbonyl, di-$C_1$-$C_8$-alkylaminocarbonyl, $C_1$-$C_8$-alkylsulphonyl, $C_1$-$C_8$-halogenoalkylsulphonyl comprising up to 9 halogen atoms which can be the same or different, ($C_1$-$C_8$-alkoxyimino)-$C_1$-$C_8$-alkyl, ($C_1$-$C_8$-alkenyloxyimino)-$C_1$-$C_8$-alkyl, ($C_2$-$C_8$-alkynyloxyimino)-$C_1$-$C_8$-alkyl, a (benzyloxyimino)-$C_1$-$C_8$-alkyl, tri($C_1$-$C_8$-alkyl)silyl, tri($C_1$-$C_8$-alkyl)silyl-$C_1$-$C_8$-alkyl, benzyloxy which can be substituted by up to 5 groups Q, benzylamino which can be substituted by up to 5 groups Q, phenyl which can be substituted by up to 5 groups Q; naphthyl which can be substituted by up to 6 groups Q, phenoxy which can be substituted by up to 5 groups Q, phenylamino which can be substituted by up to 5 groups Q, phenylmethylene which can be substituted by up to 5 groups Q, provided that when n represents 1 then $R^2$, $R^3$ and $R^4$ do not represent simultaneously a hydrogen atom, when Het represents Het 42, $Y^1$ and $Y^2$ represent O, $R^1$ represents ethyl, then $Z^3$ does not represent hydrogen or $NO_2$, when Het represents Het 8 and n represents O, then $R^4$ does not represent an unsubstituted phenyl group, when Het represents an indole ring then $R^{13}$ does not represent —$CH_2$—$CH_2$—OH, —$CH_2$—$OCOC_2H_5$, —$CH_2$—$CH_2$—$N(C_2H_5)_2$, when Het represents a 4,5,6,7-tetrahydro-1H-indole then $R^A$ does not represent n-butyl, as well as salts, N-oxides, metallic complexes, metalloidic complexes and optically active or geometric isomers thereof.

Depending on the nature of the substituents defined above, the compounds of the formula (I) have acidic or basic properties and can form salts, if appropriate also inner salts or adducts, with inorganic or organic acids or with inorganic or organic bases or with metal ions. Suitable metal ions are in particular the ions of the elements of the second main group, in particular calcium and magnesium, of the third and fourth main group, in particular aluminum, tin and lead, and also of the first to eighth transition group, in particular chromium, manganese, iron, cobalt, nickel, copper, zinc and others. Particular preference is given to the metal ions of the elements of the fourth period. Here, the metals can be present in the various valencies they can assume.

If the compounds of the formula (I) carry hydroxyl groups, carboxyl groups or other groups which induce acidic properties, these compounds can be converted with bases into salts. Suitable bases are, for example, the hydroxides, carbonates and bicarbonates of the alkali metals and the alkaline earth metals, in particular those of sodium, potassium, magnesium and calcium, furthermore ammonia, primary, secondary and tertiary amines having $C_1$-$C_4$-alkyl radicals, mono-, di- and trialkanolamines of $C_1$-$C_4$-alkanols, choline and also chlorocholine.

If the compounds of the formula (I) carry amino groups, alkylamino groups or other groups which induce basic properties, these compounds can be converted with acids into salts. Examples of inorganic acids are hydrohalic acids, such as hydrofluoric acid, hydrochloric acid, hydrobromic acid and hydroiodic acid, sulphuric acid, phosphoric acid and nitric acid, and acidic salts, such as $NaHSO_4$ and $KHSO_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulphonic acids (sulphonic acids having straight-chain or branched alkyl radicals of 1 to 20 carbon atoms), arylsulphonic acids or disulphonic acids (aromatic radicals, such as phenyl and naphthyl which carry one or two sulphonic acid groups), alkylphosphonic acids (phosphonic acids having straight-chain or branched alkyl radicals of 1 to 20 carbon atoms), arylphosphonic acids or -diphosphonic acids (aromatic radicals, such as phenyl and naphthyl, which carry one or two phosphonic acid radicals, where the alkyl radicals and aryl radicals may carry further substituents, for example p-toluenesulphonic acid, salicylic acid, p-aminosalicylic acid, 2-phenoxybenzoic acid, 2-acetoxybenzoic acid, etc.

The salts which can be obtained in this manner also have fungicidal properties.

Compounds of the formula (I) according to the invention can, if appropriate, be present as mixtures of various possible isomeric forms, in particular of stereoisomers, such as, for example, E and Z, threo and erythro, and also optical isomers, atropoisomers, and, if appropriate, also of tautomers. What is claimed are both the E and the Z isomers and the threo and erythro and also the optical isomers, any mixtures of these isomers, and also the possible tautomeric forms.

In particular the aminopropenoate derivatives of the formula (I) may exist in Z-form or in E-form, where the correct assignment of Z and E according to the IUPAC nomenclature depends on the definitions of the different substituents. For easy reference in this patent application the assignment is made as shown. In all formulas below and above the E-form is used. Nevertheless the Z-form is also part of this invention.

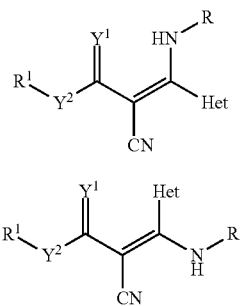

(E)-(I)

(Z)-(I)

According to the invention, the following generic terms are generally used with the following meanings:

Halogen means fluorine, chlorine, bromine or iodine.

Heteroatom can be nitrogen, oxygen or sulphur.

Aryl means phenyl or naphthyl, optionally substituted by one to five groups selected from the group consisting of halogen, $C_1$-$C_6$-alkyl, $C_1$-$C_6$-haloalkyl, $C_2$-$C_6$-alkenyl, $C_2$-$C_6$-haloalkenyl, $C_2$-$C_8$-alkynyl, $C_2$-$C_6$-haloalkynyl, $C_1$-$C_6$-alkoxy, $C_1$-$C_4$-alkoxy-$C_1$-$C_4$-alkyl, $C_1$-$C_4$-alkoxy-$C_1$-$C_4$-alkoxy, $C_1$-$C_6$-haloalkoxy and $C_1$-$C_4$-haloalkoxy-$C_1$-$C_4$-alkyl.

Any alkyl, alkenyl or alkynyl group can be linear or branched.

The formula (I) provides a general definition of the aminopropenoate derivatives which can be used according to the invention. Preferred radical definitions of the formulae given above and below are indicated below. These definitions apply both to the end products of the formula (I) and likewise to all intermediates. These definitions apply both to the end products of the formula (I) and likewise to all intermediates.

Preferred compounds of formula (I) according to the invention are those wherein R represents $R^A$. Other preferred compounds of formula (I) according to the invention are those wherein R represents $R^B$.

Preferred compounds of formula (I) according to the invention are those wherein n represents 0, 1, 2 or 3. More preferred compounds of formula (I) according to the invention are those wherein n represents 0, 1 or 2.

Preferred compounds of formula (I) according to the invention are those wherein m represents 1, 2 or 3. More preferred compounds of formula (I) according to the invention are those wherein m represents 1 or 2.

Preferred compounds of formula (I) according to the invention are those wherein $Y^1$ represents S, O. More preferred compounds of formula (I) according to the invention are those wherein $Y^1$ represents O.

Preferred compounds of formula (I) according to the invention are those wherein $Y^2$ represents O or $NR^6$. More preferred compounds of formula (I) according to the invention are those wherein $Y^2$ represents O or $NR^6$ wherein $R^6$ represents hydrogen, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, $C_1$-$C_8$-alkoxy.

Even more preferred compounds of formula (I) according to the invention are those wherein $Y^2$ represents O or $NR^6$ wherein $R^6$ represents hydrogen, methyl, methoxy or ethoxy.

Preferred compounds of formula (I) according to the invention are those wherein $Y^3$ represents O or $NR^8$. More preferred compounds of formula (I) according to the invention are those wherein $Y^3$ represents O or $NR^8$ wherein $R^8$ represents hydrogen, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, $C_1$-$C_6$-alkoxy, $C_3$-$C_6$-cycloalkoxy, $C_1$-$C_6$-halogenoalkoxy comprising up to 9 halogen atoms which can be the same or different, $C_3$-$C_6$-cycloalkyl-$C_1$-$C_6$-alkoxy, $C_2$-$C_6$-alkenyl-$C_1$-$C_6$-alkoxy, $C_2$-$C_6$-alkynyl-$C_1$-$C_6$-alkoxy, $C_1$-$C_6$-halogeno-$C_3$-$C_6$-cycloalkoxy comprising up to 9 halogen atoms which can be the same or different, $C_3$-$C_6$-cycloalkenyloxy, $C_1$-$C_6$-alkoxy-$C_1$-$C_6$-alkoxy, $C_3$-$C_6$-cycloalkoxy-$C_1$-$C_6$-alkoxy, $C_1$-$C_6$-halogenoalkoxy-$C_1$-$C_6$-alkoxy comprising up to 9 halogen atoms which can be the same or different, $C_1$-$C_6$-alkylsulfanyl-$C_1$-$C_6$-alkoxy, $C_1$-$C_6$-alkylamino-$C_1$-$C_6$-alkoxy, $C_1$-$C_6$-halogenoalkylamino-$C_1$-$C_6$-alkoxy comprising up to 9 halogen atoms which can be the same or different, $C_3$-$C_6$-cycloalkylamino-$C_1$-$C_6$-alkoxy, $C_1$-$C_6$-trialkylsilyl-$C_1$-$C_6$-alkoxy, aryloxy which can be substituted by up to 5 groups Q, benzyloxy which can be substituted by up to 5 groups Q.

Even more preferred compounds of formula (I) according to the invention are those wherein $Y^3$ represents O or $NR^8$ wherein $R^8$ represents hydrogen or methyl, methoxy, ethoxy, n-propoxy, isopropoxy, n-, s- or t-butoxy, trifluoromethoxy, difluoromethoxy.

Preferred compounds of formula (I) according to the invention are those wherein $Y^4$ represents a bond, O or $NR^9$.

More preferred compounds of formula (I) according to the invention are those wherein $Y^4$ represents a bond, O or $NR^9$ wherein $R^9$ represents hydrogen or $C_1$-$C_6$-alkyl.

Even more preferred compounds of formula (I) according to the invention are those wherein $Y^4$ represents a bond, O or $NR^9$ wherein $R^9$ represents hydrogen, methyl or ethyl.

Preferred compounds of formula (I) according to the invention are those wherein $R^1$ represents hydrogen, $C_1$-$C_8$-alkyl, $C_3$-$C_8$-cycloalkyl, $C_1$-$C_8$-halogenoalkyl comprising up to 9 halogen atoms which can be the same or different, $C_2$-$C_4$-alkenyl, $C_2$-$C_4$-alkynyl, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogeno alkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl, $C_1$-$C_8$-trialkylsilyl-$C_1$-$C_8$-alkyl.

More preferred compounds of formula (I) according to the invention are those wherein $R^1$ represents hydrogen, $C_1$-$C_8$-alkyl, $C_3$-$C_6$-cycloalkyl, $C_1$-$C_4$-halogenoalkyl comprising up to 9 halogen atoms which can be the same or different, $C_2$-$C_4$-alkenyl, $C_2$-$C_4$-alkynyl, $C_1$-$C_4$-alkoxy-$C_1$-$C_4$-alkyl.

Even more preferred compounds of formula (I) according to the invention are those wherein $R^1$ represents hydrogen, methyl, ethyl, n-propyl, isopropyl, n-, s-, t-butyl, cyclopropyl, cyclobutyl, trifluoropropyl, trifluoroethyl, allyl, propargyl, methoxymethyl, ethoxyethyl, ethoxymethyl, methoxyethyl.

Preferred compounds of formula (I) according to the invention are those wherein Het is selected in the list of Het 1 to Het 61, wherein $Z^1$, $Z^2$, $Z^3$, $Z^4$ and $Z^5$ which can be the same or different, independently of one another represent hydrogen, halogen, $NO_2$, CN, OH, SH, $NH_2$, $C_1$-$C_6$-alkyl, $C_1$-$C_6$-halogenoalkyl comprising up to 9 halogen atoms which can be the same or different, $C_1$-$C_6$-alkylamino, di-$C_1$-$C_6$-alkylamino, $C_1$-$C_6$-alkoxy, $C_1$-$C_6$-halogenoalkoxy comprising up to 9 halogen atoms which can be the same or different, $C_1$-$C_6$-alkylsulfanyl, $C_1$-$C_6$-halogenoalkylsulfanyl comprising up to 9 halogen atoms which can be the same or different, $C_2$-$C_6$-alkenyl, $C_2$-$C_6$-halogenoalkenyl comprising up to 9 halogen atoms which can be the same or different, $C_2$-$C_6$-alkynyl, $C_2$-$C_6$-halogenoalkynyl comprising up to 9 halogen atoms which can be the same or different, $C_3$-$C_7$-cycloalkyl, $C_3$-$C_7$-cycloalkyl-$C_1$-$C_8$-alkyl, $C_3$-$C_7$-halogenocycloalkyl comprising up to 9 halogen atoms which can be the same or different, formyl, formyloxy, formylamino, carbamoyl, $C_1$-$C_6$-alkylcarbonyl, $C_1$-$C_6$-halogenoalkylcarbonyl comprising up to 9 halogen atoms which can be the same or different, $C_1$-$C_6$-alkylcarbamoyl, di-$C_1$-$C_6$-alkylcarbamoyl, $C_1$-$C_6$-alkylcarbonyl, $C_1$-$C_6$-alkoxycarbonyl, $C_1$-$C_6$-halogenoalkoxycarbonyl comprising up to 9 halogen atoms which can be the same or different, $C_1$-$C_6$-alkylaminocarbonyl, di-$C_1$-$C_6$-alkylaminocarbonyl, $C_1$-$C_6$-alkylcarbonyloxy, $C_1$-$C_6$-halogenoalkylcarbonyloxy comprising up to 9 halogen atoms which can be the same or different, $C_1$-$C_6$-alkylcarbonylamino, $C_1$-$C_6$-halogenoalkylcarbonylamino comprising up to 9 halogen atoms which can be the same or different, $C_1$-$C_6$-alkylsulphinyl, $C_1$-$C_6$-halogenoalkylsulphinyl comprising up to 9 halogen atoms which can be the same or different, $C_1$-$C_6$-alkylsulphonyl, $C_1$-$C_6$-halogenoalkylsulphonyl comprising up to 9 halogen atoms which can be the same or different, tri($C_1$-$C_6$-alkyl)silyl, tri($C_1$-$C_6$-alkyl)silyl-$C_1$-$C_6$-alkyl, benzyloxy which can be substituted by up to 5 groups Q, benzylamino which can be substituted by up to 5 groups Q, phenyl which can be substituted by up to 5 groups Q; naphthyl which can be substituted by up to 6 groups Q, phenoxy which can be substituted by up to 5 groups Q, phenylamino which can be substituted by up to 5 groups Q, phenylsulfanyl which can be substituted by up to 5 groups Q, or two vicinal substituents Z together with the consecutive carbon atoms to which they are linked form a 5- or 6-membered, saturated, carbo- or heterocycle comprising up to 3 heteroatoms, which can be substituted by up to four groups Q which can be the same or different and the other substituents Z are as herein-described and Q, which can be the same or different, represents a halogen atom, cyano group, nitro group, $C_1$-$C_6$-alkyl, $C_1$-$C_6$-alkoxy, $C_1$-$C_6$-halogenoalkyl comprising up to 9 halogen atoms which can be the same or different, $C_1$-$C_6$-halogenoalkoxy comprising up to 9 halogen atoms which can be the same or different, tri($C_1$-$C_6$)alkylsilyl or tri($C_1$-$C_6$)alkylsilyl-$C_1$-$C_6$-alkyl. And $G^1$ and $G^2$ which can be the same or different, represent a hydrogen atom, cyano group, hydroxyl, amino, $C_1$-$C_6$-alkyl, $C_1$-$C_6$-halogenoalkyl comprising up to 9 halogen atoms which can be the same or different, $C_1$-$C_6$-alkoxy-$C_1$-$C_6$-alkyl, $C_3$-$C_7$-cycloalkyl, $C_3$-$C_7$-cycloalkyl-$C_1$-$C_6$-alkyl, $C_3$-$C_7$-halogenocycloalkyl comprising up to 9 halogen atoms which can be the same or different, formyl, $C_1$-$C_6$-alkylcarbonyl, $C_1$-$C_6$-halogenoalkylcarbonyl comprising up to 9 halogen atoms which can be the same or different, $C_1$-$C_6$-alkylcarbamoyl, $C_1$-$C_6$-alkoxycarbonyl, $C_1$-$C_6$-halogenoalkoxycarbonyl comprising up to 9 halogen atoms which can be the same or different, $C_1$-$C_6$-alkylaminocarbonyl, di-$C_1$-$C_6$-alkylaminocarbonyl, $C_1$-$C_6$-alkylsulphonyl, $C_1$-$C_6$-halogenoalkylsulphonyl comprising up to 9 halogen atoms which can be the same or different, tri($C_1$-$C_6$-alkyl)silyl, tri($C_1$-$C_6$-alkyl)silyl-$C_1$-$C_6$-alkyl, phenyl which can be substituted by up to 5 groups Q; phenylmethylene which can be substituted by up to 5 groups Q.

More preferred compounds of formula (I) according to the invention are those wherein Het is selected in the list of Het 1 to Het 12, Het 15 to Het 22, Het 25, Het 27, Het 28, Het 30, Het 33 to Het 43, Het 46 to Het 53, Het 55 to Het 59 and Het 61, wherein $Z^1$, $Z^2$, $Z^3$, $Z^4$ and $Z^5$ which can be the same or different, independently of one another represent hydrogen, halogen, $NO_2$, CN, OH, SH, $NH_2$, $C_1$-$C_4$-alkyl, $C_1$-$C_4$-halogenoalkyl comprising up to 9 halogen atoms which can be the same or different, $C_1$-$C_4$-alkylamino, di-$C_1$-$C_4$-alkylamino, $C_1$-$C_4$-alkoxy, $C_1$-$C_4$-halogenoalkoxy comprising up to 9 halogen atoms which can be the same or different, $C_2$-$C_4$-alkenyl, $C_2$-$C_4$-alkynyl, $C_3$-$C_7$-cycloalkyl, $C_3$-$C_7$-halogenocycloalkyl comprising up to 9 halogen atoms which can be the same or different, $C_1$-$C_4$-alkylcarbonyl, $C_1$-$C_4$-halogenoalkylcarbonyl comprising up to 9 halogen atoms which can be the same or different, $C_1$-$C_4$-alkoxycarbonyl, $C_1$-$C_4$-halogenoalkoxycarbonyl comprising up to 9 halogen atoms which can be the same or different, $C_1$-$C_4$-alkylcarbonyloxy, $C_1$-$C_4$-halogenoalkylcarbonyloxy comprising up to 9 halogen atoms which can be the same or different, $C_1$-$C_4$-alkylcarbonylamino, $C_1$-$C_4$-halogenoalkylcarbonylamino comprising up to 9 halogen atoms which can be the same or different, $C_1$-$C_4$-alkylsulfanyl, $C_1$-$C_4$-halogenoalkylsulfanyl comprising up to 9 halogen atoms which can be the same or different, $C_1$-$C_4$-alkylsulphonyl, $C_1$-$C_4$-halogenoalkylsulphonyl comprising up to 9 halogen atoms which can be the same or different, tri($C_1$-$C_4$-alkyl)silyl, phenyl which can be substituted by up to 5 groups Q; naphthyl which can be substituted by up to 6 groups Q, or two vicinal substituents Z together with the consecutive carbon atoms to which they are linked form 6-membered, unsaturated carbocycle which can be substituted by up to four groups Q which can be the same or different and the other substituents Z are as herein-described and Q, which can be the same or different, represents a halogen atom, cyano group, nitro group, $C_1$-$C_4$-alkyl, $C_1$-$C_4$-alkoxy, $C_1$-$C_4$-halogenoalkyl comprising up to 9 halogen atoms which can be the same or different, $C_1$-$C_4$-halogenoalkoxy comprising up to 9 halogen atoms which can be the same or different, tri($C_1$-$C_4$)alkylsilyl And $G^1$ and $G^2$ which can be the same or different, represent a hydrogen atom, $C_1$-$C_4$ alkyl, $C_1$-$C_4$-alkoxy-$C_1$-$C_4$-alkyl, $C_3$-$C_7$-cycloalkyl, $C_3$-$C_7$-halogenocycloalkyl comprising up to 9 halogen atoms which can be the same or different, formyl, $C_1$-$C_4$-alkylcarbonyl, $C_1$-$C_4$-halogenoalkylcarbonyl comprising up to 9 halogen atoms which can be the same or different.

Even more preferred compounds of formula (I) according to the invention are those wherein Het is selected in the list of Het 1 to Het 3, Het 8 to Het 11, Het 25, Het 30, Het 36, Het 37, Het 39 to Het 43, Het 46 to Het 50, Het 52, Het 53 and Het 61, wherein $Z^1$, $Z^2$, $Z^3$, $Z^4$ and $Z^5$ which can be the same or different, independently of one another represent hydrogen, halogen, $NO_2$, CN, OH, SH, $NH_2$, methyl, ethyl, n-propyl, isopropyl, n-, s- or t-butyl, difluoromethyl, trifluoromethyl, fluoroethyl, difluoroethyl, methylamino, ethylamino, dimethylamino, diethylamino, methoxy, ethoxy, trifluoromethoxy, vinyl, allyl, ethinyl, propargyl, cyclopropyl, cyclohexyl, acetyl, $C_1$-$C_3$-halogenoalkylcarbonyl comprising up to 5 halogen atoms which can be the same or different, carboxyl, methoxycarbonyl, ethoxycarbonyl, $C_1$-$C_4$-alkylcarbonyloxy, $C_1$-$C_4$-alkylcarbonylamino, $C_1$-$C_4$-halogenoalkylcarbonylamino comprising up to 5 halogen atoms which can be the same or different, methylthio, ethylthio, trimethylsilyl, phenyl which can be substituted by up to 3 groups Q; naphthyl which can be substituted by up to 6 groups Q.

Q, which can be the same or different, independently preferably represents halogen, CN, $NO_2$, $C_1$-$C_8$-alkyl, $C_1$-$C_6$-alkoxy, $C_1$-$C_6$-halogenoalkyl comprising up to 5 halogen atoms which can be the same or different, $C_1$-$C_6$-halogenoalkoxy comprising up to 5 halogen atoms which can be the same or different, tri($C_1$-$C_8$-alkylsilyl.

$G^1$ and $G^2$ which can be the same or different, independently of one another represent hydrogen, $C_1$-$C_6$-alkyl, $C_3$-$C_6$-cycloalkyl, $C_1$-$C_6$-halogenoalkyl comprising up to 5 halogen atoms which can be the same or different, $C_3$-$C_6$-halogenocycloalkyl comprising up to 5 halogen atoms which can be the same or different, $C_1$-$C_6$-alkylcarbonyl, $C_1$-$C_6$-halogenoalkylcarbonyl comprising up to 5 halogen atoms which can be the same or different.

More preferred $G^1$ and $G^2$ which can be the same or different, independently of one another represent hydrogen, $C_1$-$C_4$-alkyl, $C_3$-$C_6$-cycloalkyl, $C_1$-$C_6$-alkylcarbonyl.

Even more preferred $G^1$ and $G^2$ which can be the same or different, independently of one another represent hydrogen or methyl.

Preferred compounds of formula (I) according to the invention are those wherein $R^2$ and $R^3$, which can be the same or different, independently of one another represent hydrogen, halogen, CN, $NH_2$, $C_1$-$C_6$-alkyl, $C_1$-$C_6$-hydroxyalkyl, $C_3$-$C_6$-cycloalkyl, $C_3$-$C_6$-halogenocycloalkyl comprising up to 9 halogen atoms which can be the same or different, $C_1$-$C_6$-halogenoalkyl comprising up to 9 halogen atoms which can be the same or different, $C_3$-$C_6$-cycloalkyl-$C_1$-$C_6$-alkyl, $C_2$-$C_6$-alkenyl, $C_2$-$C_6$-alkynyl, $C_2$-$C_6$-alkenyl-$C_1$-$C_6$-alkyl, $C_2$-$C_6$-alkynyl-$C_1$-$C_6$-alkyl, $C_3$-$C_6$-halogenocycloalkyl comprising up to 9 halogen atoms which can be the same or different, $C_1$-$C_6$-alkoxy-$C_1$-$C_6$-alkyl, $C_3$-$C_6$-cycloalkoxy-$C_1$-$C_6$-alkyl, $C_1$-$C_6$-halogenoalkoxy-$C_1$-$C_6$-alkyl comprising up to 9 halogen atoms which can be the same or different, $C_1$-$C_6$-alkylsulfanyl-$C_1$-$C_6$-alkyl, $C_1$-$C_6$-alkylamino-$C_1$-$C_6$-alkyl, $C_1$-$C_6$-halogenoalkylamino-$C_1$-$C_6$-alkyl comprising up to 9 halogen atoms which can be the same or different, $R_2$ and $R_3$ together with the carbon atom to which they are linked can form a $C_3$-$C_7$ cycloalkyl.

More preferred compounds of formula (I) according to the invention are those wherein $R^2$ and $R^3$, which can be the same or different, independently of one another represent hydrogen, halogen, CN, $C_1$-$C_4$-alkyl, $C_3$-$C_6$-cycloalkyl, $C_1$-$C_4$-halogenoalkyl comprising up to 5 halogen atoms which can be the same or different, $C_3$-$C_6$-cycloalkyl-$C_1$-$C_4$-alkyl, $C_2$-$C_4$-alkenyl, $C_2$-$C_4$-alkynyl, $C_2$-$C_4$-alkenyl-$C_1$-$C_4$-alkyl, $C_2$-$C_4$-alkynyl-$C_1$-$C_4$-alkyl, $C_3$-$C_4$-halogenocycloalkyl comprising up to 5 halogen atoms which can be the same or different, $C_1$-$C_4$-alkoxy-$C_1$-$C_4$-alkyl, $C_3$-$C_6$-cycloalkoxy-$C_1$-$C_4$-alkyl, $C_1$-$C_4$-halogenoalkoxy-$C_1$-$C_4$-alkyl comprising up to 5 halogen atoms which can be the same or different, $R_2$ and $R_3$ together with the carbon atom to which they are linked can form a $C_3$-$C_6$-cycloalkyl which may be substituted by 1 to 4 identical or different substituents selected from by fluorine, chlorine, bromine, OH, methyl, ethyl, n-propyl, isopropyl, n-, s- or t-butyl, trifluoromethyl, methoxy, ethoxy, methylthio, ethylthio, or phenyl.

Even more preferred compounds of formula (I) according to the invention are those wherein $R^2$ and $R^3$, which can be the same or different, independently of one another represent hydrogen, halogen, CN, methyl, ethyl, n-propyl, isopropyl, n-, s- or t-butyl, cyclopropyl, 1-chlorocyclopropyl, trifluoromethyl, trifluoroethyl, $C_3$-$C_6$-cycloalkyl-$C_1$-$C_6$-alkyl, $C_2$-$C_6$-alkenyl, $C_2$-$C_6$-alkynyl, $C_2$-$C_6$-alkenyl-$C_1$-$C_6$-alkyl, $C_2$-$C_6$-alkynyl-$C_1$-$C_8$-alkyl, $C_3$-$C_6$-halogenocycloalkyl comprising up to 5 halogen atoms which can be the same or different, $R_2$ and $R_3$ together with the carbon atom to which they are linked can form a $C_3$-$C_6$-cycloalkyl which may be substituted by 1 to 4 identical or different substituents selected from by fluorine, chlorine, bromine, OH, methyl, ethyl, n-propyl, isopropyl, n-, s- or t-butyl, trifluoromethyl, methoxy, ethoxy, methylthio, ethylthio, or phenyl.

Preferred compounds of formula (I) according to the invention are those wherein $R^4$ is selected from the group consisting of E 1 to E 144, wherein $Z^1$, $Z^2$, $Z^3$, $Z^4$, $Z^5$, $Z^6$, $Z^7$, $Z^8$, $Z^9$, $Z^{10}$ and $Z^{11}$ which can be the same or different, independently of one another represent hydrogen, halogen, $NO_2$, CN, OH, SH, $NH_2$, $C_1$-$C_6$-alkyl, $C_1$-$C_6$-halogenoalkyl comprising up to 9 halogen atoms which can be the same or different and optionally in addition one hydroxy group, $C_1$-$C_6$-alkylamino, di-$C_1$-$C_6$-alkylamino, $C_1$-$C_6$-alkoxy, $C_1$-$C_6$-halogenoalkoxy comprising up to 9 halogen atoms which can be the same or different, $C_1$-$C_6$-alkylsulfanyl, $C_1$-$C_6$-halogenoalkylsulfanyl comprising up to 9 halogen atoms which can be the same or different, $C_2$-$C_6$-alkenyl, $C_2$-$C_6$-halogenoalkenyl comprising up to 9 halogen atoms which can be the same or different, $C_2$-$C_6$-alkynyl, $C_2$-$C_6$-halogenoalkynyl comprising up to 9 halogen atoms which can be the same or different, $C_2$-$C_6$-alkenyloxy, $C_2$-$C_6$-alkynyloxy, $C_2$-$C_6$-alkenylsulfanyl, $C_2$-$C_6$-alkynylsulfanyl, $C_3$-$C_7$-cycloalkyl, $C_3$-$C_7$-cycloalkyl-$C_1$-$C_6$-alkyl, $C_3$-$C_7$-halogenocycloalkyl comprising up to 9 halogen atoms which can be the same or different, formyl, formyloxy, formylamino, carbamoyl, $C_1$-$C_6$-alkylcarbonyl, ($C_3$-$C_6$-cycloalkyl)carbonyl, $C_1$-$C_6$-halogenoalkylcarbonyl comprising up to 9 halogen atoms which can be the same or different, $C_1$-$C_6$-alkylcarbamoyl, di-$C_1$-$C_6$-alkylcarbamoyl, $C_1$-$C_6$-alkoxycarbonyl, $C_1$-$C_6$-halogenoalkoxycarbonyl comprising up to 9 halogen atoms which can be the same or different, $C_1$-$C_6$-alkylaminocarbonyl, di-$C_1$-$C_6$-alkylaminocarbonyl, $C_1$-$C_6$-alkylcarbonyloxy, $C_1$-$C_6$-halogenoalkylcarbonyloxy comprising up to 9 halogen atoms which can be the same or different, $C_1$-$C_6$-alkylcarbonylamino, $C_1$-$C_6$-halogenoalkylcarbonylamino comprising up to 9 halogen atoms which can be the same or different, $C_1$-$C_6$-alkylsulfanyl, $C_1$-$C_6$-halogenoalkylsulfanyl comprising up to 9 halogen atoms which can be the same or different, $C_1$-$C_6$-alkylsulphinyl, $C_1$-$C_6$-halogenoalkylsulphinyl comprising up to 9 halogen atoms which can be the same or different, $C_1$-$C_6$-alkylsulphonyl, $C_1$-$C_6$-halogenoalkylsulphonyl comprising up to 9 halogen atoms which can be the same or different, tri($C_1$-$C_6$-alkyl)silyl, tri($C_1$-$C_6$-alkyl)silyl-$C_1$-$C_6$-alkyl, benzyloxy which can be substituted by up to 5 groups Q, benzylamino which can be substituted by up to 5 groups Q, phenyl which can be substituted by up to 5 groups Q; naphthyl which can be substituted by up to 6 groups Q, phenoxy which can be substituted by up to 5 groups Q, phenylamino which can be substituted by up to 5 groups Q, phenylsulfanyl which can be substituted by up to 5 groups Q, or two vicinal substituents Z together with the consecutive carbon atoms to which they are linked form a 5- or 6-membered, saturated, carbo- or heterocycle comprising up to 3 heteroatoms, which can be substituted by up to four groups Q which can be the same or different and the other substituents Z are as herein-described and Q, which can be the same or different, represents a halogen atom, cyano group, nitro group, $C_1$-$C_6$-alkyl, $C_1$-$C_6$-alkoxy, $C_1$-$C_6$-halogenoalkoxy comprising up to 9 halogen atoms which can be the same or different, tri($C_1$-$C_6$)alkylsilyl or tri($C_1$-$C_6$)alkylsilyl-$C_1$-$C_6$-alkyl. And $G^1$ and $G^2$ which can be the same or different, represent a hydrogen atom, cyano group, hydroxyl, amino, $C_1$-$C_6$-alkyl, $C_1$-$C_6$-halogenoalkyl comprising up to 9 halogen atoms which can be the same or different, $C_1$-$C_6$-alkoxy-$C_1$-$C_6$-alkyl, $C_3$-$C_7$-cycloalkyl, $C_3$-$C_7$-cycloalkyl-$C_1$-$C_6$-alkyl, $C_3$-$C_7$-halogenocycloalkyl comprising up to 9 halogen atoms which can be the same or different, formyl, $C_1$-$C_6$-alkylcarbonyl, $C_1$-$C_6$-halogenoalkylcarbonyl comprising up to 9 halogen atoms which can be the same or different, $C_1$-$C_6$-alkylcarbamoyl, $C_1$-$C_6$-alkoxycarbonyl, $C_1$-$C_6$-halogenoalkoxycarbonyl comprising up to 9 halogen atoms which can be the same or different, $C_1$-$C_6$-alkylaminocarbonyl, di-$C_1$-$C_6$-alkylaminocarbonyl, $C_1$-$C_6$-alkylsulphonyl, $C_1$-$C_6$-halogenoalkylsulphonyl comprising up to 9 halogen atoms which can be the same or different, tri($C_1$-$C_6$-alkyl)silyl, tri($C_1$-$C_6$-alkyl)silyl-$C_1$-$C_6$-alkyl, phenyl which can be substituted by up to 5 groups Q; phenylmethylene which can be substituted by up to 5 groups Q.

In the case $Z^1$, $Z^2$, $Z^3$, $Z^4$, $Z^5$, $Z^6$, $Z^7$, $Z^8$, $Z^9$, $Z^{10}$, $Z^{11}$ are geminals they could also be fused to represent (=O); (=S), Two geminal substituents Z together with the carbon atom to which they are linked could preferably also be fused to represent C(=O) or C(=S).

More preferred compounds of formula (I) according to the invention are those wherein $R^4$ is selected in the list of E 1 to E 86, E 89 to E 95, E 98 to E 112, E 129, E 130 and E 133 to E 141 wherein $Z^1$, $Z^2$, $Z^3$, $Z^5$, $Z^6$, $Z^7$, $Z^8$, $Z^9$, $Z^{10}$ and $Z^{11}$ which can be the same or different, independently of one another represent hydrogen, halogen, $NO_2$, CN, OH, SH, $NH_2$, $C_1$-$C_4$-alkyl, $C_1$-$C_4$-halogenoalkyl comprising up to 9 halogen atoms which can be the same or different and optionally in addition one hydroxy group, $C_1$-$C_4$-alkylamino, di-$C_1$-$C_4$-alkylamino, $C_1$-$C_4$-alkoxy, $C_1$-$C_4$-halogenoalkoxy comprising up to 9 halogen atoms which can be the same or different, $C_2$-$C_4$-alkenyl, $C_2$-$C_4$-alkynyl, $C_2$-$C_4$-alkenyloxy, $C_2$-$C_4$-alkynyloxy, $C_1$-$C_4$-alkylsulfanyl, $C_2$-$C_4$-alkenylsulfanyl, $C_2$-$C_4$-alkynylsulfanyl, $C_1$-$C_4$-alkylsulphinyl, $C_1$-$C_4$-alkylsulphonyl, $C_1$-$C_4$-halogenoalkylsulfanyl comprising up to 9 halogen atoms which can be the same or different, $C_1$-$C_4$-halogenoalkylsulphenyl comprising up to 9 halogen atoms which can be the same or different, $C_1$-$C_4$-halogenoalkylsulphonyl comprising up to 9 halogen atoms which can be the same or different, $C_3$-$C_7$-cycloalkyl, $C_3$-$C_7$-halogenocycloalkyl comprising up to 9 halogen atoms which can be the same or different, $C_1$-$C_4$-alkylcarbonyl, $C_1$-$C_4$-halogenoalkylcarbonyl comprising up to 9 halogen atoms which can be the same or different, $C_1$-$C_4$-alkoxycarbonyl, $C_1$-$C_4$-halogenoalkoxycarbonyl comprising up to 9 halogen atoms which can be the same or different, $C_1$-$C_4$-alkylcarbonyloxy, $C_1$-$C_4$-halogenoalkylcarbonyloxy comprising up to 9 halogen atoms which can be the same or different, $C_1$-$C_4$-alkylcarbonylamino, $C_1$-$C_4$-halogenoalkylcarbonylamino comprising up to 9 halogen atoms which can be the same or different, $C_1$-$C_4$-alkylsulfanyl, $C_1$-$C_4$-halogenoalkylsulfanyl comprising up to 9 halogen atoms which can be the same or different, $C_1$-$C_4$-alkylsulphonyl, halogenoalkylsulphonyl comprising up to 9 halogen atoms which can be the same or different, tri($C_1$-$C_4$-alkyl)silyl, phenyl which can be substituted by up to 5 groups Q; naphthyl which can be substituted by up to 6 groups Q, phenoxy or phenylthio, or two vicinal substituents Z together with the consecutive carbon atoms to which they are linked form 6-membered, unsaturated which can be substituted by up to four groups Q which can be the same or different and the other substituents Z are as herein-described and Q, which can be the same or different, represents a halogen atom, cyano group, nitro group, $C_1$-$C_4$-alkyl, $C_1$-$C_4$-alkoxy, $C_1$-$C_4$-halogenoalkyl comprising up to 9 halogen atoms which can be the same or different, $C_1$-$C_4$-halogenoalkoxy comprising up to 9 halogen atoms which can be the same or different, tri($C_1$-$C_4$)alkylsilyl And $G^1$ and $G^2$ which can be the same or different, represent a hydrogen atom, $C_1$-$C_4$-alkyl, $C_1$-$C_4$-alkoxy-$C_1$-$C_4$-alkyl, $C_3$-$C_7$-cycloalkyl, $C_3$-$C_7$-halogenocycloalkyl comprising up to 9 halogen atoms which can be the same or different, formyl, $C_1$-$C_4$-alkylcarbonyl, $C_1$-$C_8$-halogenoalkylcarbonyl comprising up to 9 halogen atoms which can be the same or different.

Even more preferred compounds of formula (I) according to the invention are those wherein $R^4$ is selected in the list of E 1 to E 48, E 52 to E 56, E 63, E 64, E 69 to E 77, E 98 to E 100, E 105, E 106, E 109 to E 112, E 129 and E 130, wherein $Z^1$, $Z^2$, $Z^3$, $Z^4$, $Z^5$, $Z^6$, $Z^7$, $Z^8$, $Z^9$, $Z^{10}$ an $Z^{11}$ which can be the same or different, independently of one another represent hydrogen, halogen, $NO_2$, CN, OH, SH, $NH_2$, methyl, ethyl, n-propyl, isopropyl, n-, s- or t-butyl, difluoromethyl, trifluoromethyl, fluoroethyl, difluoroethyl, methylamino, ethylamino, dimethylamino, diethylamino, methoxy, ethoxy, trifluoromethoxy, vinyl, allyl, ethinyl, propargyl, cyclopropyl, cyclohexyl, acetyl, $C_1$-$C_3$-halogenoalkylcarbonyl comprising up to 5 halogen atoms which can be the same or different, carboxyl, methoxycarbonyl, ethoxycarbonyl, $C_1$-$C_4$-alkylcarbonyloxy, $C_1$-$C_4$-alkylcarbonylamino, methylthio, ethylthio, trimethylsilyl, phenyl which can be substituted by up to 3 groups Q; naphthyl which can be substituted by up to 6 groups Q.

Two geminal substituents Z together with the carbon atom to which they are linked could preferably also be fused to represent C(=O).

$G^1$ and $G^2$ which can be the same or different, independently of one another represent hydrogen, $C_1$-$C_6$-alkyl, $C_3$-$C_6$-cycloalkyl, $C_3$-$C_6$-halogenocycloalkyl comprising up to 5 halogen atoms which can be the same or different, $C_1$-$C_6$-alkylcarbonyl, $C_1$-$C_6$-halogenoalkylcarbonyl comprising up to 5 halogen atoms which can be the same or different.

Preferred compounds of formula (I) according to the invention are those wherein at least one substituent Z of a group Het 1 to Het 61 is not hydrogen.

More preferred compounds of formula (I) according to the invention are those wherein the substituent $Z^1$ of a group Het 1 to Het 61 is not hydrogen.

Preferred compounds of formula (I) according to the invention are those wherein $R^5$ represents hydrogen, OH, $C_1$-$C_6$-alkyl, $C_3$-$C_6$-cycloalkyl, $C_1$-$C_6$-halogenoalkyl comprising up to 9 halogen atoms which can be the same or different, $C_3$-$C_6$-cycloalkyl-$C_1$-$C_6$-alkyl, $C_2$-$C_6$-alkenyl-$C_1$-$C_6$-alkyl, $C_2$-$C_6$-alkynyl-$C_1$-$C_6$-alkyl, halogeno-$C_3$-$C_6$-cycloalkyl comprising up to 9 halogen atoms which can be the same or different, $C_3$-$C_6$-cycloalkenyl, $C_1$-$C_6$-alkoxy-$C_1$-$C_6$-alkyl, $C_3$-$C_6$-cycloalkoxy-$C_1$-$C_6$-alkyl, $C_1$-$C_6$-halogenoalkoxy-$C_1$-$C_6$-alkyl comprising up to 9 halogen atoms which can be the same or different, $C_1$-$C_6$-alkylsulfanyl-$C_1$-$C_6$-alkyl, $C_1$-$C_6$-alkylamino-$C_1$-$C_6$-alkyl, $C_1$-$C_6$-halogenoalkylamino-$C_1$-$C_6$-alkyl comprising up to 9 halogen atoms which can be the same or different, $C_3$-$C_6$-cycloalkylamino-$C_1$-$C_6$-alkyl, $C_1$-$C_6$-trialkylsilyl-$C_1$-$C_6$-alkyl, an aryl which can be substituted by up to 5 groups Q, an aryl-$C_1$-$C_6$-alkyl which can be substituted by up to 5 groups Q, an aryl-$C_3$-$C_6$-cycloalkyl which can be substituted by up to 5 groups Q.

More preferred compounds of formula (I) according to the invention are those wherein $R^5$ represents hydrogen, OH, $C_1$-$C_4$-alkyl, $C_3$-$C_6$-cycloalkyl, $C_1$-$C_2$-halogenoalkyl comprising up to 5 halogen atoms which can be the same or different, $C_3$-$C_6$-cycloalkyl-$C_1$-$C_2$-alkyl, $C_2$-$C_4$-alkenyl-$C_1$-$C_4$-alkyl, $C_2$-$C_4$-alkynyl-$C_1$-$C_4$-alkyl, halogeno-$C_3$-$C_6$-cycloalkyl comprising up to 9 halogen atoms which can be the same or different, cyclohexenyl, $C_1$-$C_4$-alkoxy-$C_1$-$C_4$-alkyl, $C_1$-$C_6$-cycloalkoxy-$C_1$-$C_4$-alkyl, $C_1$-$C_4$-halogenoalkoxy-$C_1$-$C_4$-alkyl comprising up to 9 halogen atoms which can be the same or different, $C_1$-$C_4$-alkylsulfanyl-$C_1$-$C_4$-alkyl, $C_1$-$C_4$-alkylamino-$C_1$-$C_4$-alkyl, $C_1$-$C_4$-halogenoalkylamino-$C_1$-$C_4$-alkyl comprising up to 9 halogen atoms which can be the same or different, $C_1$-$C_4$-trialkylsilyl-$C_1$-$C_4$-alkyl, phenyl or naphthyl, each of which can be substituted by up to 5 groups Q, benzyl which can be substituted by up to 5 groups Q.

Preferred compounds of formula (I) according to the invention are those wherein $R^6$ represents hydrogen, OH, $C_1$-$C_6$-alkyl, $C_3$-$C_6$-cycloalkyl, $C_1$-$C_6$-halogenoalkyl comprising up to 9 halogen atoms which can be the same or different, $C_3$-$C_6$-cycloalkyl-$C_1$-$C_6$-alkyl, $C_7$-$C_6$-alkenyl-$C_1$-$C_6$-alkyl, $C_2$-$C_6$-alkynyl-$C_1$-$C_6$-alkyl, halogeno-$C_3$-$C_6$-cycloalkyl comprising up to 9 halogen atoms which can be the same or different, $C_3$-$C_6$-cycloalkenyl, $C_1$-$C_6$-alkoxy-$C_1$-$C_6$-alkyl, $C_3$-$C_6$-cycloalkoxy-$C_1$-$C_6$-alkyl, $C_1$-$C_6$-halogenoalkoxy-$C_1$-$C_8$-alkyl comprising up to 9 halogen atoms which can be the same or different, $C_1$-$C_6$-alkylsulfanyl-$C_1$-$C_6$-alkyl, $C_1$-$C_6$-alkylamino-$C_1$-$C_6$-alkyl, $C_1$-$C_6$-halogenoalkylamino-$C_1$-$C_6$-alkyl comprising up to 9 halogen atoms which can be the same or different, $C_3$-$C_6$-cycloalkylamino-$C_1$-$C_6$-alkyl, $C_1$-$C_6$-trialkylsilyl-$C_1$-$C_6$-alkyl, $C_1$-$C_6$-alkoxy, $C_3$-$C_6$-cycloalkoxy, $C_1$-$C_6$-halogenoalkoxy comprising up to 9 halogen atoms which can be the same or different, $C_3$-$C_6$-cycloalkyl-$C_1$-$C_6$-alkoxy, $C_2$-$C_6$-alkenyl-$C_1$-$C_6$-alkoxy, $C_2$-$C_6$-alkynyl-$C_1$-$C_6$-alkoxy, $C_1$-$C_6$-halogeno-$C_3$-$C_6$-cycloalkoxy comprising up to 9 halogen atoms which can be the same or different, $C_3$-$C_6$-cycloalkenyloxy, $C_1$-$C_6$-alkoxy-$C_1$-$C_6$-alkoxy, $C_3$-$C_6$-cycloalkoxy-$C_1$-$C_6$-alkoxy, $C_1$-$C_6$-halogenoalkoxy-$C_1$-$C_6$-alkoxy comprising up to 9 halogen atoms which can be the same or different, $C_1$-$C_6$-alkylsulfanyl-$C_1$-$C_6$-alkoxy, $C_1$-$C_6$-alkylamino-$C_1$-$C_6$-alkoxy, $C_1$-$C_6$-halogenoalkylamino-$C_1$-$C_6$-alkoxy comprising up to 9 halogen atoms which can be the same or different, $C_3$-$C_6$-cycloalkylamino-$C_1$-$C_6$-alkoxy, $C_1$-$C_6$-trialkylsilyl-$C_1$-$C_6$-alkoxy, aryloxy which can be substituted by up to 5 groups Q, benzyloxy which can be substituted by up to 5 groups Q; $C_1$-$C_6$-alkylamino, ($C_1$-$C_4$-alkyl)carbonylamino, $C_3$-$C_6$-cycloalkylamino, $C_1$-$C_6$-halogenoalkylamino comprising up to 9 halogen atoms which can be the same or different, $C_3$-$C_6$-cycloalkyl-$C_1$-$C_6$-alkylamino, $C_2$-$C_6$-alkenyl-$C_1$-$C_6$-alkylamino, $C_2$-$C_6$-alkynyl-$C_1$-$C_6$-alkylamino, halogeno-$C_3$-$C_6$-cycloalkylamino comprising up to 9 halogen atoms which can be the same or different, arylamino which can be substituted by up to 5 groups Q, benzylamino which can be substituted by up to 5 groups Q, an aryl-$C_3$-$C_6$-cycloalkyl which can be substituted by up to 5 groups Q.

More preferred compounds of formula (I) according to the invention are those wherein $R^6$ represents hydrogen, OH, $C_1$-$C_4$-alkyl, $C_3$-$C_6$-cycloalkyl, $C_1$-$C_4$-halogenoalkyl comprising up to 5 halogen atoms which can be the same or different, $C_3$-$C_6$-cycloalkyl-$C_1$-$C_2$-alkyl, halogeno-$C_3$-$C_6$-cycloalkyl comprising up to 5 halogen atoms which can be the same or different, cyclohexenyl, $C_1$-$C_2$-alkoxy-$C_1$-$C_2$-alkyl, $C_1$-$C_2$-halogenoalkoxy-$C_1$-$C_2$-alkyl comprising up to 9 halogen atoms which can be the same or different, $C_1$-$C_2$-alkylsulfanyl-$C_1$-$C_2$-alkyl, $C_1$-$C_4$ trialkylsilyl $C_1$-$C_2$ alkyl, $C_1$-$C_4$-alkoxy, $C_1$-$C_4$-halogenoalkoxy comprising up to 5 halogen atoms which can be the same or different, alkenyl-$C_1$-$C_4$-alkoxy, $C_2$-$C_4$-alkynyl-$C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_1$-$C_4$-alkylamino-$C_1$-$C_4$-alkoxy, $C_1$-$C_4$-halogenoalkylamino-$C_1$-$C_4$-alkoxy comprising up to 9 halogen atoms which can be the same or different, $C_3$-$C_4$-cycloalkylamino-$C_1$-$C_4$-alkoxy, $C_1$-$C_4$ trialkylsilyl $C_1$-$C_4$ alkoxy, phenyloxy which can be substituted by up to 5 groups Q, benzyloxy which can be substituted by up to 5 groups Q; $C_1$-$C_4$-alkylamino, Acetylamino, $C_1$-$C_4$-halogenoalkylamino comprising up to 9 halogen atoms which can be the same or different, $C_2$-$C_4$-alkenyl-$C_1$-$C_4$-alkylamino, $C_2$-$C_4$-alkynyl-$C_1$-$C_4$-alkylamino, phenylamino which can be substituted by up to 5 groups Q, benzylamino which can be substituted by up to 5 groups Q.

Preferred compounds of formula (I) according to the invention are those wherein $R^7$ represents hydrogen, CN, $C_1$-$C_6$-alkyl, $C_3$-$C_6$-cycloalkyl, $C_1$-$C_6$-halogenoalkyl comprising up to 9 halogen atoms which can be the same or different, $C_3$-$C_6$-cycloalkyl-$C_1$-$C_6$-alkyl, $C_2$-$C_6$-alkenyl, $C_2$-$C_6$-alkynyl, halogeno-$C_3$-$C_6$-cycloalkyl comprising up to 9 halogen atoms which can be the same or different, $C_3$-$C_6$-cycloalkenyl, $C_1$-$C_6$-alkoxy-$C_1$-$C_6$-alkyl, $C_1$-$C_6$-halogenoalkoxy-$C_1$-$C_6$-alkyl comprising up to 9 halogen atoms which can be the same or different, $C_1$-$C_6$-alkylsulfanyl-$C_1$-$C_6$-alkyl, $C_1$-$C_6$-trialkylsilyl-$C_1$-$C_6$-alkyl, phenyl or naphthyl, each of which can be substituted by up to 5 groups Q, benzyl which can be substituted by up to 5 groups Q, phenyl-$C_1$-$C_2$-alkylimino.

More preferred compounds of formula (I) according to the invention are those wherein $R^7$ represents hydrogen, CN, methyl, ethyl, n-propyl, isopropyl, n-, s- or t-butyl, trifluoromethyl, cyclohexenyl, vinyl, allyl propargyl, $C_2$-$C_4$-alkenyl, $C_2$-$C_4$-alkynyl, halogeno-$C_3$-$C_4$-cycloalkyl comprising up to 9 halogen atoms which can be the same or different, phenyl or naphthyl, each of which can be substituted by up to 5 groups Q, benzyl which can be substituted by up to 5 groups Q.

Preferred compounds of formula (I) according to the invention are those wherein $R^8$ represents hydrogen, OH, $C_1$-$C_6$-alkyl, $C_3$-$C_6$-cycloalkyl, $C_1$-$C_6$-halogenoalkyl comprising up to 9 halogen atoms which can be the same or different, $C_3$-$C_6$-cycloalkyl-$C_1$-$C_6$-alkyl, $C_2$-$C_6$-alkenyl-$C_1$-$C_6$-alkyl, $C_2$-$C_6$-alkynyl-$C_1$-$C_6$-alkyl, $C_1$-$C_6$-halogeno-$C_3$-$C_6$-cycloalkyl comprising up to 9 halogen atoms which can be the same or different, $C_3$-$C_6$-cycloalkenyl, $C_1$-$C_6$-alkoxy-$C_1$-$C_6$-alkyl, $C_3$-$C_6$-cycloalkoxy-$C_1$-$C_6$-alkyl, $C_1$-$C_6$-halogenoalkoxy-$C_1$-$C_6$-alkyl comprising up to 9 halogen atoms which can be the same or different, $C_1$-$C_6$-alkylsulfanyl-$C_1$-$C_6$-alkyl, $C_1$-$C_6$-alkylamino-$C_1$-$C_6$-alkyl, $C_1$-$C_6$-halogenoalkylamino-$C_1$-$C_6$-alkyl comprising up to 9 halogen atoms which can be the same or different, $C_3$-$C_6$-cycloalkylamino-$C_1$-$C_6$-alkyl, $C_1$-$C_6$-trialkylsilyl-$C_1$-$C_6$-alkyl, phenyl which can be substituted by up to 5 groups Q, benzyl which can be substituted by up to 5 groups Q, $C_1$-$C_6$-alkoxy, $C_3$-$C_6$-cycloalkoxy, $C_1$-$C_6$-halogenoalkoxy comprising up to 9 halogen atoms which can be the same or different, $C_3$-$C_6$-cycloalkyl-$C_1$-$C_6$-alkoxy, $C_2$-$C_6$-alkenyl-$C_1$-$C_6$-alkoxy, $C_2$-$C_6$-alkynyl-$C_1$-$C_6$-alkoxy, $C_1$-$C_6$-halogeno-$C_3$-$C_6$-cycloalkoxy comprising up to 9 halogen atoms which can be the same or different, $C_3$-$C_6$-cycloalkenyloxy, $C_1$-$C_6$-alkoxy-$C_1$-$C_6$-alkoxy, $C_3$-$C_5$-cycloalkoxy-$C_1$-$C_6$-alkoxy, $C_1$-$C_6$-halogenoalkoxy-$C_1$-$C_6$-alkoxy comprising up to 9 halogen atoms which can be the same or different, $C_1$-$C_6$-alkylsulfanyl-$C_1$-$C_6$-alkoxy, $C_1$-$C_6$-alkylamino-$C_1$-$C_6$-alkoxy, $C_1$-$C_6$-halogenoalkylamino-$C_1$-$C_6$-alkoxy comprising up to 9 halogen atoms which can be the same or different, $C_3$-$C_6$-cycloalkylamino-$C_1$-$C_6$-alkoxy, $C_1$-$C_6$-trialkylsilyl-$C_1$-$C_6$-alkoxy, aryloxy which can be substituted by up to 5 groups Q, benzyloxy which can be substituted by up to 5 groups Q.

More preferred compounds of formula (I) according to the invention are those wherein $R^8$ represents hydrogen, OH, $C_1$-$C_4$-alkyl, $C_3$-$C_6$-cycloalkyl, $C_1$-$C_2$-halogenoalkyl comprising up to 5 halogen atoms which can be the same or different, cyclohexenyl, phenyl which can be substituted by up to 5 groups Q, benzyl which can be substituted by up to 5 groups Q, $C_1$-$C_4$-alkoxy, $C_1$-$C_4$-halogenoalkoxy comprising up to 5 halogen atoms which can be the same or different, alkenyl-$C_1$-$C_4$-alkoxy, $C_2$-$C_4$-alkynyl-$C_1$-$C_4$-alkoxy, $C_1$-$C_4$-alkoxy-$C_1$-$C_4$-alkoxy, $C_1$-$C_4$-alkylsulfanyl-$C_1$-$C_4$-alkoxy, $C_1$-$C_4$-alkylamino-$C_1$-$C_4$-alkoxy, $C_1$-$C_4$-halogenoalkylamino-$C_1$-$C_4$-alkoxy comprising up to 9 halogen atoms which can be the same or different, $C_3$-$C_4$-cycloalkylamino-$C_1$-$C_4$-alkoxy, $C_1$-$C_4$-trialkylsilyl-$C_1$-$C_4$-alkoxy, phenyloxy which can be substituted by up to 5 groups Q, benzyloxy which can be substituted by up to 5 groups Q.

Preferred compounds of formula (I) according to the invention are those wherein $R^9$ represents hydrogen, OH, $C_1$-$C_6$-alkyl, $C_3$-$C_6$-cycloalkyl, $C_1$-$C_6$-halogenoalkyl comprising up to 9 halogen atoms which can be the same or different, $C_3$-$C_6$-cycloalkyl-$C_1$-$C_6$-alkyl, $C_2$-$C_6$-alkenyl-$C_1$-$C_6$-alkyl, $C_2$-$C_6$-alkynyl-$C_1$-$C_6$-alkyl, $C_3$-$C_6$-halogenocycloalkyl comprising up to 9 halogen atoms which can be the same or different, $C_3$-$C_6$-cycloalkenyl, $C_1$-$C_6$-alkoxy-$C_1$-$C_6$-alkyl, $C_3$-$C_6$-cycloalkoxy-$C_1$-$C_6$-alkyl, $C_1$-$C_6$-halogenoalkoxy-$C_1$-$C_6$-alkyl comprising up to 9 halogen atoms which can be the same or different, $C_1$-$C_6$-alkylsulfanyl-$C_1$-$C_6$-alkyl, $C_1$-$C_6$-alkylamino-$C_1$-$C_6$-alkyl, $C_1$-$C_6$-halogenoalkylamino-$C_1$-$C_6$-alkyl comprising up to 9 halogen atoms which can be the same or different, $C_1$-$C_6$-trialkylsilyl-$C_1$-$C_6$-alkyl, phenyl which can be substituted by up to 5 groups Q, benzyl which can be substituted by up to 5 groups Q; $C_1$-$C_6$-alkoxy, $C_3$-$C_6$-cycloalkoxy, $C_1$-$C_6$-halogenoalkoxy comprising up to 9 halogen atoms which can be the same or different, $C_3$-$C_6$-cycloalkyl-$C_1$-$C_6$-alkoxy, $C_2$-$C_6$-alkenyl-$C_1$-$C_6$-alkoxy, $C_2$-$C_6$-alkynyl-$C_1$-$C_8$-alkoxy, halogeno-$C_3$-$C_6$-cycloalkoxy comprising up to 9 halogen atoms which can be the same or different, $C_3$-$C_6$-cycloalkenyloxy, $C_1$-$C_6$-alkoxy-$C_1$-$C_6$-alkoxy, $C_1$-$C_6$-halogenoalkoxy-$C_1$-$C_6$-alkoxy comprising up to 9 halogen atoms which can be the same or different, $C_1$-$C_6$-alkylsulfanyl-$C_1$-$C_6$-alkoxy, $C_1$-$C_6$-alkylamino-$C_1$-$C_6$-alkoxy, $C_1$-$C_6$-halogenoalkylamino-$C_1$-$C_6$-alkoxy comprising up to 9 halogen atoms which can be the same or different, $C_1$-$C_6$-trialkylsilyl-$C_1$-$C_6$-alkoxy, phenyloxy which can be substituted by up to 5 groups Q, benzyloxy which can be substituted by up to 5 groups Q.

More preferred compounds of formula (I) according to the invention are those wherein $R^9$ represents hydrogen, OH, $C_1$-$C_4$-alkyl, $C_3$-$C_6$-cycloalkyl, $C_1$-$C_2$-halogenoalkyl comprising up to 5 halogen atoms which can be the same or different, cyclohexenyl, phenyl which can be substituted by up to 5 groups Q, benzyl which can be substituted by up to 5 groups Q; $C_1$-$C_4$-alkoxy, $C_1$-$C_4$-halogenoalkoxy comprising up to 9 halogen atoms which can be the same or different, phenoxy which can be substituted by up to 5 groups Q, benzyloxy which can be substituted by up to 5 groups Q.

Preferred compounds of formula (I) according to the invention are those wherein Q which can be the same or different, independently represents halogen, CN, $NO_2$, $C_1$-$C_6$-alkyl, $C_1$-$C_6$-alkoxy, $C_1$-$C_6$-alkylsulfanyl, $C_1$-$C_6$-halogenoalkyl comprising up to 9 halogen atoms which can be the same or different, $C_1$-$C_6$-halogenoalkoxy comprising up to 9 halogen atoms which can be the same or, tri($C_1$-$C_6$)alkylsilyl or tri($C_1$-$C_6$)alkylsilyl-$C_1$-$C_6$-alkyl.

More preferred compounds of formula (I) according to the invention are those wherein Q which can be the same or different, independently represents fluorine, chlorine, bromine, CN, $NO_2$, $C_1$-$C_4$-alkyl, $C_1$-$C_4$-alkoxy, $C_1$-$C_4$-alkylsulfanyl, $C_1$-$C_4$-halogenoalkyl comprising up to 9 halogen atoms which can be the same or different, $C_1$-$C_4$-halogenoalkoxy comprising up to 9 halogen atoms which can be the same or different, tri($C_1$-$C_4$)alkylsilyl or tri($C_1$-$C_4$)alkylsilyl-$C_1$-$C_4$-alkyl.

Preferred compounds of formula (I) according to the invention are those wherein R represents $R^B$, wherein
t represents 1
$Y^2$ represents S or O
$Y^3$ represents S or O,
$Y^4$ represents O, S or $NR^9$,
$R^7$ and $R^9$ are as herein defined.

Preferred compounds of formula (I) according to the invention are those wherein R represents $R^B$, wherein
t represents 1,
$Y^2$ represents O
$Y^3$ represents O,
$Y^4$ represents O or $NR^9$,
$R^7$ and $R^9$ are as herein defined.

Preferred compounds of formula (I) according to the invention are those wherein R represents $R^B$, wherein
t represents 1,
$Y^2$ represents O
$Y^3$ represents O,
$Y^4$ represents $NR^9$,
$R^7$ and $R^9$ are as herein defined.

Preferred compounds of formula (I) according to the invention are those wherein R represents $R^B$, wherein
t represents O,
$Y^3$ represents O or S,
$Y^4$ represents O, S or $NR^9$,
$R^7$ is as herein defined,
$R^9$ represents hydrogen, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_4$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl which can be substituted by up to 5 groups Q, benzyl which can be substituted by up to 5 groups Q.

Preferred compounds of formula (I) according to the invention are those wherein R represents $R^B$, wherein
t represents O,
$Y^3$ represents O,
$Y^4$ represents O or $NR^9$,
$R^7$ is as herein defined,
$R^9$ represents hydrogen, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl which can be substituted by up to 5 groups Q, benzyl which can be substituted by up to 5 groups Q.

Preferred compounds of formula (I) according to the invention are those wherein R represents $R^B$, wherein t represents O, $Y^3$ represents O, $Y^4$ represents $NR^9$, $R^7$ is as herein defined, $R^9$ represents hydrogen, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl which can be substituted by up to 5 groups Q, benzyl which can be substituted by up to 5 groups Q.

Preferred compounds according to the invention are those, wherein R represents $R^A$

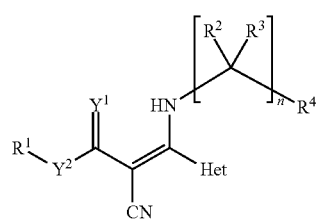

(I-a)

Preferred compounds according to the invention are those, wherein R represents $R^B$

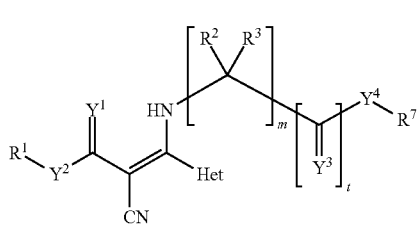

(I-b)

However, the general or preferred radical definitions or illustrations given above can also be combined with one another as desired, i.e. including combinations between respective ranges and preferred ranges. They apply both to the end products and, correspondingly, to precursors and intermediates. Moreover, individual definitions may not apply.

Preference is given to using those compounds of the formula (I) in which all radicals each have the meanings mentioned above as being preferred.

Particular preference is given to using those compounds of the formula (I) in which all radicals each have the meanings mentioned above as being more preferred.

Very particular preference is given to using those compounds of the formula (I) in which all radicals each have the meanings mentioned above as being even more preferred.

In these combinations of preferred features of the substituents of the compounds according to the invention, the said preferred features can also be selected among the more preferred features of each of $R^1$, $R^2$, $R^3$, $R^4$, n, $Y^1$, $Y^2$ and Het, so as to form most preferred subclasses of compounds according to the invention.

According to the invention, the following generic terms are generally used with the following meanings:

Halogen means fluorine, chlorine, bromine or iodine.

Heteroatom can be nitrogen, oxygen or sulphur.

Alkyl: saturated straight-chain or branched hydrocarbon radicals having 1 to 8 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl.

Haloalkyl: straight-chain or branched alkyl groups having 1 to 8 carbon atoms (as mentioned above), where in these groups some or all of the hydrogen atoms may be replaced by halogen atoms as mentioned above, for example $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

Alkenyl: unsaturated straight-chain or branched hydrocarbon radicals having 2 to 8 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl: straight-chain or branched hydrocarbon groups having 2 to 8 carbon atoms and a triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Cycloalkyl: monocyclic saturated hydrocarbon groups having 3 to 8 carbon ring members, such as cyclopropyl, cyclobutyl, cyclopentyl, cyclohexyl, cycloheptyl and cyclooctyl.

Cycloalkenyl: monocyclic nonaromatic hydrocarbon groups having 3 to 8 carbon ring members and at least one double bond, such as cyclopenten-1-yl, cyclohexen-1-yl, cyclohepta-1,3-dien-1-yl.

Alkoxycarbonyl: an alkoxy group having 1 to 6 carbon atoms (as mentioned above) which is attached to the skeleton via a carbonyl group (—CO—).

The present invention also relates to a process for the preparation of compounds of formula (I). Thus, according to a further aspect of the present invention, there is provided a process P1 for the preparation of compounds of formula (I), as herein-defined, as illustrated by the following reaction schemes. If not stated otherwise all radicals have the meanings as defined above.

Scheme 1: Process P1

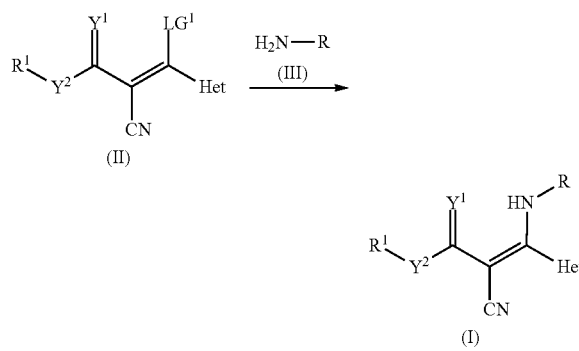

$LG^1$ represents a leaving group, preferably selected from the group consisting of chlorine, bromine, iodine, methoxy, methylsufanyl, methylsulphonyloxy and trifluoromethylsulphonyloxy.

According to the invention process P1 may be performed if appropriate in the presence of a solvent, if appropriate in the presence of a catalyst and if appropriate in the presence of a base.

Compounds of formula (III) are commercially available or prepared from known procedures such as reductive amination of carbonyls, nucleophilic displacement, and reduction of amides, cyanides, oximes or nitro groups (cf. R. C. Larock Comprehensive organic transformations, 1989, VCH publishers).

The present invention also relates to a process for the preparation of compounds of formula (I-c) and (I-d).

Thus, according to a further aspect of the present invention, there is provided a process P2 for the preparation of compounds of formula (I-c) and (I-d), as herein-defined, as illustrated by the following reaction scheme:

Scheme 2: Process P2

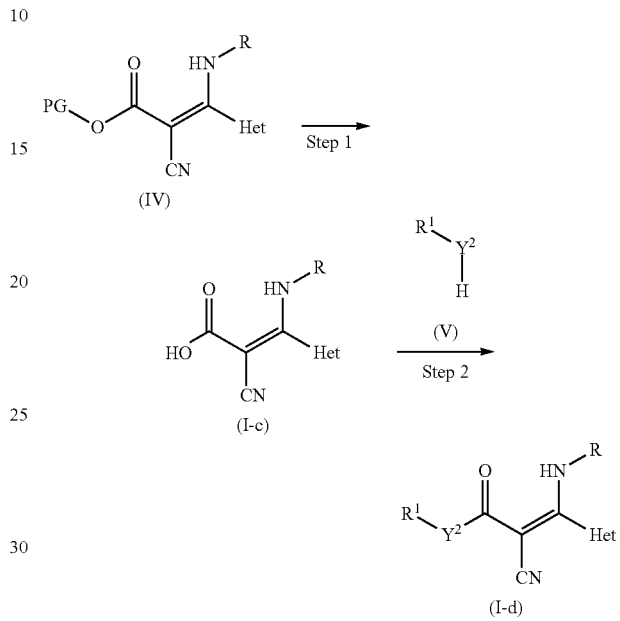

PG represents a protecting group, preferably selected from the group consisting of allyl, propargyl, benzyl, t-butyl-dimethylsilyl and tert-butyl.

In Step 1 the carboxylic acid-protecting group is cleaved according to known methods (cf. T. W. Greene and P. G. M. Wuts, Protective Group in Organic Chemistry, 3$^{rd}$ ed., John Wiley & Sons).

According to the invention, Step 2 of process P2 may be performed if appropriate in the presence of a solvent, if appropriate in the presence of a base and if appropriate in the presence of a condensing reagent or a catalyst.

Suitable condensing reagents for carrying out Step 2 of process P2 according to the invention may be chosen as being acid halide former, such as phosgene, phosphorous tri-bromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromotripyrrolidino-phosphonium-hexafluorophosphate.

Suitable catalysts for carrying out Step 2 of process P2 according to the invention may be chosen as being 4-dimethyl-aminopyridine, 1-hydroxy-benzotriazole or dimethylformamide.

Compounds of formula (IV) could be prepared according to process P1.

Compounds of formula (V) are commercially available or prepared from known procedures such as reductive amination of carbonyls, nucleophilic displacement, and reduction of amides, cyanides or nitro groups (cf. R. C. Larock *Comprehensive organic transformations*, 1989, VCH publishers).

The present invention also relates to a process for the preparation of compounds of (I-e). Thus, according to a further aspect of the present invention, there is provided a process P3 for the preparation of compounds of formula (I-e), as herein-defined, as illustrated by the following reaction scheme:

Scheme 3: Process P3

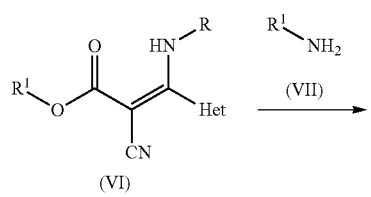

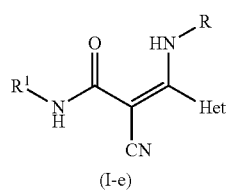

According to the invention process P3 may be performed if appropriate in the presence of a solvent, if appropriate in the presence of a base and if appropriate in the presence of a condensing reagent or a catalyst.

Suitable condensing reagents for carrying process P3 according to the invention may be chosen as being a Lewis acid such as for example $MgCl_2$, $MgBr_2$, $AlMe_3$, $AlEt_3$, $AlCl_3$, $AlBr_3$, $ZnCl_2$, $ZnBr_2$, $SnCl_4$, $TiCl_4$ or complex thereof such as, amongst others, $MgBr_2.Et_2O$, $ZnCl_2.Et_2O$, $AlMe_3.DABCO$, $AlCl_3.THF$.

The present invention also relates to a process for the preparation of compounds of formula (I-g). Thus, according to a further aspect of the present invention, there is provided a process P4 for the preparation of compounds of formula (I-g), as herein-defined, as illustrated by the following reaction scheme:

Scheme 4: Process P4

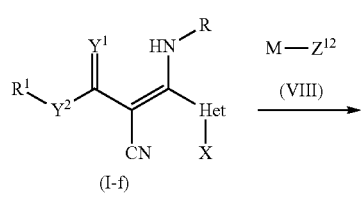

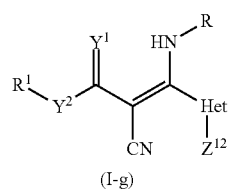

X represents halogen, phenylsulphonyloxy which can be substituted by up to 5 groups Q, $C_1$-$C_8$-halogenoalkylsufonyloxy comprising up to 5 halogen atoms which can be the same or different.

$Z^{12}$ represents $C_1$-$C_8$-alkyl, $C_3$-$C_8$-cycloalkyl, $C_1$-$C_8$-halogenoalkyl comprising up to 9 halogen atoms which can be the same or different, $C_2$-$C_8$-alkynyl, $C_2$-$C_8$-halogenoalkynyl comprising up to 9 halogen atoms which can be the same or different, $C_2$-$C_8$-halogenoalkynyl comprising up to 9 halogen atoms which can be the same of different, phenyl which can be substituted by up to 5 groups Q; naphthyl which can be substituted by up to 6 groups Q.

M represents MgCl, MgBr, ZnCl, ZnBr, B(OH)$_2$, BF$_3$K, B($C_1$-$C_8$-alkoxy)$_2$, SnMe$_3$, SnBu$_3$, CuCl, CuBr, CuCN, AgCl, AgBr or Al($C_1$-$C_8$-alkyl)$_2$.

Compound (VIII) can be prepared according to known methods either in situ or prior to the reaction.

Compounds of formula (I-f) can be prepared according to process P1.

Suitable catalyst for carrying out processes P1, P4 according to the invention may be chosen from metal salt or complex. Suitable metal derivatives for this purpose are based on palladium. Suitable metal salts or complexes for this purpose are palladium chloride, palladium acetate, tetrakis(triphenylphosphine)palladium, bis(triphenylphosphine)palladium dichloride or 1,1'-bis(diphenylphosphino) ferrocenepalladium(II) chloride.

It is also possible to generate a palladium complex in the reaction mixture by separate addition to the reaction of a palladium salt and a ligand or salt, such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino) ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl]ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine or 1,3-bis(2,4,6-trimethylphenyl)imidazolium chloride.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

The present invention also relates to a process for the preparation of compounds of formula (I-i). Thus, according to a further aspect of the present invention, there is provided a process P5 for the preparation of compounds of formula (I-i), as herein-defined, as illustrated by the following reaction scheme:

Scheme 5: Process P5

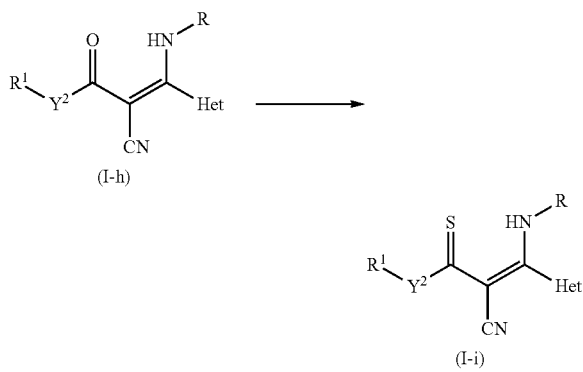

According to the invention, process P5 may be performed if appropriate in the presence of a solvent, if appropriate in the presence of a base and in the presence of a thionating agent.

Suitable thionating agents for carrying out process P5 according to the invention can be sulphur (S), sulfhydric acid ($H_{2S}$), sodium sulfide ($Na_2S$), sodium hydrosulfide (NaHS), boron trisulfide ($B_2S_3$), bis(diethylaluminium) sulfide [$(AlEt_2)_2S$], ammonium sulfide [$(NH_4)_2S$], phosphorous pentasulfide ($P_2S_5$), Lawesson's reagent [2,4-bis(4-methoxyphenyl)-1,2,3,4-dithiadiphosphetane 2,4-disulfide] or a polymer-supported thionating reagent (cf. *J. Chem. Soc. Perkin* 1, 2001, 358).

The present invention also relates to a process for the preparation of compounds of formula (I-j). Thus, according to a further aspect of the present invention, there is provided a process P6 for the preparation of compounds of formula (I-j), as herein-defined, as illustrated by the following reaction scheme:

Scheme 6: Process P6

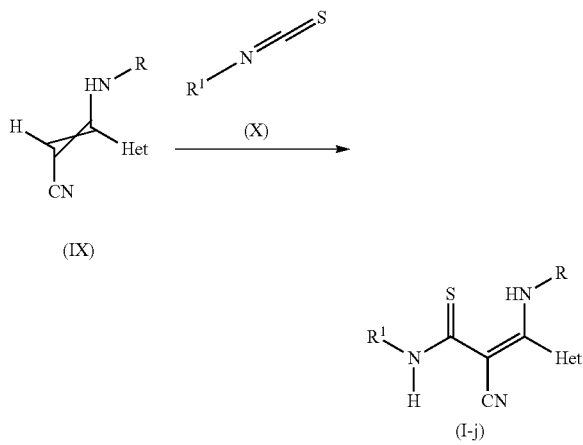

According to the invention, process P6 may be performed if appropriate in the presence of a solvent and if appropriate in the presence of a base.

Compounds of formula (X) are commercially available or can be prepared according to known methods.

The present invention also relates to a process for the preparation of compounds of formula (I-k). Thus, according to a further aspect of the present invention, there is provided a process P7 for the preparation of compounds of formula (I-k), as herein-defined, as illustrated by the following reaction scheme:

Scheme 7: Process P7

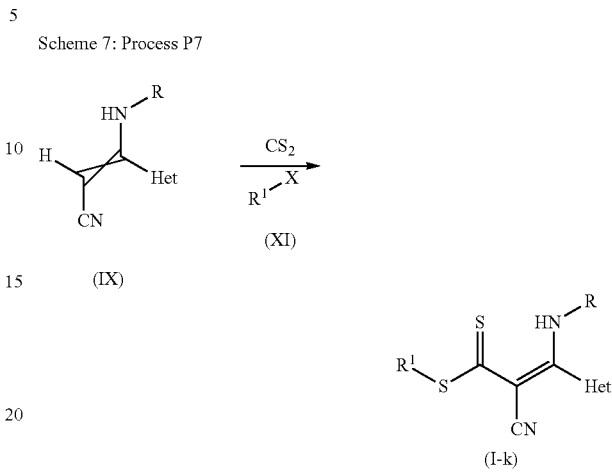

X represents halogen, phenylsulphonyloxy which can be substituted by up to 5 groups Q, $C_1$-$C_8$-halogenoalkylsufonyloxy comprising up to 5 halogen atoms which can be the same or different.

According to the invention, process P7 may be performed if appropriate in the presence of a solvent and if appropriate in the presence of a base.

Compounds of formula (XI) are commercially available or can be prepared according to known methods.

Compounds of formula (II), useful as synthetic intermediates, could be prepared according to process P8 as illustrated by the following reaction scheme:

Scheme 8: Process P8

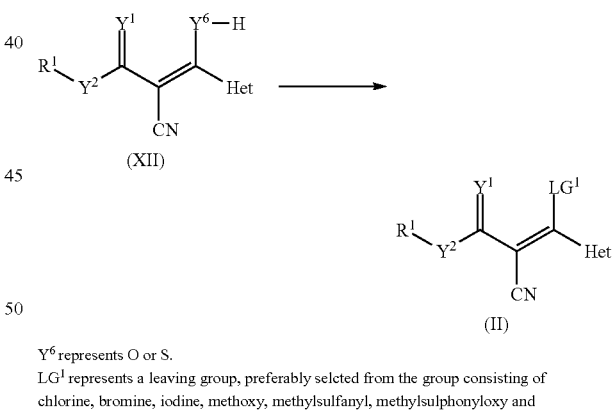

$Y^6$ represents O or S.
$LG^1$ represents a leaving group, preferably selcted from the group consisting of chlorine, bromine, iodine, methoxy, methylsulfanyl, methylsulphonyloxy and trifluoromethylsulphonyloxy.

According to the invention, suitable reagents to perform process P8 may be chosen from the following groups:
provided that $Y^6$ represents an oxygen atom: phosphorous (V)oxychloride, phosphorous(V)oxybromide, phosphorous pentachloride, thionyl chloride, thionyl bromide, diazomethane, methylbromide, methyliodide, methyltriflate, carbon tetrachloride and triphenylphosphine, carbon tetrabromide and triphenylphosphine, N-chlorosuccinimide and triphenylphosphine, N-bromosuccinimide and triphenylphosphine, N-iodosuccinimide and triphenylphosphine, triflic anhydride, methanesulfonyl chloride, p-tolylsulfonylchloride, sulfuryl chloride, sulfuryl bromide, chlorine, phosgene, triphosgene, oxalyl chloride.

provided that $Y^6$ represents a sulphur atom: methyliodide, methylbromide, methylchloride, methyltrifluoromethanesulfonate, dimethylsulfate.

According to the invention process P8 may be performed if appropriate in the presence of a solvent and if appropriate in the presence of a base.

Compounds of formula (XII) are prepared from known procedures such as condensation of a malonic derivative with an activated carboxylic acid (cf. Perez M. A., Soto J. L. *Journal of heterocyclic chemistry*, 1982, 19(1), 177-179)

Compounds of formula (XII) may exist in Z-form or in E-form when they are present in enol-form, where the correct assignment of Z and E according to the IUPAC nomenclature depends on the definitions of the different substituents. For easy reference in this patent application the assignment is made as shown. In all formulas below and above the E-form is used. Nevertheless the Z-form is also part of this invention. In addition compounds of formula (XII) may exist in ketoform.

Compounds of formula (IX), useful as synthetic intermediates, could be prepared according to process P9 as illustrated by the following reaction scheme:

Scheme 9: Process P9

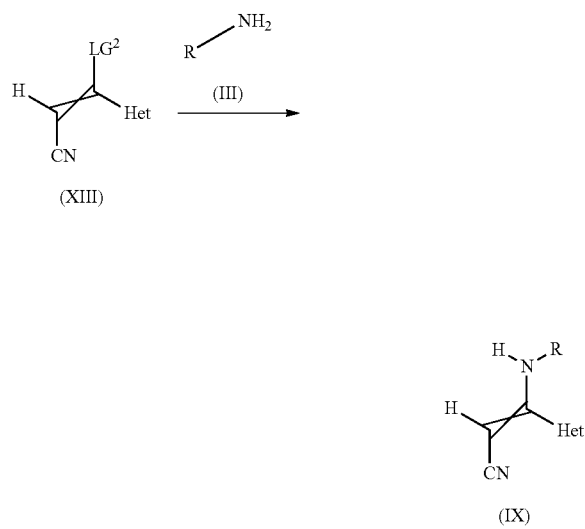

$LG^2$ represents a leaving group, preferably selected from the group consisting of chlorine or bromine.

According to the invention process P9 may be performed if appropriate in the presence of a solvent, if appropriate in the presence of a catalyst and if appropriate in the presence of a base.

Compounds of formula (IX) may exist in Z-form or in E-form where the correct assignment of Z and E according to the IUPAC nomenclature depends on the definitions of the different substituents Compounds of formula (XIII), useful as synthetic intermediates, could be prepared according to process P9 as illustrated by the following reaction scheme:

Scheme 10: Process P10

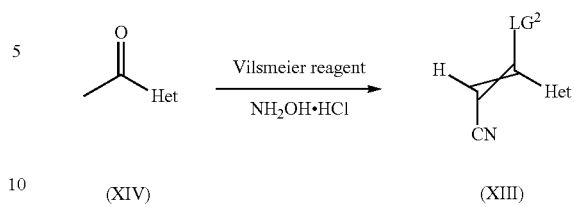

$LG^2$ represents a leaving group, preferably selected from the group consisting of chlorine or bromine.

According to the invention process P10 may be performed if appropriate in the presence of a solvent.

Compounds of formula (XIII) may exist in Z-form or in E-form where the correct assignment of Z and E according to the IUPAC nomenclature depends on the definitions of the different substituents Compounds of formula (XIV) are commercially available or prepared from known procedures such as alkylation of corresponding Weinreb amides or oxidation of alcohols (cf. R. C. Larock *Comprehensive organic transformations*, 1989, VCH publishers).

The Vilsmeier reagent can be prepared by mixing an activating reagent such as for example $SOCl_2$, $SOBr_2$, $POCl_3$, $POBr_3$, $PCl_5$, $PBr_5$, $(COCl)_2$, $COCl_2$ with a N,N-dialkylformamide such as for example DMF either in situ or prior to the reaction.

A crossed double bond in the formulae above means that either cis or trans configuration may be present as shown in the following example:

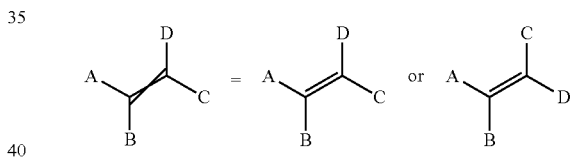

Suitable solvents for carrying out processes P1, P2, P3, P4, P5, P6, P7, P8, P9 and P10 according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin, chlorobenzene, dichlorobenzene, dichloromethane, chloroform, carbon tetrachloride, dichlorethane or trichlorethane, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, nitriles, such as acetonitrile, propionitrile, n- or iso-butyronitrile or benzonitrile, amides, such as N,N-dimethylformamide, N,N-dimethylacetamide, N-methylformanilide, N-methylpyrrolidone or hexamethylphosphoric triamide, esters, such as methyl acetate or ethyl acetate, sulphoxides, such as dimethyl sulphoxide, or sulphones, such as sulpholane.

Suitable bases for carrying out processes P1, P2, P3, P4, P5, P6, P7, P8, P9 and P10 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

When carrying out processes P1, P2, P3, P4, P5, P6, P7, P8, P9 and P10 according to the invention, the reaction temperatures can be varied within a relatively wide range. In general, these processes are carried out at temperatures from 0° C. to 160° C., preferably from 10° C. to 120° C. A way to control the temperature for the processes according to the invention is to use micro-wave technology.

Processes P1, P2, P3, P4, P5, P6, P7, P8, P9 and P10 according to the invention are generally carried out under atmospheric pressure. It is also possible to operate under elevated or reduced pressure.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesized.

The present invention furthermore relates to compositions for combating/controlling undesirable microorganisms comprising the active compounds according to the invention. Preferably, the compositions are fungicidal compositions comprising agriculturally suitable auxiliaries, solvents, carriers, surfactants or extenders.

Furthermore the invention relates to a method of combating undesirable microorganisms, characterized in that the compounds according to the invention are applied to the phytopathogenic fungi and/or their habitat.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid is generally inert and should be suitable for use in agriculture.

Suitable solid or liquid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable liquefied gaseous extenders or carriers are liquids which are gaseous at ambient temperature and under atmospheric pressure, for example aerosol propellants, such as butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils and waxes, optionally modified.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or non-ionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions according to the invention comprise between 0.05 and 99 percent by weight, 0.01 and 98 percent by weight, preferable between 0.1 and 95 percent by weight, particularly preferred between 0.5 and 90 percent by weight of the active compound according to the invention, very particularly preferable between 10 and 70 percent by weight.

The active compound combinations or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds or the active compound combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

The compositions according to the invention do not only comprise ready-to-use compositions which can be applied with suitable apparatus to the plant or the seed, but also commercial concentrates which have to be diluted with water prior to use.

The active compound combinations according to the invention can be present in (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and Semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more layers, etc. It is furthermore possible to apply the active compounds by the ultra-low volume method, or to inject the active compound preparation or the active compound itself into the soil.

The invention furthermore comprises a method for treating seed. The invention furthermore relates to seed treated according to one of the methods described in the preceding paragraph.

The active compounds or compositions according to the invention are especially suitable for treating seed. A large part of the damage to crop plants caused by harmful organisms is triggered by an infection of the seed during storage or after sowing as well as during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or which at least considerably reduce additional application. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

Accordingly, the present invention also relates in particular to a method for protecting seed and germinating plants against attack by phytopathogenic fungi by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compounds applied.

One of the advantages of the present invention is that, because of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the mixtures according to the invention can be used in particular also for transgenic seed where the plant growing from this seed is capable of expressing a protein which acts against pests. By treating such seed with the active compound combinations or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety employed in agriculture, in the greenhouse, in forests or in horticulture or viticulture. In particular, this takes the form of seed of cereals (such as wheat, barley, rye, triticale, millet, oats), maize (corn), cotton, soya bean, rice, potatoes, sunflowers, beans, coffee, beets (e.g. sugar beets and fodder beets), peanuts, oilseed rape, poppies, olives, coconuts, cacao, sugar cane, tobacco, vegetables (such as tomatoes, cucumbers, onions and lettuce), lawn and ornamental plants (also see below). The treatment of seeds of cereals (such as wheat, barley, rye, triticale, and oats), maize (corn) and rice is of particular importance.

As also described further below, the treatment of transgenic seed with the active compound combinations or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

In the context of the present invention, the active compound combinations or compositions according to the invention are applied on their own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. No. 4,272,417, U.S. Pat. No. 4,245,432, U.S. Pat. No. 4,808,430, U.S. Pat. No. 5,876,739, US 2003/0176428 A, WO 2002/080675, WO 2002/028186.

The active compound combinations which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compound combinations with customary additives, such as, for example, customary extenders and also solvents or diluents, colorants, wetting agents, dispersants, emulsifiers, defoamers, preservatives, secondary thickeners, adhesives, gibberellins and water as well.

Suitable colorants that may be present in the seed dressing formulations which can be used according to the invention include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1.

Suitable wetting agents that may be present in the seed dressing formulations which can be used according to the invention include all substances which promote wetting and are customary in the formulation of active agrochemical substances. With preference it is possible to use alkylnaphthalene-sulphonates, such as diisopropyl- or diisobutylnaphthalene-sulphonates.

Suitable dispersants and/or emulsifiers that may be present in the seed dressing formulations which can be used according to the invention include all nonionic, anionic, and cationic dispersants which are customary in the formulation of active agrochemical substances. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates.

Defoamers that may be present in the seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof.

Preservatives that may be present in the seed dressing formulations to be used according to the invention include all compounds which can be used for such purposes in agrochemical compositions. By way of example, mention may be made of dichlorophen and benzyl alcohol hemiformal.

Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations to be used according to the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of Crop Protection Agents and Pesticides], Vol. 2, Springer Verlag, 1970, pp. 401-412).

The seed dressing formulations which can be used according to the invention may be used directly or after dilution with water beforehand to treat seed of any of a very wide variety of types. The seed dressing formulations which can be used according to the invention or their dilute preparations may also be used to dress seed of transgenic plants. In this context, synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

The active compounds or compositions according to the invention have strong microbicidal activity and can be used for controlling unwanted microorganisms, such as fungi and bacteria, in crop protection and material protection.

In crop protection, fungicides can be used for controlling Plasmodiophoromycetes, Oomycetes, Chytridiomycetes, Zygomycetes, Ascomycetes, Basidiomycetes and Deuteromycetes.

In crop protection, bactericides can be used for controlling Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compound combinations or compositions according to the invention, which are applied to the seed, the plant or plant parts, the fruit or the soil in which the plants grow. Preference is given to application onto the plant or the plant parts, the fruits or the soil in which the plants grow.

The compositions according to the invention for combating phytopathogenic fungi in crop protection comprise an active, but non-phytotoxic amount of the compounds according to the invention. "Active, but non-phytotoxic amount" shall mean an amount of the composition according to the invention which is sufficient to control or to completely kill the plant disease caused by fungi, which amount at the same time does not exhibit noteworthy symptoms of phytotoxicity. These application rates generally may be varied in a broader range, which rate depends on several factors, e.g. the phytopathogenic fungi, the plant or crop, the climatic conditions and the ingredients of the composition according to the invention.

The fact that the active compounds, at the concentrations required for the controlling of plant diseases, are well tolerated by plants permits the treatment of aerial plant parts, of vegetative propagation material and seed, and of the soil.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant variety protection rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings, tubers, rhizomes, cuttings and seeds. Preference is given to the treatment of the plants and the above-ground and below-ground parts and organs of the plants, such as shoot, leaf, flower and root, examples which may be mentioned being leaves, needles, stems, trunks, flowers, and fruits.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material. They may be preferably employed as crop protection agents. They are active against normally sensitive and resistant species and against all or some stages of development.

The following plants may be mentioned as plants which can be treated according to the invention: cotton, flax, grapevines, fruit, vegetable, such as *Rosaceae* sp. (for example pomaceous fruit, such as apples and pears, but also stone fruit, such as apricots, cherries, almonds and peaches and soft fruit such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, or anges and grapefruit), *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leek, onions), *Papilionaceae* sp. (for example peas); major crop plants, such *Gramineae* sp. (for example maize, lawn, cereals such as wheat, rye, rice, barley, oats, millet and triticale), *Asteraceae* sp. (for example sunflowers), *Brassicaceae* sp. (for example white cabbage, red cabbage, broccoli, cauliflowers, Brussels sprouts, pak choi, kohlrabi, garden radish, and also oilseed rape, mustard, horseradish and cress), *Fabacae* sp. (for example beans, peas, peanuts), *Papilionaceae* sp. (for example soya beans), *Solanaceae* sp. (for example potatoes), *Chenopodiaceae* sp. (for example sugar beet, fodder beet, Swiss chard, beetroot); crop plants and ornamental plants in garden and forest; and also in each case genetically modified varieties of these plants.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts", "parts of plants" and "plant parts" have been explained above. Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

The method of treatment according to the invention is used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by down regulating or silencing other gene(s) which are present in the plant (using for example, antisense technology, co-suppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in super-additive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these phytopathogenic fungi and/ or microorganisms and/or viruses, Thus, the substances according to the invention can be employed for protecting plants against attack by the above-mentioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium Agrobacterium sp, the genes encoding a Petunia EPSPS, a Tomato EPSPS, or an *Eleusine* EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyoxy(thio)benzoates, and/or sulfonylaminocarbonyltriazolinone herbicides. Different mutations in the ALS enzyme (also known as acetohydroxy acid synthase, AHAS) are known to confer tolerance to different herbicides and groups of herbicides. The production of sulfonylurea-tolerant plants and imidazolinone-tolerant plants is described in WO 1996/033270. Other imidazolinone-tolerant plants are also described. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Aa, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or
3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;
5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g. proteins from the VIP3Aa protein class; or
6) secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or
7) hybrid insecticidal protein comprising parts from different secreted proteins from *Bacillus* thuringiensis or *Bacillus cereus*, such as a hybrid of the proteins in 1) above or a hybrid of the proteins in 2) above; or
8) protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:
a. plants which contain a transgene capable of reducing the expression and/or the activity of poly(ADP-ribose)polymerase (PARP) gene in the plant cells or plants
b. plants which contain a stress tolerance enhancing transgene capable of reducing the expression and/or the activity of the PARG encoding genes of the plants or plants cells.
c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:
1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.
2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1,4-glucans, plants producing alternan,
3) transgenic plants which produce hyaluronan.

Plants or plant cultivars (that can be obtained by plant biotechnology methods such as genetic engineering) which may also be treated according to the invention are plants, such as cotton plants, with altered fiber characteristics. Such plants can be obtained by genetic transformation or by selection of plants contain a mutation imparting such altered fiber characteristics and include:
a) Plants, such as cotton plants, containing an altered form of cellulose synthase genes,
b) Plants, such as cotton plants, containing an altered form of rsw2 or rsw3 homologous nucleic acids,
c) Plants, such as cotton plants, with increased expression of sucrose phosphate synthase,
d) Plants, such as cotton plants, with increased expression of sucrose synthase,
e) Plants, such as cotton plants, wherein the timing of the plasmodesmatal gating at the basis of the fiber cell is altered, e.g. through downregulation of fiberselective β1,3-glucanase,
f) Plants, such as cotton plants, having fibers with altered reactivity, e.g. through the expression of N-acteylglucosaminetransferase gene including nodC and chitinsynthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:
a) Plants, such as oilseed rape plants, producing oil having a high oleic acid content,
b) Plants such as oilseed rape plants, producing oil having a low linolenic acid content,
c) Plant such as oilseed rape plants, producing oil having a low level of saturated fatty acids.

Particularly useful transgenic plants which may be treated according to the invention are plants which comprise one or more genes which encode one or more toxins, such as the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

In material protection the substances of the invention may be used for the protection of technical materials against infestation and destruction by undesirable fungi and/or microorganisms.

Technical materials are understood to be in the present context non-living materials that have been prepared for use in engineering. For example, technical materials that are to be protected against microbiological change or destruction by the active materials of the invention can be adhesives, glues, paper and cardboard, textiles, carpets, leather, wood, paint and plastic articles, cooling lubricants and other materials that can be infested or destroyed by micro-organisms. Within the context of materials to be protected are also parts of production plants and buildings, for example cooling circuits, cooling and heating systems, air conditioning and ventilation systems, which can be adversely affected by the propagation of fungi and/or microorganisms. Within the context of the present invention, preferably mentioned as technical materials are adhesives, glues, paper and cardboard, leather, wood, paints, cooling lubricants and heat exchanger liquids, particularly preferred is wood. The combinations according to the invention can prevent disadvantageous effects like decaying, dis- and decoloring, or molding. The active compound combinations and compositions according to the invention can likewise be employed for protecting against colonization of objects, in particular ship hulls, sieves, nets, buildings, quays and signalling installations, which are in contact with sea water or brackish water.

The method of treatment according to the invention can also be used in the field of protecting storage goods against attack of fungi and microorganisms. According to the present invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

Some pathogens of fungal diseases which can be treated according to the invention may be mentioned by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

Diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

Diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

Leaf blotch diseases and leaf wilt diseases caused, for example, by *Alternaria* species, such as, for example, *Alternaria solani*; *Cercospora* species, such as, for example, *Cercospora beticola*; *Cladiosporium* species, such as, for example, *Cladiosporium cucumerinum*; *Cochliobolus* species, such as, for example, *Cochliobolus sativus* (conidia form: *Drechslera*, Syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola* and *M. fijiensis*; *Phaeosphaeria* species, such as, for example, *Phaeosphaeria nodorum*; *Pyrenophora* species, such as, for example, *Pyrenophora teres*; *Ramularia* species, such as, for example, *Ramularia collo-cygni*; *Rhynchosporium* species, such as, for example, *Rhynchosporium secalis*; *Septoria* species, such as, for example, *Septoria apii*; *Typhula* species, such as, for example, *Typhula incamata*; *Venturia* species, such as, for example, *Venturia inaequalis*;

Root and stem diseases caused, for example, by *Corticium* species, such as, for example, *Corticium graminearum*; *Fusarium* species, such as, for example, *Fusarium oxysporum*; *Gaeumannomyces* species, such as, for example, *Gaeumannomyces graminis*; *Rhizoctonia* species, such as, for example *Rhizoctonia solani*; *Tapesia* species, such as, for example, *Tapesia acuformis*; *Thielaviopsis* species, such as, for example, *Thielaviopsis basicola*;

Ear and panicle diseases (including maize cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*, *Gibberella fujikuroi*; *Monographella* species, such as, for example, *Monographella nivalis*; *Septoria* species, such as for example, *Septoria nodorum*;

Diseases caused by smut fungi, such as, for example, *Sphacelotheca* species, such as, for example, *Sphacelotheca reiliana*; *Tilletia* species, such as, for example, *Tilletia caries*; *T. controversa*; *Urocystis* species, such as, for example, *Urocystis occulta*; *Ustilago* species, such as, for example, *Ustilago nuda*; *U. nuda tritici*;

Fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* and *P. purpurogenum*; *Sclerotinia* species, such as, for example, *Sclerotinia sclerotionim*; *Verticilium* species, such as, for example, *Verticilium alboatrum*;

Seed- and soil-home rot and wilt diseases, and also diseases of seedlings, caused, for example, by Fusarium species, such as, for example, *Fusarium culmorum*; *Phytophthora* species, such as, for example, *Phytophthora cactorum*; *Pythium* species, such as, for example, *Pythium ultimum*; *Rhizoctonia* species, such as, for example, *Rhizoctonia solani*; *Sclerotium* species, such as, for example, *Sclerotium rolfsii*;

Cancerous diseases, galls and witches' broom caused, for example, by *Nectria* species, such as, for example, *Nectria galligena*;

Wilt diseases caused, for example, by *Monilinia* species, such as, for example, *Monilinia laxa*;

Deformations of leaves, flowers and fruits caused, for example, by *Taphrina* species, such as, for example, *Taphrina deformans*;

Degenerative diseases of woody plants caused, for example, by *Esca* species, such as, for example, *Phaemoniella clamydospora* and *Phaeoacremonium aleophilum* and *Fomitiporia mediterranea*;

Diseases of flowers and seeds caused, for example, by *Botrytis* species, such as, for example, *Botrytis cinerea*;

Diseases of plant tubers caused, for example, by *Rhizoctonia* species, such as, for example, *Rhizoctonia solani*; *Helminthosporium* species, such as, for example, *Helminthosporium solani*;

Diseases caused by bacteriopathogens, such as, for example, *Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Erwinia amylovora*.

Preference is given to controlling the following diseases of soya beans:

fungal diseases on leaves, stems, pods and seeds caused, for example, by alternaria leaf spot (*Alternaria* spec. *atrans tenuissima*), anthracnose (*Colletotrichum gloeosporioides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermaturn, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

It is also possible to control resistant strains of the organisms mentioned above.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae. Microorganisms of the following genera may be mentioned as examples: *Alternaria*, such as *Alternaria tenuis*, *Aspergillus*, such as *Aspergillus niger*, *Chaetomium*, such as *Chaetomium globosum*, *Coniophora*, such as *Coniophora puetana*, *Lentinus*, such as *Lentinus tigrinus*, *Penicillium*, such as *Penicillium glaucum*, *Polyporus*, such as *Polyporus versicolor*, *Aureobasidium*, such as *Aureobasidium pullulans*, *Sclerophoma*, such as *Sclerophoma pityophila*, *Trichoderma*, such as *Trichoderma viride*, *Escherichia*, such as *Escherichia coli*, *Pseudomonas*, such as *Pseudomonas aeruginosa*, and *Staphylococcus*, such as *Staphylococcus aureus*.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum*, *Aspergillus* species such as *Aspergillus niger* and *Aspergillus fumigatus*, *Trichophyton* species such as *Trichophyton mentagrophytes*, *Microsporon* species such as *Microsporon canis* and *audouinii*. The list of these fungi by no means limits the mycotic spectrum which can be covered, but is only for illustration.

When applying the compounds according to the invention the application rates can be varied within a broad range. The dose of active compound/application rate usually applied in the method of treatment according to the invention is generally and advantageously for treatment of part of plants, e.g. leafs (foliar treatment): from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;

for seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

for soil treatment: from 0.1 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

The combination according to the invention can be used in order to protect plants within a certain time range after the treatment against pests and/or phytopathogenic fungi and/or microorganisms. The time range, in which protection is effected, spans in general 1 to 28 days, preferably 1 to 14 days, more preferably 1 to 10 days, even more preferably 1 to 7 days after the treatment of the plants with the combinations or up to 200 days after the treatment of plant propagation material.

Furthermore combinations and compositions according to the invention may also be used to reduce the contents of mycotoxins in plants and the harvested plant material and therefore in foods and animal feed stuff made therefrom. Especially but not exclusively the following mycotoxins can be specified: Deoxynivalenole (DON), Nivalenole, 15-Ac-DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalkaloides und Aflatoxins, which are caused for example by the following fungal diseases: *Fusarium* spec., like *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea*, *Stachybotrys* spec. and others.

The invention is illustrated by the examples below. However, the invention is not limited to the examples.

PREPARATION EXAMPLES

Examples of Process P1

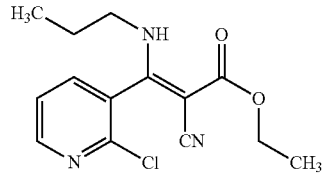

To a solution of ethyl 3-chloro-3-(2-chloropyridin-3-yl)-2-cyanoacrylate (0.3 g, 1.10 mmol, 1 eq.) in 5 ml of tetrahydrofuran was added propylamine (0.131 g, 2.21 mmol, 2 eq.) at room temperature. After being stirred for 8 h at 80° C., the mixture was evaporated. The residue was diluted with AcOEt and the precipitate was filtered off. The filtrate was evaporated and the residual oil was subjected to column chromatography to give ethyl (2Z)-3-(2-chloropyridin-3-yl)-2-cyano-3-(propylamino)acrylate (0.240 g, 74% yield).

$^1$H-NMR (400 MHz, $CDCl_3/CDCl_3$=7.26): 9.96 (bs, 1H), 8.55-8.58 (m, 1H), 7.67-7.71 (m, 1H), 7.39-7.44 (m, 3H), 7.39-7.50 (m, 3H), 4.27 (q, 2H), 3.08-3.14 (m, 1H), 2.88-2.94 (m, 1H), 1.35-1.63 (m, 2H), 1.32 (t, 3H), 0.92 (t, 3H).

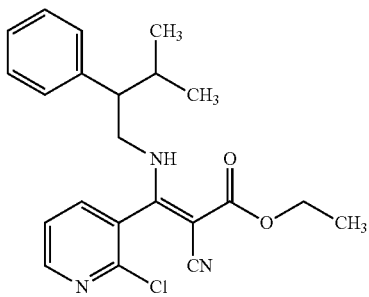 [SMILES: CCOC(=O)/C(C#N)=C(\NCC(c1ccccc1)C(C)C)c1cccnc1Cl]

To a solution of ethyl 3-chloro-3-(2-chloropyridin-3-yl)-2-cyanoacrylate (0.2 g, 0.738 mmol, 1 eq.) in 3 ml of acetonitril was added 2-phenyl-3-methylbutylamine hydrochloride (0.147 g, 0.738 mmol, 1 eq.) at room temperature followed by triethylamine (TEA) (0.164 g, 1.62 mmol, 2.2 eq.). The reaction was microwaved (130° C., 600 s, fixed hold, high absorption) and the solvent evaporated. The residual oil was subjected to column chromatography to give ethyl (2Z)-3-(2-chloropyridin-3-yl)-2-cyano-3-[(3-methyl-2-phenylbutyl)amino]acrylate (0.253 g, 85% yield) as a mixture of 2 atropoisomers.

$^1$H-NMR (400 MHz, DMSO-$d_6$/DMSO-$d_5$=2.50, water signal=3.33): 9.73 (m, 1H for isomer 1), 9.65 (m, 1H for isomer 2), 8.63 (m, 1H for isomerl and 1H for isomer 2), 7.96 (m, 1H for isomer 1), 7.66-7.53 (m, 1H for isomer 1 and 2H for isomer 2), 7.37-7.25 (m, 3H for isomer 1 and 3H for isomer 2), 7.19 (m, 1H for isomer 1 and 1H for isomer 2), 7.13 (m, 1H for isomer 1 and 1H for isomer 2), 4.13 (2H for isomer 1 and 2H for isomer 2), 3.50 (m, 2H for isomer 1), 3.34 (bs, 1H for isomer 1 and 1H for isomer 2), 3.25 (m, 2H for isomer 2), 2.55 (m, 1H for isomer 1), 2.45 (m, 1H for isomer 2), 1.79 (m, 1H for isomer 1 and 1H for isomer 2), 1.18-0.5 (m, 9H for isomer 1 and 9H for isomer 2).

LogP: 4.21

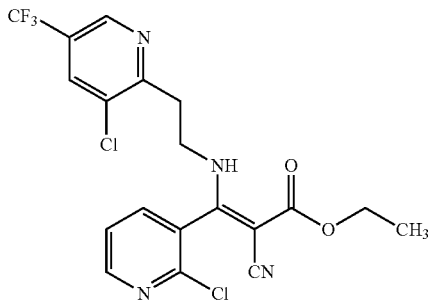 [SMILES: CCOC(=O)/C(C#N)=C(\NCCc1ncc(C(F)(F)F)cc1Cl)c1cccnc1Cl]

To a solution of ethyl 3-chloro-3-(2-chloropyridin-3-yl)-2-cyanoacrylate (0.1 g, 0.369 mmol, 1 eq.) in 5 ml of tetrahydrofuran were added 2-[3-chloro-5-(trifluoromethyl)pyridin-2-yl]ethanamine hydrochloride (0.106 g, 0.40 mmol, 1.1 eq.) and triethylamine (TEA) (0.112 g, 1.10 mmol, 3 eq.) at room temperature. After being stirred for 8 h at 80° C., the mixture was evaporated. The residue was diluted with AcOEt and the precipitate was filtered off. The filtrate was evaporated and the residual oil was subjected to column chromatography to give ethyl (2Z)-3-(2-chloropyridin-3-yl)-3-({2-[3-chloro-5-(trifluoromethyl)pyridin-2-yl]ethyl}amino)-2-cyanoacrylate (0.170 g, 99% yield).

$^1$H-NMR (400 MHz, CDCl$_3$/CDCl$_3$=7.26): 10.46 (bs, 1H), 8.76 (S, 1H), 8.57-8.60 (m, 1H), 7.92 (s, 1H), 7.68 (dd, 1H), 7.44 (dt, 1H), 4.26 (q, 2H), 3.50-3.69 (m, 2H), 3.18-3.28 (m, 2H), 1.33 (t, 3H).

LogP: 3.57

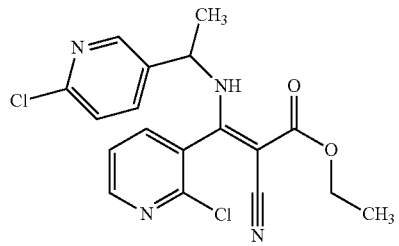 [SMILES: CCOC(=O)/C(C#N)=C(\NC(C)c1ccc(Cl)nc1)c1cccnc1Cl]

To a solution of ethyl 3-chlor-3-(2-chloropyridin-3-yl)-2-cyanoacrylate (0.150 g, 0.55 mmol, 1 eq.) in 3 ml of acetonitrile was added 1-(6-chloropyridin-3-yl)ethanamine (0.103 g, 0.66 mmol, 1.2 eq.) followed by triethylamine (TEA) (0.167 g, 1.66 mmol, 3 eq.). The reaction was microwaved (130° C., 600 s, fixed hold, high absorption) and the solvent evaporated. The residual oil was subjected to column chromatography to give ethyl (2Z)-3-(2-chloropyridin-3-yl)-3-{[1-(6-chloropyridin-3-yl)ethyl]amino}-2-cyanoacrylate (0.157 g, 68% yield) as a mixture of 2 atropoisomers.

$^1$H-NMR (250 MHz, CDCl$_3$/CDCl$_3$=7.26): 10.32-10.29 (bm, 1H for isomer 1 and 1H for isomer 2), 8.58 (dd, 1H for isomer 1, J=1.9 and 4.8 Hz), 8.53 (dd, 1H for isomer 2, J=2.3 and 4.8 Hz), 8.15 (d, J=2.5 Hz, 1H for isomer 1), 7.85 (d, 1H for isomer 2, J=2.3 Hz), 7.9 (dd, 1H for isomer 1, J=2.0 and 7.7 Hz), 7.56-7.19 (m, 4H for isomer 1 and 4H for isomer 2), 4.36-4.27 (m, 3H for isomer 1 and 3H for isomer 2), 1.64 (d, 3H for isomer 2, J=6.7 Hz), 1.52 (td, 3H for isomer 1, J=7.0 Hz), 1.981-1.41 (m, 3H for isomer 1 and 3H for isomer 2)

LogP: 2.80

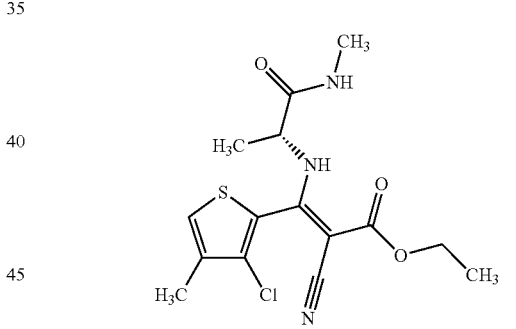

To a solution of ethyl 3-chloro-3-(3-chloro-4-methyl-2-thienyl)-2-cyanoacrylate (0.351 g, 1.21 mmol, 1 eq.) in 3 ml of acetonitrile was added N-methyl-L-alaninamide hydrochloride (0.201 g, 1.45 mmol, 1.2 eq.) followed by triethylamine (TEA) (0.490 g, 4.84 mmol, 4 eq.). The reaction was microwaved (130° C., 300 s, fixed hold, high absorption) and the solvent evaporated. The residual oil was triturated in ethyl acetate and the white solid removed by filtration. After concentration under vacuum, the residual oil was subjected to column chromatography to give ethyl (2Z)-3-(3-chloro-4-methyl-2-thienyl)-2-cyano-3-{[(2R)-1-(methylamino)-1-oxopropan-2-yl]amino}acrylate (0.26 g, 57% yield) as a mixture of atropoisomers.

$^1$H-NMR (400 MHz, DMSO-$d_6$/DMSO-$d_5$=2.50, water signal=3.33): 10.25 (m, 1H), 8.05 (m, 1H) 7.75 (m, 1H), 4.2 (m, 2H), 3.93 (m, 1H), 2.60 (m, 3H), 2.20 (m, 3H), 1.26 (m, 6H).

LogP: 3.61

Example of Process P2

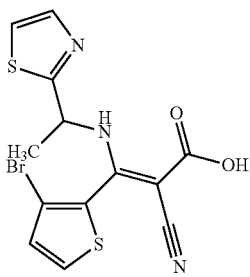 [SMILES: CC(N/C(=C(/C#N)C(=O)O)c1sccc1Br)c1nccs1]

Allyl (2Z)-3-(3-bromo-2-thienyl)-2-cyano-3-{[1-(1,3-thiazol-2-yl)ethyl]amino}acrylate (0.1 g, 0.212 mmol, 1 eq.) was dissolved in 5 ml of DCM under Argon and cooled to 0° C. Pyrrolidine (0.018 g, 0.255 mmol, 1.2 eq.) added followed by triphenylphosphine (0.010 g, 0.038 mmol, 0.18 eq.) and tetrakis(triphenylphosphine)palladium(0) (0.012 g, 0.011 mmol, 0.05 eq.). The reaction was stirred at 0° C. for 2 h at which point no starting material remained. The reaction medium was quenched with aqueous HCl 1N (5 ml) and diluted with water. The organic layer was basified with aqueous 1N NaOH until pH 9 and was extracted again with aqueous 1N NaOH. The aqueous layers were combined, acidified with aqueous 1N HCl and extracted with DCM ($CH_2Cl_2$). The organic layers were combined, dried over $MgSO_4$ and concentrated under vacuum to give (2Z)-3-(3-bromo-2-thienyl)-2-cyano-3-{[1-(1,3-thiazol-2-yl)ethyl]amino}acrylic acid (0.075 g, 87% yield) as a white solid and a mixture of atropoisomers.

$^1$H-NMR (250 MHz, DMSO-$d_6$/DMSO-$d_5$=2.50, water signal=3.33): 13.14 (bs, 1H), 10.57 (d, 1H for isomer 1, J=8.6 Hz), 10.45 (d, 1H for isomer 2, J=8.9 Hz), 8.04 (d, in for isomer 1, J=5.1 Hz), 7.94 (d, 1H for isomer 2, J=5.4 Hz), 7.80 (m, 1H for isomer 1 and 1H for isomer 2), 7.73 (m, 1H for isomer 1 and 1H for isomer 2), 7.32 (d, 1H for isomer 2, J=5.4 Hz), 7.29 (d, 1H for isomer 1, J=5.1 Hz), 4.79 (m, 1H for isomer 1 and 1H for isomer 2), 1.65 (d, 3H for isomer 2, J=7.0 Hz), 1.57 (d, 3H for isomer 1, J=6.7 Hz).

LogP: 1.23

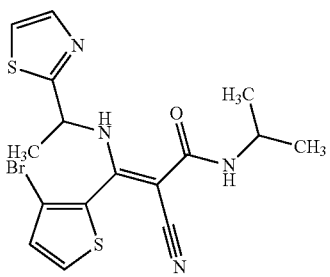 [SMILES: CC(C)NC(=O)/C(C#N)=C(\NC(C)c1nccs1)c1sccc1Br]

To a solution of (2Z)-3-(3-bromo-2-thienyl)-2-cyano-3-{[1-(1,3-thiazol-2-yl)ethyl]amino}acrylic acid (0.18 g, 0.468 mmol, 1 eq.) in 5 ml of DCM ($CH_2Cl_2$) were added isopropylamine (0.083 g, 1.40 mmol, 3 eq.), hydroxybenzotriazole (HOBT) (0.066 g, 0.49 mmol, 1.05 eq.) and diisopropylethylamine (DIPEA) (0.090 g, 0.70 mmol, 1.5 eq.). The reaction was cooled to 0° C. and dicyclohexylcarbodiimide (DCC) (0.101 g, 0.49 mmol, 1.05 eq.) was added. Stirring was allowed overnight and the solid formed removed by filtration. The solvent was removed under reduced pressure and the residual oil submitted to chromatography on silica gel to give 2Z)-3-(3-bromo-2-thienyl)-2-cyano-N-isopropyl-3-{[1-(1,3-thiazol-2-yl)ethyl]amino}acrylamide (0.090 g, 43% yield) as a white solid and a mixture of atropoisomers.

$^1$H-NMR (250 MHz, DMSO-$d_6$/DMSO-$d_5$=2.50, water signal=3.33): 11.36 (d, 1H of isomer 1, J=9.2 Hz), 11.30 (d, 1H of isomer 2, J=9.8 Hz), 8.01 (d, 1H of isomer 1, J=5.6 Hz), 7.91 (d, 1H of isomer 2, J=5.1 Hz), 7.79 (m, 1H for isomer 1 and 1H for isomer 2), 7.71 (m, 1H for isomer 1 and 1H for isomer 2), 7.29 (m, 2H of isomer 1 and 2H of isomer 2), 4.69 (m, 1H of isomer 1 and 11-1 of isomer 2), 4.01 (m, 1H of isomer 1 and 1H of isomer 2), 1.64 (d, 3H for isomer 2, J=7.0 Hz), 1.54 (d, 3H for isomer 1, J=6.6 Hz), 1.14 (m, 6H of isomer 1 and 6H of isomer 2).

LogP: 3.11

Example of Process P3

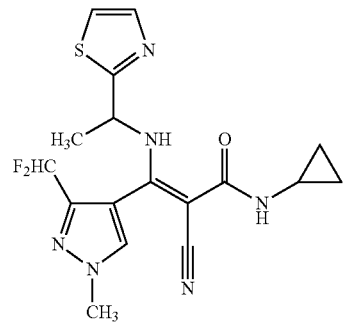 [SMILES: CC(N/C(=C(/C#N)C(=O)NC1CC1)c1cn(C)nc1C(F)F)c1nccs1]

A solution of ethyl (2Z)-2-cyano-3-[3-(difluoromethyl)-1-methyl-1H-pyrazol-4-yl]-3-{[1-(1,3-thiazol-2-yl)ethyl]amino}acrylate (0.122 g, 0.32 mmol, 1 eq.) in 3 ml of toluene was treated with ethylamine (1 M solution in tetrahydrofurane, 0.96 ml, 0.96 mmol, 3 eq.) and $AlMe_3$ (1 M solution in toluene, 0.96 ml, 0.96 mmol, 3 eq.). The reaction was microwaved at 110° C. for 1800s (fixed hold, high absorption). The reaction was quenched with aqueous saturated $NH_4Cl$ and extracted with ethylacetate. The organic layers were combined and dried over $MgSO_4$ and concentrated under vacuum. The residue was purified by chromatography on silica gel to give (2Z)-2-cyano-N-cyclopropyl-3-[3-(difluoromethyl)-1-methyl-1H-pyrazol-4-yl]-3-{[1-(1,3-thiazol-2-yl)ethyl]amino}acrylamide (0.068 g, 51% yield) as a mixture of atropoisomers.

$^1$H-NMR (250 MHz, $CDCl_3$/$CDCl_3$=7.26): 11.40 (d, 1H for isomer 1, J=9.5 Hz), 11.22 (d, 1H for isomer 2, J=9.5 Hz), 7.73 (m, 1H for isomer 1 and 1H for isomer 2), 7.60 (s, 1H for isomer 1), 7.38 (s, 1H for isomer 2), 7.30 (m, 1H for isomer 1 and 1H for isomer 2), 6.78 (t, 1H for isomer 2, J=54.7 Hz), 6.67 (t, 1H for isomer 1, J=54.7 Hz), 6.11 (bs, 1H for isomer 1 and 1H for isomer 2), 4.77 (m, 1H for isomer 1 and 1H for isomer 2), 4.02 (s, 3H for isomer 1), 3.91 (s, 3H for isomer 2), 2.73 (m, 1H for isomer 1 and 1H for isomer 2), 1.70 (d, 3H for isomer 2, J=7 Hz), 1.61 (d, 3H for isomer 1, J=7 Hz), 0.83 (m, 2H for isomer 1 and 2H for isomer 2), 0.59 (m, 2H for isomer 1 and 2H for isomer 2).

LogP: 2.04

Example of Process P4

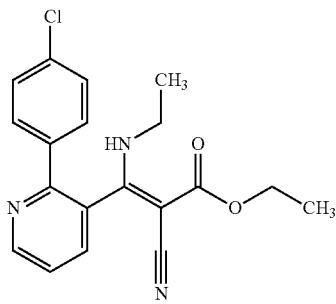 [SMILES: CCN/C(=C(/C#N)C(=O)OCC)c1cccnc1-c1ccc(Cl)cc1]

A mixture of ethyl (2Z)-3-(2-chloropyridin-3-yl)-2-cyano-3-(ethylamino)acrylate (0.284 g, 1.01 mmol, 1 eq.) 4-chloro-pjhenylboronic acid (0.207 g, 1.32 mmol, 1.3 eq.) and $K_2CO_3$ (in 1 ml of water, 0.281 g, 2.02 mmol, 2 eq.) in 20 ml of dimethyl ether (DME) and 0.6 ml of ethanol was degassed with argon. Tetrakis(triphenylphosphine)palladium(0) (0.117 g, 0.1 mmol, 0.1 eq.) was added to the mixture under argon atmosphere and the mixture was heated under reflux for 6 h. The reaction mixture was cooled, extracted with AcOEt. After drying over $MgSO_4$, the solution was concentrated in vacuo to obtain crude product, which was purified by column chromatography to give ethyl (2Z)-3-[2-(4-chlorophenyl)pyridin-3-yl]-2-cyano-3-(ethylamino)acrylate (0.24 g, 66% yield).

$^1$H-NMR (400 MHz, $CDCl_3/CDCl_3$=7.26): 9.76 (bs, 1H), 8.84 (dd, 1H), 7.75 (dd, 1H), 7.63-7.66 (dd, 1H), 7.40-7.46 (m, 4H), 4.23-4.31 (m, 2H), 2.76-2.87 (m, 2H), 1.36 (t, 3H), 1.24 (t, 3H).

LogP: 2.96

Example of Process P6

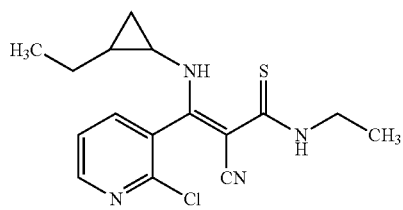 [SMILES: CCNC(=S)/C(C#N)=C(\NC1CC1CC)c1cccnc1Cl]

A solution of 3-(2-chloropyridin-3-yl)-3-[(2-ethylcyclopropyl)amino]acrylonitrile (0.15 g, 0.606 mmol, 1 eq.) in 2 ml of dimethyl formamide (DMF) was treated with NaH (60% in mineral oil, 0.029 g, 0.727 mmol, 1.2 eq.) and stirring allowed for 1 h. ethylisothiocyanate (0.105 g, 1.21 mmol, 2 eq.) was added and stirring continued overnight. The reaction was quenched with water and extracted with AcOEt. The organic layers were combined, dried over $MgSO_4$ and concentrated under vacuum. The residue was purified by chromatography on silica gel to give (2Z)-3-(2-chloropyridin-3-yl)-2-cyano-N-ethyl-3-[(2-ethylcyclopropyl)amino]-prop-2-enethioamide (0.059 g, 27% yield) as a white solid.

$^1$H-NMR (500 MHz, DMSO-$d_6$/DMSO-$d_5$=2.50, water signal=3.33): 12.77 (bd, 1H, J=3.1 Hz), 8.96 (m, 1H), 8.68 (m, 1H), 8.26 (m, 1H), 7.73 (m, 1H), 3.65 (m, 2H), 2.31 (m, 1H), 1.18 (t, 3H, J=7.2 Hz), 1.05-0.83 (m, 5H), 0.62 (dd, 2H, J=6.3 and 13.5 Hz), 0.56 (m, 1H).

LogP: 3.87

Example of Process P8

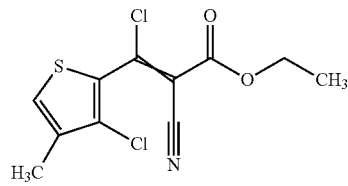 [SMILES: CCOC(=O)C(C#N)=C(Cl)c1scc(C)c1Cl]

To a solution of ethyl 3-(3-chloro-4-methyl-2-thienyl)-2-cyano-3-oxopropanoate (15.40 g, 56.67 mmol, 1 eq.) in 200 ml of $CHCl_3$ was added $POCl_3$ (86.9 g, 566 mmol, 10 eq.). $Et_3N$ (14.33 g, 141.6 mmol, 2.5 eq.) was added dropwise with stirring at 5° C., and the mixture was refluxed for 4 h. The mixture was evaporated. After evaporation, the mixture was diluted with DCM ($CH_2Cl_2$) and with ice water and was extracted with DCM ($CH_2Cl_2$) and washed with brine. The organic layers were combined and dried over $MgSO_4$ before concentration under reduced pressure. The residue was subjected to column chromatography on silica gel to give ethyl 3-chloro-3-(3-chloro-4-methyl-2-thienyl)-2-cyanoacrylate (11 g, 66% yield) as a mixture of 2 isomers $^1$H-NMR (400 MHz, DMSO-$d_6$/DMSO-$d_5$=2.50, water signal=3.33): 8.13 (s, 1H for isomer 1), 7.91 (s, 1H for isomer 2), 4.42 (q, 2H for isomer 1, J=7 Hz), 4.152 (q, 2H for isomer 2, J=7.1 Hz), 2.24 (s, 3H for isomer 1), 2.18 (s, 3H for isomer 2), 1.30 (t, 3H for isomer 1, J=7 Hz), 1.10 (t, 3H for isomer 2, J=7.1 Hz).

LogP: 3.65, 3.70

Example of Process P9

To a solution of 3-chloro-3-(2-chloropyridin-3-yl)acrylonitrile (1.4 g, 7.03 mmol, 1 eq.) in 15 ml of acetonitrile was added 2-ethylcyclopropanamine hydrochloride (1.02 g, 8.44 mmol, 1.2 eq.) followed by triethylamine (TEA) (1.06 g, 10.55 mmol, 1.5 eq.). The reaction was microwaved (130° C., 2000 s, fixed hold, high absorption) and the solvent evaporated. The residual oil was triturated in ethyl acetate and the white solid removed by filtration. After concentration under vacuum, the residual oil was subjected to column chromatography to give 3-(2-chloropyridin-3-yl)-3-[(2-ethylcyclopropyl)amino]acrylonitrile (0.998 g, 51% yield).

$^1$H-NMR (400 MHz, DMSO-$d_6$/DMSO-$d_5$=2.50, water signal=3.33): 8.50 (m, 1H), 7.87 (bd, 1H, J=7.9 Hz), 7.53 (m, 1H), 4.43 (s, 1H), 2.20 (bs, 1H), 1.44 (bs, 1H), 1.20 (m, 1H), 0.95 (m, 4H), 0.67 (bs, 1H), 0.59 (m, 1H)

LogP: 2.53 .

Example of Process P10

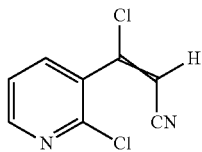 [SMILES: N#CC=C(Cl)c1cccnc1Cl]

100 ml of dimethyl formamide (DMF) were cooled to 0° C. and POCl$_3$ (35.47 g, 231 mmol, 3 eq.) added dropwise. The reaction was stirred 30 min at 0° C. and a solution of 2-chloro-3-acetyl-pyridine (12 g, 77.12 mmol, 1 eq.) in 15 ml of dimethyl formamide (DMF) was added. Once all added the reaction was warmed to 50° C. and stirred for 8 h. The mixture was cooled to 0° C. and hydroxylamine hydrochloride (21.43 g, 308 mmol, 4 eq.) was added by portions very carefully (exothermic). Once all added the reaction was stirred at room temperature for 2 h and quenched with water. The medium was basified until pH 2-3 was reached with 1N aqueous NaOH and extracted with ethylacetate. The organic layer was washed with brine and dried over MgSO$_4$. Removal of all volatiles under reduced pressure afforded 3-chloro-3-(2-chloropyridin-3-yl)acrylonitrile (13.21 g, 81% yield) as a mixture of isomers which was used without further purification.

LogP: 1.94, 2.03

In analogy to the examples above and according to the general description of the processes of preparing the compounds according to the invention the compounds in the following Table 1 may be obtained.

TABLE 1

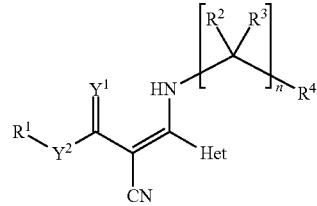

(I)

| No. | R$^1$ | Y$^2$ | Y$^1$ | Het | R | Log P | M+ |
|---|---|---|---|---|---|---|---|
| 1 | Et | O | O | 3,6-dichloropyridin-2-yl | (1R)-1-(1-naphthyl)ethyl | 4.4[a] | |
| 2 | Et | O | O | 3,5-dichloropyridin-2-yl | (1S)-1-(1-naphthyl)ethyl | 4.65[a] | 440 |
| 3 | Et | O | O | 4,6-dichloropyridin-3-yl | (1S)-1-(1-naphthyl)ethyl | 4.4[a] | |
| 4 | Me | O | O | 6-chloropyridin-2-yl | 1-(1,3-thiazol-2-yl)ethyl | | |
| 5 | Me | O | O | 2-chloropyridin-3-yl | 1-(1,3-thiazol-2-yl)ethyl | | |
| 6 | Et | O | O | 2-chloropyridin-3-yl | 1-(1,3-thiazol-2-yl)ethyl | 2.58[a]; 2.5[c] I2; 2.5[c] T1; 2.65[c] T2; 2.34[c] I1; 2.4[b]; 2.41[b] I2; 2.41[b] I1 | 363 |
| 7 | Et | O | O | 2-chloropyridin-3-yl | 1-(1,3-thiazol-2-yl)propyl | 2.79[c] T2; 2.61[c] T1; 2.71[b] T1; 2.71[b] T2 | |
| 8 | Me | O | O | 2-chloropyridin-3-yl | 1-(1,3-thiazol-2-yl)propyl | 2.29[c] T1; 2.46[c] T2; 2.39[b] T2; 2.39[b] T1 | |
| 9 | Me | O | O | 2-chloropyridin-3-yl | 2-methyl-1-(1,3-thiazol-2-yl)propyl | 2.56[c] T1; 2.73[c] T2; 2.66[b] T1; 2.72[b] T2 | |
| 10 | nBu | O | O | 2-chloropyridin-3-yl | 1-(1,3-thiazol-2-yl)ethyl | 3.04[c] T1; 3.23[c] T2; 3.15[b] T1; 3.15[b] T2 | |
| 11 | Me | O | O | 2-chloropyridin-3-yl | 1-(1,3-thiazol-2-yl)butyl | 2.82[c] T2; 2.64[c] T1; 2.75[b] T1; 2.75[b] T2 | |
| 12 | 2-EtOEt | O | O | 2-chloropyridin-3-yl | 1-(1,3-thiazol-2-yl)ethyl | 2.46[c] T2; 2.32[c] T1; 2.4[b] T1; 2.4[b] T2 | |
| 13 | Me | O | O | 2-chloropyridin-3-yl | pyrimidin-2-ylmethyl | 1.57[c]; 1.57[b] | |
| 14 | Me | O | O | 2-chloropyridin-3-yl | 1,3-dioxolan-2-ylmethyl | 1.79[c]; 1.77[b] | |
| 15 | Me | O | O | 2-chloropyridin-3-yl | 1-(1,3-benzothiazol-2-yl)ethyl | 2.88[c] T1; 3.03[c] T2; 2.95[b] | |
| 16 | Me | O | O | 2-chloropyridin-3-yl | tetrahydrofuran-2-ylmethyl | 2.06[c] I2; 2.03[c] I1; 2.03[b] | |
| 17 | Me | O | O | 2-methyl-4-trifluoromethyl-1,3-thiazol-5-yl | 1-(1,3-thiazol-2-yl)ethyl | 2.78[a]; 2.66[c]; 2.63[b] | 403 |
| 18 | Me | O | O | 3-chlorothiophen-2-yl | 1-(1,3-thiazol-2-yl)ethyl | 2.61[c]; 2.59[b] | |
| 19 | Me | O | O | 2-chloropyridin-3-yl | 1-(4,5-dimethyl-1,3-thiazol-2-yl)ethyl | 2.74[c] T1; 2.91[c] T2; 2.69[b] | |
| 20 | Me | O | O | 2-chloropyridin-3-yl | tetrahydrothiophen-2-ylmethyl | 2.63[c]; 2.47[b] | |
| 21 | Me | O | O | 2-bromopyridin-3-yl | 1-(1,3-thiazol-2-yl)ethyl | 2.36[c] T2; 2.2[c] T1; 2.12[b] | |
| 22 | Me | O | O | 2-chloropyridin-3-yl | tetrahydrothiophen-3-yl | 2.4[c]; 2.23[b] | |
| 23 | iPr | O | O | 2-chloropyridin-3-yl | 1-(1,3-thiazol-2-yl)ethyl | 2.96[c] T2; 2.78[c] T1; 2.7[b] | |
| 24 | Et | O | O | 2-chloro-6-methylpyridin-3-yl | 1-(1,3-thiazol-2-yl)ethyl | 2.71[c] T1; 2.87[c] T2; 2.62[b] | |
| 25 | tBu | O | O | 2-chloropyridin-3-yl | 1-(1,3-thiazol-2-yl)ethyl | 3.3[c] T2; 3.1[c] T1; 3.07[b] | |
| 26 | Me | O | O | 2-chloropyridin-3-yl | 1-(2,4-dimethyl-1,3-thiazol-5-yl)ethyl | 2.11[c] T1; 2.37[c] T2; 2.17[b] | |
| 27 | Me | O | O | 3-chloro-4-methylthiophen-2-yl | 1-(1,3-thiazol-2-yl)ethyl | 3.03[c]; 2.91[b] | |
| 28 | iBu | O | O | 2-chloropyridin-3-yl | 1-(1,3-thiazol-2-yl)ethyl | 3.16[c] T1; 3.36[c] T2; 3.13[b] | |
| 29 | iPr | O | O | 2-chloropyridin-3-yl | 1-(1,3-benzothiazol-2-yl)ethyl | 3.68[c] T1; 3.89[c] T2; 3.63[b] | |
| 30 | CH$_2$CF$_3$ | O | O | 2-chloropyridin-3-yl | 1-(1,3-thiazol-2-yl)ethyl | 2.9[c] T2; 2.77[c] T1; 2.67[b] | |
| 31 | Et | O | O | 2,5-dichloropyridin-3-yl | 1-(1,3-thiazol-2-yl)ethyl | 2.98[c] T1; 3.15[c] T2; 2.95[b] | |
| 32 | Et | O | O | 3-(difluoromethyl)-1-methyl-1H-pyrazol-4-yl | pyridin-2-ylmethyl | 1.94[a] | 362 |
| 33 | Et | O | O | 3-(difluoromethyl)-1-methyl-1H-pyrazol-4-yl | 1-(4,5-dimethyl-1,3-thiazol-2-yl)ethyl | 2.96[a] | 410 |

TABLE 1-continued

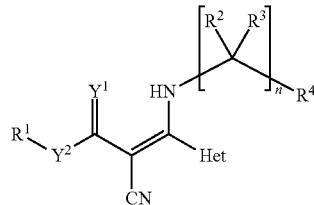

(I)

| No. | R¹ | Y² | Y¹ | Het | R | Log P | M+ |
|---|---|---|---|---|---|---|---|
| 34 | Et | O | O | 3-(difluoromethyl)-1-methyl-1H-pyrazol-4-yl | 1-(1,3-thiazol-2-yl)ethyl | 2.4[a] | 382 |
| 35 | Et | O | O | 3-(difluoromethyl)-1-methyl-1H-pyrazol-4-yl | 1-(1H-indol-3-yl)propan-2-yl | 3.25[a] | 428 |
| 36 | Et | O | O | 3-(difluoromethyl)-1-methyl-1H-pyrazol-4-yl | 1-(pyridin-2-yl)ethyl | 2.33[a] | 376 |
| 37 | Et | O | O | 3-chloro-5-(trifluoromethyl)pyridin-2-yl | 1-(4,5-dimethyl-1,3-thiazol-2-yl)ethyl | 4.04[a] | 459 |
| 38 | Et | O | O | 5-fluoro-1,3-dimethyl-1H-pyrazol-4-yl | 1-(1,3-thiazol-2-yl)ethyl | 2.37[a] | 364 |
| 39 | Et | O | O | 5-fluoro-1,3-dimethyl-1H-pyrazol-4-yl | pyridin-2-ylmethyl | 1.91[a] | 344 |
| 40 | Et | O | O | 3-chloro-5-(trifluoromethyl)pyridin-2-yl | 1-(1,3-thiazol-2-yl)ethyl | 3.37[a] | 431 |
| 41 | Et | O | O | 3-chloro-5-(trifluoromethyl)pyridin-2-yl | 1-(1H-indol-3-yl)propan-2-yl | 4.07[a] | 477 |
| 42 | Et | O | O | 3-chloro-5-(trifluoromethyl)pyridin-2-yl | pyridin-2-ylmethyl | 2.98[a] | 411 |
| 43 | Et | O | O | 3-chloro-5-(trifluoromethyl)pyridin-2-yl | 1-(pyridin-2-yl)ethyl | 3.44[a] | 425 |
| 44 | Et | O | O | 2-chloropyridin-3-yl | 2-oxotetrahydrothiophen-3-yl | 2.42[c]; 2.23[b] | |
| 45 | Et | O | O | 5-fluoro-1,3-dimethyl-1H-pyrazol-4-yl | 1-(4,5-dimethyl-1,3-thiazol-2-yl)ethyl | 2.94[a] | 392 |
| 46 | Et | O | O | 5-fluoro-1,3-dimethyl-1H-pyrazol-4-yl | 1-(1H-indol-3-yl)propan-2-yl | 3.07[a] | 410 |
| 47 | Me | O | O | 3-(difluoromethyl)-1-methyl-1H-pyrazol-4-yl | 1-(4,5-dimethyl-1,3-thiazol-2-yl)ethyl | 2.65[a] | 396 |
| 48 | Et | O | O | 3-(difluoromethyl)-1-methyl-1H-pyrazol-4-yl | 1-(1-benzothiophen-2-yl)-2,2,2-trifluoroethyl | 4.1[a] | 485 |
| 49 | Et | O | O | 2-chloropyridin-3-yl | 1-[3-chloro-5-(trifluoromethyl)pyridin-2-yl]propan-2-yl | 4[c] I2; 3.9[c] I1; 3.76[b] | |
| 50 | Et | O | O | 5-fluoro-1,3-dimethyl-1H-pyrazol-4-yl | 1-(pyridin-2-yl)ethyl | 2.28[a] | 358 |
| 51 | Et | O | O | 5-fluoro-1,3-dimethyl-1H-pyrazol-4-yl | 1-(1-benzothiophen-2-yl)-2,2,2-trifluoroethyl | 4.25[a] | 467 |
| 52 | Et | O | O | 2,5-dimethylfuran-3-yl | 1-(1,3-thiazol-2-yl)ethyl | | |
| 53 | Et | O | O | 4,5-dichloro-1,2-thiazol-3-yl | 1-(4,5-dimethyl-1,3-thiazol-2-yl)ethyl | 4.01[a] | 431 |
| 54 | Et | O | O | 4,5-dichloro-1,2-thiazol-3-yl | 1-(1H-indol-3-yl)propan-2-yl | 4.1[a] | 449 |
| 55 | Et | O | O | 4,5-dichloro-1,2-thiazol-3-yl | 1-(1,3-thiazol-2-yl)ethyl | 3.29[a] | 4.03 |
| 56 | F₃iPr | O | O | 2-chloropyridin-3-yl | 1-(1,3-thiazol-2-yl)ethyl | 3.2[c] I2; 3.09[c] I1; 2.94[b] | |
| 57 | Me | O | O | 3-(difluoromethyl)-1-methyl-1H-pyrazol-4-yl | 1-(1H-indol-3-yl)propan-2-yl | 3[a] | 414 |
| 58 | Me | O | O | 3-(difluoromethyl)-1-methyl-1H-pyrazol-4-yl | pyridin-2-ylmethyl | 1.63[a] | 348 |
| 59 | Me | O | O | 3-(difluoromethyl)-1-methyl-1H-pyrazol-4-yl | 1-(pyridin-2-yl)ethyl | 2.05[a] | 362 |
| 60 | Me | O | O | 3-(difluoromethyl)-1-methyl-1H-pyrazol-4-yl | 1-(1-benzothiophen-2-yl)-2,2,2-trifluoroethyl | 3.83[a] | 471 |
| 61 | Me | O | O | 3-(difluoromethyl)-1-methyl-1H-pyrazol-4-yl | 1-(1,3-thiazol-2-yl)ethyl | 2.13[a] | 368 |
| 62 | Et | O | O | 2-(methylsulfanyl)pyridin-3-yl | 1-(1,3-thiazol-2-yl)ethyl | 2.75[c] T1; 2.94[c] T2; 2.73[b] | |
| 63 | Et | O | O | 1-methyl-3-(trifluoromethyl)-1H-pyrazol-4-yl | 1-(1,3-thiazol-2-yl)ethyl | 2.78[a] | 400 |
| 64 | Et | O | O | 1-methyl-3-(trifluoromethyl)-1H-pyrazol-4-yl | 1-(4,5-dimethyl-1,3-thiazol-2-yl)ethyl | 3.48[a] | 428 |
| 65 | Et | O | O | 1-methyl-3-(trifluoromethyl)-1H-pyrazol-4-yl | 1-(1H-indol-3-yl)propan-2-yl | 3.73[a] | 446 |
| 66 | Et | O | O | 2-chloropyridin-3-yl | 1,3-thiazol-2-ylmethyl | 2.07[a] | 348 |
| 67 | Me | O | O | 3-(difluoromethyl)-1-methyl-1H-pyrazol-4-yl | 1,3-thiazol-2-ylmethyl | 1.72[a] | 354 |
| 68 | Et | O | O | 3-(difluoromethyl)-1-methyl-1H-pyrazol-4-yl | 1,3-thiazol-2-ylmethyl | 2[a] | 368 |
| 69 | Et | O | O | 4,5-dichloro-1,2-thiazol-3-yl | 1-(1-benzothiophen-2-yl)-2,2,2-trifluoroethyl | 5.11[a] | 505 |

TABLE 1-continued

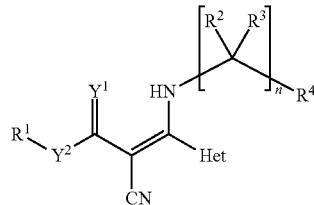

(I)

| No. | R¹ | Y² | Y¹ | Het | R | Log P | M⁺ |
|---|---|---|---|---|---|---|---|
| 70 | Et | O | O | 4,5-dichloro-1,2-thiazol-3-yl | pyridin-2-ylmethyl | 2.84[a] | 383 |
| 71 | Et | O | O | 4,5-dichloro-1,2-thiazol-3-yl | 1-(pyridin-2-yl)ethyl | 3.35[a] | 397 |
| 72 | Et | O | O | 2,6-dichloropyridin-3-yl | 1-(1,3-thiazol-2-yl)ethyl | 3.05[c] T1; 3.24[c] T2; 3.01[b] | |
| 73 | Et | O | O | 3-chloro-5-(trifluoro-methyl)pyridin-2-yl | 1-(1-benzothiophen-2-yl)-2,2,2-trifluoroethyl | 4.94[a] | 534 |
| 74 | Et | O | O | 3-methylisoxazol-4-yl | 1-(4,5-dimethyl-1,3-thiazol-2-yl)ethyl | 3.02[a] | 361 |
| 75 | Et | O | O | 3-chloro-5-(trifluoro-methyl)pyridin-2-yl | 1,3-thiazol-2-ylmethyl | 2.84[a] | 417 |
| 76 | Et | O | O | 3-methylisoxazol-4-yl | 1,3-thiazol-2-ylmethyl | 2.04[a] | 319 |
| 77 | Et | O | O | 3-methylisoxazol-4-yl | 1-(1,3-thiazol-2-yl)ethyl | 2.4[a] | 333 |
| 78 | Et | O | O | 3-methylisoxazol-4-yl | 1-(1H-indol-3-yl)propan-2-yl | 3.15[a] | 379 |
| 79 | Et | O | O | 2-fluoropyridin-3-yl | 1-(1,3-thiazol-2-yl)ethyl | 2.47[c]; 2.32[b] | |
| 80 | Et | O | O | 5-fluoro-1,3-dimethyl-1H-pyrazol-4-yl | 1,3-thiazol-2-ylmethyl | 2.01[a] | 350 |
| 81 | Et | O | O | 3-methylisoxazol-4-yl | pyridin-2-ylmethyl | 1.96[a] | 313 |
| 82 | Et | O | O | 3-methylisoxazol-4-yl | 1-(pyridin-2-yl)ethyl | 2.36[a] | 327 |
| 83 | Me | O | O | 3-chloro-5-(trifluoro-methyl)pyridin-2-yl | 1,3-thiazol-2-ylmethyl | 2.63[a] | 403 |
| 84 | Et | O | O | 2-chloropyridin-3-yl | (2S)-1-(1H-1,2,4-triazol-1-yl)propan-2-yl | 1.79[c] I2; 1.87[c]; 1.67[c] I1; 1.59[b] | |
| 85 | Et | O | O | 3-bromothiophen-2-yl | 1-(1,3-thiazol-2-yl)ethyl | 3.13[a] | 412 |
| 86 | Et | O | O | 5-chloro-1,3-dimethyl-1H-pyrazol-4-yl | 1,3-thiazol-2-ylmethyl | 2.13[a] | 366 |
| 87 | Et | O | O | 5-chloro-1,3-dimethyl-1H-pyrazol-4-yl | pyridin-2-ylmethyl | 2.02[a] | 360 |
| 88 | Et | O | O | 3-bromothiophen-2-yl | 1,3-thiazol-2-ylmethyl | 2.67[a] | 398 |
| 89 | allyl | O | O | 2-chloropyridin-3-yl | 1-(1,3-thiazol-2-yl)ethyl | 2.64[c] T1; 2.78[c] T2; 2.56[b] | |
| 90 | H | O | O | 2-chloropyridin-3-yl | 1-(1,3-thiazol-2-yl)ethyl | | |
| 91 | Et | O | O | 3-bromothiophen-2-yl | 1-(1H-indol-3-yl)propan-2-yl | 3.8[a] | 458 |
| 92 | Et | O | O | 3-bromothiophen-2-yl | 1-(4,5-dimethyl-1,3-thiazol-2-yl)ethyl | 3.8[a] | 440 |
| 93 | Et | O | O | 3-methylisoxazol-4-yl | 1-(1-benzothiophen-2-yl)-2,2,2-trifluoroethyl | 4.24[a] | 436 |
| 94 | Et | O | O | 5-chloro-1,3-dimethyl-1H-pyrazol-4-yl | 1-(4,5-dimethyl-1,3-thiazol-2-yl)ethyl | 3.12[a] | 408 |
| 95 | Et | O | O | 3-(trifluoromethyl)thiophen-2-yl | 1,3-thiazol-2-ylmethyl | 2.82[a] | 388 |
| 96 | Et | O | O | 3-(trifluoromethyl)thiophen-2-yl | 1-(1,3-thiazol-2-yl)ethyl | 3.31[a] | 402 |
| 97 | Et | O | O | 3-(trifluoromethyl)thiophen-2-yl | 1-(4,5-dimethyl-1,3-thiazol-2-yl)ethyl | 3.92[a] | 430 |
| 98 | Et | O | O | 5-chloro-1,3-dimethyl-1H-pyrazol-4-yl | 1-(1,3-thiazol-2-yl)ethyl | 2.52[a] | 380 |
| 99 | Et | O | O | 3-bromothiophen-2-yl | pyridin-2-ylmethyl | 2.61[a] | 392 |
| 100 | Et | O | O | 3-bromothiophen-2-yl | 1-(pyridin-2-yl)ethyl | 3.1[a] | 406 |
| 101 | iPr | NH | O | 2-chloropyridin-3-yl | 1-(1,3-thiazol-2-yl)ethyl | | |
| 102 | Et | O | O | 3-(trifluoromethyl)thiophen-2-yl | pyridin-2-ylmethyl | 2.84[a] | |
| 103 | Et | O | O | 3-(trifluoromethyl)thiophen-2-yl | 1-(pyridin-2-yl)ethyl | 3.27[a] | 396 |
| 104 | Et | O | O | 2-bromothiophen-3-yl | 1,3-thiazol-2-ylmethyl | 2.66[a] | 398 |
| 105 | Et | O | O | 2-bromothiophen-3-yl | 1-(1,3-thiazol-2-yl)ethyl | 3.1[a] | 412 |
| 106 | Et | O | O | 2-bromothiophen-3-yl | 1-(1H-indol-3-yl)propan-2-yl | 3.8[a] | 458 |
| 107 | Et | O | O | 3-(trifluoromethyl)thiophen-2-yl | 1-(1-benzothiophen-2-yl)-2,2,2-trifluoroethyl | 4.89[a] | 505 |
| 108 | Et | O | O | 3-(trifluoromethyl)thiophen-2-yl | 1-(1H-indol-3-yl)propan-2-yl | 3.94[a] | 448 |
| 109 | Me | O | O | 2-chloropyridin-3-yl | 1-(pyridin-3-yl)ethyl | 0.82[a] | |
| 110 | Me | O | O | 2-chloropyridin-3-yl | 1-(pyridin-2-yl)ethyl | 1.99[a] | |
| 111 | Et | O | O | 2-chloropyridin-3-yl | (2R)-1-[3,5-bis(trifluoromethyl)-1H-pyrazol-1-yl]propan-2-yl | | |
| 112 | Et | O | O | 2-bromothiophen-3-yl | 1-(4,5-dimethyl-1,3-thiazol-2-yl)ethyl | 3.7[a] | 440 |
| 113 | Et | O | O | 5-chloro-1,3-dimethyl-1H-pyrazol-4-yl | 1-(1H-indol-2-yl)propan-2-yl | 3.24[a] | 426 |

TABLE 1-continued

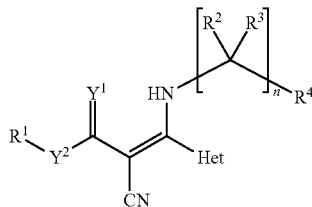

(I)

| No. | R¹ | Y² | Y¹ | Het | R | Log P | M⁺ |
|---|---|---|---|---|---|---|---|
| 114 | Et | O | O | 2-chloropyridin-3-yl | (2S)-1-[3,5-bis(trifluoromethyl)-1H-pyrazol-1-yl]propan-2-yl | | |
| 115 | Et | O | O | 2-bromothiophen-3-yl | pyridin-2-ylmethyl | 2.53[a] | 392 |
| 116 | Et | O | O | 2-bromothiophen-3-yl | 1-(pyridin-2-yl)ethyl | 3.1[a] | 406 |
| 117 | Et | O | O | 2-chloropyridin-3-yl | 2-(methylsulfanyl)pyridin-3-yl | | |
| 118 | Et | O | O | 2,5-dimethylfuran-3-yl | 1-(tetrahydrofuran-2-yl)ethyl | 3.27[a] | |
| 119 | Et | O | O | 2,5-dimethylfuran-3-yl | 2-oxoazepan-3-yl | 2.14[a] | |
| 120 | Me | O | O | 2-chloropyridin-3-yl | oxetan-3-yl | 1.35[a] | |
| 121 | Me | O | O | 2-chloropyridin-3-yl | 1-cyclopropyl-2-(morpholin-4-yl)ethyl | 1.38[a] | |
| 122 | Me | O | O | 2-chloropyridin-3-yl | thietan-3-yl | 2.08[a] | |
| 123 | Me | O | O | 2-chloropyridin-3-yl | 2-oxoazepan-3-yl | 1.57[a] | |
| 124 | Me | O | O | 2-chloropyridin-3-yl | 1-(5-bromo-3-chloropyridin-2-yl)ethyl | 3.24[a] | |
| 125 | Me | O | O | 2-chloropyridin-3-yl | 1,1-dioxidotetrahydrothiophen-3-yl | 1.33[a] | |
| 126 | Me | O | O | 2-chloropyridin-3-yl | 1-(tetrahydrofuran-2-yl)ethyl | 2.17[a] | |
| 127 | Et | O | O | 2-chloropyridin-3-yl | (2S)-1-[5-(methylsulfanyl)-3-(pentafluoroethyl)-1H-1,2,4-triazol-1-yl]propan-2-yl | 3.55[c] T1; 3.81[c] T2; 3.66[b] | |
| 128 | Et | O | O | 2-chloropyridin-3-yl | 1-(5-bromo-1,3-thiazol-2-yl)ethyl | 3.28[c] T1; 3.41[c] T2; 3.32[b] | |
| 129 | Et | O | O | 3-bromothiophen-2-yl | 1-(1-benzothiophen-2-yl)-2,2,2-trifluoroethyl | 4.9[a] | 515 |
| 130 | Et | O | O | 2-bromothiophen-3-yl | 1-(1-benzothiophen-2-yl)-2,2,2-trifluoroethyl | 4.87[a] | 515 |
| 131 | Me | O | O | 2-methyl-4-trifluoromethyl-1,3-thiazol-5-yl | 1-(4,5-dimethyl-1,3-thiazol-2-yl)ethyl | 3.46[a] | 431 |
| 132 | Me | O | O | 2-methyl-4-trifluoromethyl-1,3-thiazol-5-yl | 1,3-thiazol-2-ylmethyl | 2.33[a] | 389 |
| 133 | Me | O | O | 2-methyl-4-trifluoromethyl-1,3-thiazol-5-yl | 1-(1H-indol-3-yl)propan-2-yl | 3.6[a] | 449 |
| 134 | Me | O | O | 2-methyl-4-trifluoromethyl-1,3-thiazol-5-yl | pyridin-2-ylmethyl | 2.37[a] | 383 |
| 135 | Me | O | O | 2-methyl-4-trifluoromethyl-1,3-thiazol-5-yl | 1-(pyridin-2-yl)ethyl | 2.77[a] | 397 |
| 136 | Et | O | O | 5-chloro-1,3-dimethyl-1H-pyrazol-4-yl | 1-(pyridin-2-yl)ethyl | 2.49[a] | 374 |
| 137 | Et | O | O | 5-chloro-1,3-dimethyl-1H-pyrazol-4-yl | 1-(1-benzothiophen-2-yl)-2,2,2-trifluoroethyl | 4.46[a] | 483 |
| 138 | Et | O | O | 1-methyl-3-(trifluoromethyl)-1H-pyrazol-4-yl | 1,3-thiazol-2-ylmethyl | 2.43[a] | 386 |
| 139 | Et | O | O | 1-methyl-3-(trifluoromethyl)-1H-pyrazol-4-yl | pyridin-2-ylmethyl | 2.36[a] | 380 |
| 140 | Et | O | O | 1-methyl-3-(trifluoromethyl)-1H-pyrazol-4-yl | 1-(pyridin-2-yl)ethyl | 2.75[a] | 394 |
| 141 | Et | O | O | 2-methyl-4-trifluoromethyl-1,3-thiazol-5-yl | 1,3-thiazol-2-ylmethyl | 2.66[a] | 403 |
| 142 | Et | O | O | 2-methyl-4-trifluoromethyl-1,3-thiazol-5-yl | 1-(1,3-thiazol-2-yl)ethyl | 3.13[a] | 417 |
| 143 | Et | O | O | 2-methyl-4-trifluoromethyl-1,3-thiazol-5-yl | 1-(4,5-dimethyl-1,3-thiazol-2-yl)ethyl | 3.83[a] | 445 |
| 144 | Et | O | O | 2-methyl-4-trifluoromethyl-1,3-thiazol-5-yl | pyridin-2-ylmethyl | 2.7[a] | 397 |
| 145 | Et | O | O | 2-methyl-4-trifluoromethyl-1,3-thiazol-5-yl | 1-(1H-indol-2-yl)propan-2-yl | 3.85[a] | 463 |
| 146 | Et | O | O | 2-methyl-4-trifluoromethyl-1,3-thiazol-5-yl | 1-(pyridin-2-yl)ethyl | 3.12[a] | 411 |
| 147 | Et | O | O | 1-methyl-3-(trifluoromethyl)-1H-pyrazol-4-yl | 1-(1-benzothiophen-2-yl)-2,2,2-trifluoroethyl | 4.46[a] | 503 |
| 148 | Et | O | O | 2-ethoxypyridin-3-yl | 1-(1,3-thiazol-2-yl)ethyl | 2.92[c]; 2.89[b] | |
| 149 | Et | O | O | 3-chlorothiophen-2-yl | 1-(1,3-thiazol-2-yl)ethyl | 3.09[a] | 368 |
| 150 | Et | O | O | 3-chlorothiophen-2-yl | 1-(4,5-dimethyl-1,3-thiazol-2-yl)ethyl | 3.76[a] | 396 |
| 151 | Et | O | O | 3-chlorothiophen-2-yl | 1-(1H-indol-3-yl)propan-2-yl | 3.8[a] | 414 |
| 152 | Et | O | O | 2-methylpyridin-3-yl | 1-(1,3-thiazol-2-yl)ethyl | 2.28[c] T2; 2.12[c] T1; 2.17[b] | |
| 153 | Et | O | O | 3-chlorothiophen-2-yl | 1,3-thiazol-2-ylmethyl | 2.63[a] | 354 |

TABLE 1-continued

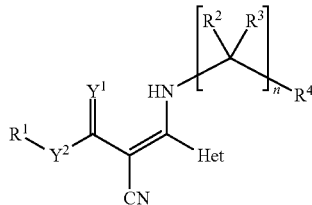

(I)

| No. | R¹ | Y² | Y¹ | Het | R | Log P | M⁺ |
|---|---|---|---|---|---|---|---|
| 154 | Et | O | O | 2-chloropyridin-3-yl | (1S)-1-(1,3-thiazol-2-yl)ethyl] | | |
| 155 | Et | O | O | 5-chloro-3-(difluoromethyl)-1-methyl-1H-pyrazol-4-yl | pyridin-2-ylmethyl | 2.37[a] | 396 |
| 156 | Et | O | O | 5-chloro-3-(difluoromethyl)-1-methyl-1H-pyrazol-4-yl | 1-(pyridin-2-yl)ethyl | 2.81[a] | 410 |
| 157 | Et | O | O | 2-iodothiophen-3-yl | 1-(4,5-dimethyl-1,3-thiazol-2-yl)ethyl | 3.75[a] | 488 |
| 158 | Et | O | O | 2-iodothiophen-3-yl | 1-(1,3-thiazol-2-yl)ethyl | 3.08[a] | 460 |
| 159 | Et | O | O | 3-chlorothiophen-2-yl | pyridin-2-ylmethyl | 2.56[a] | 348 |
| 160 | Et | O | O | 3-chlorothiophen-2-yl | 1-(pyridin-2-yl)ethyl | 3.05[a] | 362 |
| 161 | Et | O | O | 2-iodothiophen-3-yl | 1,3-thiazol-2-ylmethyl | 2.68[a] | 446 |
| 162 | Et | O | O | 3-chlorothiophen-2-yl | 1-(1-benzothiophen-2-yl)-2,2,2-trifluoroethyl | 4.89[a] | 471 |
| 163 | Et | O | O | 2-iodothiophen-3-yl | 1-(pyridin-2-yl)ethyl | 3.03[a] | 454 |
| 164 | Et | O | O | 2-iodothiophen-3-yl | 1-(1H-indol-3-yl)propan-2-yl | 3.8[a] | 506 |
| 165 | Et | O | O | 2-iodothiophen-3-yl | 1-(1-benzothiophen-2-yl)-2,2,2-trifluoroethyl | 4.81[a] | |
| 166 | Et | O | O | 2-iodothiophen-3-yl | pyridin-2-ylmethyl | 2.56[a] | 440 |
| 167 | Et | O | O | 3-bromothiophen-2-yl | 1-(4-methyl-1,3-thiazol-2-yl)ethyl | 3.44[a] | |
| 168 | Et | O | O | 3-bromothiophen-2-yl | 1-(4-methyl-1,3-thiazol-2-yl)ethyl | 2.92[a] | 412 |
| 169 | Et | O | O | 3-bromothiophen-2-yl | 1-(5-methyl-1,3-thiazol-2-yl)ethyl | 3.46[a] | 426 |
| 170 | Et | O | O | 3-bromothiophen-2-yl | 1,3-benzothiazol-2-ylmethyl | 3.53[a] | 448 |
| 171 | Et | O | O | 3-bromothiophen-2-yl | 4-(trifluoromethyl)-1,3-thiazol-2-yl]methyl | 3.37[a] | 466 |
| 172 | Et | O | O | 3-(trifluoromethyl)thiophen-2-yl | 1-(tetrahydrofuran-2-yl)ethyl | 3.55[a] | 389 |
| 173 | Et | O | O | 3-(trifluoromethyl)thiophen-2-yl | 1-(2,4-dimethyl-1,3-thiazol-5-yl)ethyl | | |
| 174 | Et | O | O | 3-(trifluoromethyl)thiophen-2-yl | 1-(4-methyl-1,3-thiazol-2-yl)ethyl | 3.58[a] | 416 |
| 175 | Et | O | O | 3-(trifluoromethyl)thiophen-2-yl | (4-methyl-1,3-thiazol-2-yl)methyl | 3.11[a] | 402 |
| 176 | Et | O | O | 3-(trifluoromethyl)thiophen-2-yl | 1,3-benzothiazol-2-ylmethyl | 3.67[a] | 438 |
| 177 | Et | O | O | 3-(trifluoromethyl)thiophen-2-yl | (4-trifluoromethyl-1,3-thiazol-2-yl)methyl | 3.51[a] | 456 |
| 178 | Me | O | O | 2-methyl-4-trifluoromethyl-1,3-thiazol-5-yl | 1-(tetrahydrofuran-2-yl)ethyl | 1.97[a] | 390 |
| 179 | Me | O | O | 2-methyl-4-trifluoromethyl-1,3-thiazol-5-yl | 1-(2,4-dimethyl-1,3-thiazol-5-yl)ethyl | 2.8[a] | 431 |
| 180 | Me | O | O | 2-methyl-4-trifluoromethyl-1,3-thiazol-5-yl | 1-(4-methyl-1,3-thiazol-2-yl)ethyl | 3.04[a] | 417 |
| 181 | Me | O | O | 2-methyl-4-trifluoromethyl-1,3-thiazol-5-yl | (4-methyl-1,3-thiazol-2-yl)methyl | 2.58[a] | 403 |
| 182 | Me | O | O | 2-methyl-4-trifluoromethyl-1,3-thiazol-5-yl | 1-(5-methyl-1,3-thiazol-2-yl)ethyl | 3.09[a] | 417 |
| 183 | Me | O | O | 2-methyl-4-trifluoromethyl-1,3-thiazol-5-yl | (5-methyl-1,3-thiazol-2-yl)methyl | 2.63[a] | 403 |
| 184 | Me | O | O | 2-methyl-4-trifluoromethyl-1,3-thiazol-5-yl | 1,3-benzothiazol-2-ylmethyl | 3.15[a] | 439 |
| 185 | Me | O | O | 2-methyl-4-trifluoromethyl-1,3-thiazol-5-yl | (4-trifluoromethyl-1,3-thiazol-2-yl)methyl | 3.06[a] | 457 |
| 186 | Et | O | O | 3-bromothiophen-2-yl | 1-(tetrahydrofuran-2-yl)ethyl | 3.35[a] | 399 |
| 187 | Et | O | O | 3-(difluoromethyl)-1-methyl-1H-pyrazol-4-yl | 1-(2,4-dimethyl-1,3-thiazol-5-yl)ethyl | 2.43[a] | 410 |
| 188 | Et | O | O | 3-(difluoromethyl)-1-methyl-1H-pyrazol-4-yl | 1-(4-methyl-1,3-thiazol-2-yl)ethyl | 2.65[a] | 396 |
| 189 | Et | O | O | 3-(difluoromethyl)-1-methyl-1H-pyrazol-4-yl | (4-methyl-1,3-thiazol-2-yl)methyl | 2.3[a] | 382 |
| 190 | Et | O | O | 3-(difluoromethyl)-1-methyl-1H-pyrazol-4-yl | 1-(5-methyl-1,3-thiazol-2-yl)ethyl | 2.68[a] | 396 |
| 191 | Et | O | O | 3-(difluoromethyl)-1-methyl-1H-pyrazol-4-yl | 1,3-benzothiazol-2-ylmethyl | 2.82[a] | 418 |

TABLE 1-continued

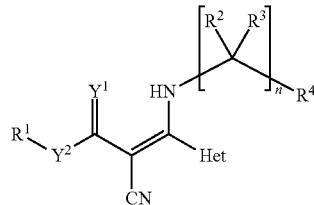

(I)

| No. | R¹ | Y² | Y¹ | Het | R | Log P | M⁺ |
|---|---|---|---|---|---|---|---|
| 192 | Et | O | O | 3-(difluoromethyl)-1-methyl-1H-pyrazol-4-yl | (4-trifluoromethyl-1,3-thiazol-2-yl)methyl | 2.78[a] | 436 |
| 193 | Et | O | O | 2-methyl-4-trifluoromethyl-1,3-thiazol-5-yl | 1-(tetrahydrofuran-2-yl)ethyl | 3.29[a] | 404 |
| 194 | Et | O | O | 2-methyl-4-trifluoromethyl-1,3-thiazol-5-yl | 1-(4-methyl-1,3-thiazol-2-yl)ethyl | 3.42[a] | 431 |
| 195 | Et | O | O | 2-methyl-4-trifluoromethyl-1,3-thiazol-5-yl | (4-methyl-1,3-thiazol-2-yl)methyl | 2.9[a] | 417 |
| 196 | Et | O | O | 2-methyl-4-trifluoromethyl-1,3-thiazol-5-yl | 1-(5-methyl-1,3-thiazol-2-yl)ethyl | 3.46[a] | 431 |
| 197 | Et | O | O | 2-methyl-4-trifluoromethyl-1,3-thiazol-5-yl | 1,3-benzothiazol-2-ylmethyl | 3.48[a] | 453 |
| 198 | Et | O | O | 2-methyl-4-trifluoromethyl-1,3-thiazol-5-yl | (4-trifluoromethyl-1,3-thiazol-2-yl)methyl | 3.35[a] | 471 |
| 199 | Et | O | O | 3-(difluoromethyl)-1-methyl-1H-pyrazol-4-yl | 1-(tetrahydrofuran-2-yl)ethyl | 2.58[a] | 369 |
| 200 | Et | O | O | 3-bromothiophen-2-yl | (5-fluoropyridin-2-yl)methyl | 3.04[a] | 410 |
| 201 | Et | O | O | 3-(trifluoromethyl)thiophen-2-yl | (5-fluoropyridin-2-yl)methyl | 3.19[a] | 400 |
| 202 | Me | O | O | 2-methyl-4-trifluoromethyl-1,3-thiazol-5-yl | (5-fluoropyridin-2-yl)methyl | 2.67[a] | 401 |
| 203 | Et | O | O | 3-(difluoromethyl)-1-methyl-1H-pyrazol-4-yl | (5-fluoropyridin-2-yl)methyl | 2.33[a] | 380 |
| 204 | Et | O | O | 2-methyl-4-trifluoromethyl-1,3-thiazol-5-yl | (5-fluoropyridin-2-yl)methyl | 2.98[a] | 415 |
| 205 | allyl | O | O | 3-bromothiophen-2-yl | 1-(1,3-thiazol-2-yl)ethyl | 3.31[a] | 424 |
| 206 | H | O | O | 3-bromothiophen-2-yl | 1-(1,3-thiazol-2-yl)ethyl | | 382* |
| 207 | Et | O | O | 2-methoxypyridin-3-yl | 1-(1,3-thiazol-2-yl)ethyl | | |
| 208 | Et | O | O | 3,6-dichloropyridin-2-yl | 1-(1,3-thiazol-2-yl)ethyl | 3.02[a] | 397 |
| 209 | Et | O | O | 3-(trifluoromethyl)thiophen-2-yl | 1-(2-thienyl)ethyl | 3.99[a] | 401 |
| 210 | Me | O | O | 2-methyl-4-trifluoromethyl-1,3-thiazol-5-yl | 1-(2-thienyl)ethyl | 3.46[a] | 402 |
| 211 | Et | O | O | 3-bromothiophen-2-yl | 1-(2-thienyl)ethyl | 3.92[a] | 411 |
| 212 | Et | O | O | 2-methyl-4-trifluoromethyl-1,3-thiazol-5-yl | 1-(2-thienyl)ethyl | 3.8[a] | 416 |
| 213 | Et | O | O | 3-(difluoromethyl)-1-methyl-1H-pyrazol-4-yl | 1-(2-thienyl)ethyl | 3.02[a] | 381 |
| 214 | iPr | NH | O | 3-bromothiophen-2-yl | 1-(1,3-thiazol-2-yl)ethyl | 3.11[a] | 425 |
| 215 | Et | O | O | 3-bromothiophen-2-yl | 1-(2,4-dimethyl-1,3-thiazol-5-yl)ethyl | 3.23[a] | 440 |
| 216 | Et | O | O | 3-(trifluoromethyl)thiophen-2-yl | 1-(5-methyl-1,3-thiazol-2-yl)ethyl | 3.67[a] | 416 |
| 217 | Et | O | O | 3-(trifluoromethyl)thiophen-2-yl | (5-methyl-1,3-thiazol-2-yl)methyl | 3.19[a] | 402 |
| 218 | Et | O | O | 2-methyl-4-trifluoromethyl-1,3-thiazol-5-yl | 1-(2,4-dimethyl-1,3-thiazol-5-yl)ethyl | 3.13[a] | 445 |
| 219 | Et | O | O | 2-methyl-4-trifluoromethyl-1,3-thiazol-5-yl | (5-methyl-1,3-thiazol-2-yl)methyl | 3[a] | 417 |
| 220 | Et | O | O | 3-bromothiophen-2-yl | (5-methyl-1,3-thiazol-2-yl)methyl | 3.04[a] | 412 |
| 221 | Et | O | O | 2,5-dichlorothiophen-3-yl | 1-(1,3-thiazol-2-yl)ethyl | 3.65[a] | 402 |
| 222 | Et | O | O | 2,5-dichlorothiophen-3-yl | 1-(pyridin-2-yl)ethyl | 2.41[a] | 396 |
| 223 | Et | O | O | 4,6-dichloropyridin-3-yl | 1-(1,3-thiazol-2-yl)ethyl | 3[a] | 397 |
| 224 | Et | O | O | 3-bromopyridin-2-yl | 1-(1,3-thiazol-2-yl)ethyl | 2.53[a] | 407 |
| 225 | Et | O | O | 3,5-dichloropyridin-2-yl | 1-(1,3-thiazol-2-yl)ethyl | 3.11[a] | 397 |
| 226 | Et | O | O | 3,6-dichloropyridin-2-yl | 1,3-thiazol-2-ylmethyl | 2.6[a] | 383 |
| 227 | Et | O | O | 4,6-dichloropyridin-3-yl | 1,3-thiazol-2-ylmethyl | 2.68[a] | 383 |
| 228 | Et | O | O | 3,5-dichloropyridin-2-yl | 1,3-thiazol-2-ylmethyl | 2.7[a] | |
| 229 | Et | O | O | 3-methoxy-1-methyl-1H-pyrazol-4-yl | 1-(1,3-thiazol-2-yl)ethyl | 2.26[a] | 362 |
| 230 | Et | O | O | 3-(trifluoromethyl)pyridin-2-yl | 1-(1,3-triazol-2-yl)ethyl | 2.78[a] | |
| 231 | Et | O | O | 2-chloropyridin-3-yl | 2-oxotetrahydrofuran-3-yl | 1.83[c] I2; 1.69[c] I1; 1.77[b] | |
| 232 | Et | O | O | 2-(trifluoromethyl)pyridin-3-yl | 1-(1,3-thiazol-2-yl)ethyl | 2.9[a] | 397 |

TABLE 1-continued

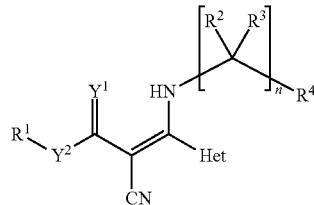

(I)

| No. | R¹ | Y² | Y¹ | Het | R | Log P | M⁺ |
|---|---|---|---|---|---|---|---|
| 233 | Et | O | O | 2-(trifluoromethyl)pyridin-3-yl | 1-(pyridin-2-yl)ethyl | 2.88[a] | 391 |
| 234 | Et | O | O | 5-chloro-3-(difluoromethyl)-1-methyl-1H-pyrazol-4-yl | 1-(1,3-thiazol-2-yl)ethyl | 2.77[a] | 416 |
| 235 | Et | O | O | 5-chloro-3-(difluoromethyl)-1-methyl-1H-pyrazol-4-yl | 1-(4,5-dimethyl-1,3-thiazol-2-yl)ethyl | 3.37[a] | 444 |
| 236 | Et | O | O | 5-chloro-3-(difluoromethyl)-1-methyl-1H-pyrazol-4-yl | 1,3-thiazol-2-ylmethyl | 2.4[a] | 402 |
| 237 | Et | O | O | 5-chloro-3-(difluoromethyl)-1-methyl-1H-pyrazol-4-yl | 1-(1H-indol-3-yl)propan-2-yl | 3.42[a] | 462 |
| 238 | Et | O | O | 3-ethenyl-1-methyl-1H-pyrazol-4-yl | 1-(1,3-thiazol-2-yl)ethyl | 2.3[a] | 358 |
| 239 | Et | O | O | 2-chloropyridin-3-yl | 2-oxopiperidin-3-yl | 1.67[c]; 1.6[b] | |
| 240 | Et | O | O | 5-bromo-2-(methylsulfanyl)pyrimidin-4-yl | 1-(1,3-thiazol-2-yl)ethyl | 3.21[a] | |
| 241 | Et | O | O | 2-chloropyridin-3-yl | (1S)-1-[(4-ethoxycarbonyl)-1,3-thiazol-2-yl]ethyl | 2.79[c] T2; 2.61[c] T1; 2.7[b] | |
| 242 | Et | O | O | 2,4-dichloro-1,3-thiazol-5-yl | 1-(1,3-thiazol-2-yl)ethyl | 3.27[a] | 403 |
| 243 | | | | 2,4-dichloro-1,3-thiazol-5-yl | 1-(pyridin-2-yl)ethyl | 2.13[a] | 397 |
| 244 | Et | O | O | 2-chloropyridin-3-yl | (1S)-1-[(4-carboxy)-1,3-thiazol-2-yl]ethyl | 1.94[c] I2; 1.75[c] I1; 1.1[b] | |
| 245 | Et | O | O | 2-chloropyridin-3-yl | (1-S)-1-(1,3-thiazol-2-yl)ethyl | | |
| 246 | Et | O | O | 2-bromothiophen-3-yl | (4-methyl-1,3-thiazol-2-yl)methyl | 2.94[a] | 413 |
| 247 | Et | O | O | 2-bromothiophen-3-yl | (5-methyl-1,3-thiazol-2-yl)methyl | 3[a] | 413 |
| 248 | Et | O | O | 2-bromothiophen-3-yl | 1,3-benzothiazol-2-ylmethyl | 3.55[a] | 449 |
| 249 | Et | O | O | 2-bromothiophen-3-yl | (4-trifluoromethyl-1,3-thiazol-2-yl)methyl | 3.42[a] | 467 |
| 250 | Et | O | O | 2-bromothiophen-3-yl | 1-(2-thienyl)ethyl | 3.99[a] | 412 |
| 251 | Et | O | O | 2-bromothiophen-3-yl | (5-fluoropyridin-2-yl)methyl | 3.04[a] | 411 |
| 252 | Et | O | O | 2,5-dichloropyridin-4-yl | 1-(1,3-thiazol-2-yl)ethyl | 3.15[a] | 397 |
| 253 | Et | O | O | 2,5-dichloropyridin-4-yl | 1-(3-isopropyl-1,2,4-oxadiazol-5-yl)ethyl | 2.2[a] | 425 |
| 254 | Et | O | O | 2,5-dichloropyridin-4-yl | 1-(3-trifluoromethyl-1,2,4-oxadiazol-5-yl)ethyl | 3.83[a] | 450 |
| 255 | Et | O | O | 2,5-dichloropyridin-4-yl | 1-(1,4-dimethyl-5-oxo-4,5-dihydro-1H-1,2,4-triazol-3-yl)ethyl | 3.76[a] | 425 |
| 256 | Et | O | O | 4-(trifluoromethyl)pyridin-3-yl | 1-(1,3-thiazol-2-yl)ethyl | 2.7[a] | 397 |
| 257 | Et | O | O | 4-bromopyridin-3-yl | 1-(1,3-thiazol-2-yl)ethyl | 2.88[a] | 407 |
| 258 | Et | O | O | 4-chloropyridin-3-yl | 1-(1,3-thiazol-2-yl)ethyl | 2.78[a] | 363 |
| 259 | Et | O | O | 3-chloropyridin-4-yl | 1,3-thiazol-2-ylmethyl | 2.11[a] | 349 |
| 260 | Et | O | O | 3-chloropyridin-4-yl | 1-(pyridin-2-yl)ethyl | 2.54[a] | 357 |
| 261 | Et | O | O | 2-bromothiophen-3-yl | 1-(2,4-dimethyl-1,3-thiazol-5-yl)ethyl | 2.9[a] | 440 |
| 262 | Et | O | O | 2-chloropyridin-3-yl | 1-(4-{[1-(4-methylphenyl)ethyl]carbamoyl}-1,3-thiazol-2-yl)ethyl] | | |
| 263 | Et | O | O | 2-(difluoromethyl)pyridin-3-yl | 1-(1-methyl-1H-pyrazol-3-yl)ethyl | 2.18[a] | 376 |
| 264 | Et | O | O | 2-(difluoromethyl)pyridin-3-yl | 1-(pyridin-2-yl)ethyl | 2.46[a] | 373 |
| 265 | Et | O | O | 4,6-dichloropyridin-2-yl | 1-(1,3-thiazol-2-yl)ethyl | 3.31[a] | 397 |
| 266 | Et | O | O | 2-(difluoromethyl)pyridin-3-yl | 1-(1,3-thiazol-2-yl)ethyl | 2.39[a] | 379 |
| 267 | propargyl | O | O | 2-chloropyridin-3-yl | 1-(1,3-thiazol-2-yl)ethyl | 2.19[c] T1; 2.31[c] T2; 2.26[b] | |
| 268 | cBu | O | O | 2-chloropyridin-3-yl | 1-(1,3-thiazol-2-yl)ethyl | 3[c] T2; 2.79[c] T1; 2.88[b] | |
| 269 | Me | NH | O | 2-chloropyridin-3-yl | 1-(1,3-thiazol-2-yl)ethyl | 1.63[c] T1; 1.76[c] T2; 1.69[b] | |
| 270 | Et | O | O | 1-methyl-4-(trifluoromethyl)-1H-pyrrol-3-yl | 1-(pyridin-2-yl)ethyl | 2.92[a] | 393 |
| 271 | Et | O | O | 1-methyl-4-(trifluoromethyl)-1H-pyrrol-3-yl | 1-(1,3-thiazol-2-yl)ethyl | 2.97[a] | 399 |
| 272 | Et | O | O | 4-(trifluoromethyl)pyridin-3-yl | 1,3-thiazol-2-ylmethyl | 2.4[a] | |
| 273 | Et | O | O | 2-chloropyridin-3-yl | 1-(piperidin-1-yl)propan-2-yl | 1.2[a] | 377 |
| 274 | Et | O | O | 2-chloropyridin-3-yl | 1-(morpholin-4-yl)propan-2-yl | 1.3[a] | 379 |
| 275 | Et | O | O | 2-chloropyridin-3-yl | 1-(1,3-thiazol-4-yl)ethyl | 2.4[a] | 363 |
| 276 | Et | O | O | 2-chloropyridin-3-yl | 1-(1-methyl-1H-pyrazol-3-yl)ethyl | 2.3[a] | 360 |

TABLE 1-continued

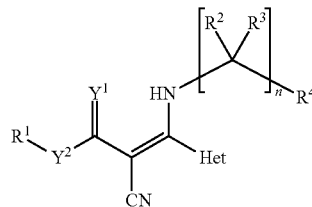

| No. | R¹ | Y² | Y¹ | Het | R | Log P | M⁺ |
|---|---|---|---|---|---|---|---|
| 277 | Et | O | O | 2-chloropyridin-3-yl | 1-(1,3,5-trimethyl-1H-pyrazol-4-yl)ethyl | 2.3[a] | 388 |
| 278 | Et | O | O | 2-chloropyridin-3-yl | 1-(1H-pyrazol-1-yl)propan-2-yl | 2.23[a] | 360 |
| 279 | Et | O | O | 2-chloropyridin-3-yl | 1-(1H-benzimidazol-2-yl)ethyl | 2[a] | 396 |
| 280 | Et | O | O | 2-chloropyridin-3-yl | 1-(2-methyl-4,5,6,7-tetrahydro-1-benzothiophen-3-yl)ethyl | 4.4[a] | 430 |
| 281 | Et | O | O | 2-chloropyridin-3-yl | 1-(5-chlorothiophen-2-yl)ethyl | 3.8[a] | |
| 282 | Et | O | O | 2-chloropyridin-3-yl | 1-[3-(propan-2-yl)-1,2,4-oxadiazol-5-yl]ethyl | 3.2[a] | 390 |
| 283 | Et | O | O | 2-chloropyridin-3-yl | 1-(pyrrolidin-1-yl)propan-2-yl | 3.35[a] | |
| 284 | Et | O | O | 2-chloropyridin-3-yl | 1-(pyridin-2-yl)cyclopropyl | 2.56[a] | |
| 285 | Et | O | O | 2-chloropyridin-3-yl | 1-[5-(trifluoromethyl)pyridin-2-yl]ethyl | 3.5[a] | |
| 286 | Et | O | O | 2-chloropyridin-3-yl | 2-hydroxypyridin-3-yl | 1.9[a] | 345 |
| 287 | Et | O | O | 2-chloropyridin-3-yl | 1-(5-bromo-3-chloropyridin-2-yl)ethyl | 3.9[a] | 469 |
| 288 | Et | O | O | 2-chloropyridin-3-yl | 1-[3-chloro-5-(trifluoromethyl)-pyridin-2-yl]ethyl | 3.9[a] | 460 |
| 289 | Et | O | O | 2,3-dichloropyridin-4-yl | 1-(pyridin-2-yl)ethyl | 3.04[a] | 392 |
| 290 | Et | O | O | 2,3-dichloropyridin-4-yl | 1-(1,3-thiazol-4-yl)ethyl | 2.92[a] | 398 |
| 291 | Et | O | O | 2,3-dichloropyridin-4-yl | 1-(1,3-thiazol-2-yl)ethyl | 2.96[a] | 398 |
| 292 | Et | O | O | 2-chloropyridin-3-yl | 1-(pyridin-2-yl)ethyl | 2.5[a] | 357 |
| 293 | Et | O | O | 2-chloropyridin-3-yl | 3-methylpyridin-4-yl | 1.45[a] | 343 |
| 294 | Et | O | O | 2-chloropyridin-3-yl | 1-(1,3-thiazol-2-yl)propan-2-yl | 2.4[a] | 377 |
| 295 | Et | O | O | 2-chloropyridin-3-yl | 1-(pyridin-2-yl)propan-2-yl | 1.82[a] | 371 |
| 296 | Et | O | O | 2-chloropyridin-3-yl | 1-(pyridin-3-yl)propan-2-yl | 1.57[a] | 371 |
| 297 | Et | O | O | 3-bromopyridin-4-yl | 1-(1,3-thiazol-2-yl)ethyl | 2.4[a] | |
| 298 | Et | O | O | 3-bromopyridin-4-yl | 1-(1,3-thiazol-4-yl)ethyl | 2.4[a] | 407 |
| 299 | Et | O | O | 3-bromopyridin-4-yl | 1-(pyridin-2-yl)ethyl | 2.5[a] | 401 |
| 300 | Et | O | O | 3-fluoropyridin-4-yl | 1-(pyridin-2-yl)ethyl | 2.28[a] | 341 |
| 301 | Et | O | O | 3-fluoropyridin-4-yl | 1-(1,3-thiazol-4-yl)ethyl | 2.22[a] | 347 |
| 302 | Et | O | O | 3-fluoropyridin-4-yl | 1-(1,3-thiazol-2-yl)propan-2-yl | 2.19[a] | 361 |
| 303 | Et | O | O | 3-(trifluoromethyl)pyridin-4-yl | 1-(1,3-thiazol-4-yl)ethyl | 2.6[a] | 397 |
| 304 | Et | O | O | 2-chloropyridin-3-yl | 1-[4-(dimethylcarbamoyl)-1,3-thiazol-2-yl]ethyl | 1.98[c] T1; 2.18[c] T2; 2.08[b] | |
| 305 | allyl | O | O | 3-(difluoromethyl)-1-methyl-1H-pyrazol-4-yl | 1-(1,3-thiazol-2-yl)ethyl | 2.59[a] | 394 |
| 306 | allyl | O | O | 3-(difluoromethyl)-1-methyl-1H-pyrazol-4-yl | 1,3-thiazol-2-ylmethyl | 2.25[a] | 380 |
| 307 | allyl | O | O | 3-(difluoromethyl)-1-methyl-1H-pyrazol-4-yl | 1-(pyridin-2-yl)ethyl | 2.56[a] | 388 |
| 308 | Et | O | O | 5-fluoro-1-methyl-3-(trifluoromethyl)-1H-pyrazol-4-yl | 1-(1,3-thiazol-2-yl)ethyl | 3.09[a] | 418 |
| 309 | Et | O | O | 3-(difluoromethyl)-5-fluoro-1-methyl-1H-pyrazol-4-yl | 1-(1,3-thiazol-2-yl)ethyl | 2.73[a] | 400 |
| 310 | Et | O | O | 5-fluoro-1-methyl-3-(trifluoromethyl)-1H-pyrazol-4-yl | 1-(pyridin-2-yl)ethyl | 3.12[a] | 412 |
| 311 | Et | O | O | 5-chloro-1-methyl-3-(trifluoromethyl)-1H-pyrazol-4-yl | 1-(1,3-thiazol-2-yl)ethyl | 3.2[a] | 434 |
| 312 | Et | O | O | 3-(1,1-difluoroethyl)-1-methyl-1H-pyrazol-4-yl | 1-(1,3-thiazol-2-yl)ethyl | 2.62[a] | 396 |
| 313 | Et | O | O | 2-chloropyridin-3-yl | 1-[4-(ethylcarbamoyl)-1,3-thiazol-2-yl]ethyl | | |
| 314 | Et | O | O | 5-chloro-1-methyl-3-(trifluoromethyl)-1H-pyrazol-4-yl | 1-(pyridin-2-yl)ethyl | 3.24[a] | 428 |
| 315 | Et | O | O | 3-(1,1-difluoroethyl)-1-methyl-1H-pyrazol-4-yl | 1-(pyridin-2-yl)ethyl | 2.57[a] | 390 |
| 316 | Et | O | O | 3-(difluoromethyl)-5-fluoro-1-methyl-1H-pyrazol-4-yl | 1-(pyridin-2-yl)ethyl | 2.73[a] | 394 |
| 317 | propargyl | NH | O | 2-chloropyridin-3-yl | 1-(1,3-thiazol-2-yl)ethyl | 2.03[a] | 372 |
| 318 | Et | O | O | 3-fluoropyridin-4-yl | 1-(1,3-thiazol-2-yl)ethyl | 2.41[a] | 347 |
| 319 | Et | O | O | 2-chloropyridin-3-yl | 2-phenyl-1,3-thiazol-4-yl)methyl | 3.63[a] | 425 |
| 320 | Et | O | O | 2-chloropyridin-3-yl | 1-(pyridin-4-yl)propan-2-yl | 1.64[a] | |
| 321 | Et | O | O | 2-chloropyridin-3-yl | 1-(1-methyl-1H-pyrazol-4-yl)ethyl | 2.2[a] | 360 |

TABLE 1-continued

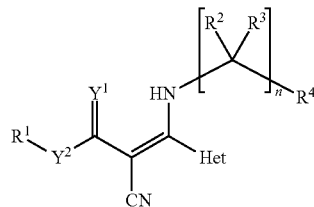

(I)

| No. | $R^1$ | $Y^2$ | $Y^1$ | Het | R | Log P | M+ |
|---|---|---|---|---|---|---|---|
| 322 | Et | O | O | 2-chloropyridin-3-yl | 1-(2-chloro-1,3-thiazol-4-yl)ethyl | 3.3[a] | 397 |
| 323 | Et | O | O | 2-chloropyridin-3-yl | quinolin-2-ylmethyl | 3.13[a] | |
| 324 | CH$_2$CF$_3$ | NH | O | 2-chloropyridin-3-yl | 1-(1,3-thiazol-2-yl)ethyl | 2.44[a] | 416 |
| 325 | Et | O | O | 3-(difluoromethyl)-1-methyl-1H-pyrazol-4-yl | 1-(pyridin-2-yl)ethyl | 2.39[a] | 376 |
| 326 | Et | O | O | 3-(difluoromethyl)-1-methyl-1H-pyrazol-4-yl | 1-(1,3-thiazol-2-yl)ethyl | 2.44[a] | 382 |
| 327 | 2-MeOEt | NH | O | 2-chloropyridin-3-yl | 1-(1,3-thiazol-2-yl)ethyl | 1.93[a] | 392 |
| 328 | Et | NH | O | 2-chloropyridin-3-yl | 1-(1,3-thiazol-2-yl)ethyl | 2.07[a]; 1.94[c] T1; 2.1[c] T2; 2.05[b] | 362 |
| 329 | Et | O | O | 2-chloropyridin-3-yl | 1-(pyrimidin-2-yl)ethyl | 2.13[a] | 358 |
| 330 | Et | O | O | 2-chloropyridin-3-yl | 1-(pyrimidin-4-yl)ethyl | 2.01[a] | 358 |
| 331 | Et | O | O | 2-chloropyridin-3-yl | 2-(1,3-thiazol-2-yl)propyl | 2.57[a] | 377 |
| 332 | Me | O | O | 2-chloropyridin-3-yl | 1-(4-chlorophenyl)ethyl | 3.24[a] | |
| 333 | Me | O | O | 2-chloropyridin-3-yl | 3-chlorophenyl | | |
| 334 | Me | O | O | 2-chloropyridin-3-yl | 2-(methylsulfanyl)phenyl | 2.82[c]; 2.82[b] | |
| 335 | Me | O | O | 2-chloropyridin-3-yl | 2-methoxyphenyl | 2.58[c]; 2.56[b] | |
| 336 | Me | O | O | 2-chloropyridin-3-yl | 4-chlorobenzyl | 2.98[c]; 2.96[b] | |
| 337 | Me | O | O | 2-chloropyridin-3-yl | 2-(4-chlorophenyl)propan-2-yl | 3.33[c] | |
| 338 | Me | O | O | 2-chloropyridin-3-yl | (6-chloropyridin-3-yl)methyl | 2.11[c]; 2.1[b] | |
| 339 | Me | O | O | 2-chloropyridin-3-yl | 3-(methylsulfanyl)phenyl | 3.04[c]; 2.83[b] | |
| 340 | Me | O | O | 2-chloropyridin-3-yl | 2-(ethylsulfanyl)phenyl | | |
| 341 | Et | O | O | 2-chloropyridin-3-yl | 2-(methylsulfanyl)phenyl | 3.32[c]; 3.17[b] | |
| 342 | Et | O | O | 2-chloropyridin-3-yl | 1-(4-chlorophenyl)ethyl | 3.88[c] T2; 3.68[c] T1; 3.61[b] | |
| 343 | Et | O | O | 2-chloro-6-methylpyridin-3-yl | 2-(methylsulfanyl)phenyl | 3.57[c]; 3.41[b] | |
| 344 | CH$_2$CF$_3$ | O | O | 2-chloropyridin-3-yl | 2-(methylsulfanyl)phenyl | 3.55[c]; 3.21[b] | |
| 345 | Et | O | O | 2-chloropyridin-3-yl | (1R)-1-(4-chlorophenyl)ethyl | 3.69[c] T1; 3.88[c] T2; 3.63[b] | |
| 346 | Et | O | O | 2,5-dichloropyridin-3-yl | 2-(methylsulfanyl)phenyl | 3.94[c]; 3.7[b] | |
| 347 | iBu | O | O | 2-chloropyridin-3-yl | 2-(methylsulfanyl)phenyl | 4.15[c]; 3.94[b] | |
| 348 | Et | O | O | 3-(difluoromethyl)-1-methyl-1H-pyrazol-4-yl | 1-(4-chlorophenyl)ethyl | 3.6[a] | 409 |
| 349 | Et | O | O | 3-(difluoromethyl)-1-methyl-1H-pyrazol-4-yl | 2-(methylsulfanyl)phenyl | 3.13[a] | 393 |
| 350 | Et | O | O | 3-chloro-5-(trifluoromethyl)-pyridin-2-yl | 2-(methylsulfanyl)phenyl | 4.26[a] | 442 |
| 351 | Et | O | O | 3-chloro-5-(trifluoromethyl)pyridin-2-yl | 1-(4-chlorophenyl)ethyl | 4.56[a] | 458 |
| 352 | Et | O | O | 5-fluoro-1,3-dimethyl-1H-pyrazol-4-yl | 1-(4-chlorophenyl)ethyl | 3.62[a] | 391 |
| 353 | Me | O | O | 2-chloropyridin-3-yl | 2,2,2-trifluoro-1-phenylethyl | | |
| 354 | Et | O | O | 5-fluoro-1,3-dimethyl-1H-pyrazol-4-yl | 2-(methylsulfanyl)phenyl | 3.21[a] | 375 |
| 355 | Et | O | O | 4,5-dichloro-1,2-thiazol-3-yl | 1-(4-chlorophenyl)ethyl | 4.65[a] | 430 |
| 356 | Me | O | O | 3-(difluoromethyl)-1-methyl-1H-pyrazol-4-yl | 1-(4-chlorophenyl)ethyl | 3.31[a] | 395 |
| 357 | Me | O | O | 3-(difluoromethyl)-1-methyl-1H-pyrazol-4-yl | 2-(methylsulfanyl)phenyl | 2.8[a] | 379 |
| 358 | Et | O | O | 4,5-dichloro-1,2-thiazol-3-yl | 2-(methylsulfanyl)phenyl | 4.31[a] | 414 |
| 359 | Me | O | O | 2-chloropyridin-3-yl | 2-(cyclopropylcarbonyl)phenyl | | |
| 360 | Et | O | O | 2,6-dichloropyridin-3-yl | 2-(methylsulfanyl)phenyl | 3.97[c]; 3.79[b] | |
| 361 | Et | O | O | 2-chloropyridin-3-yl | 2-(1,1,1,3,3,3-hexafluoro-2-hydroxypropan-2-yl)phenyl | | |
| 362 | Et | O | O | 3-methylisoxazol-4-yl | 1-(4-chlorophenyl)ethyl | 3.62[a] | 360 |
| 363 | Et | O | O | 3-methylisoxazol-4-yl | 2-(methylsulfanyl)phenyl | 3.21[a] | 344 |
| 364 | Et | O | O | 2-chloropyridin-3-yl | biphenyl-2-yl | | |
| 365 | Et | O | O | 3-bromothiophen-2-yl | 1-(4-chlorophenyl)ethyl | 4.42[a] | 439 |
| 366 | Et | O | O | 3-bromothiophen-2-yl | 2-(methylsulfanyl)phenyl | 3.96[a] | 423 |
| 367 | Et | O | O | 5-chloro-1,3-dimethyl-1H-pyrazol-4-yl | 1-(4-chlorophenyl)ethyl | 3.8[a] | 407 |
| 368 | Et | O | O | 3-(trifluoromethyl)thiophen-2-yl | 1-(4-chlorophenyl)ethyl | 4.47[a] | 429 |
| 369 | Et | O | O | 3-(trifluoromethyl)thiophen-2-yl | 2-(methylsulfanyl)phenyl | 4.01[a] | 413 |
| 370 | Me | O | O | 2-chloropyridin-3-yl | 2-phenylpropan-2-yl | 2.98[a] | |
| 371 | Me | O | O | 2-chloropyridin-3-yl | 1-(pyridin-4-yl)ethyl | 1.24[a] | |
| 372 | Me | O | O | 2-chloropyridin-3-yl | 1-(3-chlorophenyl)propyl | 3.58[a] | |
| 373 | Me | O | O | 2-chloropyridin-3-yl | 1-(2-methylphenyl)ethyl | 3.15[a] | |

TABLE 1-continued

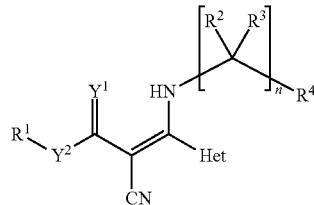

| No. | R¹ | Y² | Y¹ | Het | R | Log P | M⁺ |
|---|---|---|---|---|---|---|---|
| 374 | Me | O | O | 2-chloropyridin-3-yl | 1-(2,4-dichlorophenyl)ethyl | 3.73[a] | |
| 375 | Me | O | O | 2-chloropyridin-3-yl | 1-(2-chlorophenyl)ethyl | 3.19[a] | |
| 376 | Me | O | O | 2-chloropyridin-3-yl | 1-(4-chlorophenyl)propyl | 3.58[a] | |
| 377 | Me | O | O | 2-chloropyridin-3-yl | 1-(3-methoxyphenyl)ethyl | 2.89[a] | |
| 378 | Me | O | O | 2-chloropyridin-3-yl | 1-(4-ethoxyphenyl)ethyl | 3.02[a] | |
| 379 | Me | O | O | 2-chloropyridin-3-yl | 1-(4-isopropylphenyl)ethyl | 4[a] | |
| 380 | Me | O | O | 2-chloropyridin-3-yl | 1-(2,6-difluorophenyl)cyclopropyl | 2.8[a] | |
| 381 | Me | O | O | 2-chloropyridin-3-yl | (4-chloro-phenyl)(cyclopropyl)methyl | 3.58[a] | |
| 382 | Me | O | O | 2-chloropyridin-3-yl | 1-(2-chlorophenyl)cyclopropyl | 2.61[a] | |
| 383 | Me | O | O | 2-chloropyridin-3-yl | 1-(3-chlorophenyl)cyclopropyl | 3.11[a] | |
| 384 | Me | O | O | 2-chloropyridin-3-yl | 1-(4-chlorophenyl)cyclopropyl | 3.19[a] | |
| 385 | Me | O | O | 2-chloropyridin-3-yl | 2-(2,6-difluorophenyl)propan-2-yl | 2.98[a] | |
| 386 | Me | O | O | 2-chloropyridin-3-yl | 2-(4-methoxyphenyl)propan-2-yl | 3.02[a] | |
| 387 | Me | O | O | 2-chloropyridin-3-yl | 1-(3,4-dichlorophenyl)ethyl | 3.58[a] | |
| 388 | Me | O | O | 2-chloropyridin-3-yl | 1-(3,5-dichlorophenyl)ethyl | 3.68[a] | |
| 389 | Me | O | O | 2-chloropyridin-3-yl | 3,3,3-trifluoro-1-phenylpropyl | 2.98[a] | |
| 390 | Me | O | O | 2-chloropyridin-3-yl | (3-chlorophenyl)(cyclopropyl)methyl | 2.93[a] | |
| 391 | Me | O | O | 2-chloropyridin-3-yl | 1-(2-methoxyphenyl)propyl | 3.15[a] | |
| 392 | Me | O | O | 2-chloropyridin-3-yl | 1-(2-methoxyphenyl)ethyl | 2.84[a] | |
| 393 | Me | O | O | 2-chloropyridin-3-yl | 2-(2-chlorophenyl)propan-2-yl | 3.15[a] | |
| 394 | Me | O | O | 2-chloropyridin-3-yl | 1-(2,5-dichlorophenyl)ethyl | 3.28[a] | |
| 395 | Me | O | O | 2-chloropyridin-3-yl | 1-(4-trifluoromethylphenyl)ethyl | 3.37[a] | |
| 396 | Me | O | O | 2-chloropyridin-3-yl | 1-(3-methylphenyl)ethyl | 3.02[a] | |
| 397 | Me | O | O | 2-chloropyridin-3-yl | 1-(4-fluorophenyl)ethyl | 2.89[a] | |
| 398 | Me | O | O | 2-chloropyridin-3-yl | (phenyl)(cyclopropyl)methyl | 3.24[a] | |
| 399 | Me | O | O | 2-chloropyridin-3-yl | 2-(4-fluorophenyl)propan-2-yl | 2.98[a] | |
| 400 | Me | O | O | 2-chloropyridin-3-yl | 1-(3,4-dimethoxyphenyl)ethyl | 2.34[a] | |
| 401 | Me | O | O | 2-chloropyridin-3-yl | 1-(3-trifluoromethylphenyl)ethyl | 3.28[a] | |
| 402 | Me | O | O | 2-chloropyridin-3-yl | 1-(1,3-benzodioxol-5-yl)ethyl | 2.53[a] | |
| 403 | Me | O | O | 2-chloropyridin-3-yl | 1-(3-chlorophenyl)ethyl | 3.19[a] | |
| 404 | Me | O | O | 2-chloropyridin-3-yl | 1-phenylethyl | 2.89[a] | |
| 405 | Me | O | O | 2-chloropyridin-3-yl | 1-phenylpropyl | 3.02[a] | |
| 406 | Me | O | O | 2-chloropyridin-3-yl | 1-(4-tert-butylphenyl)ethyl | 4.23[a] | |
| 407 | Me | O | O | 2-chloropyridin-3-yl | 1-(4-ethylphenyl)ethyl | 3.63[a] | |
| 408 | Me | O | O | 2-chloropyridin-3-yl | 1-(4-methoxyphenyl)ethyl | 2.65[a] | |
| 409 | Me | O | O | 2-chloropyridin-3-yl | 1-(4-methylphenyl)ethyl | 3.28[a] | |
| 410 | Et | O | O | 5-chloro-1,3-dimethyl-1H-pyrazol-4-yl | 2-(methylsulfanyl)phenyl | 3.42[a] | 391 |
| 411 | Et | O | O | 2-bromothiophen-3-yl | 1-(4-chlorophenyl)ethyl | 4.35[a] | 439 |
| 412 | Et | O | O | 2-bromothiophen-3-yl | 2-(methylsulfanyl)phenyl | 3.99[a] | 423 |
| 413 | Et | O | O | 2-chloropyridin-3-yl | 2-(methylsulfanyl)-5-(trifluoromethyl)phenyl | | |
| 414 | Et | O | O | 2,5-dimethylfuran-3-yl | 2-(methylsulfanyl)phenyl | 3.84[a] | |
| 415 | Et | O | O | 2,5-dimethylfuran-3-yl | 2-[(pentafluoroethyl)-sulfanyl]phenyl | 4.7[a] | |
| 416 | Et | O | O | 2,5-dimethylfuran-3-yl | 2-[(trifluoroethyl)-sulfanyl]phenyl | 4.3[a] | |
| 417 | Et | O | O | 2,5-dimethylfuran-3-yl | 2-(methylsulfonyl)phenyl | 2.65[a] | |
| 418 | Et | O | O | 2,5-dimethylfuran-3-yl | 2-[(2-chloro-1,1,2-trifluoroethyl)-sulfanyl]phenyl | 4.25[a] | |
| 419 | Et | O | O | 2,5-dimethylfuran-3-yl | 2-[(4-methylphenyl)sulfanyl]phenyl | 5.08[a] | |
| 420 | Et | O | O | 2,5-dimethylfuran-3-yl | 2-(prop-2-en-1-ylsulfanyl)phenyl | 4.25[a] | |
| 421 | Et | O | O | 2,5-dimethylfuran-3-yl | 2-(propan-2-ylsulfanyl)phenyl | 4.57[a] | |
| 422 | Et | O | O | 2,5-dimethylfuran-3-yl | 2-bromophenyl | 3.99[a] | |
| 423 | Me | O | O | 2-chloropyridin-3-yl | 1-(2-methylphenyl)propan-2-yl | 3.23[a] | |
| 424 | Me | O | O | 2-chloropyridin-3-yl | 4-phenylbutan-2-yl | 3.27[a] | |
| 425 | Me | O | O | 2-chloropyridin-3-yl | 4-(3-methylphenyl)butan-2-yl | 3.68[a] | |
| 426 | Me | O | O | 2-chloropyridin-3-yl | 1-phenylpropan-2-yl | 2.98[a] | |
| 427 | Me | O | O | 2-methyl-4-trifluoromethyl-1,3-thiazol-5-yl | 1-(4-chlorophenyl)ethyl | 3.98[a] | 430 |
| 428 | Me | O | O | 2-methyl-4-trifluoromethyl-1,3-thiazol-5-yl | 2-(methylsulfanyl)phenyl | 3.46[a] | 414 |

TABLE 1-continued

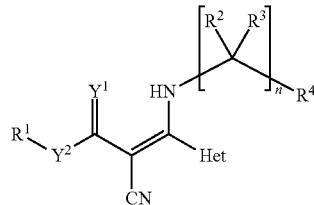

(I)

| No. | R¹ | Y² | Y¹ | Het | R | Log P | M⁺ |
|---|---|---|---|---|---|---|---|
| 429 | Et | O | O | 2-chloropyridin-3-yl | 4-(2,6-dichlorophenyl)butan-2-yl | 4.69[c] I2; 4.58[c] I1; 4.62[b] | |
| 430 | Et | O | O | 1-methyl-3-(trifluoromethyl)-1H-pyrazol-4-yl | 1-(4-chlorophenyl)ethyl | 3.95[a] | 427 |
| 431 | Et | O | O | 1-methyl-3-(trifluoromethyl)-1H-pyrazol-4-yl | 2-(methylsulfanyl)phenyl | 3.48[a] | 411 |
| 432 | Et | O | O | 2-methyl-4-trifluoromethyl-1,3-thiazol-5-yl | 2-(methylsulfanyl)phenyl | 3.8[a] | 428 |
| 433 | Et | O | O | 2-methyl-4-trifluoromethyl-1,3-thiazol-5-yl | 1-(4-chlorophenyl)ethyl | 4.27[a] | |
| 434 | Et | O | O | 3-chlorothiophen-2-yl | 1-(4-chlorophenyl)ethyl | 4.4[a] | 395 |
| 435 | Et | O | O | 3-chlorothiophen-2-yl | 2-(methylsulfanyl)phenyl | 3.92[a] | 379 |
| 436 | Et | O | O | 2-iodothiophen-3-yl | 2-(methylsulfanyl)phenyl | 3.94[a] | 471 |
| 437 | Et | O | O | 3-(trifluoromethyl)thiophen-2-yl | 4-phenylbutan-2-yl | 4.56[a] | 423 |
| 438 | Et | O | O | 3-(trifluoromethyl)thiophen-2-yl | 1-(4-fluorophenyl)ethyl | 4.14[a] | 413 |
| 439 | Et | O | O | 3-(trifluoromethyl)thiophen-2-yl | 1-(4-methylphenyl)ethyl | 4.54[a] | 409 |
| 440 | Et | O | O | 3-(trifluoromethyl)thiophen-2-yl | 1-phenylethyl | 4.16[a] | 395 |
| 441 | Me | O | O | 2-methyl-4-trifluoromethyl-1,3-thiazol-5-yl | 4-phenylbutan-2-yl | 4.01[a] | 424 |
| 442 | Me | O | O | 2-methyl-4-trifluoromethyl-1,3-thiazol-5-yl | 1-(4-fluorophenyl)ethyl | 3.64[a] | 414 |
| 443 | Me | O | O | 2-methyl-4-trifluoromethyl-1,3-thiazol-5-yl | 1-(4-methylphenyl)ethyl | 4.01[a] | 410 |
| 444 | Me | O | O | 2-methyl-4-trifluoromethyl-1,3-thiazol-5-yl | 1-phenylethyl | 3.62[a] | 396 |
| 445 | Et | O | O | 3-bromothiophen-2-yl | 4-phenylbutan-2-yl | 4.51[a] | 433 |
| 446 | Et | O | O | 3-bromothiophen-2-yl | 1-(4-fluorophenyl)ethyl | 4.06[a] | 423 |
| 447 | Et | O | O | 3-bromothiophen-2-yl | 1-(4-methylphenyl)ethyl | 4.49[a] | 419 |
| 448 | Et | O | O | 3-bromothiophen-2-yl | 1-phenylethyl | 4.09[a] | 405 |
| 449 | Et | O | O | 2-methyl-4-trifluoromethyl-1,3-thiazol-5-yl | 4-phenylbutan-2-yl | 4.36[a] | 438 |
| 450 | Et | O | O | 2-methyl-4-trifluoromethyl-1,3-thiazol-5-yl | 1-(4-fluorophenyl)ethyl | 3.96[a] | 428 |
| 451 | Et | O | O | 2-methyl-4-trifluoromethyl-1,3-thiazol-5-yl | 1-(4-methylphenyl)ethyl | 4.36[a] | 424 |
| 452 | Et | O | O | 2-methyl-4-trifluoromethyl-1,3-thiazol-5-yl | 1-phenylethyl | 3.99[a] | 410 |
| 453 | Et | O | O | 3-(difluoromethyl)-1-methyl-1H-pyrazol-4-yl | 4-phenylbutan-2-y | 3.62[a] | 403 |
| 454 | Et | O | O | 3-(difluoromethyl)-1-methyl-1H-pyrazol-4-yl | 1-(4-fluorophenyl)ethyl | 3.21[a] | 393 |
| 455 | Et | O | O | 3-(difluoromethyl)-1-methyl-1H-pyrazol-4-yl | 1-(4-methylphenyl)ethyl | 3.51[a] | 389 |
| 456 | Et | O | O | 3-(difluoromethyl)-1-methyl-1H-pyrazol-4-yl | 1-phenylethyl | 3.17[a] | 375 |
| 457 | Et | O | O | 3-bromothiophen-2-yl | 4-chlorophenyl | 4.11[a] | 411 |
| 458 | Et | O | O | 3-bromothiophen-2-yl | 2-(methylsulfanyl)benzyl | 4.01[a] | 437 |
| 459 | Et | O | O | 3-bromothiophen-2-yl | 3-chlorophenyl | 4.09[a] | 411 |
| 460 | Et | O | O | 3-(trifluoromethyl)thiophen-2-yl | 2-(propan-2-yloxy)phenyl | 4.54[a] | 425 |
| 461 | Et | O | O | 3-(trifluoromethyl)thiophen-2-yl | 4-(difluoromethoxy)phenyl | 3.78[a] | 433 |
| 462 | Et | O | O | 3-(trifluoromethyl)thiophen-2-yl | 4-(methylsulfanyl)phenyl | 4.09[a] | 413 |
| 463 | Et | O | O | 3-(trifluoromethyl)thiophen-2-yl | 2-(methylsulfanyl)benzyl | 4.09[a] | 427 |
| 464 | Et | O | O | 2-methyl-4-trifluoromethyl-1,3-thiazol-5-yl | 2-(methylsulfanyl)benzyl | 3.87[a] | 442 |
| 465 | Me | O | O | 2-methyl-4-trifluoromethyl-1,3-thiazol-5-yl | 1,3-benzothiazol-6-yl | 2.64[a] | 425 |
| 466 | Me | O | O | 2-methyl-4-trifluoromethyl-1,3-thiazol-5-yl | 2-(methylsulfanyl)benzyl | 3.55[a] | 428 |
| 467 | Et | O | O | 3-bromothiophen-2-yl | 2-(propan-2-yloxy)phenyl | 4.46[a] | 435 |

TABLE 1-continued

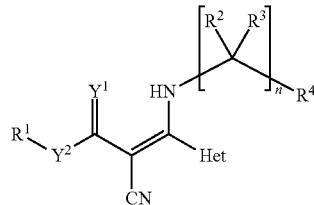

(I)

| No. | R¹ | Y² | Y¹ | Het | R | Log P | M⁺ |
|---|---|---|---|---|---|---|---|
| 468 | Et | O | O | 3-bromothiophen-2-yl | 4-(difluoromethoxy)phenyl | 3.73[a] | |
| 469 | Et | O | O | 3-bromothiophen-2-yl | 1,3-benzothiazol-6-yl | 3.09[a] | 434 |
| 470 | Et | O | O | 3-bromothiophen-2-yl | 4-(methylsulfanyl)phenyl | 4.01[a] | 423 |
| 471 | Et | O | O | 3-(difluoromethyl)-1-methyl-1H-pyrazol-4-yl | 2-(propan-2-yloxy)phenyl | 3.53[a] | 405 |
| 472 | Et | O | O | 3-(difluoromethyl)-1-methyl-1H-pyrazol-4-yl | 4-(difluoromethoxy)phenyl | 3.04[a] | 413 |
| 473 | Et | O | O | 3-(difluoromethyl)-1-methyl-1H-pyrazol-4-yl | 1,3-benzothiazol-6-yl | 2.44[a] | 404 |
| 474 | Et | O | O | 3-(difluoromethyl)-1-methyl-1H-pyrazol-4-yl | 4-(methylsulfanyl)phenyl | 3.19[a] | 393 |
| 475 | Et | O | O | 3-(difluoromethyl)-1-methyl-1H-pyrazol-4-yl | 4-chlorophenyl | 3.23[a] | 381 |
| 476 | Et | O | O | 3-(difluoromethyl)-1-methyl-1H-pyrazol-4-yl | 2-(methylsulfanyl)benzyl | 3.17[a] | 407 |
| 477 | Et | O | O | 3-(difluoromethyl)-1-methyl-1H-pyrazol-4-yl | 3-chlorophenyl | 3.21[a] | 381 |
| 478 | Et | O | O | 2-methyl-4-trifluoromethyl-1,3-thiazol-5-yl | 4-(difluoromethoxy)phenyl | | |
| 479 | Et | O | O | 2-methyl-4-trifluoromethyl-1,3-thiazol-5-yl | 1,3-benzothiazol-6-yl | 2.98[a] | 439 |
| 480 | Et | O | O | 2-methyl-4-trifluoromethyl-1,3-thiazol-5-yl | 4-(methylsulfanyl)phenyl | 3.87[a] | 428 |
| 481 | Et | O | O | 3-(trifluoromethyl)thiophen-2-yl | 4-(propan-2-yl)phenyl | 4.75[a] | 409 |
| 482 | Et | O | O | 3-(trifluoromethyl)thiophen-2-yl | 3-(methylsulfanyl)phenyl | 4.04[a] | 413 |
| 483 | Et | O | O | 3-(trifluoromethyl)thiophen-2-yl | 4-methoxyphenyl | 3.62[a] | 397 |
| 484 | Et | O | O | 3-(trifluoromethyl)thiophen-2-yl | 4-(dimethylamino)phenyl | 3.89[a] | 410 |
| 485 | Me | O | O | 2-methyl-4-trifluoromethyl-1,3-thiazol-5-yl | 4-methoxyphenyl | 3.06[a] | 398 |
| 486 | Me | O | O | 2-methyl-4-trifluoromethyl-1,3-thiazol-5-yl | 4-(dimethylamino)phenyl | 3.31[a] | 411 |
| 487 | Me | O | O | 2-methyl-4-trifluoromethyl-1,3-thiazol-5-yl | 4-(propan-2-yl)phenyl | 4.14[a] | |
| 488 | Et | O | O | 3-bromothiophen-2-yl | 4-methoxyphenyl | 3.55[a] | 407 |
| 489 | Et | O | O | 3-bromothiophen-2-yl | 4-(dimethylamino)phenyl | 3.76[a] | 420 |
| 490 | Et | O | O | 3-bromothiophen-2-yl | 4-(propan-2-yl)phenyl | 4.73[a] | 419 |
| 491 | Et | O | O | 3-bromothiophen-2-yl | 3-(methylsulfanyl)phenyl | 3.96[a] | 423 |
| 492 | Et | O | O | 2-methyl-4-trifluoromethyl-1,3-thiazol-5-yl | 4-methoxyphenyl | 3.44[a] | 412 |
| 493 | Et | O | O | 2-methyl-4-trifluoromethyl-1,3-thiazol-5-yl | 4-(dimethylamino)phenyl | 3.71[a] | 425 |
| 494 | Et | O | O | 2-methyl-4-trifluoromethyl-1,3-thiazol-5-yl | 4-(propan-2-yl)phenyl | 4.54[a] | 424 |
| 495 | Et | O | O | 3-(difluoromethyl)-1-methyl-1H-pyrazol-4-yl | 4-methoxyphenyl | 2.77[a] | 377 |
| 496 | Et | O | O | 3-(difluoromethyl)-1-methyl-1H-pyrazol-4-yl | 4-(dimethylamino)phenyl | 2.71[a] | 390 |
| 497 | Et | O | O | 3-(difluoromethyl)-1-methyl-1H-pyrazol-4-yl | 4-(propan-2-yl)phenyl | 3.76[a] | 389 |
| 498 | Et | O | O | 3-(difluoromethyl)-1-methyl-1H-pyrazol-4-yl | 3-(methylsulfanyl)phenyl | 3.17[a] | 393 |
| 499 | Et | O | O | 2,5-dichlorothiophen-3-yl | 1-(4-chlorophenyl)ethyl | 4.96[a] | 429 |
| 500 | Et | O | O | 2,5-dichlorothiophen-3-yl | 2-(methylsulfanyl)phenyl | 4.59[a] | |
| 501 | Et | O | O | 2,5-dichlorothiophen-3-yl | 1-(2,6-difluorophenyl)cyclopropyl | 4.62[a] | 443 |
| 502 | Et | O | O | 3,6-dichloropyridin-2-yl | 2-(methylsulfanyl)phenyl | 3.99[a] | 408 |
| 503 | Et | O | O | 3,5-dichloropyridin-2-yl | 2-(methylsulfanyl)phenyl | 4.09[a] | |
| 504 | Me | O | O | 2-methyl-4-trifluoromethyl-1,3-thiazol-5-yl | 3-(methylsulfanyl)phenyl | 3.53[a] | 414 |
| 505 | Et | O | O | 2-methyl-4-trifluoromethyl-1,3-thiazol-5-yl | 3-(methylsulfanyl)phenyl | 3.89[a] | 428 |

TABLE 1-continued

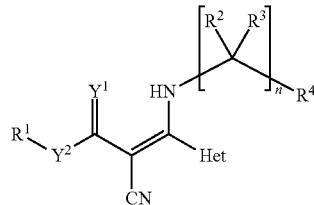

(I)

| No. | R¹ | Y² | Y¹ | Het | R | Log P | M⁺ |
|---|---|---|---|---|---|---|---|
| 506 | Et | O | O | 3-methoxy-1-methyl-1H-pyrazol-4-yl | 1-(4-chlorophenyl)ethyl | 3.51[a] | 389 |
| 507 | Et | O | O | 3-methoxy-1-methyl-1H-pyrazol-4-yl | 2-(methylsulfanyl)phenyl | 3.06[a] | 373 |
| 508 | Et | O | O | 3-methoxy-1-methyl-1H-pyrazol-4-yl | 1-(2,6-difluorophenyl)cyclopropyl | 3.02[a] | 403 |
| 509 | Et | O | O | 3-(trifluoromethyl)thiophen-2-yl | 1,3-benzothiazol-6-yl | 3.21[a] | 424 |
| 510 | Et | O | O | 3-(trifluoromethyl)thiophen-2-yl | 4-chlorophenyl | 4.14[a] | 401 |
| 511 | Et | O | O | 3-(trifluoromethyl)thiophen-2-yl | 3-chlorophenyl | 414[a] | 401 |
| 512 | Et | O | O | 2-methyl-4-trifluoromethyl-1,3-thiazol-5-yl | 4-chlorophenyl | 3.92[a] | 416 |
| 513 | Et | O | O | 2-methyl-4-trifluoromethyl-1,3-thiazol-5-yl | 3-chlorophenyl | 3.89[a] | 416 |
| 514 | Me | O | O | 2-methyl-4-trifluoromethyl-1,3-thiazol-5-yl | 2-(propan-2-yloxy)phenyl | 3.96[a] | 426 |
| 515 | Me | O | O | 2-methyl-4-trifluoromethyl-1,3-thiazol-5-yl | 4-(difluoromethoxy)phenyl | 3.31[a] | 434 |
| 516 | Me | O | O | 2-methyl-4-trifluoromethyl-1,3-thiazol-5-yl | 4-(methylsulfanyl)phenyl | 3.53[a] | 414 |
| 517 | Me | O | O | 2-methyl-4-trifluoromethyl-1,3-thiazol-5-yl | 4-chlorophenyl | 3.55[a] | 402 |
| 518 | Me | O | O | 2-methyl-4-trifluoromethyl-1,3-thiazol-5-yl | 3-chlorophenyl | 3.53[a] | 402 |
| 519 | Et | O | O | 2-methyl-4-trifluoromethyl-1,3-thiazol-5-yl | 2-(propan-2-yloxy)phenyl | 4.36[a] | 440 |
| 520 | Et | O | O | 3-(1-fluoroethyl)-1-methyl-1H-pyrazol-4-yl | 1-(4-chlorophenyl)ethyl | 3.64[a] | |
| 521 | Et | O | O | 3-(1-fluoroethyl)-1-methyl-1H-pyrazol-4-yl | 2-(methylsulfanyl)phenyl | 3.15[a] | 389 |
| 522 | Et | O | O | 2-methoxypyridin-3-yl | 2-(methylsulfanyl)phenyl | 3.32[c]; 3.32[b] | |
| 523 | Et | O | O | 2-bromothiophen-3-yl | 2-(propan-2-yloxy)phenyl | 4.46[a] | 435 |
| 524 | Et | O | O | 2-bromothiophen-3-yl | 4-(methylsulfanyl)phenyl | 4.01[a] | 422 |
| 525 | Et | O | O | 2-bromothiophen-3-yl | 4-methoxyphenyl | 3.6[a] | 407 |
| 526 | Et | O | O | 2,4-dichloro-1,3-thiazol-5-yl | 1-(4-chlorophenyl)ethyl | 4.54[a] | 430 |
| 527 | Et | O | O | 2,4-dichloro-1,3-thiazol-5-yl | 2-(methylsulfanyl)phenyl | 4.14[a] | 414 |
| 528 | Et | O | O | 2,4-dichloro-1,3-thiazol-5-yl | 1-(2,6-difluorophenyl)cyclopropyl | 4.14[a] | 444 |
| 529 | Et | O | O | 2-chloropyridin-3-yl | 2-(trifluoromethoxy)phenyl | 3.52[c]; 3.46[b] | |
| 530 | Et | O | O | 1-methyl-3-(trifluoromethyl)-1H-pyrazol-4-yl | 1-(2,6-difluorophenyl)cyclopropyl | 3.48[a] | 441 |
| 531 | Et | O | O | 2-bromothiophen-3-yl | 1-(4-fluorophenyl)ethyl | 3.89[a] | 423 |
| 532 | Et | O | O | 2-bromothiophen-3-yl | 4-(difluoromethoxy)phenyl | 3.73[a] | 444 |
| 533 | Et | O | O | 2-bromothiophen-3-yl | 1,3-benzothiazol-6-yl | 3.11[a] | 435 |
| 534 | Et | O | O | 2-bromothiophen-3-yl | 4-chlorophenyl | 4.11[a] | 412 |
| 535 | Et | O | O | 2-bromothiophen-3-yl | 2-(methylsulfanyl)benzyl | 4.01[a] | 438 |
| 536 | Et | O | O | 2-bromothiophen-3-yl | 4-(propan-2-yl)phenyl | 4.78[a] | 420 |
| 537 | Et | O | O | 2-bromothiophen-3-yl | 3-(methylsulfanyl)phenyl | 4.04[a] | 424 |
| 538 | Et | O | O | 2-bromothiophen-3-yl | 4-phenylbutan-2-yl | 4.56[a] | 434 |
| 539 | Et | O | O | 2-bromothiophen-3-yl | 3-chlorophenyl | 4.09[a] | 412 |
| 540 | Et | O | O | 2-bromothiophen-3-yl | 4-(dimethylamino)phenyl | 3.76[a] | 421 |
| 541 | Et | O | O | 3-chloropyridin-4-yl | 1-(4-chlorophenyl)ethyl | 3.78[a] | 391 |
| 542 | Et | O | O | 1-methyl-4-(trifluoromethyl)-1H-pyrrol-3-yl | 1-(4-chlorophenyl)ethyl | 4.2[a] | 426 |
| 543 | Et | O | O | 2-chloropyridin-3-yl | 1-(2,6-difluorophenyl)cyclopropyl | 3.39[a] | 404 |
| 544 | Et | O | O | 2,3-dichloropyridin-4-yl | 1-(4-chlorophenyl)ethyl | 4.21[a] | 425 |
| 545 | Et | O | O | 2-chloropyridin-3-yl | 3-methyl-2-phenylbutyl | 4.21[a] | 398 |
| 546 | Et | O | O | 3-fluoropyridin-4-yl | 1-(4-chlorophenyl)ethyl | 3.48[a] | 374 |
| 547 | Et | O | O | 1-methyl-4-(trifluoromethyl)-1H-pyrrol-3-yl | 1-(2,6-difluorophenyl)cyclopropyl | 3.85[a] | 440 |
| 548 | Et | O | O | 1-methyl-4-(trifluoromethyl)-1H-pyrrol-3-yl | 2-(methylsulfanyl)phenyl | 3.73[a] | 410 |

TABLE 1-continued

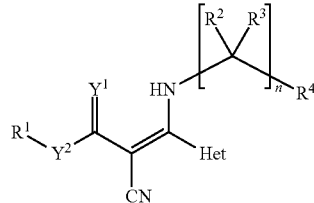

(I)

| No. | R[1] | Y[2] | Y[1] | Het | R | Log P | M+ |
|---|---|---|---|---|---|---|---|
| 549 | Et | O | O | 3-(1-fluoroethyl)-1-methyl-1H-pyrazol-4-yl | 1-(2,6-difluorophenyl)cyclopropyl | 3.23[a] | 419 |
| 550 | Et | O | O | 3-(difluoromethyl)-1-methyl-1H-pyrazol-4-yl | 1-(4-isopropylphenyl)ethyl | 4.2[a] | 417 |
| 551 | Et | O | O | 3-(difluoromethyl)-1-methyl-1H-pyrazol-4-yl | 2-phenylpropan-2-yl | 3.33[a] | 389 |
| 552 | Et | O | O | 3-(difluoromethyl)-1-methyl-1H-pyrazol-4-yl | 1-(2,4-dichlorophenyl)ethyl | 3.96[a] | 443 |
| 553 | Et | O | O | 3-(difluoromethyl)-1-methyl-1H-pyrazol-4-yl | 1-(2-chlorophenyl)ethyl | 3.46[a] | 409 |
| 554 | Et | O | O | 3-(difluoromethyl)-1-methyl-1H-pyrazol-4-yl | 1-(3-chlorophenyl)ethyl | 3.55[a] | 409 |
| 555 | Et | O | O | 3-(difluoromethyl)-1-methyl-1H-pyrazol-4-yl | (4-chlorophenyl)methyl | 3.31[a] | 395 |
| 556 | Et | O | O | 3-(difluoromethyl)-1-methyl-1H-pyrazol-4-yl | 1-[4-(dimethylamino)phenyl]-2,2,2-trifluoroethyl | 3.78[a] | 472 |
| 557 | Et | O | O | 3-(difluoromethyl)-1-methyl-1H-pyrazol-4-yl | 1-(2-methoxyphenyl)propyl | 3.62[a] | 419 |
| 558 | Et | O | O | 3-(difluoromethyl)-1-methyl-1H-pyrazol-4-yl | 1-(3-chlorophenyl)propyl | 3.87[a] | 423 |
| 559 | Et | O | O | 3-(difluoromethyl)-1-methyl-1H-pyrazol-4-yl | 1-(2,6-difluorophenyl)cyclopropyl | 3.17[a] | 423 |
| 560 | Et | O | O | 2-chloropyridin-3-yl | 1-(phenoxymethyl)cyclopropyl | 3.6[a] | 398 |
| 561 | Et | O | O | 3-(difluoromethyl)-1-methyl-1H-pyrazol-4-yl | 1-(phenoxymethyl)cyclopropyl | 3.37[a] | 417 |
| 562 | Et | O | O | 2-chloropyridin-3-yl | 1-(methylsulfanyl)propan-2-yl | 2.77[c] I2; 2.71[c] I1; 2.73[b] I2; 2.73[b] I1 | |
| 563 | Me | O | O | 2-chloropyridin-3-yl | (2R)-1-amino-1-oxopropan-2-yl | 1.47[c] T2; 1.26[c] T1; 1.18[b] | |
| 564 | Me | O | O | 2-chloropyridin-3-yl | 1-methoxypropan-2-yl | 2.16[c] I2; 2.1[c] I1; 2.13[b] | |
| 565 | Me | O | O | 2-chloropyridin-3-yl | 2-methyl-1-(methylsulfanyl)propan-2-yl | | |
| 566 | Me | O | O | 2-chloropyridin-3-yl | [(4-methylphenyl)sulfanyl]propan-2-yl | 3.54[c]; 3.53[b] | |
| 567 | Me | O | O | 2-chloropyridin-3-yl | [(2S)-1-(methylamino)-1-oxopropan-2-yl | 1.5[c] T2; 1.37[c] T1; 1.43[b] T1; 1.43[b] T2 | |
| 568 | Me | O | O | 2-chloropyridin-3-yl | (2S)-1-amino-1-oxopropan-2-yl | 1.39[c] T2; 1.2[c] T1; 1.32[b] T2; 1.32[b] T1 | |
| 569 | Me | O | O | 2-chloropyridin-3-yl | 2-amino-2-oxoethyl | 1.14[c]; 0.94[b] | |
| 570 | Me | O | O | 2-chloropyridin-3-yl | (2S)-1-amino-3-hydroxy-1-oxopropan-2-yl | 0.97[c]; 0.79[b] | |
| 571 | Et | O | O | 2-chloropyridin-3-yl | (2S)-3-methyl-1-(methoxy)-1-oxobutan-2-yl | | |
| 572 | Me | O | O | 2-chloropyridin-3-yl | (2S)-1-amino-3-methyl-1-oxobutan-2-yl | 1.9[c] T2; 1.65[c] T1; 1.58[b] | |
| 573 | Me | O | O | 2-chloropyridin-3-yl | 1-(dimethylamino)propan-2-yl | | |
| 574 | Me | O | O | 2-chloropyridin-3-yl | 4-methyl-1-(methoxy)-1-oxopentan-3-yl | | |
| 575 | Me | O | O | 2-chloropyridin-3-yl | (2S)-1-(methylsulfanyl)propan-2-yl | 2.48[c] I1; 2.54[c] I2; 2.38[b] | |
| 576 | Me | O | O | 2-chloropyridin-3-yl | 1-(methylsulfanyl)propan-2-yl | 2.54[c] I2; 2.48[c] I1; 2.38[b] | |
| 577 | Me | O | O | 2-chloropyridin-3-yl | (2S)-1-(ethylsulfanyl)propan-2-yl | 2.83[c] I1; 2.87[c] I2; 2.72[b] | |
| 578 | Et | O | O | 3-(difluoromethyl)-1-methyl-1H-pyrazol-4-yl | 1-(dimethylamino)propan-2-yl | 1.13[a] | 356 |
| 579 | Et | O | O | 3-(difluoromethyl)-1-methyl-1H-pyrazol-4-yl | 2-aminopropyl | 0.84[a] | 328 |
| 580 | Me | O | O | 2-chloropyridin-3-yl | (2S)-3-methyl-1-(methoxy)-1-oxobutan-2-yl | 2.8[c] T2; 2.61[c] T1; 2.56[b] | |
| 581 | CH$_2$CF$_3$ | O | O | 2-chloropyridin-3-yl | (2S)-3-methyl-1-(methoxy)-1-oxobutan-2-yl | 3.43[c] T2; 3.24[c] T1; 3.14[b] | |
| 582 | Et | O | O | 2-chloropyridin-3-yl | (2S)-1-(methoxy)-1-oxobutan-2-yl | 2.5[c] T2; 2.37[c] T1; 2.27[b] | |
| 583 | Et | O | O | 3-chloro-5-(trifluoromethyl)-pyridin-2-yl | 1-(dimethylamino)propan-2-yl | 1.63[a] | 405 |
| 584 | Et | O | O | 5-fluoro-1,3-dimethyl-1H-pyrazol-4-yl | 1-(dimethylamino)propan-2-yl | 0.96[a] | 338 |
| 585 | CH$_2$CF$_3$ | O | O | 2-chloropyridin-3-yl | (2S)-1-(methylsulfanyl)propan-2-yl | 3.14[c] I1; 3.19[c] I2; 2.98[b] | |

TABLE 1-continued

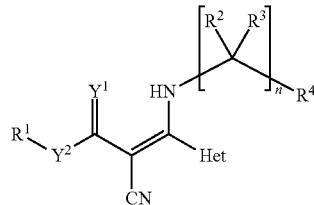

(I)

| No. | R¹ | Y² | Y¹ | Het | R | Log P | M⁺ |
|---|---|---|---|---|---|---|---|
| 586 | Et | O | O | 2-chloropyridin-3-yl | (2S)-1-(ethylsulfanyl)propan-2-yl | 3.19[c] I1; 3.25[c] I2; 3.06[b] | |
| 587 | Me | O | O | 3-(difluoromethyl)-1-methyl-1H-pyrazol-4-yl | 1-(dimethylamino)propan-2-y | 0.82[a] | 342 |
| 588 | Et | O | O | 4,5-dichloro-1,2-thiazol-3-yl | 1-(dimethylamino)propan-2-yl | 1.41[a] | 377 |
| 589 | Et | O | O | 3-chloro-5-(trifluoro-methyl)pyridin-2-yl | 1-aminopropan-2-yl | 1.59[a] | 377 |
| 590 | Et | O | O | 3-(difluoromethyl)-1-methyl-1H-pyrazol-4-yl | 1-amino-1-oxopropan-2-yl | 1.5[a] | 342 |
| 591 | Me | O | O | 3-(difluoromethyl)-1-methyl-1H-pyrazol-4-yl | 1-aminopropan-2-yl | 0.58[a] | 314 |
| 592 | Et | O | O | 3-chloro-5-(trifluoro-methyl)pyridin-2-yl | 1-amino-1-oxopropan-2-yl | 2.17[a] | 391 |
| 593 | Et | O | O | 2-chloropyridin-3-yl | (2S)-1-(methylsulfanyl)propan-2-yl | 2.81[c] I1; 2.88[c] I2; 2.84[c] I2; 2.71[b] | |
| 594 | Et | O | O | 3-methylisoxazol-4-yl | 1-(dimethylamino)propan-2-yl | 0.76[a] | 307 |
| 595 | Et | O | O | 2,6-dichloropyridin-3-yl | (2S)-1-(methylsulfanyl)propan-2-yl | 3.52[c]; 3.59[c]; 3.43[c] I1; 3.47[c] I2; 3.45[b]; 3.34[b] | |
| 596 | Et | O | O | 3-methylisoxazol-4-yl | (2S)-1-amino-1-oxopropan-2-yl | 1.41[a] | 293 |
| 597 | iPr | O | O | 2-chloropyridin-3-yl | (2S)-1-(methylsulfanyl)propan-2-yl | 3.21[c] I2; 3.16[c] I1; 3.03[b] | |
| 598 | Me | O | O | 3-(difluoromethyl)-1-methyl-1H-pyrazol-4-yl | 1-amino-1-oxopropan-2-yl | 1.3[a] | 328 |
| 599 | Et | O | O | 3-(difluoromethyl)-1-methyl-1H-pyrazol-4-yl | 1-(methylamino)-1-oxopropan-2-yl | 1.66[a] | 356 |
| 600 | Et | O | O | 3-chloro-5-(trifluoro-methyl)pyridin-2-yl | 1-(methylamino)-1-oxopropan-2-yl | 2.41[a] | 405 |
| 601 | Me | O | O | 3-(difluoromethyl)-1-methyl-1H-pyrazol-4-yl | 1-(methylamino)-1-oxopropan-2-yl | 1.38[a] | 342 |
| 602 | Et | O | O | 1-methyl-3-(trifluoromethyl)-1H-pyrazol-4-yl | 1-(dimethylamino)propan-2-yl | 1.36[a] | 374 |
| 603 | Et | O | O | 5-chloro-1,3-dimethyl-1H-pyrazol-4-yl | 2-aminopropyl | 0.96[a] | 326 |
| 604 | Et | O | O | 3-bromothiophen-2-yl | 1-(dimethylamino)propan-2-yl | 1.24[a] | 286 |
| 605 | Et | O | O | 5-chloro-1,3-dimethyl-1H-pyrazol-4-yl | 1-(dimethylamino)propan-2-yl | 1.13[a] | |
| 606 | Et | O | O | 5-chloro-1,3-dimethyl-1H-pyrazol-4-yl | 1-(methylamino)-1-oxopropan-2-yl | 1.7[a] | 354 |
| 607 | Et | O | O | 5-chloro-1,3-dimethyl-1H-pyrazol-4-yl | 1-amino-1-oxopropan-2-yl | 1.58[a] | |
| 608 | Et | O | O | 3-(trifluoromethyl)thiophen-2-yl | 1-(dimethylamino)propan-2-yl | 1.63[a] | 376 |
| 609 | Et | O | O | 3-(trifluoromethyl)thiophen-2-yl | 2-aminopropyl | 1.42[a] | 348 |
| 610 | Et | O | O | 3-(trifluoromethyl)thiophen-2-yl | 1-amino-1-oxopropan-2-yl | 2.07[a] | 362 |
| 611 | Et | O | O | 3-bromothiophen-2-yl | (2S)-1-amino-1-oxopropan-2-yl | 1.9[a] | 372 |
| 612 | Et | O | O | 3-bromothiophen-2-yl | (2S)-1-(methylamino)-1-oxopropan-2-yl | 2.07[a] | 386 |
| 613 | Et | O | O | 2-bromothiophen-3-yl | 1-(dimethylamino)propan-2-yl | 1.44[a] | 386 |
| 614 | allyl | O | O | 2-chloropyridin-3-yl | (2S)-1-(methylsulfanyl)propan-2-yl | | |
| 615 | Et | O | O | 2-chloropyridin-3-yl | 4-(ethoxy)-4-oxobutan-2-yl | | |
| 616 | Me | NH | O | 2-chloropyridin-3-yl | 4-(methylamino)-4-oxobutan-2-yl | 1.17[c] T1; 1.34[c] T2; 0.98[b] T1; 1.13[b] T2 | |
| 617 | Et | O | O | 2,5-dimethylfuran-3-yl | 1-ethoxypropan-2-yl | 3.42[a] | |
| 618 | Et | O | O | 2,5-dimethylfuran-3-yl | 1-[(butan-2-yloxy)carbonyl]-cyclopropyl | 3.94[a] | |
| 619 | Et | O | O | 2,5-dimethylfuran-3-yl | 2-methyl-1-(methylsulfanyl)propan-2-yl | 3.58[a] | |
| 620 | Me | O | O | 2-chloropyridin-3-yl | 1-(methoxycarbonyl)propan-2-yl | 2.11[a] | |
| 621 | Me | O | O | 2-chloropyridin-3-yl | 1-[(butan-2-yloxy)carbonyl]-cyclopropyl | 2.23[a] | |
| 622 | Me | O | O | 2-chloropyridin-3-yl | 1-(diethylamino)propan-2-yl | 0.86[a] | |
| 623 | Me | O | O | 2-chloropyridin-3-yl | 1-(ethoxycarbonyl)cyclopropyl | 1.66[a] | |
| 624 | Me | O | O | 2-chloropyridin-3-yl | 1-ethoxypropan-2-yl | 2.42[a] | |
| 625 | Me | O | O | 2-chloropyridin-3-yl | 1-ethoxybutan-2-yl | 2.76[a] | |

TABLE 1-continued

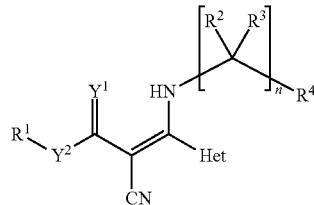
(I)

| No. | R¹ | Y² | Y¹ | Het | R | Log P | M⁺ |
|---|---|---|---|---|---|---|---|
| 626 | Me | O | O | 2-chloropyridin-3-yl | 1-ethoxypentan-2-yl | 3.15[a] | |
| 627 | Me | O | O | 2-chloropyridin-3-yl | 1-ethoxy-3-methylbutan-2-yl | 3.11[a] | |
| 628 | Et | O | O | 2-bromothiophen-3-yl | (2S)-1-amino-1-oxopropan-2-yl | 1.9[a] | 372 |
| 629 | Et | O | O | 3-methylisoxazol-4-yl | (2S)-1-(methylamino)-1-oxopropan-2-yl | 1.57[a] | 307 |
| 630 | Me | O | O | 2-methyl-4-trifluoromethyl-1,3-thiazol-5-yl | 1-(dimethylamino)propan-2-yl | 1.17[a] | 377 |
| 631 | Me | O | O | 2-methyl-4-trifluoromethyl-1,3-thiazol-5-yl | 2-aminopropyl | 0.94[a] | 349 |
| 632 | Et | O | O | 1-methyl-3-(trifluoromethyl)-1H-pyrazol-4-yl | 1-aminopropan-2-yl | 1.11[a] | 346 |
| 633 | Et | O | O | 2-chloro-6-methylpyridin-3-yl | (2S)-1-(methylsulfanyl)propan-2-yl | 3.14[c] I2; 3.09[c] I1; 3.09[b] | |
| 634 | Me | O | O | 2-methyl-4-trifluoromethyl-1,3-thiazol-5-yl | 1-amino-1-oxopropan-2-yl | 1.69[a] | 363 |
| 635 | Et | O | O | 1-methyl-3-(trifluoromethyl)-1H-pyrazol-4-yl | 1-amino-1-oxopropan-2-yl | 1.78[a] | 360 |
| 636 | Et | O | O | 1-methyl-3-(trifluoromethyl)-1H-pyrazol-4-yl | (2S)-1-(methylamino)-1-oxopropan-2-yl | 1.95[a] | 374 |
| 637 | Et | O | O | 2-bromothiophen-3-yl | (2S)-1-(methylamino)-1-oxopropan-2-yl | 2.05[a] | 386 |
| 638 | Me | O | O | 2-methyl-4-trifluoromethyl-1,3-thiazol-5-yl | 1-(methylamino)-1-oxopropan-2-yl | 1.93[a] | 377 |
| 639 | Et | O | O | 3-(trifluoromethyl)thiophen-2-yl | 1-(methylamino)-1-oxopropan-2-yl | 2.25[a] | 376 |
| 640 | Et | O | O | 2-methyl-4-trifluoromethyl-1,3-thiazol-5-yl | 1-(dimethylamino)propan-2-yl | 1.35[a] | 391 |
| 641 | Et | O | O | 2-methyl-4-trifluoromethyl-1,3-thiazol-5-yl | 1-amino-1-oxopropan-2-yl | 1.96[a] | 377 |
| 642 | Et | O | O | 2-methyl-4-trifluoromethyl-1,3-thiazol-5-yl | 1-(methylamino)-1-oxopropan-2-yl | 2.07[a] | 391 |
| 643 | Et | O | O | 2-methyl-4-trifluoromethyl-1,3-thiazol-5-yl | 2-aminopropyl | 1.11[a] | 363 |
| 644 | Et | O | O | 3-chlorothiophen-2-yl | (2S)-1-amino-1-oxopropan-2-yl | 1.9[a] | 328 |
| 645 | Et | O | O | 3-chlorothiophen-2-yl | (2S)-1-(methylamino)-1-oxopropan-2-yl | 2.08[a] | 342 |
| 646 | Et | O | O | 2-iodothiophen-3-yl | 1-(methylamino)-1-oxopropan-2-yl | 2.07[a] | 434 |
| 647 | Et | O | O | 2-iodothiophen-3-yl | 1-amino-1-oxopropan-2-yl | 1.91[a] | |
| 648 | Et | O | O | 2-methylpyridin-3-yl | (2S)-1-(methylsulfanyl)propan-2-yl | 2.2[c]; 2.44[b] | |
| 649 | Et | O | O | 3-bromothiophen-2-yl | (2S)-1-methoxy-1-oxopropan-2-yl | 2.96[a] | 387 |
| 650 | Et | O | O | 3-bromothiophen-2-yl | 3-methyl-1-(methoxy)-1-oxobutan-2-yl | 3.67[a] | 415 |
| 651 | Et | O | O | 3-bromothiophen-2-yl | (2S)-3-methyl-1-(methoxy)-1-oxobutan-2-yl | 3.67[a] | 415 |
| 652 | Et | O | O | 3-bromothiophen-2-yl | 1-amino-1-oxopropan-2-yl | 1.94[a] | 372 |
| 653 | Et | O | O | 3-(trifluoromethyl)thiophen-2-yl | 1-(2-naphthylamino)-1-oxopropan-2-yl | 4.01[a] | 488 |
| 654 | Et | O | O | 3-(trifluoromethyl)thiophen-2-yl | 1-(2,6-dimethylphenoxy)propan-2-yl | 4.89[a] | 453 |
| 655 | Et | O | O | 3-(trifluoromethyl)thiophen-2-yl | 1-methoxypropan-2-yl | 3.31[a] | 363 |
| 656 | Et | O | O | 3-(trifluoromethyl)thiophen-2-yl | 1-ethoxy-1-oxopropan-2-yl | 3.44[a] | 391 |
| 657 | Et | O | O | 3-(trifluoromethyl)thiophen-2-yl | (2S)-1-methoxy-1-oxopropan-2-yl | 3.11[a] | 377 |
| 658 | Et | O | O | 3-(trifluoromethyl)thiophen-2-yl | 3-methyl-1-methoxy-1-oxobutan-2-yl | 3.62[a] | 405 |
| 659 | Et | O | O | 3-(trifluoromethyl)thiophen-2-yl | (2S)-3-methyl-1-methoxy-1-oxobutan-2-yl | 3.62[a] | 405 |
| 660 | Et | O | O | 3-(trifluoromethyl)thiophen-2-yl | 1-amino-1-oxopropan-2-yl | 2.13[a] | 362 |
| 661 | Me | O | O | 2-methyl-4-trifluoromethyl-1,3-thiazol-5-yl | 1-(2-naphthylamino)-1-oxopropan-2-yl | 3.69[a] | 489 |

TABLE 1-continued

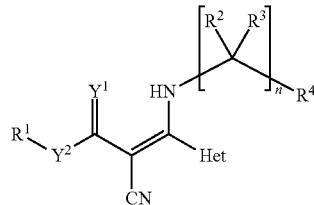

(I)

| No. | R¹ | Y² | Y¹ | Het | R | Log P | M⁺ |
|---|---|---|---|---|---|---|---|
| 662 | Me | O | O | 2-methyl-4-trifluoromethyl-1,3-thiazol-5-yl | 1-(2,6-dimethylphenoxy)propan-2-yl | 4.34[a] | 454 |
| 663 | Me | O | O | 2-methyl-4-trifluoromethyl-1,3-thiazol-5-yl | 1-methoxypropan-2-yl | 2.75[a] | 364 |
| 664 | Me | O | O | 2-methyl-4-trifluoromethyl-1,3-thiazol-5-yl | 1-ethoxy-1-oxopropan-2-yl | 2.96[a] | 392 |
| 665 | Me | O | O | 2-methyl-4-trifluoromethyl-1,3-thiazol-5-yl | (2S)-1-methoxy-1-oxopropan-2-yl | 2.62[a] | |
| 666 | Me | O | O | 2-methyl-4-trifluoromethyl-1,3-thiazol-5-yl | 3-methyl-1-methoxy-1-oxobutan-2-yl | 3.29[a] | 406 |
| 667 | Me | O | O | 2-methyl-4-trifluoromethyl-1,3-thiazol-5-yl | (2S)-3-methyl-1-methoxyl-1-oxobutan-2-yl | 3.29[a] | 406 |
| 668 | Me | O | O | 2-methyl-4-trifluoromethyl-1,3-thiazol-5-yl | 1-amino-1-oxopropan-2-yl | 1.78[a] | 363 |
| 669 | Et | O | O | 3-bromothiophen-2-yl | 1-(2-naphthylamino)-1-oxopropan-2-yl | 3.89[a] | 498 |
| 670 | Et | O | O | 3-bromothiophen-2-yl | 1-(2,6-dimethylphenoxy)propan-2-yl | 4.86[a] | 463 |
| 671 | Et | O | O | 3-bromothiophen-2-yl | 1-methoxypropan-2-yl | 3.17[a] | 373 |
| 672 | Et | O | O | 3-bromothiophen-2-yl | 1-ethoxy-1-oxopropan-2-y | 3.33[a] | 401 |
| 673 | Et | O | O | 3-(difluoromethyl)-1-methyl-1H-pyrazol-4-yl | (2S)-1-methoxy-1-oxopropan-2-yl | 2.31[a] | 357 |
| 674 | Et | O | O | 3-(difluoromethyl)-1-methyl-1H-pyrazol-4-yl | 3-methyl-1-methoxy-1-oxobutan-2-yl | 2.84[a] | 385 |
| 675 | Et | O | O | 3-(difluoromethyl)-1-methyl-1H-pyrazol-4-yl | (2S)-3-methyl-1-methoxyl-1-oxobutan-2-yl | 2.84[a] | 385 |
| 676 | Et | O | O | 2-methyl-4-trifluoromethyl-1,3-thiazol-5-yl | 1-(2-naphthylamino)-1-oxopropan-2-yl | 3.99[a] | 503 |
| 677 | Et | O | O | 2-methyl-4-trifluoromethyl-1,3-thiazol-5-yl | 1-(2,6-dimethylphenoxy)propan-2-yl | 4.7[a] | 468 |
| 678 | Et | O | O | 2-methyl-4-trifluoromethyl-1,3-thiazol-5-yl | 1-methoxypropan-2-yl | 3.11[a] | 378 |
| 679 | Et | O | O | 2-methyl-4-trifluoromethyl-1,3-thiazol-5-yl | 1-ethoxy-1-oxopropan-2-yl | 3.29[a] | 406 |
| 680 | Et | O | O | 2-methyl-4-trifluoromethyl-1,3-thiazol-5-yl | (2S)-1-methoxy-1-oxopropan-2-yl | 2.94[a] | 392 |
| 681 | Et | O | O | 2-methyl-4-trifluoromethyl-1,3-thiazol-5-yl | 3-methyl-1-methoxy-1-oxobutan-2-yl | 3.64[a] | 420 |
| 682 | Et | O | O | 2-methyl-4-trifluoromethyl-1,3-thiazol-5-yl | (2S)-3-methyl-1-methoxyl-1-oxobutan-2-yl | 3.64[a] | 420 |
| 683 | Et | O | O | 3-(difluoromethyl)-1-methyl-1H-pyrazol-4-yl | 1-(2-naphthylamino)-1-oxopropan-2-yl | 3.31[a] | 468 |
| 684 | Et | O | O | 3-(difluoromethyl)-1-methyl-1H-pyrazol-4-yl | 1-(2,6-dimethylphenoxy)propan-2-yl | 3.96[a] | 433 |
| 685 | Et | O | O | 3-(difluoromethyl)-1-methyl-1H-pyrazol-4-yl | 1-methoxypropan-2-yl | 2.41[a] | 343 |
| 686 | Et | O | O | 3-(difluoromethyl)-1-methyl-1H-pyrazol-4-yl | 1-ethoxy-1-oxopropan-2-yl | 2.62[a] | 371 |
| 687 | Et | O | O | 2-methoxypyridin-3-yl | (2S)-1-(methylsulfanyl)propan-2-yl | 2.96[c]; 2.95[b] | |
| 688 | Et | O | O | 3-(trifluoromethyl)thiophen-2-yl | 1-(benzyloxy)but-3-en-2-yl | 4.36[a] | 451 |
| 689 | Et | O | O | 3-bromothiophen-2-yl | 1-(benzyloxy)but-3-en-2-yl | 4.31[a] | 461 |
| 690 | Me | O | O | 2-methyl-4-trifluoromethyl-1,3-thiazol-5-yl | 1-(benzyloxy)but-3-en-2-yl | 3.89[a] | 452 |
| 691 | Et | O | O | 3-(difluoromethyl)-1-methyl-1H-pyrazol-4-yl | 1-(benzyloxy)but-3-en-2-yl | 3.51[a] | 431 |
| 692 | Et | O | O | 2-methyl-4-trifluoromethyl-1,3-thiazol-5-yl | 1-(benzyloxy)but-3-en-2-yl | 4.21[a] | 466 |
| 693 | Et | O | O | 3-bromothiophen-2-yl | 2-methyl-1-methoxy-1-oxopropan-2-yl | 3.23[a] | |
| 694 | Et | O | O | 3-(trifluoromethyl)thiophen-2-yl | 2-methyl-1-methoxy-1-oxopropan-2-yl | 3.37[a] | |
| 695 | Me | O | O | 2-methyl-4-trifluoromethyl-1,3-thiazol-5-yl | 2-methyl-1-methoxy-1-oxopropan-2-yl | 2.9[a] | |

TABLE 1-continued

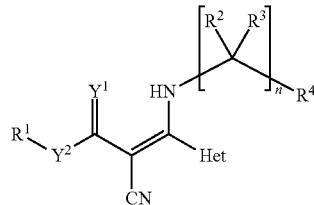

(I)

| No. | R¹ | Y² | Y¹ | Het | R | Log P | M⁺ |
|---|---|---|---|---|---|---|---|
| 696 | Et | O | O | 3-(difluoromethyl)-1-methyl-1H-pyrazol-4-yl | 2-methyl-1-methoxy-1-oxopropan-2-yl | 2.51[a] | |
| 697 | Et | O | O | 2-methyl-4-trifluoromethyl-1,3-thiazol-5-yl | 2-methyl-1-methoxy-1-oxopropan-2-yl | 3.23[a] | |
| 698 | Et | O | O | 3,6-dichloropyridin-2-yl | (2S)-1-amino-1-oxopropan-2-yl | 1.97[a] | 357 |
| 699 | Et | O | O | 3,5-dichloropyridin-2-yl | (2S)-1-amino-1-oxopropan-2-yl | 2.01[a] | 357 |
| 700 | Et | O | O | 3-(trifluoromethyl)thiophen-2-yl | 2-methyl-1-(methylsulfanyl)propan-2-yl | 3.8[a] | 393 |
| 701 | Et | O | O | 3-bromothiophen-2-yl | 2-methyl-1-(methylsulfanyl)propan-2-yl | 3.73[a] | 403 |
| 702 | Me | O | O | 2-methyl-4-trifluoromethyl-1,3-thiazol-5-yl | 2-methyl-1-(methylsulfanyl)propan-2-yl | 3.27[a] | 394 |
| 703 | Et | O | O | 3-(difluoromethyl)-1-methyl-1H-pyrazol-4-yl | 2-methyl-1-(methylsulfanyl)propan-2-yl | 2.84[a] | 373 |
| 704 | Et | O | O | 2-methyl-4-trifluoromethyl-1,3-thiazol-5-yl | 2-methyl-1-(methylsulfanyl)propan-2-yl | 3.62[a] | 408 |
| 705 | Et | O | O | 2-(trifluoromethyl)pyridin-3-yl | (2S)-1-amino-1-oxopropan-2-yl | 1.91[a] | 357 |
| 706 | Et | O | O | 2-(trifluoromethyl)pyridin-3-yl | 1-(methylamino)-1-oxopropan-2-yl | 2.05[a] | 371 |
| 707 | Et | O | O | 3-bromothiophen-2-yl | 1-aminopropan-2-yl | 1.1[a] | 358 |
| 708 | Et | O | O | 2-chloropyridin-3-yl | (2S)-1-amino-1-thioxopropan-2-yl | 1.96[c] T2; 1.79[c] T1; 1.87[b] | |
| 709 | Et | O | O | 5-bromo-2-(methylsulfanyl)-pyrimidin-4-yl | (2S)-1-amino-1-oxopropan-2-yl | 2.13[a] | 414 |
| 710 | Et | O | O | 2,4-dichloro-1,3-thiazol-5-yl | 3-methyl-1-methoxy-1-oxobutan-2-yl | 3.82[a] | 406 |
| 711 | Et | O | O | 3-methoxy-1-methyl-1H-pyrazol-4-yl | 3-methyl-1-methoxy-1-oxobutan-2-yl | 2.71[a] | 365 |
| 712 | Et | O | O | 2,5-dichlorothiophen-3-yl | 3-methyl-1-methoxy-1-oxobutan-2-yl | 4.14[a] | 405 |
| 713 | Et | O | O | 1-methyl-3-(trifluoromethyl)-1H-pyrazol-4-yl | 3-methyl-1-methoxy-1-oxobutan-2-yl | 3.09[a] | 403 |
| 714 | Et | O | O | 2-bromothiophen-3-yl | 1-methoxypropan-2-yl | 3.21[a] | 374 |
| 715 | Et | O | O | 2-bromothiophen-3-yl | 3-methyl-1-methoxy-1-oxobutan-2-yl | 3.48[a] | 416 |
| 716 | Et | O | O | 2-bromothiophen-3-yl | (2-S)-3-methyl-1-methoxy-1-oxobutan-2-yl | 3.71[a] | 416 |
| 717 | Et | O | O | 2-bromothiophen-3-yl | 1-(2-naphthylamino)-1-oxopropan-2-yl | 3.94[a] | 499 |
| 718 | Et | O | O | 2-bromothiophen-3-yl | 1-(2,6-dimethylphenoxy)propan-2-yl | 4.86[a] | 464 |
| 719 | Et | O | O | 3-ethenyl-1-methyl-1H-pyrazol-4-yl | 3-methyl-1-methoxy-1-oxobutan-2-yl | 2.94[a] | 361 |
| 720 | Et | O | O | 2,5-dichloropyridin-4-yl | 1-(methylamino)-1-oxopropan-2-yl | 2.19[a] | 371 |
| 721 | Et | O | O | 2,5-dichloropyridin-4-yl | 1-amino-1-oxopropan-2-yl | 2.64[a] | 357 |
| 722 | Et | O | O | 3-chloropyridin-4-yl | 1-amino-1-oxopropan-2-yl | 1.65[a] | 323 |
| 723 | Et | O | O | 3-chloropyridin-4-yl | 1-(methylamino)-1-oxopropan-2-yl | 1.78[a] | 337 |
| 724 | Et | O | O | 2-(difluoromethyl)pyridin-3-yl | (2S)-1-(methylamino)-1-oxopropan-2-yl | 1.62[a] | 353 |
| 725 | Et | O | O | 2-(difluoromethyl)pyridin-3-yl | (2R)-1-(methylamino)-1-oxopropan-2-yl | 1.45[a] | 339 |
| 726 | Et | O | O | 1-methyl-4-(trifluoromethyl)-1H-pyrrol-3-yl | 3-methyl-1-methoxy-1-oxobutan-2-yl | 3.43[a] | 402 |
| 727 | Et | O | O | 4-(trifluoromethyl)pyridin-3-yl | 1-amino-1-oxopropan-2-yl | 1.8[a] | |
| 728 | Et | O | O | 2-chloropyridin-3-yl | 1-(ethylamino)-1-oxopropan-2-yl | 2.1[a] | 351 |
| 729 | Et | O | O | 2,3-dichloropyridin-4-yl | (2S)-1-amino-1-oxopropan-2-yl | 1.88[a] | 358 |
| 730 | Et | O | O | 2,3-dichloropyridin-4-yl | (2S)-1-(methylamino)-1-oxopropan-2-yl | 2.08[a] | 372 |
| 731 | Et | O | O | 2-chloropyridin-3-yl | 1-{[4-(trifluoromethyl)-benzyl]oxy}propan-2-yl | 4.2[a] | 468 |
| 732 | Et | O | O | 2-chloropyridin-3-yl | 1-amino-3-methyl-1-oxobutan-2-yl | 2.07[a] | 351 |
| 733 | Et | O | O | 3-fluoropyridin-4-yl | (2S)-1-amino-1-oxopropan-2-yl | 1.37[a] | 307 |
| 734 | Et | O | O | 3-bromothiophen-2-yl | 1-methoxy-propan-2-yl | 3.21[a] | 373 |

TABLE 1-continued

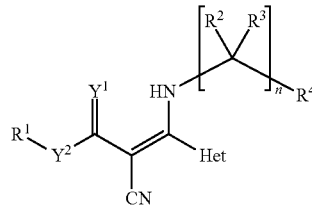

| No. | R¹ | Y² | Y¹ | Het | R | Log P | M⁺ |
|---|---|---|---|---|---|---|---|
| 735 | Et | O | O | 3-(difluoromethyl)-1-methyl-1H-pyrazol-4-yl | 1-(4-methylphenoxy)propan-2-yl | 3.71[a] | 419 |
| 736 | Et | O | O | 3-(difluoromethyl)-1-methyl-1H-pyrazol-4-yl | 1-(4-fluorophenoxy)propan-2-yl | 3.42[a] | 423 |
| 737 | Et | O | O | 3-(difluoromethyl)-1-methyl-1H-pyrazol-4-yl | 3-(phenylsulfanyl)butan-2-yl | 3.87[a] | 435 |
| 738 | Et | O | O | 3-(difluoromethyl)-1-methyl-1H-pyrazol-4-yl | 1-phenoxypropan-2-yl | 3.37[a] | 405 |
| 739 | Et | O | O | 3-(difluoromethyl)-1-methyl-1H-pyrazol-4-yl | 1-(benzyloxy)propan-2-yl | 3.48[a] | 419 |
| 740 | Et | O | O | 3-(difluoromethyl)-1-methyl-1H-pyrazol-4-yl | 1-[(2-fluorobenzyl)oxy]propan-2-yl | 3.48[a] | 437 |
| 741 | Et | O | O | 3-(difluoromethyl)-1-methyl-1H-pyrazol-4-yl | 1-(2-chlorophenoxy)propan-2-yl | 3.6[a] | 439 |
| 742 | Et | O | O | 3-(difluoromethyl)-1-methyl-1H-pyrazol-4-yl | 1-(3-methoxyphenoxy)propan-2-yl | 3.35[a] | 435 |
| 743 | Et | O | O | 2-chloropyridin-3-yl | (2S)-1-chloropropan-2-yl | 2.72[c] I1; 2.75[c] I2; 2.7[b] | |
| 744 | Me | O | O | 2-chloropyridin-3-yl | 1-fluoro-2-methylpropan-2-yl | 2.31[a] | |
| 745 | Et | O | O | 2,5-dimethylfuran-3-yl | 1-fluoropropan-2-yl | 2.8[a] | |
| 746 | Me | O | O | 2-chloropyridin-3-yl | 1-fluoropropan-2-yl | 2.05[a] | |
| 747 | Et | O | O | 2,5-dichlorothiophen-3-yl | 1-fluoropropan-2-yl | 3.49[a] | 351 |
| 748 | Et | O | O | 3-methoxy-1-methyl-1H-pyrazol-4-yl | 1-fluoropropan-2-yl | 2.23[a] | 311 |
| 749 | Et | O | O | 3-ethenyl-1-methyl-1H-pyrazol-4-yl | 1-fluoropropan-2-yl | 2.25[a] | 307 |
| 750 | Et | O | O | 3-chloropyridin-4-yl | 1-fluoropropan-2-yl | 2.42[a] | 312 |
| 751 | Et | O | O | 1-methyl-3-(trifluoromethyl)-1H-pyrazol-4-yl | 1-fluoropropan-2-yl | 2.72[a] | 349 |
| 752 | Et | O | O | 1-methyl-4-(trifluoromethyl)-1H-pyrrol-3-yl | 1-fluoropropan-2-yl | 2.95[a] | 348 |
| 753 | Et | O | O | 3-(difluoromethyl)-1-methyl-1H-pyrazol-4-yl | 2,3,3-trimethylbutan-2-yl | 3.46[a] | 369 |
| 754 | Me | O | O | 2-methyl-4-trifluoromethyl-1,3-thiazol-5-yl | 2,3,3-trimethylbutan-2-yl | 4.02[a] | |
| 755 | Et | O | O | 3-bromothiophen-2-yl | 2,3,3-trimethylbutan-2-yl | 4.67[a] | 399 |
| 756 | Me | O | O | 2-chloropyridin-3-yl | pentan-3-yl | 2.76[a] | |
| 757 | Me | O | O | 2-chloropyridin-3-yl | 4,4,4-trifluorobutan-2-yl | 2.34[a] | |
| 758 | Me | O | O | 2-chloropyridin-3-yl | 4,4,4-trifluoro-2-methylbutan-2-yl | 2.34[a] | |
| 759 | Me | O | O | 2-chloropyridin-3-yl | 2-fluorocyclopropyl | 1.87[a] | |
| 760 | Et | O | O | 2-chloropyridin-3-yl | 1-(cyclohex-3-en-1-yl)ethyl | 3.9[a] | |
| 761 | Et | O | O | 2-chloropyridin-3-yl | cyclohexyl | 3.55[a] | |
| 762 | Me | O | O | 2-chloropyridin-3-yl | 1-cyclohexylpropyl | 4.07[a] | |
| 763 | Me | O | O | 2-chloropyridin-3-yl | cyclopentyl | 2.61[a] | |
| 764 | Et | O | O | 2-chloropyridin-3-yl | cyclopropyl | 2.5[c]; 2.36[b] | |
| 765 | Me | O | O | 2-chloropyridin-3-yl | dicyclopropylmethyl | 2.85[a] | |
| 766 | Me | O | O | 2-chloropyridin-3-yl | 1-cyclopropylpropan-2-yl | 2.84[a] | |
| 767 | Et | O | O | 2-chloropyridin-3-yl | (2S)-1-bromopropan-2-yl | 2.83[c] I1; 2.87[c] I2; 2.79[b] | |
| 768 | Me | O | O | 2-chloropyridin-3-yl | 1-(1-chlorocyclopropyl)ethyl | 2.72[a] | |
| 769 | Et | O | O | 3-(trifluoromethyl)thiophen-2-yl | 1-(1-chlorocyclopropyl)ethyl | 4.04[a] | 393 |
| 770 | Me | O | O | 2-methyl-4-trifluoromethyl-1,3-thiazol-5-yl | 1-(1-chlorocyclopropyl)ethyl | 3.53[a] | 394 |
| 771 | Et | O | O | 3-bromothiophen-2-yl | 1-(1-chlorocyclopropyl)ethyl | 3.94[a] | 403 |
| 772 | Et | O | O | 2-methyl-4-trifluoromethyl-1,3-thiazol-5-yl | 1-(1-chlorocyclopropyl)ethyl | 3.89[a] | 408 |
| 773 | Et | O | O | 3-(difluoromethyl)-1-methyl-1H-pyrazol-4-yl | 1-(1-chlorocyclopropyl)ethyl | | 373 |
| 774 | Et | O | O | 2-bromothiophen-3-yl | 1-(1-chlorocyclopropyl)ethyl | 3.92[a] | 404 |
| 775 | Me | O | O | 2-chloropyridin-3-yl | tBu | 2.31[a] | |
| 776 | Et | O | O | 5-bromo-2-(methylsulfanyl)pyrimidin-4-yl | tBu | 3.82[a] | 401 |
| 777 | Et | O | O | 5-bromo-2-(methylsulfanyl)pyrimidin-4-yl | tBu | 3.06[a] | |
| 778 | Et | O | O | 2-chloropyridin-3-yl | 4-methylpentan-2-yl | 3.76[c] I2; 3.72[c] I1; 3.62[b] | |
| 779 | Et | O | O | 2,5-dimethylfuran-3-yl | 4-methylpentan-2-yl | 4.35[a] | |

TABLE 1-continued

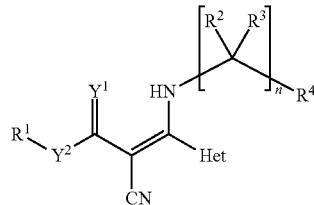

(I)

| No. | R¹ | Y² | Y¹ | Het | R | Log P | M⁺ |
|---|---|---|---|---|---|---|---|
| 780 | Et | O | O | 3-(difluoromethyl)-1-methyl-1H-pyrazol-4-yl | 4-methylpentan-2-yl | 3.46[a] | 355 |
| 781 | Et | O | O | 3-(trifluoromethyl)thiophen-2-yl | 4-methylpentan-2-yl | 4.54[a] | 375 |
| 782 | Me | O | O | 2-methyl-4-trifluoromethyl-1,3-thiazol-5-yl | 4-methylpentan-2-yl | 3.9[a] | 376 |
| 783 | Et | O | O | 3-bromothiophen-2-yl | 4-methylpentan-2-yl | 4.46[a] | 385 |
| 784 | Et | O | O | 2-methyl-4-trifluoromethyl-1,3-thiazol-5-yl | 4-methylpentan-2-yl | 4.29[a] | 390 |
| 785 | Et | O | O | 2-bromothiophen-3-yl | 4-methylpentan-2-yl | 4.41[a] | 386 |
| 786 | Et | O | O | 3-(trifluoromethyl)thiophen-2-yl | cyanomethyl | | |
| 787 | Me | O | O | 2-methyl-4-trifluoromethyl-1,3-thiazol-5-yl | cyanomethyl | 2.01[a] | 331 |
| 788 | Et | O | O | 3-(difluoromethyl)-1-methyl-1H-pyrazol-4-yl | cyanomethyl | 1.79[a] | 310 |
| 789 | Et | O | O | 3-bromothiophen-2-yl | cyanomethyl | 2.33[a] | 340 |
| 790 | Et | O | O | 2-methyl-4-trifluoromethyl-1,3-thiazol-5-yl | cyanomethyl | 2.35[a] | 345 |
| 791 | Et | O | O | 2-bromothiophen-3-yl | cyanomethyl | 2.32[a] | 341 |
| 792 | Et | O | O | 2-chloropyridin-3-yl | (2S)-1-cyanopropan-2-yl | 2.22[c]; 2.09[c] I1; 2.17[c] I2; 2.13[b] | |
| 793 | Me | O | O | 2-chloropyridin-3-yl | cyclobutyl | 2.34[a] | |
| 794 | Et | O | O | 3,6-dichloropyridin-2-yl | cBu | 3.58[a] | 340 |
| 795 | Et | O | O | 3,5-dichloropyridin-2-yl | cBu | 3.67[a] | 340 |
| 796 | Et | O | O | 4,6-dichloropyridin-3-yl | cBu | 3.55[a] | |
| 797 | Et | O | O | 2,5-dichloropyridin-4-yl | cBu | 3.55[a] | 340 |
| 798 | Et | O | O | 3-chloropyridin-4-yl | cBu | 2.84[a] | 306 |
| 799 | Et | O | O | 2-(difluoromethyl)pyridin-3-yl | cBu | 2.76[a] | 322 |
| 800 | Et | O | O | 4-(trifluoromethyl)pyridin-3-yl | cBu | 3.06[a] | 340 |
| 801 | Et | O | O | 4,6-dichloropyridin-2-yl | cBu | 3.79[a] | |
| 802 | Et | O | O | 2,3-dichloropyridin-4-yl | cBu | 3.52[a] | 341 |
| 803 | Et | O | O | 3-bromopyridin-4-yl | cBu | 2.9[a] | 350 |
| 804 | Et | O | O | 3-fluoropyridin-4-yl | cBu | 2.66[a] | 290 |
| 805 | Et | O | O | 3-(trifluoromethyl)pyridin-4-yl | cBu | 3.6[a] | 340 |
| 806 | Et | O | O | 2-chloropyridin-3-yl | F₃iPr | 3.1[c] I2; 2.99[c] I1; 2.9[b] | |
| 807 | Et | O | O | 2-methoxypyridin-3-yl | F₃iPr | 3.05[c]; 3.04[b] | |
| 808 | Et | O | O | 3-methoxy-1-methyl-1H-pyrazol-4-yl | F₃iPr | 2.82[a] | 347 |
| 809 | Et | O | O | 2,4-dichloro-1,3-thiazol-5-yl | F₃iPr | 3.75[a] | 388 |
| 810 | Et | O | O | 2,5-dichlorothiophen-3-yl | F₃iPr | 4.11[a] | 387 |
| 811 | Et | O | O | 1-methyl-3-(trifluoromethyl)-1H-pyrazol-4-yl | F₃iPr | 3.29[a] | 285 |
| 812 | Et | O | O | 1-methyl-4-(trifluoromethyl)-1H-pyrrol-3-yl | F₃iPr | 3.64[a] | 384 |
| 813 | Et | O | O | 5-fluoro-1,3-dimethyl-1H-pyrazol-4-yl | octan-2-yl | 4.51[a] | 365 |
| 814 | Et | O | O | 3-bromothiophen-2-yl | octan-2-yl | 5.48[a] | 413 |
| 815 | Et | O | O | 3-(trifluoromethyl)thiophen-2-yl | octan-2-yl | 5.48[a] | 403 |
| 816 | Me | O | O | 2-methyl-4-trifluoromethyl-1,3-thiazol-5-yl | octan-2-yl | 4.86[a] | 404 |
| 817 | Et | O | O | 3-(difluoromethyl)-1-methyl-1H-pyrazol-4-yl | octan-2-yl | 4.36[a] | 383 |
| 818 | Et | O | O | 2-methyl-4-trifluoromethyl-1,3-thiazol-5-yl | octan-2-yl | 5.22[a] | 418 |
| 819 | Et | O | O | 2-chloropyridin-3-yl | octan-2-yl | 4.53[c]; 4.55[b] | |
| 820 | Et | O | O | 2-bromothiophen-3-yl | octan-2-yl | 5.41[a] | 414 |
| 821 | Et | O | O | 2-chloropyridin-3-yl | (2S)-hexan-2-yl | 3.69[c] I1; 3.71[c] I2 | |
| 822 | Me | O | O | 2-chloropyridin-3-yl | iPr | 2.11[a] | |
| 823 | Et | O | O | 2-chloropyridin-3-yl | iPr | 2.66[a]; 2.54[c]; 2.53[b] | |
| 824 | Et | O | O | 2-chloropyridin-3-yl | sBu | | |
| 825 | Et | O | O | 2,5-dimethylfuran-3-yl | (2S)-butan-2-yl | 3.63[a] | |
| 826 | Me | O | O | 2-chloropyridin-3-yl | (2S)-butan-2-yl | 2.55[a] | |
| 827 | Et | O | O | 3-bromothiophen-2-yl | (2S)-butan-2-yl | 3.76[a] | 357 |
| 828 | Et | O | O | 3-bromothiophen-2-yl | (2R)-butan-2-yl | 3.76[a] | 357 |

TABLE 1-continued

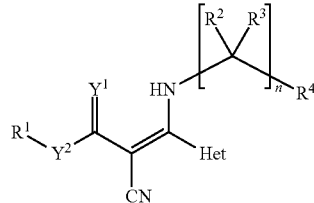

| No. | R¹ | Y² | Y¹ | Het | R | Log P | M⁺ |
|---|---|---|---|---|---|---|---|
| 829 | Et | O | O | 3-(trifluoromethyl)thiophen-2-yl | (2R)-butan-2-yl | 3.83[a] | 347 |
| 830 | Et | O | O | 3-(trifluoromethyl)thiophen-2-yl | (2S)-butan-2-yl | 3.83[a] | 347 |
| 831 | Me | O | O | 2-methyl-4-trifluoromethyl-1,3-thiazol-5-yl | (2S)-butan-2-yl | 3.23[a] | 348 |
| 832 | Me | O | O | 2-methyl-4-trifluoromethyl-1,3-thiazol-5-yl | (2R)-butan-2-yl | 3.23[a] | 348 |
| 833 | Et | O | O | 3-(difluoromethyl)-1-methyl-1H-pyrazol-4-yl | (2R)-butan-2-yl | 2.82[a] | 327 |
| 834 | Et | O | O | 3-(difluoromethyl)-1-methyl-1H-pyrazol-4-yl | (2S)-butan-2-yl | 2.82[a] | 327 |
| 835 | Et | O | O | 2-methyl-4-trifluoromethyl-1,3-thiazol-5-yl | (2S)-butan-2-yl | 3.59[a] | 362 |
| 836 | Et | O | O | 2-methyl-4-trifluoromethyl-1,3-thiazol-5-yl | (2R)-butan-2-yl | 3.59[a] | 362 |
| 837 | Et | O | O | 3,6-dichloropyridin-2-yl | sBu | 3.67[a] | 342 |
| 838 | Et | O | O | 4,6-dichloropyridin-3-yl | sBu | 3.64[a] | 342 |
| 839 | Et | O | O | 3,5-dichloropyridin-2-yl | sBu | 3.78[a] | 342 |
| 840 | Et | O | O | 2-(trifluoromethyl)pyridin-3-yl | sBu | 3.27[a] | 342 |
| 841 | Et | O | O | 5-bromo-2-(methylsulfanyl)pyrimidin-4-yl | sBu | 3.89[a] | 399 |
| 842 | Et | O | O | 2-(difluoromethyl)pyridin-3-yl | sBu | 2.87[a] | 324 |
| 843 | Et | O | O | 4-(trifluoromethyl)pyridin-3-yl | sBu | 3.17[a] | |
| 844 | Et | O | O | 3-bromothiophen-2-yl | (2R)-heptan-2-yl | 5.03[a] | 399 |
| 845 | Et | O | O | 3-bromothiophen-2-yl | (2S)-heptan-2-yl | 5.03[a] | 399 |
| 846 | Et | O | O | 3-bromothiophen-2-yl | heptan-2-yl | 5.03[a] | 399 |
| 847 | Et | O | O | 3-(trifluoromethyl)thiophen-2-yl | (2R)-heptan-2-yl | 5.05[a] | 389 |
| 848 | Et | O | O | 3-(trifluoromethyl)thiophen-2-yl | (2S)-heptan-2-yl | 5.05[a] | 389 |
| 849 | Et | O | O | 3-(trifluoromethyl)thiophen-2-yl | heptan-2-yl | 5.05[a] | 389 |
| 850 | Me | O | O | 2-methyl-4-trifluoromethyl-1,3-thiazol-5-yl | (2R)-heptan-2-yl | 4.41[a] | 390 |
| 851 | Me | O | O | 2-methyl-4-trifluoromethyl-1,3-thiazol-5-yl | (2S)-heptan-2-yl | 4.41[a] | 390 |
| 852 | Me | O | O | 2-methyl-4-trifluoromethyl-1,3-thiazol-5-yl | heptan-2-yl | 4.41[a] | 390 |
| 853 | Et | O | O | 3-(difluoromethyl)-1-methyl-1H-pyrazol-4-yl | (2S)-heptan-2-yl | 3.94[a] | 369 |
| 854 | Et | O | O | 3-(difluoromethyl)-1-methyl-1H-pyrazol-4-yl | (2R)-heptan-2-yl | 3.94[a] | 369 |
| 855 | Et | O | O | 3-(difluoromethyl)-1-methyl-1H-pyrazol-4-yl | heptan-2-yl | 3.94[a] | 369 |
| 856 | Et | O | O | 2-methyl-4-trifluoromethyl-1,3-thiazol-5-yl | (2S)-heptan-2-yl | 4.81[a] | 404 |
| 857 | Et | O | O | 2-methyl-4-trifluoromethyl-1,3-thiazol-5-yl | (2R)-heptan-2-yl | 4.81[a] | 404 |
| 858 | Et | O | O | 2-methyl-4-trifluoromethyl-1,3-thiazol-5-yl | heptan-2-yl | 4.81[a] | 404 |
| 859 | Et | O | O | 2-chloropyridin-3-yl | heptan-2-yl | 4.1[c] I1; 4.12[c] I2; 4.1[b] | |
| 860 | Et | O | O | 2-bromothiophen-3-yl | (2R)-heptan-2-yl | 4.94[a] | |
| 861 | Et | O | O | 2-bromothiophen-3-yl | (2S)-heptan-2-yl | 4.94[a] | 400 |
| 862 | Et | O | O | 2-bromothiophen-3-yl | heptan-2-yl | 4.99[a] | 400 |
| 863 | Et | O | O | 2-chloropyridin-3-yl | pentan-2-yl | | |
| 864 | Et | O | O | 3-(difluoromethyl)-1-methyl-1H-pyrazol-4-yl | pentan-2-yl | 3.19[a] | 341 |
| 865 | Et | O | O | 3-(trifluoromethyl)thiophen-2-yl | pentan-2-yl | 4.21[a] | 361 |
| 866 | Me | O | O | 2-methyl-4-trifluoromethyl-1,3-thiazol-5-yl | pentan-2-yl | 3.61[a] | 362 |
| 867 | Et | O | O | 3-bromothiophen-2-yl | pentan-2-yl | 4.16[a] | 371 |
| 868 | Et | O | O | 2-methyl-4-trifluoromethyl-1,3-thiazol-5-yl | pentan-2-yl | 3.96[a] | 376 |

TABLE 1-continued

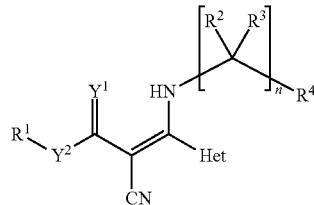

(I)

| No. | R¹ | Y² | Y¹ | Het | R | Log P | M⁺ |
|---|---|---|---|---|---|---|---|
| 869 | Me | O | O | 2-chloropyridin-3-yl | 1-cyanoethyl | 1.85[c]; 1.86[b] | |
| 870 | Me | O | O | 2-chloropyridin-3-yl | (1S)-1-cyclohexylethyl | 3.9[c] I2; 3.87[c] I1; 3.76[b] | |
| 871 | Me | O | O | 2-chloropyridin-3-yl | (1R)-1-cyclohexylethyl | 3.9[c] I2; 3.87[c] I1; 3.76[b] | |
| 872 | Et | O | O | 3-(difluoromethyl)-1-methyl-1H-pyrazol-4-yl | 1-cyclohexylethyl | 3.92[a] | 381 |
| 873 | Et | O | O | 3-(trifluoromethyl)thiophen-2-yl | 1-cyclohexylethyl | 5.11[a] | 401 |
| 874 | Me | O | O | 2-methyl-4-trifluoromethyl-1,3-thiazol-5-yl | 1-cyclohexylethyl | 4.46[a] | 402 |
| 875 | Et | O | O | 3-bromothiophen-2-yl | 1-cyclohexylethyl | 5.11[a] | 411 |
| 876 | Et | O | O | 2-methyl-4-trifluoromethyl-1,3-thiazol-5-yl | 1-cyclohexylethyl | 4.86[a] | 416 |
| 877 | Et | O | O | 2-bromothiophen-3-yl | 1-cyclohexylethyl | 5.03[a] | 412 |
| 878 | Et | O | O | 2-chloropyridin-3-yl | 1-cyclopropylethyl | 3.1[c] I2; 3.05[c] I1; 2.93[b] | |
| 879 | Et | O | O | 2,5-dimethylfuran-3-yl | 1-cyclopropylethyl | 3.63[a] | |
| 880 | Me | O | O | 2-chloropyridin-3-yl | 1-cyclopropylethyl | 2.58[a] | |
| 881 | Et | O | O | 2-chloro-6-methylpyridin-3-yl | 1-cyclopropylethyl | 3.32[c] I1; 3.37[c] I2; 3.32[b] | |
| 882 | Et | O | O | 3-(difluoromethyl)-1-methyl-1H-pyrazol-4-yl | 1-cyclopropylethyl | 2.88[a] | 339 |
| 883 | Et | O | O | 3-(trifluoromethyl)thiophen-2-yl | 1-cyclopropylethyl | 3.83[a] | 359 |
| 884 | Me | O | O | 2-methyl-4-trifluoromethyl-1,3-thiazol-5-yl | 1-cyclopropylethyl | 3.27[a] | 360 |
| 885 | Et | O | O | 3-bromothiophen-2-yl | 1-cyclopropylethyl | 3.76[a] | 369 |
| 886 | Et | O | O | 2-methyl-4-trifluoromethyl-1,3-thiazol-5-yl | 1-cyclopropylethyl | 3.61[a] | 374 |
| 887 | Et | O | O | 2,5-dichlorothiophen-3-yl | 1-cyclopropylethyl | 4.36[a] | 359 |
| 888 | Et | O | O | 3,6-dichloropyridin-2-yl | 1-cyclopropylethyl | 3.73[a] | 354 |
| 889 | Et | O | O | 3,5-dichloropyridin-2-yl | 1-cyclopropylethyl | 3.8[a] | 354 |
| 890 | Et | O | O | 4,6-dichloropyridin-3-yl | 1-cyclopropylethyl | 3.64[a] | 354 |
| 891 | Et | O | O | 3-methoxy-1-methyl-1H-pyrazol-4-yl | 1-cyclopropylethyl | 2.8[a] | 319 |
| 892 | Et | O | O | 2-(trifluoromethyl)pyridin-3-yl | 1-cyclopropylethyl | 3.35[a] | 354 |
| 893 | Et | O | O | 2,4-dichloro-1,3-thiazol-5-yl | 1-cyclopropylethyl | 3.87[a] | 360 |
| 894 | Et | O | O | 1-methyl-3-(trifluoromethyl)-1H-pyrazol-4-yl | 1-cyclopropylethyl | 3.29[a] | 357 |
| 895 | Et | O | O | 3-(1-fluoroethyl)-1-methyl-1H-pyrazol-4-yl | 1-cyclopropylethyl | 2.84[a] | 335 |
| 896 | Et | O | O | 2,5-dichloropyridin-4-yl | 1-cyclopropylethyl | 3.69[a] | 354 |
| 897 | Et | O | O | 4-(trifluoromethyl)pyridin-3-yl | 1-cyclopropylethyl | 3.2[a] | 354 |
| 898 | Et | O | O | 3-chloropyridin-4-yl | 1-cyclopropylethyl | 3.03[a] | 320 |
| 899 | Et | O | O | 2-(difluoromethyl)pyridin-3-yl | 1-cyclopropylethyl | 2.9[a] | 336 |
| 900 | Et | O | O | 4,6-dichloropyridin-2-yl | 1-cyclopropylethyl | 3.92[a] | |
| 901 | Et | O | O | 1-methyl-4-(trifluoromethyl)-1H-pyrrol-3-yl | 1-cyclopropylethyl | 3.56[a] | 356 |
| 902 | Et | O | O | 2,3-dichloropyridin-4-yl | 1-cyclopropylethyl | 3.61[a] | 355 |
| 903 | Et | O | O | 3-bromopyridin-4-yl | 1-cyclopropylethyl | 3[a] | 364 |
| 904 | Et | O | O | 3-fluoropyridin-4-yl | 1-cyclopropylethyl | 2.8[a] | 304 |
| 905 | Et | O | O | 3-(trifluoromethyl)pyridin-4-yl | 1-cyclopropylethyl | 3.2[a] | 354 |
| 906 | allyl | O | O | 2-chloropyridin-3-yl | 1-cyclopropylethyl | 3.06[c] I1; 3.11[c] I2; 3.08[b] | |
| 907 | Et | NH | O | 2-chloropyridin-3-yl | 1-cyclopropylethyl | 2.54[c] I1; 2.59[c] I2; 2.53[b] I1; 2.58[b] I2 | |
| 908 | Me | NH | O | 2-chloropyridin-3-yl | 1-cyclopropylethyl | 2.2[c]; 2.2[b] | |
| 909 | Et | O | O | 2-chloropyridin-3-yl | (1S)-1-cyclopropylethyl | 3.1[a] | |
| 910 | Et | O | O | 2-chloropyridin-3-yl | (1R)-1-cyclopropylethyl | 3.1[a] | |
| 911 | Me | NOMe | O | 2-chloropyridin-3-yl | 1-cyclopropylethyl | 2.4[c]; 2.41[b] | |
| 912 | H | N(NHCOMe) | O | 2-chloropyridin-3-yl | 1-cyclopropylethyl | 1.53[c]; 1.5[b] | |
| 913 | Et | O | O | 2-chloropyridin-3-yl | (1S)-1-cyclopropylethyl | 2.9[c] I1; 2.96[c] I2; 2.9[b] | |
| 914 | Et | O | O | 2,6-dichloropyridin-3-yl | (1S)-1-cyclopropylethyl | 3.59[c] I2; 3.54[c] I1; 3.54[b] | |
| 915 | allyl | O | O | 2-chloropyridin-3-yl | (1S)-1-cyclopropylethyl | 3.11[c] I2; 3.06[c] I1; 3.08[b] | |
| 916 | Me | O | O | 2-chloropyridin-3-yl | (2S)-3,3-dimethylbutan-2-yl | 3.28[c] I2; 3.24[c] I1; 3.14[b] | |
| 917 | Me | O | O | 2-chloropyridin-3-yl | (2S)-3,3-dimethylbutan-2-yl | 3.28[c] I2; 3.24[c] I1; 3.14[b] | |
| 918 | Et | O | O | 3-(difluoromethyl)-1-methyl-1H-pyrazol-4-yl | 3,3-dimethylbutan-2-yl | 3.37[a] | 355 |

TABLE 1-continued

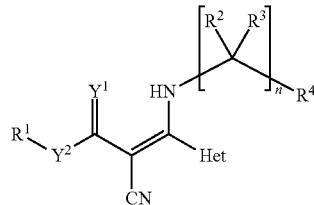

(I)

| No. | R¹ | Y² | Y¹ | Het | R | Log P | M⁺ |
|---|---|---|---|---|---|---|---|
| 919 | Et | O | O | 3-(trifluoromethyl)thiophen-2-yl | 3,3-dimethylbutan-2-yl | 4.46[a] | 375 |
| 920 | Me | O | O | 2-methyl-4-trifluoromethyl-1,3-thiazol-5-yl | 3,3-dimethylbutan-2-yl | 3.83[a] | 376 |
| 921 | Et | O | O | 3-bromothiophen-2-yl | 3,3-dimethylbutan-2-yl | 4.41[a] | 385 |
| 922 | Et | O | O | 2-methyl-4-trifluoromethyl-1,3-thiazol-5-yl | 3,3-dimethylbutan-2-yl | 4.21[a] | 390 |
| 923 | Et | O | O | 2-bromothiophen-3-yl | 3,3-dimethylbutan-2-yl | 4.36[a] | 386 |
| 924 | Et | O | O | 2-chloropyridin-3-yl | (2S)-3,3-dimethylbutan-2-yl | 3.6[a] | |
| 925 | Et | O | O | 3-(difluoromethyl)-1-methyl-1H-pyrazol-4-yl | 6-methylheptan-2-yl | 4.26[a] | 383 |
| 926 | Et | O | O | 3-(trifluoromethyl)thiophen-2-yl | 6-methylheptan-2-yl | 5.39[a] | 403 |
| 927 | Me | O | O | 2-methyl-4-trifluoromethyl-1,3-thiazol-5-yl | 6-methylheptan-2-yl | 4.78[a] | 404 |
| 928 | Et | O | O | 3-bromothiophen-2-yl | 6-methylheptan-2-yl | 5.36[a] | 413 |
| 929 | Et | O | O | 2-methyl-4-trifluoromethyl-1,3-thiazol-5-yl | 6-methylheptan-2-yl | 5.14[a] | 418 |
| 930 | Et | O | O | 2-bromothiophen-3-yl | 6-methylheptan-2-yl | 5.32[a] | 414 |
| 931 | Me | O | O | 2-chloropyridin-3-yl | 3-methylbutan-2-yl | 2.76[a]; 3[c]; 2.83[b] | |
| 932 | Me | O | O | 2-chloropyridin-3-yl | (2S)-3-methylbutan-2-yl | 2.99[c] I2; 2.96[c] I1; 2.85[b] | |
| 933 | Et | O | O | 3-(difluoromethyl)-1-methyl-1H-pyrazol-4-yl | 3-methylbutan-2-yl | 3.13[a] | 341 |
| 934 | Et | O | O | 2-chloropyridin-3-yl | 3-methylbutan-2-yl | 3.36[c] I2; 3.33[c] I1; 3.21[b] | |
| 935 | Et | O | O | 3-chloro-5-(trifluoromethyl)pyridin-2-yl | 3-methylbutan-2-yl | 4.29[a]] | 390 |
| 936 | Et | O | O | 5-fluoro-1,3-dimethyl-1H-pyrazol-4-yl | 3-methylbutan-2-yl | 3.19[a] | 323 |
| 937 | Et | O | O | 4,5-dichloro-1,2-thiazol-3-yl | 3-methylbutan-2-yl | 4.39[a] | 362 |
| 938 | Me | O | O | 3-(difluoromethyl)-1-methyl-1H-pyrazol-4-yl | 3-methylbutan-2-yl | 2.8[a] | 327 |
| 939 | Et | O | O | 1-methyl-3-(trifluoromethyl)-1H-pyrazol-4-yl | 3-methylbutan-2-yl | 3.64[a] | 359 |
| 940 | Et | O | O | 3-methylisoxazol-4-yl | 3-methylbutan-2-yl | 3.15[a] | 292 |
| 941 | Et | O | O | 3-bromothiophen-2-yl | 3-methylbutan-2-yl | 4.12[a] | 371 |
| 942 | Me | O | O | 2-bromopyridin-3-yl | (2S)-3-methylbutan-2-yl | 3.02[c]; 2.88[b] | |
| 943 | Et | O | O | 5-chloro-1,3-dimethyl-1H-pyrazol-4-yl | 3-methylbutan-2-yl | 3.67[a] | 339 |
| 944 | Et | O | O | 3-(trifluoromethyl)thiophen-2-yl | 3-methylbutan-2-yl | 4.21[a] | 361 |
| 945 | Et | O | O | 2-bromothiophen-3-yl | 3-methylbutan-2-yl | 4.1[a] | 371 |
| 946 | iPr | O | O | 2-chloropyridin-3-yl | (2S)-3-methylbutan-2-yl | 3.73[c] I2; 3.7[c] I1; 3.69[b] | |
| 947 | Et | O | O | 2,5-dimethylfuran-3-yl | 3-methylbutan-2-yl | 3.99[a] | |
| 948 | Me | O | O | 2-methyl-4-trifluoromethyl-1,3-thiazol-5-yl | 3-methylbutan-2-yl | 3.63[a] | 362 |
| 949 | Et | O | O | 2-methyl-4-trifluoromethyl-1,3-thiazol-5-yl | 3-methylbutan-2-yl | 3.95[a] | 376 |
| 950 | Et | O | O | 2-chloro-6-methylpyridin-3-yl | (2S)-3-methylbutan-2-yl | 3.64[c] I1; 3.67[c] I2; 3.63[b] | |
| 951 | Et | O | O | 3-chlorothiophen-2-yl | 3-methylbutan-2-yl | 4.08[a] | 327 |
| 952 | Et | O | O | 2-chloropyridin-3-yl | (2S)-3-methylbutan-2-yl | 3.37[a]; 3.34[c] I1; 3.36[c] I2; 3.33[b] | |
| 953 | Et | O | O | 2-methylpyridin-3-yl | (2S)-3-methylbutan-2-yl | 2.63[c]; 2.89[b] | |
| 954 | Et | O | O | 5-chloro-3-(difluoromethyl)-1-methyl-1H-pyrazol-4-yl | 3-methylbutan-2-yl | 3.63[a] | 375 |
| 955 | allyl | O | O | 2-chloropyridin-3-yl | (2S)-3-methylbutan-2-yl | 3.55[a]; 3.53[c] I2; 3.5[c] I1; 3.49[b] | |
| 956 | H | O | O | 2-chloropyridin-3-yl | (2S)-3-methylbutan-2-yl | 2.2[a] | |
| 957 | iPr | NH | O | 2-chloropyridin-3-yl | (2S)-3-methylbutan-2-yl | 3.37[c]; 3.39[b] | |
| 958 | Et | NH | O | 2-chloropyridin-3-yl | (2S)-3-methylbutan-2-yl | 2.94[a]; 2.95[c]; 2.82[c]; 2.95[b]; 2.82[b] | |
| 959 | Me | NMe | O | 2-chloropyridin-3-yl | (2S)-3-methylbutan-2-yl | | |
| 960 | OMe | NH | O | 2-chloropyridin-3-yl | (2S)-3-methylbutan-2-yl | 2.31[c]; 2.26[b] | |
| 961 | Et | O | O | 2-methoxypyridin-3-yl | (2S)-3-methylbutan-2-yl | 3.52[c]; 3.52[b] | |
| 962 | allyl | O | O | 3-bromothiophen-2-yl | 3-methylbutan-2-yl | 4.34[a] | 383 |
| 963 | Et | O | O | 2-hydroxypyridin-3-yl | (2S)-3-methylbutan-2-yl | | |
| 964 | H | O | O | 3-bromothiophen-2-yl | 3-methylbutan-2-yl | 2.74[a] | 343 |
| 965 | Et | O | O | 2,5-dichlorothiophen-3-yl | 3-methylbutan-2-yl | 4.72[a] | 361 |
| 966 | Et | O | O | 3,6-dichloropyridin-2-yl | 3-methylbutan-2-yl | 4.06[a] | 356 |
| 967 | Et | O | O | 3,5-dichloropyridin-2-yl | 3-methylbutan-2-yl | 4.19[a] | 356 |

TABLE 1-continued

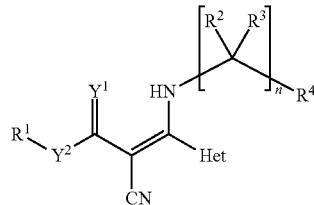

| No. | R¹ | Y² | Y¹ | Het | R | Log P | M⁺ |
|---|---|---|---|---|---|---|---|
| 968 | Et | O | O | 4,6-dichloropyridin-3-yl | 3-methylbutan-2-yl | 3.96[a] | 356 |
| 969 | Et | O | O | 3-methoxy-1-methyl-1H-pyrazol-4-yl | 3-methylbutan-2-yl | 3.06[a] | 321 |
| 970 | Et | O | O | 2-(trifluoromethyl)pyridin-3-yl | 3-methylbutan-2-yl | 3.62[a] | 356 |
| 971 | Et | O | O | 3-ethenyl-1-methyl-1H-pyrazol-4-yl | 3-methylbutan-2-yl | 3.06[a] | 317 |
| 972 | Et | O | O | 5-bromo-2-(methylsulfanyl)pyrimidin-4-yl | 3-methylbutan-2-yl | 4.26[a] | |
| 973 | Et | O | O | 2,4-dichloro-1,3-thiazol-5-yl | 3-methylbutan-2-yl | 4.23[a] | 362 |
| 974 | Et | O | O | 2-(4-chlorophenyl)pyridin-3-yl | (2S)-3-methylbutan-2-yl | 4.09[c]; 4.08[b] | |
| 975 | Et | O | O | 2-(3,5-dichlorophenyl)-pyridin-3-yl | (2S)-3-methylbutan-2-yl | 4.68[c]; 4.67[b] | |
| 976 | Et | O | O | 2-ethenylpyridin-3-yl | (2S)-3-methylbutan-2-yl | 3.24[c]; 3.26[b] | |
| 977 | Et | O | O | 2,5-dichloropyridin-4-yl | 3-methylbutan-2-yl | 3.96[a] | 356 |
| 978 | Et | O | O | 3-chloropyridin-4-yl | 3-methylbutan-2-yl | 3.29[a] | 322 |
| 979 | Et | O | O | 2-(1-ethoxyethenyl)pyridin-3-yl | (2S)-3-methylbutan-2-yl | | |
| 980 | Et | O | O | 2-acetylpyridin-3-yl | (2S)-3-methylbutan-2-yl | 3.11[c]; 3.08[b] | |
| 981 | Et | O | O | 2-(difluoromethyl)pyridin-3-yl | 3-methylbutan-2-yl | 3.15[a] | 338 |
| 982 | Et | O | O | 4-(trifluoromethyl)pyridin-3-yl | 3-methylbutan-2-yl | 3.5[a] | 356 |
| 983 | Et | O | O | 4,6-dichloropyridin-2-yl | 3-methylbutan-2-yl | 4.26[a] | |
| 984 | Et | O | O | 2-chloropyridin-3-yl | (2S)-3-methylbutan-2-yl | 3.33[a]; 3.22[c]; 3.22[b] | |
| 985 | Et | O | O | 2-(N-hydroxyethanimidoyl)pyridin-3-yl | (2S)-3-methylbutan-2-yl | 2.69[c]; 2.67[b] | |
| 986 | Et | O | O | 2,6-dichloropyridin-3-yl | (2S)-3-methylbutan-2-yl | 3.85[c]; 3.85[b] | |
| 987 | Et | O | O | 1-methyl-4-(trifluoromethyl)-1H-pyrrol-3-yl | 3-methylbutan-2-yl | 3.84[a] | 358 |
| 988 | nPr | NH | O | 2-chloropyridin-3-yl | (2S)-3-methylbutan-2-yl | 3.24[c]; 3.22[b] | |
| 989 | Me | NH | O | 2-chloropyridin-3-yl | (2S)-3-methylbutan-2-yl | 2.41[c]; 2.41[b] | |
| 990 | 1H-benzotriazol-1-yl | O | O | 2-chloropyridin-3-yl | (2S)-3-methylbutan-2-yl | 3.22[c]; 3.21[b] | |
| 991 | propargyl | NH | O | 2-chloropyridin-3-yl | (2S)-3-methylbutan-2-yl | 2.69[c]; 2.68[b] | |
| 992 | CH₂CF₃ | NH | O | 2-chloropyridin-3-yl | (2S)-3-methylbutan-2-yl | 3.17[c]; 3.16[b] | |
| 993 | H | NH | O | 2-chloropyridin-3-yl | (2S)-3-methylbutan-2-yl | 1.97[c]; 1.96[b] | |
| 994 | Et | O | O | 2,3-dichloropyridin-4-yl | (2S)-3-methylbutan-2-yl | 3.92[a] | 357 |
| 996 | Et | O | O | 3-bromopyridin-4-yl | (2S)-3-methylbutan-2-yl | 3.33[a] | 366 |
| 997 | Et | O | O | 3-fluoropyridin-4-yl | (2S)-3-methylbutan-2-yl | 3.08[a] | 306 |
| 998 | allyl | O | O | 3-(difluoromethyl)-1-methyl-1H-pyrazol-4-yl | (2S)-3-methylbutan-2-yl | 3.31[a] | 353 |
| 999 | Et | O | O | 5-fluoro-1-methyl-3-(trifluoromethyl)-1H-pyrazol-4-yl | (2S)-3-methylbutan-2-yl | 3.93[a] | 377 |
| 1000 | Et | O | O | 3-(difluoromethyl)-5-fluoro-1-methyl-1H-pyrazol-4-yl | 3-methylbutan-2-yl | 3.53[a] | 359 |
| 1001 | Et | O | O | 5-chloro-1-methyl-3-(trifluoromethyl)-1H-pyrazol-4-yl | 3-methylbutan-2-yl | 4.06[a] | 393 |
| 1002 | Et | O | O | 3-(1,1-difluoroethyl)-1-methyl-1H-pyrazol-4-yl | 3-methylbutan-2-yl | 3.39[a] | 355 |
| 1003 | Et | O | O | 3-(difluoromethyl)-1-methyl-1H-pyrazol-4-yl | (2S)-3-methylbutan-2-yl | 3.15[a] | 341 |
| 1004 | CH₂CF₃ | NH | O | 3-(difluoromethyl)-1-methyl-1H-pyrazol-4-yl | (2S)-3-methylbutan-2-yl | | 392* |
| 1005 | 2-MeOEt | NH | O | 3-(difluoromethyl)-1-methyl-1H-pyrazol-4-yl | (2S)-3-methylbutan-2-yl | 2.59[a] | 370 |
| 1006 | cPr | NH | O | 3-(difluoromethyl)-1-methyl-1H-pyrazol-4-yl | (2S)-3-methylbutan-2-yl | 2.66[a] | 352 |
| 1007 | allyl | NH | O | 3-(difluoromethyl)-1-methyl-1H-pyrazol-4-yl | (2S)-3-methylbutan-2-yl | 2.9[a] | 352 |
| 1008 | allyl | NH | O | 3-(difluoromethyl)-1-methyl-1H-pyrazol-4-yl | (2S)-3-methylbutan-2-yl | 2.68[a] | 350 |
| 1009 | Me | O | O | 2-chloropyridin-3-yl | 1-methylcyclohexyl | 3.13[a] | |
| 1010 | Me | O | O | 2-methyl-4-trifluoromethyl-1,3-thiazol-5-yl | 2-cyanopropan-2-yl | 3.04[a] | 358 |
| 1011 | Et | O | O | 3,6-dichloropyridin-2-yl | 2-cyanopropan-2-yl | 2.98[a] | 353 |
| 1012 | Et | O | O | 2-chloropyridin-3-yl | allyl | | |

TABLE 1-continued

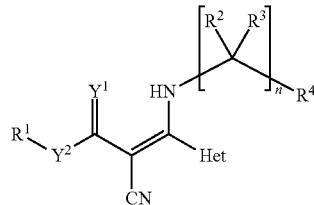

(I)

| No. | R[1] | Y[2] | Y[1] | Het | R | Log P | M+ |
|---|---|---|---|---|---|---|---|
| 1013 | Et | O | O | 5-chloro-1,3-dimethyl-1H-pyrazol-4-yl | octa-1,7-dien-3-yl | 4.04[a] | 377 |
| 1014 | Et | O | O | 3-(trifluoromethyl)thiophen-2-yl | octa-1,7-dien-3-yl | 4.7[a] | 399 |
| 1015 | Et | O | O | 3-chloro-5-(trifluoromethyl)-pyridin-2-yl | octa-1,7-dien-3-yl | 4.82[a] | 428 |
| 1016 | Et | O | O | 3-(difluoromethyl)-1-methyl-1H-pyrazol-4-yl | octa-1,7-dien-3-yl | 3.73[a] | 379 |
| 1017 | Et | O | O | 3-bromothiophen-2-yl | octa-1,7-dien-3-yl | 4.67[a] | 409 |
| 1018 | Et | O | O | 2-bromothiophen-3-yl | octa-1,7-dien-3-yl | 4.67[a] | 409 |
| 1019 | Me | O | O | 2-methyl-4-trifluoromethyl-1,3-thiazol-5-yl | octa-1,7-dien-3-yl | 4.19[a] | 400 |
| 1020 | Et | O | O | 3-methylisoxazol-4-yl | octa-1,7-dien-3-yl | 3.81[a] | 330 |
| 1021 | Et | O | O | 1-methyl-3-(trifluoromethyl)-1H-pyrazol-4-yl | octa-1,7-dien-3-yl | 4.14[a] | 397 |
| 1022 | Et | O | O | 2-methyl-4-trifluoromethyl-1,3-thiazol-5-yl | octa-1,7-dien-3-yl | 4.49[a] | 414 |
| 1023 | Et | O | O | 3-chlorothiophen-2-yl | octa-1,7-dien-3-yl | 4.65[a] | 365 |
| 1024 | Et | O | O | 2-iodothiophen-3-yl | octa-1,7-dien-3-yl | 4.65[a] | 457 |
| 1025 | Me | O | O | 2-chloropyridin-3-yl | 2-methylhex-3-yn-2-yl | 2.98[a] | |
| 1026 | Et | O | O | 3-(difluoromethyl)-1-methyl-1H-pyrazol-4-yl | 2-methylbut-3-yn-2-yl | 2.53[a] | 338 |
| 1027 | Et | O | O | 3-bromothiophen-2-yl | 2-methylbut-3-yn-2-yl | 3.42[a] | 367 |
| 1028 | Me | O | O | 2-chloropyridin-3-yl | 2-methylbut-3-yn-2-yl | 2.23[a] | |
| 1029 | Et | O | O | 2-bromothiophen-3-yl | 2-methylbut-3-yn-2-yl | 3.42[a] | 367 |
| 1030 | Et | O | O | 3-methylisoxazol-4-yl | 2-methylbut-3-yn-2-yl | 2.66[a] | 288 |
| 1031 | Et | O | O | 1-methyl-3-(trifluoromethyl)-1H-pyrazol-4-yl | 2-methylbut-3-yn-2-yl | 3.02[a] | 355 |
| 1032 | Et | O | O | 3-chlorothiophen-2-yl | 2-methylbut-3-yn-2-yl | 3.41[a] | 323 |
| 1033 | Et | O | O | 2,5-dichlorothiophen-3-yl | 2-methylbut-3-yn-2-yl | 3.99[a] | 357 |
| 1034 | Et | O | O | 3-methoxy-1-methyl-1H-pyrazol-4-yl | 2-methylbut-3-yn-2-yl | 2.44[a] | 317 |
| 1035 | Et | O | O | 3-ethenyl-1-methyl-1H-pyrazol-4-yl | 2-methylbut-3-yn-2-yl | 2.54[a] | 313 |
| 1036 | Et | O | O | 2,4-dichloro-1,3-thiazol-5-yl | 2-methylbut-3-yn-2-yl | 3.61[a] | 358 |
| 1037 | Et | O | O | 2,3-dichloropyridin-4-yl | 2-methylbut-3-yn-2-yl | | |
| 1038 | Et | O | O | 1-methyl-4-(trifluoromethyl)-1H-pyrrol-3-yl | 2-methylbut-3-yn-2-yl | 3.21[a] | |
| 1039 | Me | O | O | 2-chloropyridin-3-yl | 2-methylpent-3-yn-2-yl | 2.57[a] | |
| 1040 | Et | O | O | 3-(trifluoromethyl)thiophen-2-yl | 2-methylpent-3-yn-2-yl | 3.92[a] | 371 |
| 1041 | Et | O | O | 3-bromothiophen-2-yl | 2-methylpent-3-yn-2-yl | 3.85[a] | 381 |
| 1042 | Me | O | O | 2-methyl-4-trifluoromethyl-1,3-thiazol-5-yl | 2-methylpent-3-yn-2-yl | 3.35[a] | 372 |
| 1043 | Et | O | O | 3-(difluoromethyl)-1-methyl-1H-pyrazol-4-yl | 2-methylpent-3-yn-2-yl | 2.9[a] | 351 |
| 1044 | Et | O | O | 2-chloropyridin-3-yl | prop-2-yn-1-yl | 2.18[c]; 2.05[b] | |
| 1045 | Me | O | O | 2-chloropyridin-3-yl | but-3-yn-2-yl | 2.14[a] | |
| 1046 | Et | O | O | 3-(trifluoromethyl)thiophen-2-yl | but-3-yn-2-yl | 3.25[a] | 343 |
| 1047 | Et | O | O | 3-bromothiophen-2-yl | but-3-yn-2-yl | 3.17[a] | 353 |
| 1048 | Me | O | O | 2-methyl-4-trifluoromethyl-1,3-thiazol-5-yl | but-3-yn-2-yl | 2.73[a] | 344 |
| 1049 | Et | O | O | 3-(difluoromethyl)-1-methyl-1H-pyrazol-4-yl | but-3-yn-2-yl | 2.44[a] | 323 |
| 1050 | Et | O | O | 2-methyl-4-trifluoromethyl-1,3-thiazol-5-yl | but-3-yn-2-yl | 3.06[a] | 358 |
| 1051 | Me | O | O | 2-chloropyridin-3-yl | pent-3-yn-2-yl | 2.5[a] | |
| 1052 | Et | O | O | 2-chloropyridin-3-yl | pent-3-yn-2-yl | 2.86[a] | 318 |
| 1053 | Et | O | O | 2-chloropyridin-3-yl | 3-(methylsulfanyl)cyclohexyl | 3.57[c] I1; 3.68[c] I2; 3.54[b]; 3.43[b] I1 | |
| 1054 | Et | O | O | 2-chloropyridin-3-yl | 2-(trifluoromethyl)cyclopropyl | 2.9[a] | 360 |
| 1055 | Et | O | O | 2-chloropyridin-3-yl | 2,2-dimethylcyclopropyl | 3.25[a] | |
| 1056 | Me | O | O | 2-chloropyridin-3-yl | 2,4-dimethylcyclohexyl | 3.73[a] | |
| 1057 | Me | O | O | 2-chloropyridin-3-yl | 2,5-dimethylcyclohexyl | 3.73[a] | |
| 1058 | Me | O | O | 2-chloropyridin-3-yl | 2,6-dimethylcyclohexyl | 3.63[a] | |
| 1059 | Me | O | O | 2-chloropyridin-3-yl | 2-ethoxycyclopentyl | 2.93[a] | |

TABLE 1-continued

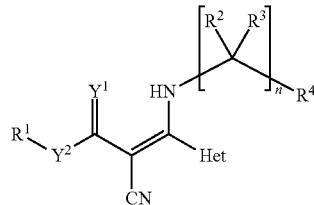

(I)

| No. | R¹ | Y² | Y¹ | Het | R | Log P | M⁺ |
|---|---|---|---|---|---|---|---|
| 1060 | Me | O | O | 2-chloropyridin-3-yl | 2-ethyl-6-methylcyclohexyl | 3.99[a] | |
| 1061 | Me | O | O | 2-chloropyridin-3-yl | 2-ethylcyclohexyl | 3.63[a] | |
| 1062 | Et | O | O | 2-chloropyridin-3-yl | 2-ethylcyclopropyl | 3.27[a] | 320 |
| 1063 | Me | O | O | 2-chloropyridin-3-yl | 2-ethynylcyclohexyl | 2.99[a] | |
| 1064 | Et | O | O | 2-chloropyridin-3-yl | 2-hydroxycyclohexyl | 2.03[c] T1; 2.33[c] T2; 2.27[b] | |
| 1065 | Et | O | O | 2-chloropyridin-3-yl | 2-methylcyclobutyl | 3.37[a] | |
| 1066 | Et | O | O | 2-chloropyridin-3-yl | 2-methylcyclohexyl | 3.84[c]; 3.7[b] | |
| 1067 | Et | O | O | 2-chloropyridin-3-yl | 2-methylcyclopropyl | 2.86[a] | 306 |
| 1068 | Et | O | O | 2-chloropyridin-3-yl | 2-phenylcyclopropyl | 3.44[a] | 368 |
| 1069 | Me | O | O | 2-chloropyridin-3-yl | 3-(trifluoromethyl)cyclohexyl | 3.09[a] | |
| 1070 | Me | O | O | 2-chloropyridin-3-yl | 3,4-dimethylcyclohexyl | 3.73[a] | |
| 1071 | Me | O | O | 2-chloropyridin-3-yl | 3,5-bis(trifluoromethyl)-cyclohexyl | 3.42[a] | |
| 1072 | Et | O | O | 2-bromothiophen-3-yl | 3-ethyl-3,5,5-trimethyl-cyclohexyl | | 454 |
| 1073 | Et | O | O | 2-chloropyridin-3-yl | 3-methylcyclobutyl | 3.3[a] | |
| 1074 | Me | O | O | 2-chloropyridin-3-yl | 3-methylcyclohexyl | 3.37[a] | |
| 1075 | Me | O | O | 2-chloropyridin-3-yl | 4-(trifluoromethyl)cyclohexyl | 3.04[a] | |
| 1076 | Me | O | O | 2-chloropyridin-3-yl | 4-methylcyclohexyl | 3.37[a] | |
| 1077 | Me | O | O | 2-chloropyridin-3-yl | 4-tert-butylcyclohexyl | 4.51[a] | |
| 1078 | Me | O | O | 2-chloropyridin-3-yl | 2,3-dihydro-1H-inden-1-yl | 3.06[a] | |
| 1079 | Et | O | O | 3-(difluoromethyl)-1-methyl-1H-pyrazol-4-yl | 2,3-dihydro-1H-indene-1-yl | 3.42[a] | 387 |
| 1080 | Et | O | O | 2-chloropyridin-3-yl | bicyclo[2.2.1]hept-2-yl | 3.59[c]; 3.57[b] | |
| 1081 | Et | O | O | 2-chloropyridin-3-yl | (1S,4R)-bicyclo[2.2.1]hept-2-yl | 3.7[a] | 346 |
| 1082 | Et | O | O | 2-chloropyridin-3-yl | (1R,4S)-bicyclo[2.2.1]hept-2-yl | 3.74[a] | |
| 1083 | Et | O | O | 2-chloropyridin-3-yl | bicyclo[4.1.0]hept-7-yl | 3.73[a] | 346 |
| 1084 | Me | O | O | 2-chloropyridin-3-yl | decahydronaphthalen-1-yl | 4.25[a] | |
| 1085 | Et | O | O | 2-chloropyridin-3-yl | (trimethylsilyl)methyl | 3.59[c]; 3.46[b] | |
| 1086 | Et | O | O | 3-bromothiophen-2-yl | 2-ethoxy-2-oxo-1-phenylethyl | | |
| 1087 | Et | O | O | 2-chloropyridin-3-yl | 2-(methylamino)-2-oxo-1-phenylethyl | 2.43[a] | 399 |
| 1088 | Me | O | O | 2-chloropyridin-3-yl | 1-ethynylcyclohexyl | 2.99[a] | |
| 1089 | Et | O | O | 3-bromothiophen-2-yl | 4-(4-cyanophenyl)-2-methylbut-3-yn-2-yl | 4.16[a] | 468 |
| 1090 | Et | O | O | 3-(difluoromethyl)-1-methyl-1H-pyrazol-4-yl | 4-(4-cyanophenyl)-2-methylbut-3-yn-2-yl | 3.37[a] | 438 |
| 1091 | Et | O | O | 3-(trifluoromethyl)thiophen-2-yl | 4-(4-cyanophenyl)-2-methylbut-3-yn-2-yl | 4.24[a] | 458 |
| 1092 | Me | O | O | 2-methyl-4-trifluoromethyl-1,3-thiazol-5-yl | 4-(4-cyanophenyl)-2-methylbut-3-yn-2-yl | 3.78[a] | 459 |
| 1093 | Et | O | O | 2-methyl-4-trifluoromethyl-1,3-thiazol-5-yl | 4-(4-cyanophenyl)-2-methylbut-3-yn-2-yl | 4.04[a] | 473 |
| 1094 | Et | O | O | 2-bromothiophen-3-yl | 4-(4-cyanophenyl)-2-methylbut-3-yn-2-yl | 4.21[a] | 469 |
| 1095 | Me | O | O | 2-methyl-4-trifluoromethyl-1,3-thiazol-5-yl | 2-methyl-4-(4-methylphenyl)but-3-yn-2-yl | 4.51[a] | 448 |
| 1096 | Et | O | O | 3-bromothiophen-2-yl | 2-methyl-4-(4-methylphenyl)but-3-yn-2-yl | 5.05[a] | 457 |
| 1097 | Et | O | O | 3-(difluoromethyl)-1-methyl-1H-pyrazol-4-yl | 2-methyl-4-(4-methylphenyl)but-3-yn-2-yl | 4.11[a] | 427 |
| 1098 | Et | O | O | 2-methyl-4-trifluoromethyl-1,3-thiazol-5-yl | 2-methyl-4-(4-methylphenyl)but-3-yn-2-yl | 4.92[a] | 462 |
| 1099 | Et | O | O | 3-(trifluoromethyl)thiophen-2-yl | 5-methoxy-2-methylpent-3-yn-2-yl | 3.55[a] | 401 |
| 1100 | Me | O | O | 2-methyl-4-trifluoromethyl-1,3-thiazol-5-yl | 5-methoxy-2-methylpent-3-yn-2-yl | 3.06[a] | 402 |
| 1101 | Et | O | O | 3-(difluoromethyl)-1-methyl-1H-pyrazol-4-yl | 5-methoxy-2-methylpent-3-yn-2-yl | 2.73[a] | 381 |
| 1102 | Et | O | O | 2-methyl-4-trifluoromethyl-1,3-thiazol-5-yl | 5-methoxy-2-methylpent-3-yn-2-yl | 3.42[a] | 416 |
| 1103 | Et | O | O | 3-(trifluoromethyl)thiophen-2-yl | 4,4-dichloro-2-methylbut-3-en-2-yl | 4.26[a] | 427 |
| 1104 | Me | O | O | 2-methyl-4-trifluoromethyl-1,3-thiazol-5-yl | 4,4-dichloro-2-methylbut-3-en-2-yl | 3.73[a] | 428 |

TABLE 1-continued

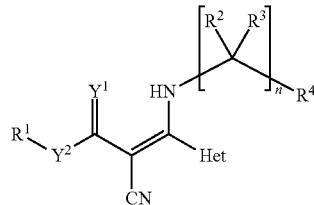

(I)

| No. | R[1] | Y[2] | Y[1] | Het | R | Log P | M[+] |
|---|---|---|---|---|---|---|---|
| 1105 | Et | O | O | 3-bromothiophen-2-yl | 4,4-dichloro-2-methylbut-3-en-2-yl | 4.21[a] | 437 |
| 1106 | Et | O | O | 3-(difluoromethyl)-1-methyl-1H-pyrazol-4-yl | 4,4-dichloro-2-methylbut-3-en-2-yl | 3.31[a] | |
| 1107 | Et | O | O | 2-chloropyridin-3-yl | (2S)-1-[(methylsulfonyl)oxy]propan-2-yl | 2.28[c] T2; 2.12[c] T1; 2.17[b] | |
| 1108 | Et | O | O | 2-chloropyridin-3-yl | 1-(methylsulfonyl)propan-2-yl | 1.69[c] I1; 1.77[c] I2; 1.86[b]; 1.8[b] I2; 1.8[b]; 1.77[b] I1 | |
| 1109 | Et | O | O | 2-chloropyridin-3-yl | (2S)-1-thiocyanatopropan-2-yl | 2.44[c] T2; 2.32[c] T1; 2.35[b] | |
| 1111 | Et | O | O | 2-chloropyridin-3-yl | 1-{[(1-phenylethylidene)amino]oxy}propan-2-yl | 3.96[a] | 427 |
| 1112 | Et | O | O | 3-(difluoromethyl)-1-methyl-1H-pyrazol-4-yl | 1-{[(1-phenylethylidene)amino]oxy}propan-2-yl | 3.83[a] | 446 |
| 1113 | Me | O | O | 2-chloropyridin-3-yl | 1-(trifluoromethyl)cyclohexyl | 2.99[a] | |
| 1114 | Et | NH | O | 2-chloropyridin-3-yl | (1S)-1-cyclopropylethyl | 2.54[c] I1; 2.59[c] I2; 2.58[b] I2; 2.53[b] I1 | |
| 1115 | cPr | NH | O | 2-chloropyridin-3-yl | 1-cyclopropylethyl | 2.54[c] I2; 2.48[c] I1; 2.47[b] I1; 2.53[b] I2 | |
| 1116 | OMe | NH | O | 2-chloropyridin-3-yl | (1S)-1-cyclopropylethyl | | |
| 1117 | Et | O | O | 2-chloropyridin-3-yl | 1-(5,6-dihydro-1,4,2-dioxazin-3-yl)ethyl | 2.11[a] | 365 |
| 1118 | Et | NH | O | 2-chloropyridin-3-yl | 1-(pyrimidin-4-yl)ethyl | 1.62[a] | 357 |
| 1119 | Et | NH | O | 2-chloropyridin-3-yl | pent-3-yn-2-yl | 2.5[a] | 317 |
| 1120 | Et | NH | O | 2-chloropyridin-3-yl | 2-(1,3-thiazol-2-yl)propyl | 2.14[a] | 376 |
| 1121 | Et | O | O | 2-cyanopyridin-3-yl | (2S)-3-methylbutan-2-yl | | 313 |
| 1122 | Et | O | O | 3-(difluoromethyl)-1-methyl-1H-pyrazol-4-yl | 2-methylcyclohexyl | 3.6[a] | 367 |
| 1123 | Et | O | O | 3-(difluoromethyl)-1-methyl-1H-pyrazol-4-yl | cBu | 2.73[a] | 325 |
| 1124 | Et | O | O | 3-(difluoromethyl)-1-methyl-1H-pyrazol-4-yl | cPr | 2.35[a] | 311 |
| 1125 | Et | O | O | 3-(difluoromethyl)-1-methyl-1H-pyrazol-4-yl | (2S)-hexan-2-yl | 3.58[a] | 355 |
| 1126 | Et | O | O | 3-(difluoromethyl)-1-methyl-1H-pyrazol-4-yl | (trimethylsilyl)methyl | 3.35[a] | 357 |
| 1127 | Et | O | O | 3-(difluoromethyl)-1-methyl-1H-pyrazol-4-yl | allyl | 2.35[a] | 311 |
| 1128 | Et | O | O | 3-(difluoromethyl)-1-methyl-1H-pyrazol-4-yl | propargyl | 2.13[a] | 309 |
| 1129 | Et | O | O | 3-(difluoromethyl)-1-methyl-1H-pyrazol-4-yl | 1-ethoxy-4-methyl-1-oxopentan-2-yl | 3.53[a] | 413 |
| 1130 | Et | O | O | 3-(difluoromethyl)-1-methyl-1H-pyrazol-4-yl | 2-methylcyclopropyl | 2.68[a] | 325 |
| 1131 | Et | O | O | 3-(difluoromethyl)-1-methyl-1H-pyrazol-4-yl | bicyclo[4.1.0]hept-7-yl | 3.44[a] | 365 |
| 1132 | Et | O | O | 3-(difluoromethyl)-1-methyl-1H-pyrazol-4-yl | 1-cyanocyclopropyl | 2.1[a] | 336 |
| 1133 | Et | O | O | 3-(difluoromethyl)-1-methyl-1H-pyrazol-4-yl | 1-cyclobutylethyl | 3.33[a] | 353 |
| 1134 | Et | O | O | 3-(difluoromethyl)-1-methyl-1H-pyrazol-4-yl | 1-(bicyclo[2.2.1]hept-2-yl)ethyl | 4.03[a] | 393 |
| 1135 | Et | O | O | 3-(difluoromethyl)-1-methyl-1H-pyrazol-4-yl | 1-(2,2-dimethylpropoxy)propan-2-yl | 4.08[a] | 399 |
| 1136 | Et | O | O | 3-(difluoromethyl)-1-methyl-1H-pyrazol-4-yl | 1-cyclopropylpropan-2-yl | 3.23[a] | 353 |
| 1137 | Et | O | O | 3-(difluoromethyl)-1-methyl-1H-pyrazol-4-yl | 2-(methylamino)-2-oxo-1-phenylethyl | 2.27[a] | 418 |
| 1138 | Et | O | O | 3-(difluoromethyl)-1-methyl-1H-pyrazol-4-yl | 4-[(2-methylphenyl)amino]-4-oxobutan-2-yl | 2.68[a] | 446 |
| 1139 | Et | O | O | 3-(difluoromethyl)-1-methyl-1H-pyrazol-4-yl | 4-ethoxy-4-oxobutan-2-yl | 2.66[a] | 385 |
| 1140 | Et | O | O | 3-(difluoromethyl)-1-methyl-1H-pyrazol-4-yl | 2-methoxy-2-oxo-1-phenylethyl | 2.94[a] | 419 |
| 1141 | Et | O | O | 3-(difluoromethyl)-1-methyl-1H-pyrazol-4-yl | 1-(cyclohex-3-en-1-yl)ethyl | 3.62[a] | 379 |

TABLE 1-continued

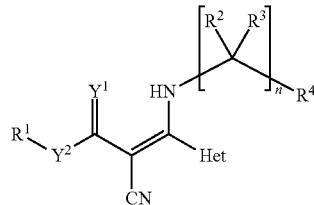

(I)

| No. | R¹ | Y² | Y¹ | Het | R | Log P | M⁺ |
|---|---|---|---|---|---|---|---|
| 1142 | Et | O | O | 3-(difluoromethyl)-1-methyl-1H-pyrazol-4-yl | pent-3-yn-2-yl | 2.8[a] | 337 |
| 1143 | Et | O | O | 3-(difluoromethyl)-1-methyl-1H-pyrazol-4-yl | 1-(prop-1-yn-1-yl)cyclopentyl | 3.39[a] | 377 |
| 1144 | Et | O | O | 3-(difluoromethyl)-1-methyl-1H-pyrazol-4-yl | (1R,2R,4S)-bicyclo[2.2.1]hept-2-yl | 3.46[a] | 365 |
| 1145 | Et | O | O | 3-(difluoromethyl)-1-methyl-1H-pyrazol-4-yl | (1S,4R)-bicyclo[2.2.1]hept-2-yl | 3.42[a] | 365 |
| 1146 | Et | O | O | 3-(difluoromethyl)-1-methyl-1H-pyrazol-4-yl | 2-ethylcyclopropyl | 3.04[a] | 339 |
| 1147 | Et | O | O | 3-(difluoromethyl)-1-methyl-1H-pyrazol-4-yl | 2-(trifluoromethyl)cyclopropyl | 2.75[a] | 379 |
| 1148 | Et | O | O | 3-(difluoromethyl)-1-methyl-1H-pyrazol-4-yl | 2,2-dimethylcyclopropyl | 3[a] | 339 |
| 1149 | Et | O | O | 2-chloropyridin-3-yl | 1-(4-fluorophenyl)ethyl | 3.51[a] | 374 |
| 1150 | Et | O | O | 2-chloropyridin-3-yl | 1-(4-methylphenyl)ethyl | 3.87[a] | 370 |
| 1151 | Et | O | O | 2-chloropyridin-3-yl | 1-phenylethyl | 3.48[a] | 356 |
| 1152 | Et | O | O | 2-chloropyridin-3-yl | 1-(3-chlorophenyl)ethyl | 3.83[a] | 390 |
| 1153 | Et | O | O | 2-chloropyridin-3-yl | 4-methoxyphenyl | 2.98[a] | 358 |
| 1154 | Et | O | O | 2-chloropyridin-3-yl | 4-(propan-2-yl)phenyl | 4.08[a] | 370 |
| 1155 | Et | O | O | 2-chloropyridin-3-yl | 1-(2-methylphenoxy)propan-2-yl | 4.01[a] | 400 |
| 1156 | Et | O | O | 2-chloropyridin-3-yl | 1-[(4-chlorophenyl)sulfanyl]-propan-2-yl | 4.08[a] | 436 |
| 1157 | Et | O | O | 2-chloropyridin-3-yl | 1-[(2,5-dichlorophenyl)-sulfanyl]propan-2-yl | 4.27[a] | 470 |
| 1158 | Et | O | O | 2-chloropyridin-3-yl | 1-[(3,4-dichlorophenyl)-sulfanyl]propan-2-yl | 4.41[a] | 470 |
| 1159 | Et | O | O | 2-chloropyridin-3-yl | 3-(phenylsulfanyl)butan-2-yl | 4.13[a] | 416 |
| 1160 | Et | O | O | 2-chloropyridin-3-yl | 1-[3-(trifluoromethyl)-phenoxy]propan-2-yl | 4.13[a] | 454 |
| 1161 | Et | O | O | 2-chloropyridin-3-yl | 1-phenoxypropan-2-yl | 3.58[a] | 386 |
| 1162 | Et | O | O | 2-chloropyridin-3-yl | 1-(benzyloxy)propan-2-yl | 3.71[a] | 400 |
| 1163 | Et | O | O | 2-chloropyridin-3-yl | 1-[(2-fluorobenzyl)oxy]propan-2-yl | 3.69[a] | 418 |
| 1164 | Et | O | O | 2-chloropyridin-3-yl | 1-(2-chlorophenoxy)propan-2-yl | 3.78[a] | 420 |
| 1165 | Et | O | O | 2-chloropyridin-3-yl | 1-(4-methylphenoxy)propan-2-yl | 3.94[a] | 400 |
| 1166 | Et | O | O | 2-chloropyridin-3-yl | 1-(4-fluorophenoxy)propan-2-yl | 3.62[a] | 404 |
| 1167 | Et | O | O | 2-chloropyridin-3-yl | 4-phenylbutan-2-yl | 3.92[a] | 384 |
| 1168 | Et | O | O | 2-chloropyridin-3-yl | 2-(propan-2-yloxy)phenyl | 3.8[a] | 386 |
| 1169 | Et | O | O | 2-chloropyridin-3-yl | 4-(difluoromethoxy)phenyl | 3.19[a] | 394 |
| 1170 | Et | O | O | 2-chloropyridin-3-yl | 4-(methylsulfanyl)phenyl | 3.37[a] | 374 |
| 1171 | Et | O | O | 2-chloropyridin-3-yl | 2-(methylsulfanyl)benzyl | 3.37[a] | 388 |
| 1172 | Et | O | O | 2-chloropyridin-3-yl | 1-[(2-chlorobenzyl)oxy]propan-2-yl | 4.06[a] | 434 |
| 1173 | Et | O | O | 2-chloropyridin-3-yl | 1-(3-methoxyphenoxy)propan-2-yl | 3.58[a] | 416 |
| 1174 | Et | O | O | 2-chloropyridin-3-yl | (2R)-butan-2-yl | 3[a] | 308 |
| 1175 | Et | O | O | 2-chloropyridin-3-yl | pentyl | 3.53[a] | 322 |
| 1176 | Et | O | O | 2-chloropyridin-3-yl | octa-1,7-dien-3-yl | 4.01[a] | 360 |
| 1177 | Et | O | O | 2-chloropyridin-3-yl | 1-(bicyclo[2.2.1]hept-2-yl)ethyl | 4.39[a] | 374 |
| 1178 | Et | O | O | 2-chloropyridin-3-yl | 1-(2,2-dimethylpropoxy)propan-2-yl | 4.34[a] | 380 |
| 1179 | Et | O | O | 2-chloropyridin-3-yl | 1-cyclopropylpropan-yl | 3.42[a] | 334 |
| 1180 | Et | O | O | 2-chloropyridin-3-yl | 1-(2,6-dimethylphenoxy)propan-2-yl | 4.26[a] | 414 |
| 1181 | Et | O | O | 2-chloropyridin-3-yl | but-3-yn-2-yl | 2.66[a] | 304 |
| 1182 | Et | O | O | 2-chloropyridin-3-yl | 1-(1-chlorocyclopropyl)ethyl | 3.33[a] | 354 |
| 1183 | Et | O | O | 2-chloropyridin-3-yl | 2-MeOEt | 2.17[a] | 310 |
| 1184 | Et | O | O | 2-chloropyridin-3-yl | 4-hydroxybutyl | 1.75[a] | 324 |
| 1185 | Et | O | O | 2-chloropyridin-3-yl | 3-methylbutyl | 3.44[a] | 322 |
| 1186 | Et | O | O | 2-chloropyridin-3-yl | cBu | 2.92[a] | 306 |
| 1187 | Et | O | O | 2-chloropyridin-3-yl | 6-methylheptan-2-yl | 4.62[a] | 364 |
| 1188 | Et | O | O | 2-chloropyridin-3-yl | (2R)-heptan-2-yl | 4.26[a] | 350 |
| 1189 | Et | O | O | 2-chloropyridin-3-yl | (2S)-heptan-2-yl | 4.26[a] | 350 |
| 1190 | Et | O | O | 2-chloropyridin-3-yl | 2-ethylcyclopropyl | 3.23[a] | 320 |
| 1191 | Et | O | O | 2-chloropyridin-3-yl | 1-cyclobutylethyl | 3.55[a] | 334 |

TABLE 1-continued

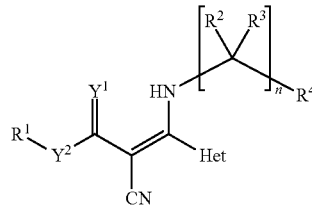

(I)

| No. | R¹ | Y² | Y¹ | Het | R | Log P | M⁺ |
|---|---|---|---|---|---|---|---|
| 1192 | Et | O | O | 2-chloropyridin-3-yl | 4-[(2-methylphenyl)amino]-4-oxobutan-2-yl | 2.8[a] | 427 |
| 1193 | Et | O | O | 2-chloropyridin-3-yl | 1-(naphthalen-2-ylamino)-1-oxopropan-2-yl | 3.51[a] | 449 |
| 1194 | Et | O | O | 2-chloropyridin-3-yl | 1-ethoxy-1-oxopropan-2-yl | 2.82[a] | 352 |
| 1195 | Et | O | O | 2-chloropyridin-3-yl | 2-methoxy-2-oxo-1-phenylethyl | 3.08[a] | 400 |
| 1196 | Et | O | O | 2-chloropyridin-3-yl | 1-ethoxy-4-methyl-1-oxopentan-2-yl | 3.89[a] | 394 |
| 1197 | Et | O | O | 2-chloropyridin-3-yl | 1-(benzyloxy)but-3-en-2-yl | 3.8[a] | 412 |
| 1198 | Et | O | O | 2-chloropyridin-3-yl | pent-3-yn-2-yl | 3.02[a] | 318 |
| 1199 | Et | NH | O | 2-cyanopyridin-3-yl | (2S)-3-methylbutan-2-yl | 2.64[a] | |
| 1200 | Et | NH | O | 2,3-dichloropyridin-4-yl | (2S)-3-methylbutan-2-yl | 3.57[a] | 356 |
| 1201 | Et | NH | O | 2,3-dichloropyridin-4-yl | 1-(pyridin-2-yl)ethyl | 2.53[a] | 391 |
| 1202 | Et | O | O | 3-iodo-1-methyl-1H-pyrazol-4-yl | 3-methylbutan-2-yl | 3.22[a] | 417 |
| 1203 | Et | O | O | 1,3-dimethyl-1H-pyrazol-4-yl | 3-methylbutan-2-yl | 2.8[a] | 305 |
| 1204 | Et | O | O | 1,3-dimethyl-1H-pyrazol-4-yl | 1-(pyridin-2-yl)ethyl | 1.99[a] | 340 |
| 1205 | Et | O | O | 3-ethyl-1-methyl-1H-pyrazol-4-yl | 3-methylbutan-2-yl | 3.13[a] | 319 |
| 1206 | Et | O | O | 3-ethyl-1-methyl-1H-pyrazol-4-yl | 1-(pyridin-2-yl)ethyl | 2.25[a] | 354 |
| 1207 | Et | O | O | 1-methyl-3-(propan-2-yl)-1H-pyrazol-4-yl | 1-(pyridin-2-yl)ethyl | 2.58[a] | 368 |
| 1208 | Et | O | O | 1-methyl-3-(propan-2-yl)-1H-pyrazol-4-yl | 3-methylbutan-2-yl | 3.46[a] | 333 |
| 1209 | Et | O | O | 2-bromo-3-chloropyridin-4-yl | (2S)-3-methylbutan-2-yl | 3.94[a] | 401 |
| 1210 | Et | NH | O | 2-bromo-3-chloropyridin-4-yl | (2S)-3-methylbutan-2-yl | 3.6[a] | 400 |
| 1211 | Et | O | O | 3-chloro-2-methylpyridin-4-yl | (2S)-3-methylbutan-2-yl | 3.51[a] | 336 |
| 1212 | Et | O | O | 1,3-dimethyl-1H-pyrazol-4-yl | 1-(1,3-thiazol-2-yl)ethyl | 2.11[a] | 346 |
| 1213 | Et | O | O | 3-ethyl-1-methyl-1H-pyrazol-4-yl | 1-(1,3-thiazol-2-yl)ethyl | 2.35[a] | 360 |
| 1214 | Et | O | O | 1-methyl-3-(propan-2-yl)-1H-pyrazol-4-yl | 1-(1,3-thiazol-2-yl)ethyl | 2.62[a] | 374 |
| 1215 | Et | O | O | 3-(difluoromethyl)-1-methyl-1H-pyrazol-4-yl | 2-(4-chlorophenyl)propan-2-yl | 3.71[a] | 423 |
| 1216 | Et | O | O | 3-(difluoromethyl)-1-methyl-1H-pyrazol-4-yl | 2-chlorophenyl | 3.15[a] | 381 |
| 1217 | Et | O | O | 3-(difluoromethyl)-1-methyl-1H-pyrazol-4-yl | 4-cyanophenyl | 2.64[a] | 372 |
| 1218 | Et | O | O | 3-(difluoromethyl)-1-methyl-1H-pyrazol-4-yl | (2-bromophenyl)(cyano)methyl | 3.13[a] | 464 |
| 1219 | Et | O | O | 3-(difluoromethyl)-1-methyl-1H-pyrazol-4-yl | cyano(2,3-dichlorophenyl)methyl | 3.44[a] | 454 |
| 1220 | Et | O | O | 3-(difluoromethyl)-1-methyl-1H-pyrazol-4-yl | 1-cyanobut-3-yn-1-yl | 2.33[a] | 348 |
| 1221 | Et | O | O | 3-(difluoromethyl)-1-methyl-1H-pyrazol-4-yl | 1-cyano-2-phenylethyl | 2.98[a] | 400 |
| 1222 | Et | O | O | 3-(difluoromethyl)-1-methyl-1H-pyrazol-4-yl | 1-(4-chlorophenyl)-2,2,2-trifluoroethyl | 4.01[a] | 463 |
| 1223 | Et | O | O | 3-(difluoromethyl)-1-methyl-1H-pyrazol-4-yl | 1,1,1-trifluoro-3-(3-methyl-pyridin-2-yl)propan-2-yl | 2.94[a] | 458 |
| 1224 | Et | O | O | 3-(difluoromethyl)-1-methyl-1H-pyrazol-4-yl | 2,2,2-trifluoro-1-phenylethyl | 3.55[a] | 429 |
| 1225 | Et | O | O | 3-(difluoromethyl)-1-methyl-1H-pyrazol-4-yl | 1-(3-methoxyphenyl)ethyl | 3.21[a] | 405 |
| 1226 | Et | O | O | 3-(difluoromethyl)-1-methyl-1H-pyrazol-4-yl | 2-(cyclopropylcarbonyl)phenyl | 3[a] | 415 |
| 1227 | Et | O | O | 3-(difluoromethyl)-1-methyl-1H-pyrazol-4-yl | 2-(trifluoromethoxy)phenyl | 3.42[a] | 431 |
| 1228 | Et | O | O | 3-(difluoromethyl)-1-methyl-1H-pyrazol-4-yl | 2-(ethylsulfanyl)phenyl | 3.46[a] | 407 |
| 1229 | Et | O | O | 3-(difluoromethyl)-1-methyl-1H-pyrazol-4-yl | 2-(4-methoxyphenyl)propan-2-yl | 3.35[a] | 419 |
| 1230 | Et | O | O | 3-(difluoromethyl)-1-methyl-1H-pyrazol-4-yl | cyano(phenyl)methyl | 2.94[a] | 386 |

TABLE 1-continued

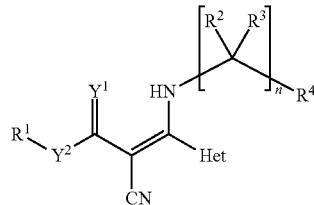

(I)

| No. | R¹ | Y² | Y¹ | Het | R | Log P | M⁺ |
|---|---|---|---|---|---|---|---|
| 1231 | Et | O | O | 3-(difluoromethyl)-1-methyl-1H-pyrazol-4-yl | cyano(2,4-dichlorophenyl)methyl | 3.55[a] | 454 |
| 1232 | Et | O | O | 3-(difluoromethyl)-1-methyl-1H-pyrazol-4-yl | cyano(1-phenyl-1H-pyrazol-4-yl)methyl | 3.15[a] | 452 |
| 1233 | Et | O | O | 3-(difluoromethyl)-1-methyl-1H-pyrazol-4-yl | 1-{[4-(trifluoromethyl)benzyl[-oxy}propan-2-yl | 3.99[a] | 487 |
| 1234 | Et | O | O | 3-(difluoromethyl)1-methyl-1H-pyrazol-4-yl | 1-[(4-chlorophenyl)sulfanyl]-propan-2-yl | 3.87[a] | 455 |
| 1235 | Et | O | O | 3-(difluoromethyl)-1-methyl-1H-pyrazol-4-yl | 1-[(2,5-dichlorophenyl)-sulfanyl]propan-2-yl | 4.08[a] | 489 |
| 1236 | Et | O | O | 3-(difluoromethyl)-1-methyl-1H-pyrazol-4-yl | 1-[(3,4-dichlorophenyl)-sulfanyl]propan-2-yl | 4.2[a] | 489 |
| 1237 | Et | O | O | 3-(difluoromethyl)-1-methyl-1H-pyrazol-4-yl | 1-[3-(trifluoromethyl)-phenoxy]propan-2-yl | 3.92[a] | 473 |
| 1238 | Et | O | O | 3-(difluoromethyl)-1-methyl-1H-pyrazol-4-yl | 4-(4-cyanophenyl)-2-methylbut-3-yn-2-yl | 3.69[a] | 438 |
| 1239 | Et | O | O | 3-(difluoromethyl)-1-methyl-1H-pyrazol-4-yl | 3-methyl-2-phenylbutyl | 3.94[a] | 417 |
| 1240 | Et | O | O | 3-(difluoromethyl)-1-methyl-1H-pyrazol-4-yl | 3-oxopentan-2-yl | 2.47[a] | 355 |
| 1241 | Et | O | O | 3-(difluoromethyl)-1-methyl-1H-pyrazol-4-yl | 1-[(2-chlorobenzyl)oxy]propan-2-yl | 3.83[a] | 453 |
| 1242 | Et | O | O | 3-(difluoromethyl)-1-methyl-1H-pyrazol-4-yl | 1-(2-methylphenoxy)propan-2-yl | 3.78[a] | 419 |
| 1243 | Et | O | O | 3-chloro-2-methylpyridin-4-yl | 1-(pyridin-2-yl)ethyl | 2.6[c] | 371 |
| 1244 | Me | NH | O | 2-chloropyridin-3-yl | (1S)-1-cyclopropylethyl | 2.16[c] I1; 2.21[c] I2; 2.16[b] I1; 2.2[b] I2 | |
| 1245 | cBu | O | O | 2-chloropyridin-3-yl | (1S)-1-cyclopropylethyl | 3.43[c] I1; 3.5[c] I2; 3.46[b] | |
| 1246 | OMe | NMe | O | 2-chloropyridin-3-yl | (2S)-3-methylbutan-2-yl | 2.68[c]; 2.67[b] | |
| 1247 | Et | O | O | 3-iodo-1-methyl-1H-pyrazol-4-yl | 1-(1,3-thiazol-2-yl)ethyl | 3.46[a] | 458 |
| 1248 | Et | O | O | 3-iodo-1-methyl-1H-pyrazol-4-yl | 1-(pyridin-2-yl)ethyl | 2.37[a] | 452 |
| 1249 | Et | NH | O | 3-chloro-2-methylpyridin-4-yl | (2S)-3-methylbutan-2-yl | 3.08[a] | 335 |
| 1250 | Et | O | O | 3-(difluoromethyl)-1-methyl-1H-pyrazol-4-yl | 1-cyanobutyl | 2.77[a] | 352 |
| 1251 | Et | O | O | 3-(difluoromethyl)-1-methyl-1H-pyrazol-4-yl | 1-cyanopropyl | 2.45[a] | 338 |
| 1252 | Et | O | O | 3-(difluoromethyl)-1-methyl-1H-pyrazol-4-yl | 1-cyano-3-methylbutyl | 3.04[a] | 366 |
| 1253 | Et | O | O | 3-(difluoromethyl)-1-methyl-1H-pyrazol-4-yl | F₃iPr | 2.92[a] | 367 |
| 1254 | Et | O | O | 3-(difluoromethyl)-1-methyl-1H-pyrazol-4-yl | 1-cyanoethyl | 2.15[a] | 324 |
| 1255 | Et | O | O | 3-(difluoromethyl)-1-methyl-1H-pyrazol-4-yl | 2-amino-2-oxoethyl | 2.1[a] | 328 |
| 1256 | Et | O | O | 3-(difluoromethyl)-1-methyl-1H-pyrazol-4-yl | 1-(ethylamino)-1-oxopropan-2-yl | 1.88[a] | 370 |
| 1257 | Et | O | O | 2-chloropyridin-3-yl | cyano(2,3-dichlorophenyl)-methyl | 3.69[a] | 435 |
| 1258 | Et | O | O | 2-chloropyridin-3-yl | 1-cyanobut-3-yn-1-yl | 2.37[a] | 329 |
| 1259 | Et | O | O | 2-chloropyridin-3-yl | 1-cyano-2-phenylethyl | 3.02[a] | 381 |
| 1260 | Et | O | O | 2-chloropyridin-3-yl | 1-[4-(dimethylamino)phenyl]-2,2,2-trifluoroethyl | 3.99[a] | 453 |
| 1261 | Et | O | O | 2-chloropyridin-3-yl | 1-(4-chlorophenyl)-2,2,2-trifluoroethyl | 4.25[a] | 444 |
| 1262 | Et | O | O | 2-chloropyridin-3-yl | 1,1,1-trifluoro-3-(3-methylpyridin-2-yl)propan-2-yl | 3.04[a] | 439 |
| 1263 | Et | O | O | 2-chloropyridin-3-yl | 2-chlorophenyl | 3.35[a] | 362 |
| 1264 | Et | O | O | 2-chloropyridin-3-yl | 4-(dimethylamino)phenyl | 3.17[a] | 371 |
| 1265 | Et | O | O | 2-chloropyridin-3-yl | 4-cyanophenyl | 2.73[a] | 353 |
| 1266 | Et | O | O | 2-chloropyridin-3-yl | 3-(methylsulfanyl)phenyl | 3.42[a] | 374 |
| 1267 | Et | O | O | 2-chloropyridin-3-yl | cyano(2,4-dichlorophenyl)methyl | 3.83[a] | 435 |
| 1268 | Et | O | O | 2-chloropyridin-3-yl | 2-methyl-4-(4-methylphenyl)but-3-yn-2-yl | 4.41[a] | 408 |

TABLE 1-continued

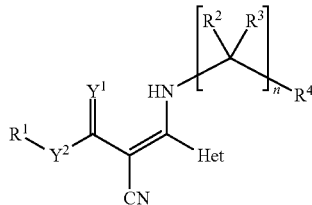

(I)

| No. | R¹ | Y² | Y¹ | Het | R | Log P | M⁺ |
|---|---|---|---|---|---|---|---|
| 1269 | Et | O | O | 2-chloropyridin-3-yl | 1,3-benzothiazol-6-yl | 2.54[a] | 385 |
| 1270 | Et | O | O | 2-chloropyridin-3-yl | 3-oxopentan-2-yl | 2.64[a] | 336 |
| 1271 | Et | O | O | 2-chloropyridin-3-yl | 4,4-dichloro-2-methylbut-3-en-2-yl | 3.55[a] | 388 |
| 1272 | Et | O | O | 2-chloropyridin-3-yl | 4-(4-cyanophenyl)-2-methylbut-3-yn-2-yl | 3.67[a] | 419 |
| 1273 | Et | O | O | 2-chloropyridin-3-yl | 2,3,3-trimethylbutan-2-yl | 3.8[a] | 350 |
| 1274 | Et | O | O | 2-chloropyridin-3-yl | 1-methoxy-2-methyl-1-oxopropan-2-yl | 2.66[a] | 352 |
| 1275 | Et | O | O | 2-chloropyridin-3-yl | 1-(prop-1-yn-1-yl)cyclopentyl | 3.69[a] | 358 |
| 1276 | Et | O | O | 2,3-dichloropyridin-4-yl | (1S)-1-(1,3-thiazol-2-yl)ethyl | 2.96[a]; 3.01[c] T2; 2.82[c] T1; 2.91[b] | 398 |
| 1277 | Et | NH | O | 3-chloro-2-methylpyridin-4-yl | 1-(pyridin-2-yl)ethyl | 2.7[a] | 370 |
| 1278 | Et | NH | O | 3-(difluoromethyl)-1-methyl-1H-pyrazol-4-yl | (2S)-3-methylbutan-2-yl | 2.71[a] | 340 |
| 1279 | cPr | NH | O | 3-(difluoromethyl)-1-methyl-1H-pyrazol-4-yl | 1-(1,3-thiazol-2-yl)ethyl | 2.04[a] | 393 |
| 1280 | cPr | NH | O | 3-(difluoromethyl)-1-methyl-1H-pyrazol-4-yl | 1-(pyridin-2-yl)ethyl | 1.84[a] | 387 |
| 1281 | oxetan-3-yl | O | O | 2-chloropyridin-3-yl | (1S)-1-cyclopropylethyl | 2.34[c] I2; 2.3[c] I1; 2.31[b] | |
| 1282 | Et | NMe | O | 2-chloropyridin-3-yl | (2S)-3-methylbutan-2-yl | 2.91[c]; 2.9[b] | |
| 1283 | (2R)-3-methylbutan-2-yl | NH | O | 2-chloropyridin-3-yl | (2S)-3-methylbutan-2-yl | 4.02[c]; 4.02[b] | |
| 1284 | cBu | O | O | 2-chloropyridin-3-yl | (2S)-3-methylbutan-2-yl | 3.79[c]; 3.79[b] | |
| 1285 | Et | O | O | 3-chloro-2-methylpyridin-4-yl | (1S)-1-(1,3-thiazol-2-yl)ethyl | 2.57[a] | 377 |
| 1286 | Me | NMe | O | 3-(difluoromethyl)-1-methyl-1H-pyrazol-4-yl | (2S)-3-methylbutan-2-yl | 2.45[a] | 340 |
| 1287 | 2-MeOEt | NH | O | 3-(difluoromethyl)-1-methyl-1H-pyrazol-4-yl | 1-(1,3-thiazol-2-yl)ethyl | 1.96[a] | 411 |
| 1288 | 2-MeOEt | NH | O | 3-(difluoromethyl)-1-methyl-1H-pyrazol-4-yl | 1-(pyridin-2-yl)ethyl | 1.75[a] | 405 |
| 1289 | Et | NH | O | 2,3-dichloropyridin-4-yl | (1S)-1-(1,3-thiazol-2-yl)ethyl | 2.57[a] | 397 |
| 1290 | Et | O | O | 2-bromo-3-chloropyridin-4-yl | (1S)-1-(1,3-thiazol-2-yl)ethyl | 3.02[a] | 442 |
| 1291 | allyl | NH | O | 3-(difluoromethyl)-1-methyl-1H-pyrazol-4-yl | 1-(pyridin-2-yl)ethyl | 2.02[a] | 387 |
| 1292 | allyl | NH | O | 3-(difluoromethyl)-1-methyl-1H-pyrazol-4-yl | 1-(1,3-thiazol-2-yl)ethyl | 2.2[a] | 393 |
| 1293 | Et | NH | O | 3-(difluoromethyl)-1-methyl-1H-pyrazol-4-yl | 1-(pyridin-2-yl)ethyl | 1.86[a] | 375 |
| 1294 | Et | NH | O | 3-(difluoromethyl)-1-methyl-1H-pyrazol-4-yl | 1-(1,3-thiazol-2-yl)ethyl | 2.05[a] | 381 |
| 1295 | Me | NMe | O | 3-(difluoromethyl)-1-methyl-1H-pyrazol-4-yl | 1-(pyridin-2-yl)ethyl | 1.59[a] | 375 |
| 1296 | Me | NMe | O | 3-(difluoromethyl)-1-methyl-1H-pyrazol-4-yl | 1-(1,3-thiazol-2-yl)ethyl | 1.81[a] | 381 |
| 1297 | propargyl | NH | O | 3-(difluoromethyl)-1-methyl-1H-pyrazol-4-yl | 1-(1,3-thiazol-2-yl)ethyl | 2.04[a] | 391 |
| 1298 | oxetan-3-yl | NH | O | 3-(difluoromethyl)-1-methyl-1H-pyrazol-4-yl | (2S)-3-methylbutan-2-yl | 1.84[a] | 368 |
| 1299 | 2-cyanoethyl | NH | O | 3-(difluoromethyl)-1-methyl-1H-pyrazol-4-yl | (2S)-3-methylbutan-2-yl | 2.44[a] | 365 |
| 1300 | Et | O | O | 5-(difluoromethyl)-1-methyl-1H-pyrazol-4-yl | 1-(pyridin-2-yl)ethyl | 2.41[a] | 376 |
| 1301 | Et | O | O | 5-(difluoromethyl)-1-methyl-1H-pyrazol-4-yl | (2S)-3-methylbutan-2-yl | 3.23[a] | 341 |
| 1302 | Et | O | O | 5-(difluoromethyl)-1-methyl-1H-pyrazol-4-yl | (1S)-1-(1,3-thiazol-2-yl)ethyl | 2.46[a] | 382 |
| 1303 | Et | O | O | 5-(difluoromethyl)-1-methyl-1H-pyrazol-4-yl | (1S)-1-cyclopropylethyl | 2.98[a] | 339 |
| 1304 | Et | O | O | 5-(difluoromethyl)-1-methyl-1H-pyrazol-4-yl | cBu | 2.84[a] | 325 |
| 1305 | Et | NH | O | 2-bromo-3-chloropyridin-4-yl | (1S)-1-(1,3-thiazol-2-yl)ethyl | 2.62[a] | 441 |
| 1306 | Et | NH | O | 3-chloro-2-methylpyridin-4-yl | (1S)-1-(1,3-thiazol-2-yl)ethyl | 2.18[a] | 376 |
| 1307 | Me | O | O | 2-chloropyridin-3-yl | (1S)-1-cyclopropylethyl | 2.61[c] I2; 2.56[c] I1; 2.58[b] | |

TABLE 1-continued

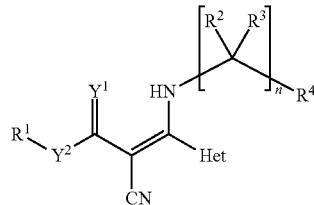

| No. | R[1] | Y[2] | Y[1] | Het | R | Log P | M[+] |
|---|---|---|---|---|---|---|---|
| 1308 | Et | NH | O | 5-(difluoromethyl)-1-methyl-1H-pyrazol-4-yl | (1S)-1-(1,3-thiazol-2-yl)ethyl | 2.11[a] | 381 |
| 1309 | Et | NH | O | 5-(difluoromethyl)-1-methyl-1H-pyrazol-4-yl | (1S)-1-cyclopropylethyl | 2.64[a] | 338 |
| 1310 | Et | O | O | 2-chloropyridin-3-yl | thieno[2,3-b]pyridin-5-yl | 2.56[c]; 2.49[b] | |
| 1311 | Et | O | O | 2-chloro-3-fluoropyridin-4-yl | (2S)-3-methylbutan-2-yl | 3.81[a] | 340 |
| 1312 | Et | O | O | 2-chloro-3-fluoropyridin-4-yl | 1-(pyridin-2-yl)ethyl | 3[a] | 375 |
| 1313 | Et | O | O | 2-chloro-3-fluoropyridin-4-yl | (1S)-1-(1,3-thiazol-2-yl)ethyl | 2.96[a] | 381 |
| 1314 | Et | O | O | 2-chloropyridin-3-yl | (2S)-1-oxopropan-2-yl | | |
| 1315 | Et | O | O | 2-bromo-3-fluoropyridin-4-yl | (2S)-3-methylbutan-2-yl | 3.87[a] | 384 |
| 1316 | Et | NH | O | 2-chloro-3-fluoropyridin-4-yl | (2S)-3-methylbutan-2-yl | 3.44[a] | 339 |
| 1317 | Et | O | O | 3-fluoro-2-methylpyridin-4-yl | (2S)-3-methylbutan-2-yl | 3.31[a] | 320 |
| 1318 | Et | O | O | 2-chloro-3-fluoropyridin-4-yl | (1R)-1-cyclopropylethyl | 3.5[a] | 338 |
| 1319 | Et | O | O | 3-fluoro-2-methylpyridin-4-yl | (1S)-1-(1,3-thiazol-2-yl)ethyl | 2.48[a] | 361 |
| 1320 | Et | O | O | 3-fluoro-2-methylpyridin-4-yl | 1-(pyridin-2-yl)ethyl | 2.5[a] | 355 |
| 1321 | Et | O | O | 2-chloro-3-fluoropyridin-4-yl | cBu | 3.39[a] | 324 |
| 1322 | Et | O | O | 2-chloropyridin-3-yl | (1E,2S)-1-(methoxyimino)-propan-2-yl | 2.5[c] I2; 2.42[c] I1; 2.56[c]; 2.49[b] | |
| 1323 | Et | NH | O | 2-bromo-3-fluoropyridin-4-yl | (2S)-3-methylbutan-2-yl | 3.46[a] | 383 |
| 1324 | Et | O | O | 2-chloro-3-fluoropyridin-4-yl | 1-(methylamino)-1-oxopropan-2-yl | 2.15[a] | 355 |
| 1325 | Et | O | O | 2-chloro-3-fluoropyridin-4-yl | pent-3-yn-2-yl | 3.39[a] | 336 |
| 1326 | R[1] & Y[2] = morpholin-4-yl | | O | 3-(difluoromethyl)-1-methyl-1H-pyrazol-4-yl | (2S)-3-methylbutan-2-yl | 2.43[a] | 382 |
| 1327 | R[1] & Y[2] = morpholin-4-yl | | O | 3-(difluoromethyl)-1-methyl-1H-pyrazol-4-yl | 1-(1,3-thiazol-2-yl)ethyl | 1.79[a] | 423 |
| 1328 | R[1] & Y[2] = morpholin-4-yl | | O | 3-(difluoromethyl)-1-methyl-1H-pyrazol-4-yl | 1-(pyridin-2-yl)ethyl | 1.63[a] | 417 |
| 1329 | Et | NH | O | 2-chloro-3-fluoropyridin-4-yl | 1-(pyridin-2-yl)ethyl | 2.5[a] | 374 |
| 1330 | Et | O | O | 2-bromo-3-fluoropyridin-4-yl | (1S)-1-(1,3-thiazol-2-yl)ethyl | 3[a] | 425 |
| 1331 | Et | O | O | 3-chloro-2-(methyl-sulfanyl)pyridin-4-yl | (1S)-1-(1,3-thiazol-2-yl)ethyl | 3.53[a] | 409 |
| 1332 | Et | O | O | 3-(difluoromethyl)-1-methyl-1H-pyrazol-4-yl | 1-methoxybutan-2-yl | 2.71[a] | 357 |
| 1333 | Et | O | O | 3-(difluoromethyl)-1-methyl-1H-pyrazol-4-yl | cyclohexyl | 3.29[a] | 353 |
| 1334 | Et | O | O | 3-(difluoromethyl)-1-methyl-1H-pyrazol-4-yl | 1-(dimethylamino)butan-2-yl | 1.22[a] | 370 |
| 1335 | Et | O | O | 3-(difluoromethyl)-1-methyl-1H-pyrazol-4-yl | 1-hydroxypentan-2-yl | 2.28[a] | 357 |
| 1336 | Et | O | O | 3-(difluoromethyl)-1-methyl-1H-pyrazol-4-yl | 1-(prop-1-yn-1-yl)cyclohexyl | 3.71[a] | 391 |
| 1337 | Et | O | O | 3-(difluoromethyl)-1-methyl-1H-pyrazol-4-yl | 4-ethoxycyclohexyl | 3.08[a] | 397 |
| 1338 | Et | O | O | 3-(difluoromethyl)-1-methyl-1H-pyrazol-4-yl | pentan-3-yl | 3.15[a] | 341 |
| 1339 | Et | O | O | 3-(difluoromethyl)-1-methyl-1H-pyrazol-4-yl | oxetan-3-yl | 1.79[a] | 327 |
| 1340 | Et | O | O | 3-(difluoromethyl)-1-methyl-1H-pyrazol-4-yl | (2-methyltetrahydrofuran-2-yl)methyl | 2.54[a] | 369 |
| 1341 | Et | O | O | 3-(difluoromethyl)-1-methyl-1H-pyrazol-4-yl | 1,3-dimethoxypropan-2-yl | 2.42[a] | 373 |
| 1342 | Et | O | O | 3-(difluoromethyl)-1-methyl-1H-pyrazol-4-yl | 1-cyanobutan-2-yl | 2.39[a] | 352 |
| 1343 | Et | O | O | 3-(difluoromethyl)-1-methyl-1H-pyrazol-4-yl | hexan-3-yl | 3.51[a] | 355 |
| 1433 | Et | O | O | 3-(difluoromethyl)-1-methyl-1H-pyrazol-4-yl | 1-methoxypentan-2-yl | 3.06[a] | 371 |
| 1435 | Et | O | O | 3-(difluoromethyl)-1-methyl-1H-pyrazol-4-yl | 1,3-diethoxypropan-2-yl | 3.13[a] | 401 |
| 1346 | Et | O | O | 3-(difluoromethyl)-1-methyl-1H-pyrazol-4-yl | 4,4,4-trifluorobutan-2-yl | 2.77[a] | 381 |
| 1347 | Et | O | O | 3-(difluoromethyl)-1-methyl-1H-pyrazol-4-yl | 2-(2-bromophenoxy)ethyl | 3.35[a] | 469 |
| 1348 | Et | O | O | 3-(difluoromethyl)-1-methyl-1H-pyrazol-4-yl | 2-(2-bromophenyl)propyl | 3.69[a] | 467 |

TABLE 1-continued

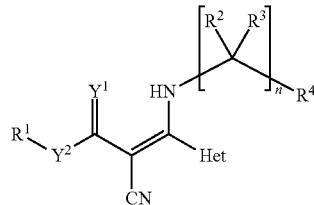

(I)

| No. | R¹ | Y² | Y¹ | Het | R | Log P | M⁺ |
|---|---|---|---|---|---|---|---|
| 1349 | Et | O | O | 3-(difluoromethyl)-1-methyl-1H-pyrazol-4-yl | 2-ethoxy-2-oxo-1-phenylethyl | 3.25[a] | 433 |
| 1350 | Et | O | O | 3-(difluoromethyl)-1-methyl-1H-pyrazol-4-yl | 1-ethoxy-3-methylbutan-2-yl | 3.39[a] | 385 |
| 1351 | Et | O | O | 3-(difluoromethyl)-1-methyl-1H-pyrazol-4-yl | 1-ethoxybutan-2-yl | 3.08[a] | 371 |
| 1352 | Et | O | O | 3-(difluoromethyl)-1-methyl-1H-pyrazol-4-yl | 2-methoxycyclopentyl | 2.78[a] | 369 |
| 1353 | Et | O | O | 3-(difluoromethyl)-1-methyl-1H-pyrazol-4-yl | 2-ethoxycyclopentyl | 3.21[a] | 383 |
| 1354 | Et | O | O | 3-(difluoromethyl)-1-methyl-1H-pyrazol-4-yl | 1-ethoxypentan-2-yl | 3.44[a] | 385 |
| 1355 | Et | O | O | 3-(difluoromethyl)-1-methyl-1H-pyrazol-4-yl | thietan-3-yl | 2.54[a] | 343 |
| 1356 | Et | O | O | 2-chloropyridin-3-yl | oxetan-3-yl | 1.84[a] | 308 |
| 1357 | Et | O | O | 2-chloropyridin-3-yl | (2-methyltetrahydrofuran-2-yl)methyl | 2.7[a] | 350 |
| 1358 | Et | O | O | 2-chloropyridin-3-yl | 1,3-dimethoxypropan-2-yl | 2.56[a] | 354 |
| 1359 | Et | O | O | 2-chloropyridin-3-yl | 1-cyanobutan-2-yl | 2.51[a] | 333 |
| 1360 | Et | O | O | 3-(difluoromethyl)-1-methyl-1H-pyrazol-4-yl | 1-(4-chlorophenyl)cyclopropyl | 3.58[a] | 421 |
| 1361 | Et | O | O | 3-(difluoromethyl)-1-methyl-1H-pyrazol-4-yl | 1-(3-chlorophenyl)cyclopropyl | 3.51[a] | 421 |
| 1362 | Et | O | O | 3-(difluoromethyl)-1-methyl-1H-pyrazol-4-yl | 1-(2-chlorophenyl)cyclopropyl | 3.35[a] | 421 |
| 1363 | Et | O | O | 3-(difluoromethyl)-1-methyl-1H-pyrazol-4-yl | (4-chlorophenyl)-(cyclopropyl)methyl | 3.89[a] | 435 |
| 1364 | Et | O | O | 3-(difluoromethyl)-1-methyl-1H-pyrazol-4-yl | 1-phenylcyclopropyl | 3.21[a] | 387 |
| 1365 | Et | O | O | 3-(difluoromethyl)-1-methyl-1H-pyrazol-4-yl | 1-(2-methylphenyl)ethyl | 3.46[a] | 389 |
| 1366 | Et | O | O | 2-chloropyridin-3-yl | 4,4,4-trifluorobutan-2-yl | 2.92[a] | 362 |
| 1367 | Et | O | O | 2-chloropyridin-3-yl | 1-methoxybutan-2-yl | 2.92[a] | 338 |
| 1368 | Et | O | O | 2-chloropyridin-3-yl | 1-hydroxypentan-2-yl | 2.45[a] | 338 |
| 1369 | Et | O | O | 2-chloropyridin-3-yl | 1,1-dioxidotetrahydrothiophen-3-yl | 1.84[a] | 370 |
| 1370 | Et | O | O | 2-chloropyridin-3-yl | 4-ethoxycyclohexyl | 3.31[a] | 378 |
| 1371 | Et | O | O | 2-chloropyridin-3-yl | pentan-3-yl | 3.35[a] | 322 |
| 1372 | Et | O | O | 2-chloropyridin-3-yl | 1-ethoxybutan-2-yl | 3.31[a] | 352 |
| 1373 | Et | O | O | 2-chloropyridin-3-yl | 2-ethoxycyclopentyl | 3.44[a] | 364 |
| 1374 | Et | O | O | 2-chloropyridin-3-yl | thietan-3-yl | 2.64[a] | 324 |
| 1375 | Et | O | O | 2-chloropyridin-3-yl | 1-methoxypentan-2-yl | 3.31[a] | 352 |
| 1376 | Et | O | O | 2-chloropyridin-3-yl | 1,3-diethoxypropan-2-yl | 3.33[a] | 382 |
| 1377 | Et | O | O | 2-chloropyridin-3-yl | 2-(2-bromophenoxy)ethyl | 3.53[a] | 450 |
| 1378 | Et | O | O | 2-chloropyridin-3-yl | 2-(2-bromophenyl)propyl | 3.94[a] | 448 |
| 1379 | Et | O | O | 2-chloropyridin-3-yl | 2-ethoxy-2-oxo-1-phenylethyl | 3.39[a] | 414 |
| 1380 | Et | O | O | 2-chloro-6-methylpyridin-3-yl | 1-(pyridin-2-yl)ethyl | 2.64[c] T2; 2.53[c] T1; 2.67[b] | |
| 1381 | Et | O | O | 2,6-dichloropyridin-3-yl | 1-(pyridin-2-yl)ethyl | 2.93[c] T1; 3.09[c] T2; 3.06[b] | |
| 1382 | Et | O | O | 3-chloro-2-propylpyridin-4-yl | (1S)-1-(1,3-thiazol-2-yl)ethyl | 3.27[a] | 405 |
| 1383 | Et | O | O | 3-chloro-2-ethylpyridin-4-yl | (1S)-1-(1,3-thiazol-2-yl)ethyl | 2.92[a] | 391 |
| 1384 | Et | O | O | 3-chloro-2-(2-methylpropyl)pyridin-4-yl | (1S)-1-(1,3-thiazol-2-yl)ethyl | 3.64[a] | 419 |
| 1385 | Et | O | O | 3-chloro-2-phenylpyridin-4-yl | (1S)-1-(1,3-thiazol-2-yl)ethyl | 3.31[a] | 439 |
| 1386 | Et | O | O | 2,3-dichloropyridin-4-yl | pent-3-yn-2-yl | 3.44[a] | 353 |
| 1387 | Et | O | O | 2,3-dichloropyridin-4-yl | (2S)-1-(methylamino)-1-oxopropan-2-yl | 2.1[a] | 372 |
| 1388 | Et | O | O | 2,3-dichloropyridin-4-yl | 2-(methylsulfanyl)phenyl | 3.89[a] | 409 |
| 1389 | Et | O | O | 2,3-dichloropyridin-4-yl | 1-(5-methyl-1,3-thiazol-2-yl)ethyl | 3.33[a] | 412 |
| 1390 | Et | O | O | 2,3-dichloropyridin-4-yl | pentan-2-yl | 3.99[a] | 357 |
| 1391 | Et | O | O | 2-bromo-3-chloropyridin-4-yl | 1-(pyridin-2-yl)ethyl | 3.09[a] | 436 |
| 1392 | Et | O | O | 2,3-dichloropyridin-4-yl | (2S)-1-methoxypropan-2-yl | 3.06[a] | 359 |
| 1393 | Et | O | O | 3-chloro-2-(methyl-sulfanyl)pyridin-4-yl | 1-(pyridin-2-yl)ethyl | 3.35[a] | 403 |
| 1394 | Et | O | O | 3-(trifluoromethyl)pyridin-4-yl | 1-(pyridin-2-yl)ethyl | 2.7[a] | 391 |

TABLE 1-continued

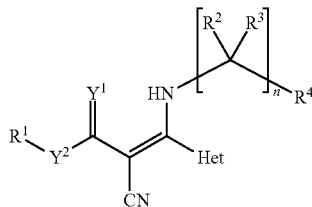

(I)

| No. | R¹ | Y² | Y¹ | Het | R | Log P | M⁺ |
|---|---|---|---|---|---|---|---|
| 1395 | Et | O | O | 2-bromo-3-fluoropyridin-4-yl | 1-(pyridin-2-yl)ethyl | 3[a] | 419 |
| 1396 | Et | O | O | 3-chloro-2-ethylpyridin-4-yl | 1-(pyridin-2-yl)ethyl | 2.96[a] | 385 |
| 1397 | Et | O | O | 3-chloro-2-propylpyridin-4-yl | 1-(pyridin-2-yl)ethyl | 3.29[a] | 399 |
| 1398 | Et | O | O | 3-chloro-2-phenylpyridin-4-yl | 1-(pyridin-2-yl)ethyl | 3.33[a] | 433 |
| 1399 | Et | O | O | 3-chloro-2-ethylpyridin-4-yl | (2S)-3-methylbutan-2-yl | 4.02[a] | 350 |
| 1400 | Et | O | O | 3-chloro-2-propylpyridin-4-yl | (2S)-3-methylbutan-2-yl | 4.41[a] | 364 |
| 1401 | Et | O | O | 3-chloro-2-(methyl-sulfanyl)pyridin-4-yl | (2S)-3-methylbutan-2-yl | 4.44[a] | 368 |
| 1402 | Et | O | O | 3-chloro-2-(2-methyl-propyl)pyridin-4-yl | (2S)-3-methylbutan-2-yl | 4.81[a] | 378 |
| 1403 | Et | O | O | 3-chloro-2-phenylpyridin-4-yl | (2S)-3-methylbutan-2-yl | 4.34[a] | 398 |
| 1404 | Et | O | O | 3-bromo-2-chloropyridin-4-yl | 1-(pyridin-2-yl)ethyl | 3.06[a] | 436 |
| 1405 | Et | O | O | 3-bromo-2-chloropyridin-4-yl | (2S)-3-methylbutan-2-yl | 3.92[a] | 401 |
| 1406 | Et | O | O | 3-bromo-2-chloropyridin-4-yl | 1-(1,3-thiazol-2-yl)ethyl | 2.96[a] | 442 |
| 1407 | propargyl | NH | O | 3-(difluoromethyl)-1-methyl-1H-pyrazol-4-yl | 1-(pyridin-2-yl)ethyl | 1.89[a] | 385 |
| 1408 | Et | NH | O | 3-bromo-2-chloropyridin-4-yl | (2S)-3-methylbutan-2-yl | 3.53[a] | 400 |
| 1409 | Et | O | O | 2,3-dibromopyridin-4-yl | 1-(pyridin-2-yl)ethyl | 3.11[a] | 481 |
| 1410 | Et | O | O | 2,3-dibromopyridin-4-yl | (2S)-3-methylbutan-2-yl | 3.96[a] | 446 |
| 1411 | Et | NH | O | 3-bromo-2-chloropyridin-4-yl | 1-(pyridin-2-yl)ethyl | 2.55[a] | 435 |
| 1412 | Et | O | O | 2-chloropyridin-3-yl | (3-chloropyridin-2-yl)methyl | 2.78[a] | 378 |
| 1413 | Et | O | O | 2-chloropyridin-3-yl | (3-chloropyridin-2-yl)methyl | 2.77[a] | 377 |
| 1414 | Et | O | O | 2-chloropyridin-3-yl | 1-(furan-1-yl)ethyl | 2.92[a] | 346 |
| 1415 | Et | O | O | 2-chloropyridin-3-yl | 1-(pyrazin-2-yl)ethyl | 2.13[a] | 358 |
| 1416 | Et | O | O | 2-chloropyridin-3-yl | (1S)-1-(4-cyclopropyl-1,3-thiazol-2-yl)ethyl | 3.37[a] | 403 |
| 1417 | Et | O | O | 3-(difluoromethyl)-1-methyl-1H-pyrazol-4-yl | 1,1,1-trifluoro-4-methylpentan-2-yl | 3.8[a] | 409 |
| 1418 | Et | O | O | 3-(difluoromethyl)-1-methyl-1H-pyrazol-4-yl | tBu | 2.66[a] | 327 |
| 1419 | Et | O | O | 3-(difluoromethyl)-1-methyl-1H-pyrazol-4-yl | iPr | 2.53[a] | 313 |
| 1420 | Et | O | O | 3-(difluoromethyl)-1-methyl-1H-pyrazol-4-yl | 1,1-dioxidotetrahydrothiophen-3-yl | 1.79[a] | 389 |
| 1421 | Et | O | O | 3-(difluoromethyl)-1-methyl-1H-pyrazol-4-yl | 2-methylbutan-2-yl | 2.96[a] | 341 |
| 1422 | Et | O | O | 3-(difluoromethyl)-1-methyl-1H-pyrazol-4-yl | 1-cyano-2-methylpropyl | 2.76[a] | 352 |
| 1423 | Et | O | O | 3-(difluoromethyl)-1-methyl-1H-pyrazol-4-yl | (3-methyloxetan-3-yl)methyl | 2.04[a] | 355 |
| 1424 | Et | O | O | 3-(difluoromethyl)-1-methyl-1H-pyrazol-4-yl | 1,1,1-trifluoropentan-2-yl | 3.53[a] | 395 |
| 1425 | Et | O | O | 2-chloropyridin-3-yl | 2-methylbutan-2-yl | 3.23[a] | 322 |
| 1426 | Et | O | O | 3-(difluoromethyl)-1-methyl-1H-pyrazol-4-yl | 2-(methylsulfanyl)-5-(trifluoromethyl)phenyl | 3.67[a] | 461 |
| 1427 | Et | O | O | 3-(difluoromethyl)-1-methyl-1H-pyrazol-4-yl | 2-(1,1,1,3,3,3-hexafluoro-2-hydroxypropan-2-yl)phenyl | 3.25[a] | 513 |
| 1428 | Et | O | O | 3-(difluoromethyl)-1-methyl-1H-pyrazol-4-yl | 3,3,3-trifluoro-1-phenylpropyl | 3.37[a] | 443 |
| 1429 | Et | O | O | 2-chloropyridin-3-yl | (3-methyloxetan-3-yl)methyl | 2.11[a] | 336 |
| 1430 | Et | O | O | 2-chloropyridin-3-yl | 1-(prop-1-yn-1-yl)cyclohexyl | 4.06[a] | 372 |
| 1431 | Et | O | O | 2-chloropyridin-3-yl | 1-ethoxy-3-methylbutan-2-yl | 3.69[a] | 366 |
| 1432 | Et | O | O | 2-chloropyridin-3-yl | 2-methoxycyclopentyl | 2.96[a] | 350 |
| 1433 | Et | O | O | 2-chloropyridin-3-yl | 1-ethoxypentan-2-yl | 3.73[a] | 366 |
| 1434 | Et | O | O | 2-chloropyridin-3-yl | hexan-3-yl | 3.8[a] | 336 |
| 1435 | Et | O | O | 2-chloropyridin-3-yl | 1-cyano-2-methylpropyl | 2.76[a] | 333 |
| 1436 | Et | O | O | 2-chloropyridin-3-yl | 6,7-dihydro-5H-cyclopenta[b]pyridin-7-yl | 2.4[a] | 369 |
| 1437 | Et | O | O | 2-chloropyridin-3-yl | 1-(6-chloropyridin-3-yl)ethyl | 2.8[a] | 392 |
| 1438 | Et | O | O | 2-chloropyridin-3-yl | 1-(6-methoxypyridin-2-yl)ethyl | 3.5[a] | 387 |
| 1439 | Et | O | O | 2-chloropyridin-3-yl | 1-(6-chloropyridin-2-yl)ethyl | 3.2[a] | 392 |
| 1440 | Et | O | O | 2-chloropyridin-3-yl | 1-(6-methylpyridin-2-yl)ethyl | 2.56[a] | 371 |
| 1441 | Et | O | O | 2-chloropyridin-3-yl | 1-(quinolin-2-yl)ethyl | 3.37[a] | 407 |
| 1442 | Et | O | O | 2-chloropyridin-3-yl | 1-(4-methylpyridin-2-yl)ethyl | 2.6[a] | 371 |
| 1443 | Et | O | O | 2-chloropyridin-3-yl | (1E,2S)-1-(hydroxyimino)-propan-2-yl | 1.68[c] T1; 1.86[c] T2; 1.78[b] | |

TABLE 1-continued

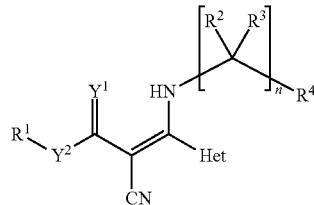

(I)

| No. | R¹ | Y² | Y¹ | Het | R | Log P | M⁺ |
|---|---|---|---|---|---|---|---|
| 1444 | Et | O | O | 2-chloropyridin-3-yl | 1-(2-chloro-1,3-thiazol-5-yl)ethyl | 3.1[a] | 397 |
| 1445 | Et | O | O | 2-chloropyridin-3-yl | 1-(5-chloropyridin-2-yl)ethyl | 3.3[a] | 391 |
| 1446 | Et | O | O | 2-chloropyridin-3-yl | 1-(4-chloro-6-methylpyridin-2-yl)ethyl | 3.4[a] | 405 |
| 1447 | Et | O | O | 2-chloropyridin-3-yl | 1-(2-phenyl-1,3-thiazol-4-yl)ethyl | 4[a] | 439 |
| 1448 | Et | O | O | 2-chloropyridin-3-yl | 1-[3-(methylsulfanyl)pyridin-2-yl]ethyl | 3.1[a] | 403 |
| 1449 | Et | O | O | 2-chloropyridin-3-yl | 1-(4-chloropyridin-2-yl)ethyl | 3[a] | 391 |
| 1450 | allyl | O | O | 2,6-dichloropyridin-3-yl | 1-(1,3-thiazol-2-yl)ethyl | 3.24[c] T2; 3.04[c] T1; 3.16[b] | |
| 1451 | cPr | NH | O | 2-chloropyridin-3-yl | (2S)-3-methylbutan-2-yl | 2.74[c]; 2.76[b] | |
| 1452 | thietan-3-yl | NH | O | 2-chloropyridin-3-yl | (2S)-3-methylbutan-2-yl | 3.22[c]; 3.22[b] | |
| 1453 | cBu | NH | O | 2-chloropyridin-3-yl | (2S)-3-methylbutan-2-yl | 3.44[c]; 3.44[b] | |
| 1454 | ethoxy | NH | O | 2-chloropyridin-3-yl | (2S)-3-methylbutan-2-yl | 2.44[c]; 2.44[b] | |
| 1455 | oxetan-3-yl | NH | O | 2-chloropyridin-3-yl | (2S)-3-methylbutan-2-yl | 2.24[c]; 2.26[b] | |
| 1456 | 2-fluoro-cyclopropyl | NH | O | 2-chloropyridin-3-yl | (2S)-3-methylbutan-2-yl | 2.83[c]; 2.83[b] | |
| 1457 | Et | O | O | 2-[4-(trifluoromethyl)-phenyl]pyridin-3-yl | (2S)-3-methylbutan-2-yl | 4.23[c]; 4.25[b] | |
| 1458 | allyl | NH | O | 2-chloropyridin-3-yl | (2S)-3-methylbutan-2-yl | 3[c]; 3[b] | |
| 1459 | OMe | NH | O | 2,6-dichloropyridin-3-yl | 1-(1,3-thiazol-2-yl)ethyl | 2[c] T1; 2.12[c] T2; 1.94[b] | |
| 1460 | Me | NH | O | 2,6-dichloropyridin-3-yl | 1-(1,3-thiazol-2-yl)ethyl | 2.37[c] T2; 2.19[c] T1; 2.29[b] | |
| 1461 | prop-2-en-1-yloxy | NH | O | 2-chloropyridin-3-yl | (2S)-3-methylbutan-2-yl | 2.66[c]; 2.62[b] | |
| 1462 | Et | O | O | 4-chloro-1,3-thiazol-5-yl | 1-(pyridin-2-yl)ethyl | 2.59[a] | 363 |
| 1463 | Et | O | O | 4-chloro-1,3-thiazol-5-yl | 1-(1,3-thiazol-2-yl)ethyl | 2.59[a] | 369 |
| 1464 | Et | O | O | 4-chloro-1,3-thiazol-5-yl | (1S)-1-(1,3-thiazol-2-yl)ethyl | 2.59[a] | 369 |
| 1465 | Et | O | O | 4-chloro-1,3-thiazol-5-yl | cBu | 3[a] | 312 |
| 1466 | Et | O | O | 4-chloro-1,3-thiazol-5-yl | (1S)-1-cyclopropylethyl | 2.02[a] | 326 |
| 1467 | Et | O | O | 4-chloro-1,3-thiazol-5-yl | (2S)-1-methoxypropan-2-yl | 2.61[a] | 330 |
| 1468 | Et | O | O | 4-chloro-1,3-thiazol-5-yl | (2S)-3-methylbutan-2-yl | 3.46[a] | 328 |
| 1469 | 1,1-dioxido-thietan-3-yl | NH | O | 2-chloropyridin-3-yl | (2S)-3-methylbutan-2-yl | 2.28[c]; 2.29[b] | |
| 1470 | (2R)-1-methoxy-1-oxopropan-2-yl | NH | O | 2-chloropyridin-3-yl | (2S)-3-methylbutan-2-yl | 2.95[c] I2; 2.85[c] I1; 2.96[b] I2; 2.87[b] I1 | |
| 1471 | Et | NH | O | 2,6-dichloropyridin-3-yl | 1-(1,3-thiazol-2-yl)ethyl | 2.54[c] T1; 2.73[c] T2; 2.65[b] | |
| 1472 | Et | O | O | 2-(4-methoxyphenyl)-pyridin-3-yl | (2S)-3-methylbutan-2-yl | 3.54[c]; 3.59[b] | |
| 1473 | Et | O | O | 2-(prop-2-en-1-yloxy)pyridin-2-yl | 1-(pyridin-2-yl)ethyl | 1.78[c]; 2.05[b] | |
| 1474 | Et | S | O | 2-chloropyridin-3-yl | (2S)-3-methylbutan-2-yl | 3.87[a] | 338 |
| 1475 | Et | O | O | 2-(3,4-dichlorophenyl)-pyridin-3-yl | (2S)-3-methylbutan-2-yl | 4.56[c]; 4.56[b] | |
| 1476 | Et | O | O | 4-chloro-1,3-thiazol-5-yl | (2S)-1-(methylamino)-1-oxopropan-2-yl | 1.81[a] | 343 |
| 1477 | Et | O | O | 4-chloro-1,3-thiazol-5-yl | (1R)-1-(2,6-dichlorophenyl)ethyl | 4[a] | 430 |
| 1478 | Et | O | O | 4-chloro-1,3-thiazol-5-yl | (5,6-dimethylpyridin-2-yl)methyl | 1.94[a] | 377 |
| 1479 | H | O | O | 2-chloropyridin-3-yl | (1S)-1-(1,3-thiazol-2-yl)ethyl | 1.01[a] | 335 |
| 1480 | Et | O | O | 4-chloro-1,3-thiazol-5-yl | 3-methoxybutan-2-yl | 2.94[a] | 344 |
| 1481 | Et | O | O | 4-chloro-1,3-thiazol-5-yl | 3-methylpentan-2-yl | 3.92[a] | 342 |
| 1482 | Et | O | O | 5-chloro-1-methyl-1H-pyrazol-4-yl | (1S)-1-cyclopropylethyl | 2.98[a] | 323 |
| 1483 | Et | O | O | 5-chloro-1-methyl-1H-pyrazol-4-yl | 1-(1,3-thiazol-2-yl)ethyl | 2.42[a] | 366 |

TABLE 1-continued

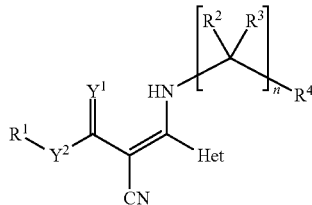
(I)

| No. | R¹ | Y² | Y¹ | Het | R | Log P | M⁺ |
|---|---|---|---|---|---|---|---|
| 1484 | Et | O | O | 5-chloro-1-methyl-1H-pyrazol-4-yl | 1-(pyridin-2-yl)ethyl | 2.35[a] | 360 |
| 1485 | Et | O | O | 5-chloro-1-methyl-1H-pyrazol-4-yl | (2S)-3-methylbutan-2-yl | 3.25[a] | 325 |
| 1486 | Et | O | O | 5-chloro-1-methyl-1H-pyrazol-4-yl | (2S)-1-methoxypropan-2-yl | 2.42[a] | 327 |
| 1487 | Et | O | O | 5-chloro-1-methyl-1H-pyrazol-4-yl | cBu | 2.82[a] | 309 |
| 1488 | Et | O | O | 5-chloro-1-methyl-1H-pyrazol-4-yl | (2S)-1-(methylamino)-1-oxopropan-2-yl | 1.63[a] | 340 |
| 1489 | Et | S | O | 2-chloropyridin-3-yl | (1S)-1-(1,3-thiazol-2-yl)ethyl | 2.9[a] | 379 |
| 1490 | allyl | O | O | 2-chloropyridin-3-yl | (1S)-1-(1,3-thiazol-2-yl)ethyl | 2.62[a] | |
| 1491 | R¹ & Y² = pyrrolidin-1-yl | | O | 2-chloropyridin-3-yl | (2S)-3-methylbutan-2-yl | 3.02[a] | 347 |
| 1492 | 2-MeOEt | NH | O | 2-chloropyridin-3-yl | (2S)-3-methylbutan-2-yl | 2.73[a] | 351 |
| 1493 | cyclopentyl | NH | O | 2-chloropyridin-3-yl | (2S)-3-methylbutan-2-yl | 3.9[a] | 361 |
| 1494 | iBu | NH | O | 2-chloropyridin-3-yl | (2S)-3-methylbutan-2-yl | 3.74[a] | 349 |
| 1495 | 2,2-dimethyl-cyclopropyl | NH | O | 2-chloropyridin-3-yl | (2S)-3-methylbutan-2-yl | 3.72[a] | 361 |
| 1496 | Et | O | O | quinolin-4-yl | (2S)-3-methylbutan-2-yl | 3.29[a] | 338 |
| 1497 | Et | O | O | quinolin-4-yl | 1-(pyridin-2-yl)ethyl | 2.5[a] | 373 |
| 1498 | Et | O | O | quinolin-4-yl | cBu | 2.88[a] | 322 |
| 1499 | Et | O | O | quinolin-4-yl | (2S)-1-methoxypropan-2-yl | 2.5[a] | 340 |
| 1500 | Et | O | O | quinolin-4-yl | 1-cyclopropylethyl | 3.02[a] | 336 |
| 1501 | Et | O | O | 5-chloro-1-methyl-1H-pyrazol-4-yl | (1S)-1-(1,3-thiazol-2-yl)ethyl | 2.42[a] | 366 |
| 1502 | Et | O | O | quinolin-4-yl | (1S)-1-(1,3-thiazol-2-yl)ethyl | 2.5[a] | 379 |
| 1503 | Et | O | O | quinolin-4-yl | (2S)-1-(methylamino)-1-oxopropan-2-yl | 1.8[a] | 353 |
| 1504 | Et | O | O | pyridin-3-yl | (2S)-3-methylbutan-2-yl | 2.61[c]; 2.67[b] | |
| 1505 | Et | O | O | 2-(thiophen-2-yl)pyridin-3-yl | (2S)-3-methylbutan-2-yl | 3.7[c]; 3.7[b] | |
| 1506 | Et | O | O | 2-(prop-2-en-1-yloxy)pyridin-3-yl | 1-(1,3-thiazol-2-yl)ethyl | 2.03[c]; 2.03[b] | |
| 1507 | R¹ & Y² = thiomorpholin-4-yl | | O | 2-chloropyridin-3-yl | (2S)-3-methylbutan-2-yl | 3.27[a] | 379 |
| 1508 | R¹ & Y² = piperidin-1-yl | | O | 2-chloropyridin-3-yl | (2S)-3-methylbutan-2-yl | 3.48[a] | 361 |
| 1509 | R¹ & Y² = 1,3-thiazolidin-3-yl | | O | 2-chloropyridin-3-yl | (2S)-3-methylbutan-2-yl | 3.19[a] | 365 |
| 1510 | 2-(methyl-sulfanyl)-ethyl | NH | O | 2-chloropyridin-3-yl | (2S)-3-methylbutan-2-yl | 3.29[a] | 367 |
| 1511 | 2-methyl-cyclobutyl | NH | O | 2-chloropyridin-3-yl | (2S)-3-methylbutan-2-yl | 4.01[a] | 361 |
| 1512 | 3-methyl-cyclobutyl | NH | O | 2-chloropyridin-3-yl | (2S)-3-methylbutan-2-yl | 4.01[a] | 361 |
| 1513 | cPr | NMe | O | 2-chloropyridin-3-yl | (2S)-3-methylbutan-2-yl | 3.02[a] | 347 |
| 1514 | Et | NOMe | O | 2-chloropyridin-3-yl | (2S)-3-methylbutan-2-yl | 3.15[a] | 351 |
| 1515 | pyridin-4-yl | NH | O | 2-chloropyridin-3-yl | (2S)-3-methylbutan-2-yl | 1.58[a] | 370 |
| 1516 | pyridin-2-yl | NH | O | 2-chloropyridin-3-yl | (2S)-3-methylbutan-2-yl | 3.21[a] | 370 |
| 1517 | pyridin-2-ylmethyl | NH | O | 2-chloropyridin-3-yl | (2S)-3-methylbutan-2-yl | 1.94[a] | 384 |
| 1518 | R¹ & Y² = morpholin-4-yl | | O | 2-chloropyridin-3-yl | (2S)-3-methylbutan-2-yl | 2.58[a] | 363 |
| 1519 | Et | O | O | 2-(thiophen-3-yl)pyridin-3-yl | (2S)-3-methylbutan-2-yl | 3.55[c]; 3.55[c]; 3.57[b]; 3.57[b] | |
| 1520 | Et | O | O | 2-chloropyridin-3-yl | 1-(5-methyl-1,3-thiazol-2-yl)ethyl | 2.92[a] | |
| 1521 | Et | O | O | 2-chloropyridin-3-yl | 4-methylpent-1-yn-3-yl | 3.37[a] | |
| 1522 | Et | O | O | 2-chloropyridin-3-yl | 1-(trimethylsilyl)ethyl | 3.87[a] | |
| 1523 | Et | O | O | 2-chloropyridin-3-yl | (1S)-1-(2,6-dichlorophenyl)ethyl | 3.73[a] | |
| 1524 | Et | O | O | 2-chloropyridin-3-yl | 1-(2-methyl-1,3-thiazol-4-yl)ethyl | 2.84[a] | |

TABLE 1-continued

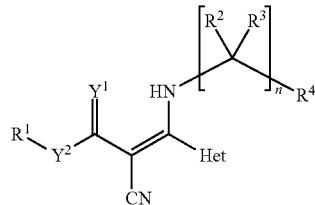

(I)

| No. | R[1] | Y[2] | Y[1] | Het | R | Log P | M[+] |
|---|---|---|---|---|---|---|---|
| 1525 | Et | O | O | 2-chloropyridin-3-yl | 3-methylpentan-2-yl | 3.76[a] | 336 |
| 1526 | Et | O | O | 2-chloropyridin-3-yl | (5,6-dimethylpyridin-2-yl)methyl | 1.91[a] | 371 |
| 1527 | Et | O | O | 2-chloropyridin-3-yl | 3-methoxybutan-2-yl | 2.8[a] | |
| 1528 | Et | O | O | 2-chloropyridin-3-yl | 1-[4-(trifluoromethyl)pyrimidin-5-yl]ethyl | 2.63[a] | |
| 1529 | Et | O | O | 2-chloropyridin-3-yl | 1-(imidazo[2,1-b][1,3]thiazol-6-yl)ethyl | 2.35[a] | |
| 1530 | Et | O | O | 2-chloropyridin-3-yl | 1-(2-bromophenyl)ethyl | 3.89[a] | |
| 1531 | Et | O | O | 2-chloropyridin-3-yl | 1-(tetrahydrofuran-2-yl)ethyl | 2.71[a] | |
| 1532 | Et | O | O | 2-chloropyridin-3-yl | 1-(2-fluorophenyl)ethyl | 3.48[a] | |
| 1533 | Et | O | O | 2-chloropyridin-3-yl | 1-(1-methylcyclopropyl)ethyl | 3.46[a] | |
| 1534 | Et | O | O | 2-chloropyridin-3-yl | (1S)-1-(2,6-dimethylphenyl)ethyl | 3.96[a] | |
| 1535 | Et | O | O | 2-chloropyridin-3-yl | (1S)-1-(2,6-difluorophenyl)ethyl | 3.27[a] | |
| 1536 | Et | O | O | 2-chloropyridin-3-yl | 1-(4-methyl-1,3-thiazol-2-yl)ethyl | 2.88[a] | |
| 1537 | Et | O | O | 2-chloropyridin-3-yl | 2-methyl-2H-indazol-7-yl | 2.68[a] | |
| 1538 | Et | O | O | 2-chloropyridin-3-yl | 2-methyl-1-(4-methylpyrimidin-5-yl)propyl | 2.28[a] | |
| 1539 | Et | O | O | 2-chloropyridin-3-yl | (2S)-1-(benzyloxy)-1-oxopropan-2-yl | 3.53[a] | |
| 1540 | Et | O | O | 2-(furan-2-yl)pyridin-3-yl | (2S)-3-methylbutan-2-yl | 3.21[c] I2; 3.21[c] I2; 3.19[c] I1; 3.19[c] I1; 3.21[c] I2; 3.19[b] I1; 3.19[b] I1; 3.21[b] I2 | |
| 1541 | Et | O | O | 2-(4-fluorophenyl)pyridin-3-yl | (2S)-3-methylbutan-2-yl | 3.7[c]; 3.7[c]; 3.68[b]; 3.7[b] | |
| 1542 | Et | O | O | 5-chloro-1-methyl-1H-pyrazol-4-yl | (5,6-dimethylpyridin-2-yl)methyl | 1.66[a] | 374 |
| 1543 | Et | O | O | 5-chloro-1-methyl-1H-pyrazol-4-yl | 3-methoxybutan-2-yl | 2.67[a] | 341 |
| 1544 | Et | O | O | 5-chloro-1-methyl-1H-pyrazol-4-yl | 3-methylpentan-2-yl | 3.6[a] | 339 |
| 1545 | Et | O | O | 2-bromopyridin-3-yl | (2S)-3-methylbutan-2-yl | 3.27[c]; 3.27[c]; 3.26[b]; 3.27[b] | |
| 1546 | Et | O | O | 2-bromopyridin-3-yl | 1-(pyridin-2-yl)ethyl | 2.46[c] T2; 2.47[c] T2; 2.34[c] T1; 2.35[c] T1; 2.49[b] T1; 2.5[b] | |
| 1547 | Et | O | O | 2-bromopyridin-3-yl | 1-(1,3-thiazol-2-yl)ethyl | 2.35[c] T1; 2.34[c] T1; 2.53[c] T2; 2.52[c] T2; 2.44[b]; 2.44[b] | |
| 1548 | Et | O | O | 2-chloropyridin-3-yl | 1-(4,5,6,7-tetrahydro-1,3-benzothiazol-2-yl)ethyl | 3.21[a] | 417 |
| 1549 | Et | O | O | 2-chloropyridin-3-yl | 2,2,2-trifluoro-1-(pyridin-2-yl)ethyl | 3.17[a] | 411 |
| 1550 | Et | O | O | 2-chloropyridin-3-yl | 1-phenylcyclobutyl | 3.73[a] | 382 |
| 1551 | Et | O | O | 2-chloropyridin-3-yl | 1-(ethoxycarbonyl)cyclobutyl | 3.17[a] | 378 |
| 1552 | Et | O | O | 2-chloropyridin-3-yl | 1-(2,5-dimethyl-1,3-thiazol-4-yl)ethyl | 2.84[a] | 391 |
| 1553 | Et | O | O | 2-chloropyridin-3-yl | 1,3-benzothiazol-4-yl | 2.61[a] | 385 |
| 1554 | Et | O | O | 2-chloropyridin-3-yl | [3-(trifluoromethyl)pyridin-2-yl]methyl | 3[a] | 411 |
| 1555 | Et | O | O | 2-chloropyridin-3-yl | 2-methyl-1,3-benzoxazol-4-yl | 3[a] | 383 |
| 1556 | Et | O | O | 2-chloropyridin-3-yl | 2,1,3-benzothiadiazol-4-yl | 3.17[a] | 386 |
| 1557 | Et | O | O | 2-chloropyridin-3-yl | 2-methyl-1-[4-(trifluoromethyl)pyrimidin-5-yl]propyl | 3.55[a] | 454 |
| 1558 | Et | O | O | 2-chloropyridin-3-yl | 1-(2,5-dichlorophenyl)ethyl | 4.13[a] | 424 |
| 1559 | Et | O | O | 5-chloro-1-methyl-1H-pyrazol-4-yl | (1R)-1-(2,6-dichlorophenyl)ethyl | 3.78[a] | 429 |
| 1560 | Et | O | O | 3-(dichloromethyl)-1-methyl-1H-pyrazol-4-yl | 1-cyclopropylethyl | 3.23[a] | 371 |
| 1561 | Et | O | O | 3-(dichloromethyl)-1-methyl-1H-pyrazol-4-yl | 1-cyclobutylethyl | 3.67[a] | 385 |
| 1562 | Et | O | O | 3-(dichloromethyl)-1-methyl-1H-pyrazol-4-yl | (2R)-3-methylbutan-2-yl | 3.46[a] | 373 |
| 1563 | 2-fluoroethyl | NH | O | 2-chloropyridin-3-yl | 1-(1,3-thiazol-2-yl)ethyl | 2[a] | 380 |

TABLE 1-continued

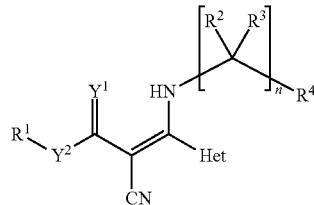

| No. | R¹ | Y² | Y¹ | Het | R | Log P | M⁺ |
|---|---|---|---|---|---|---|---|
| 1564 | Et | O | O | 3-(dichloromethyl)-1-methyl-1H-pyrazol-4-yl | (1R)-1-(1,3-thiazol-2-yl)ethyl | 2.75[a] | 414 |
| 1565 | Et | O | O | 3-(dichloromethyl)-1-methyl-1H-pyrazol-4-yl | 1-(pyridin-2-yl)ethyl | 2.7[a] | 408 |
| 1566 | Et | O | O | 3-(dichloromethyl)-1-methyl-1H-pyrazol-4-yl | cBu | 3.09[a] | 357 |
| 1567 | Et | O | O | 3-(dichloromethyl)-1-methyl-1H-pyrazol-4-yl | (2R)-1-methoxypropan-2-yl | 2.76[a] | 375 |
| 1568 | Et | O | O | 2-(3-chlorophenyl)pyridin-3-yl | (2S)-3-methylbutan-2-yl | 4.07[c]; 4.09[b] | |
| 1569 | Et | O | O | 2-(4-hydrophenyl)pyridin-3-yl | (2S)-3-methylbutan-2-yl | | |
| 1570 | Et | O | O | 2-(benzyloxy)pyridin-3-yl | (1S)-1-cyclopropylethyl | 3.08[c]; 3.08[b] | |
| 1571 | H | O | O | 2-chloropyridin-3-yl | 1-(pyridin-2-yl)ethyl | 1.37[a] | 329 |
| 1572 | allyl | O | O | 2-chloropyridin-3-yl | 1-(pyridin-2-yl)ethyl | 2.66[a] | 369 |
| 1573 | Et | O | O | 3-(dichloromethyl)-1-methyl-1H-pyrazol-4-yl | (2S)-1-(methylamino)-1-oxopropan-2-yl | 3.9[a] | 388 |
| 1574 | Et | O | O | 3-(dichloromethyl)-1-methyl-1H-pyrazol-4-yl | 1-(2,6-dichlorophenyl)ethyl | 3.94[a] | 477 |
| 1575 | Et | O | O | 3-(dichloromethyl)-1-methyl-1H-pyrazol-4-yl | (5,6-dimethylpyridin-2-yl)methyl | 2.07[a] | 422 |
| 1576 | Et | O | O | 3-(dichloromethyl)-1-methyl-1H-pyrazol-4-yl | 3-methoxybutan-2-yl | 2.98[a] | 389 |
| 1577 | Et | O | O | 3-(dichloromethyl)-1-methyl-1H-pyrazol-4-yl | 3-methylpentan-2-yl | 3.8[a] | 387 |
| 1578 | Et | O | O | 2,5-dichlorothiophen-3-yl | (1S)-1-(1,3-thiazol-2-yl)ethyl | 3.58[a] | 402 |
| 1579 | Et | O | O | 2,5-dichlorothiophen-3-yl | 1-(pyridin-2-yl)ethyl | 3.59[a] | 369 |
| 1580 | Et | O | O | 2,5-dichlorothiophen-3-yl | (2S)-3-methylbutan-2-yl | 4.68[a] | 361 |
| 1581 | Et | O | O | 2,5-dichlorothiophen-3-yl | cBu | 4.26[a] | 345 |
| 1582 | Et | O | O | 2-chloropyridin-3-yl | 6-methylheptan-2-yl | 4.47[c] I2; 4.45[c] I1; 4.47[b] | |
| 1583 | OMe | NH | O | 2-chloropyridin-3-yl | 1-(pyridin-2-yl)ethyl | 1.46[a] | 358 |
| 1584 | Et | NH | O | 2-chloropyridin-3-yl | 1-(pyridin-2-yl)ethyl | 1.93[a] | 356 |
| 1585 | Et | O | O | 2-(4-cyanophenyl)pyridin-3-yl | (2S)-3-methylbutan-2-yl | 3.26[c] I1; 3.29[c] I2; 3.29[b] I1; 3.3[b] I2 | |
| 1586 | Et | O | O | 2-[4-(trifluoromethoxy)phenyl]pyridin-3-yl | (2S)-3-methylbutan-2-yl | 4.39[c]; 4.41[b] | |
| 1587 | Et | O | O | 2,5-dichlorothiophen-3-yl | 1-cyclopropylethyl | 4.43[a] | 359 |
| 1588 | Et | O | O | 2,5-dichlorothiophen-3-yl | (2S)-1-methoxypropan-2-yl | 3.78[a] | 363 |
| 1589 | Et | O | O | 2,5-dichlorothiophen-3-yl | 1-cyclobutylethyl | 5.03[a] | 373 |
| 1590 | Et | O | O | 2-chloropyridin-3-yl | 2-fluorophenyl | 2.87[c]; 2.85[b] | |
| 1591 | Et | O | O | 2-(pyrimidin-5-yl)pyridin-3-yl | (2S)-3-methylbutan-2-yl | 2.42[c] I2; 2.38[c] I1; 2.42[b] | |
| 1592 | Et | O | O | 2-chloropyridin-3-yl | 1-methyl-2-(methylsulfanyl)-1H-pyrrol-3-yl | 3.01[c]; 3.01[b] | |
| 1593 | 2-fluoro-ethyl | NH | O | 2-chloropyridin-3-yl | 3-methylbutan-2-yl | 2.76[a] | 339 |
| 1594 | R¹ & Y² = 2-methyl-1,3-thiazolidin-3-yl | | O | 2-chloropyridin-3-yl | 1-(1,3-thiazol-2-yl)ethyl | 2.76[a] | 420 |
| 1595 | R¹ & Y² = morpholin-4-yl | | O | 2-chloropyridin-3-yl | 1-(1,3-thiazol-2-yl)ethyl | 1.84[a] | 404 |
| 1596 | 2-methoxy-2-oxoethyl | NH | O | 2-chloropyridin-3-yl | 1-(1,3-thiazol-2-yl)ethyl | 1.9[a] | 406 |
| 1597 | Et | O | O | 2-chloropyridin-3-yl | 3,4-difluorophenyl | 3[c]; 2.96[b] | |
| 1598 | ethoxy | NH | O | 2-chloropyridin-3-yl | 1-(1,3-thiazol-2-yl)ethyl | 1.8[a] | 378 |
| 1599 | R¹ & Y² = 1,2-oxazolidin-2-yl | | O | 2-chloropyridin-3-yl | 1-(1,3-thiazol-2-yl)ethyl | 1.9[a] | 390 |
| 1600 | Et | O | O | 2-chloropyridin-3-yl | 2,4-difluorophenyl | 2.95[c]; 2.9[b] | |
| 1601 | Et | O | O | 2-chloropyridin-3-yl | 1-methyl-2-(methylsulfonyl)-1H-pyrrol-3-yl | 2.07[c]; 2.08[b] | |
| 1602 | allyl | O | O | 2-chloropyridin-3-yl | 2-(methylsulfanyl)phenyl | 3.32[c]; 3.32[b] | |
| 1603 | Et | O | O | 2,5-dichlorothiophen-3-yl | 3-methoxybutan-2-yl | 4.02[a] | 377 |
| 1604 | Et | O | O | 2-chloropyridin-3-yl | 2,3-difluorophenyl | 3[c]; 2.88[b] | |
| 1605 | Et | O | O | 2-chloropyridin-3-yl | 5,6,7,8-tetrahydroquinolin-8-yl | 3[a] | 383 |
| 1606 | Et | O | O | 2-chloropyridin-3-yl | 1-cyclopentylethyl | 3.9[a] | 348 |
| 1607 | Et | O | O | 2-chloropyridin-3-yl | 1-methylcyclobutyl | 3.11[a] | 320 |

TABLE 1-continued

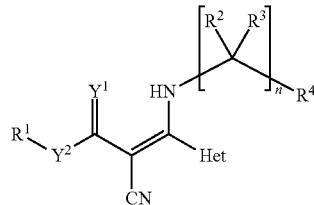

(I)

| No. | R¹ | Y² | Y¹ | Het | R | Log P | M⁺ |
|---|---|---|---|---|---|---|---|
| 1608 | Et | O | O | 2-chloropyridin-3-yl | 1-(1H-pyrazol-5-yl)ethyl | 2.1[a] | 346 |
| 1609 | Et | O | O | 2-chloropyridin-3-yl | 2,5-difluorophenyl | 2.95[c]; 2.83[b] | |
| 1610 | Et | O | O | 2-chloropyridin-3-yl | 3-fluoro-2-methylphenyl | 3.26[c]; 3.24[b] | |
| 1611 | Et | O | O | 2-chloropyridin-3-yl | 3-fluoro-2-methoxyphenyl | 3.13[c]; 3.13[b] | |
| 1612 | R¹ & Y² = 1,2-oxazolidin-2-yl | | O | 2-chloropyridin-3-yl | (2S)-3-methylbutan-2-yl | 2.55[a] | 349 |
| 1613 | 1-methoxy-cyclopropyl | NH | O | 2-chloropyridin-3-yl | (2S)-3-methylbutan-2-yl | 2.75[a] | 363 |
| 1614 | dimethyl-amino | NH | O | 2-chloropyridin-3-yl | (2S)-3-methylbutan-2-yl | 2.08[a] | 336 |
| 1615 | R¹ & Y² = 2-methyl-1,3-thiazolidin-3-yl | | O | 2-chloropyridin-3-yl | (2S)-3-methylbutan-2-yl | 3.6[a] | 379 |
| 1616 | Et | NH | O | 2-chloropyridin-3-yl | 2-(methylsulfanyl)phenyl | 2.85[c]; 2.82[b] | |
| 1617 | Et | O | O | 6-chloropyridin-3-yl | (2S)-3-methylbutan-2-yl | 3.39[c]; 3.41[b] | |
| 1618 | R¹ & Y² = 1,3-thiazolidin-3-yl | | O | 2-chloropyridin-3-yl | (2S)-3-methylbutan-2-yl | 3.1[a] | 365 |
| 1619 | (1Z)-N-methoxy-ethani-midoyl | NH | O | 2-chloropyridin-3-yl | (2S)-3-methylbutan-2-yl | 1.88[a] | 364 |
| 1620 | OMe | NH | O | 2-chloropyridin-3-yl | 2-(methylsulfanyl)phenyl | 2.19[c]; 1.96[b] | |
| 1621 | Et | O | O | 3-chloro-2-(trifluoro-methyl)pyridin-4-yl | cBu | 3.78[a] | 374 |
| 1622 | Et | O | O | 3-chloro-2-(trifluoro-methyl)pyridin-4-yl | (1S)-1-cyclopropylethyl | 3.85[a] | 388 |
| 1623 | Et | O | O | 3-chloro-2-(trifluoro-methyl)pyridin-4-yl | (2S)-1-methoxypropan-2-yl | 3.46[a] | 392 |
| 1624 | Et | O | O | 3-chloro-2-(trifluoro-methyl)pyridin-4-yl | 1-(tetrahydrofuran-2-yl)ethyl | 3.62[a] | 418 |
| 1625 | Et | O | O | 3-chloro-2-(trifluoro-methyl)pyridin-4-yl | 1-(pyridin-2-yl)ethyl | 3.33[a] | 425 |
| 1626 | Et | O | O | 3-chloro-2-(trifluoro-methyl)pyridin-4-yl | 1-(1,3-thiazol-2-yl)ethyl | 3.46[a] | 431 |
| 1627 | Et | O | O | 3-chloro-2-(trifluoro-methyl)pyridin-4-yl | (2S)-3-methylbutan-2-yl | 4.18[a] | 390 |
| 1628 | methyl-amino | NMe | O | 2-chloropyridin-3-yl | (2S)-3-methylbutan-2-yl | 1.3[a] | 336 |
| 1629 | Et | O | O | 2-chloropyridin-3-yl | 1-(4,5-dihydro-1,3-thiazol-2-yl)ethyl | 2.5[a] | 365 |
| 1630 | Et | O | O | 2,5-dichlorothiophen-3-yl | cyclohexyl | 4.92[a] | 373 |
| 1631 | Et | O | O | 2,5-dichlorothiophen-3-yl | (2S)-1-(cyclohexylamino)-1-oxopropan-2-yl | 3.83[a] | 444 |
| 1632 | Et | O | O | 2,5-dichlorothiophen-3-yl | (2S)-1-(methylamino)-1-oxopropan-2-yl | 2.46[a] | 376 |
| 1633 | Et | O | O | 2-chloropyridin-3-yl | (3Z)-3-(methoxyimino)butan-2-yl | 2.8[a] | 351 |
| 1634 | Et | O | O | 2-chloropyridin-3-yl | 1,1'-bi(cyclopropyl)-2-yl | 3.13[a] | 332 |
| 1635 | Et | O | O | 2-chloropyridin-3-yl | 2-(propan-2-yl)cyclopropyl | 3.53[a] | 334 |
| 1636 | Et | O | O | 2-chloropyridin-3-yl | (3Z)-3-(ethoxyimino)butan-2-yl | 3.29[a] | 365 |
| 1637 | Et | O | O | 2-chloropyridin-3-yl | 1-(1-methyl-1H-imidazol-2-yl)ethyl | 0.93[a] | 360 |
| 1638 | Et | O | O | 2-chloropyridin-3-yl | 1-[5-chloro-4-(trifluoromethyl)-pyridin-2-yl]ethyl | 3.9[a] | 459 |
| 1639 | Et | O | O | 2-chloropyridin-3-yl | 1-(4,6-dichloropyridin-2-yl)ethyl | 3.7[a] | 425 |
| 1640 | Et | O | O | 1-(difluoromethyl)-1H-pyrazol-5-yl | 1-cyclobutylethyl | 3.56[a] | 339 |
| 1641 | Et | O | O | 2-chloropyridin-3-yl | 1-ethylcyclopropyl | 3.13[a] | 320 |
| 1642 | Et | O | O | 2-chloropyridin-3-yl | 1-(cyclopropylmethyl)-cyclopropyl | 3.53[a] | 346 |
| 1643 | Et | O | O | 2-chloropyridin-3-yl | (2S)-1-phenylpropan-2-yl | 3.5[a] | 370 |
| 1644 | Et | O | O | 1-(difluoromethyl)-1H-pyrazol-5-yl | (1S)-1-(1,3-thiazol-2-yl)ethyl | 2.51[a] | 368 |
| 1645 | Et | O | O | 1-(difluoromethyl)-1H-pyrazol-5-yl | (2R)-3-methylbutan-2-yl | 3.27[a] | 327 |

TABLE 1-continued (I)

[Structure: R¹-Y²=Y¹ double bond system with HN-C(R²)(R³)-(CH)ₙ-R⁴ and Het, CN substituents]

| No. | R¹ | Y² | Y¹ | Het | R | Log P | M⁺ |
|---|---|---|---|---|---|---|---|
| 1646 | Et | O | O | 1-(difluoromethyl)-1H-pyrazol-5-yl | (1S)-1-(pyridin-2-yl)ethyl | 2.55[a] | 362 |
| 1647 | Et | O | O | 1-(difluoromethyl)-1H-pyrazol-5-yl | (1R)-1-cyclopropylethyl | 3.01[a] | 325 |
| 1648 | Et | O | O | 5-chloro-3-ethyl-1-methyl-1H-pyrazol-4-yl | 1-cyclobutylethyl | 3.94[a] | 365 |
| 1649 | Et | O | O | 2-chloropyridin-3-yl | (1S)-1-(2,6-dichlorophenyl)ethyl | 3.8[a] | 425 |
| 1650 | Et | O | O | 4-chloro-1,3-thiazol-5-yl | (2S)-3-methylbutan-2-yl | | 328 |

Chiral groups in table 1 show those R and/or S values, which can be found in the examples IUPAC names (product orientated chirality specification).

Abbreviations for isomers and tautomers: I1 means isomer 1; I2 means isomer 2; T1 means tautomer 1; T2 means tautomer 2.

Me=methyl, Et=ethyl, nPr=n-propyl, iPr=propan-2-yl, cPr=cyclopropyl, nBu=n-butyl, iBu=2-methylpropyl, sBu=sec-butyl, tBu=tert-butyl, cBu=cyclobutyl, Pn=pentyl, Hx=hexyl, cHx=cyclohexyl, OMe=methoxy, allyl=prop-2-en-1-yl, propargyl=prop-2-yn-1-yl, MeOEt=methoxyethyl, EtOEt=ethoxyethyl, F₃iPr=1,1,1-trifluoropropan-2-yl Measurement of logP values was performed according EEC directive 79/831 Annex V.A8 by HPLC (High Performance Liquid Chromatography) on reversed phase columns with the following methods:

[a] measurement of LC-MS was done at pH 2.7 with 0.1% formic acid in water and with acetonitrile (contains 0.1% formic acid) as eluent with a linear gradient from 10% acetonitrile to 95% acetonitrile. [b] Measurement was done at pH 7.5 with 0.005 molar aqueous KH₂PO₄ buffer and acetonitrile as eluent. [c] Measurement was done at pH 2.3 with 0.1% (w/w) phosphoric acid and acetonitrile as eluent. Calibration was done with not branched alkan2-ones (with 3 to 16 carbon atoms) with known logP-values (measurement of logP values using retention times with linear interpolation between successive alkanones). Lambda$_{max}$ values were determined using UV-spectra from 200 nm to 400 nm and the peak values of the chromatographic signals. In table 1, M⁺H (or M H) means the molecular ion peak, plus or minus 1 a.m.u. (atomic mass unit) respectively, as observed in mass spectroscopy and M (APCI⁺) means the molecular ion peak as it was found via positive atmospheric pressure chemical ionization in mass spectroscopy. *M-1 was measured for these examples.

Use Examples

Example A

*Plasmopara* Test (Grapevines)/Preventive

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet. The test is evaluated 6 days after the inoculation. 0% means an efficacy which corresponds to that of the untreated control, while an efficacy of 100% means that no disease is observed.

Under these conditions, good (at least 70%) or total protection is observed at a dose of 100 ppm with the following compounds according to the invention: 6, 34, 66, 72, 116, 124, 232, 245, 263, 292, 329, 334, 380, 543, 560, 821, 907, 909, 913, 924, 933, 934, 942, 952, 958, 959, 960, 978, 981, 984, 984, 989, 1123, 1146, 1162, 1167, 1171, 1189, 1198, 1253, 1278, 1381, 1445, 1449, 1451, 1456, 1471, 1491, 1491, 1545, 1551, 1607, 1612, 1634, 1639, 1641, 1642, 1644, 1645, 1646, 1673, 1676, 1677, 1688.

Example B

In Vivo Test on *Alternaria brassicae* (Leaf Spot of Crucifers)

The active ingredients tested are prepared by homogenization in a mixture of acetone/Tween/DMSO, then diluted with water to obtain the desired active material. Radish plants (Perrot variety), sown on a 50/50 peat soil-pozzolana substrate in starter cups and grown at 18-20° C., are treated at the cotyledon stage by spraying with the active ingredient prepared as described above. Plants, used as controls, are treated with the mixture of acetone/Tween/water not containing the active material. After 24 hours, the plants are contaminated by spraying them with an aqueous suspension of *Alternaria brassicae* spores (40,000 spores per cm³). The spores are collected from a 12 to 13 days-old culture. The contaminated radish plants are incubated for 6-7 days at about 18° C., under a humid atmosphere. Grading is carried out 6 to 7 days after the contamination, in comparison with the control plants.

Under these conditions, good protection (at least 70%) is observed at a dose of 500 ppm with the following compounds according to the invention: 155, 170, 954 and 1024.

Example C

In Vivo Test on *Sphaerotheca fuliginea* (Cucurbits Powdery Mildew)

The active ingredients tested are prepared by homogenization in a mixture of acetone/Tween/DMSO, then diluted with water to obtain the desired active material. Gherkin plants (Vert petit de Paris variety) in starter cups, sown on a 50/50 peat soil-pozzolana substrate and grown at 20° C./23° C., are treated at the cotyledon Z10 stage by spraying with the aqueous suspension described above. Plants, used as controls, are treated with an aqueous solution not containing the active material. After 24 hours, the plants are contaminated by spraying them with an aqueous suspension of *Sphaerotheca fuliginea* spores (100 000 spores per ml). The spores are collected from a contaminated plants. The contaminated gherkin plants are incubated at about 20° C./25° C. and at 60/70% relative humidity. Grading (% of efficacy) is carried out 12 days after the contamination, in comparison with the control plants.

Under these conditions, good (at least 70%) or total protection is observed at a dose of 500 ppm with the following compounds according to the invention: 94, 98, 105, 148, 149, 158, 187, 817, 818, 833, 834, 835, 836, 855, 857, 858, 868, 954, 1013, 1016, 1026 and 1085.

Example D

In Vivo Test on *Pyrenophora teres* (Barley Net Blotch)

The active ingredients tested are prepared by homogenization in a mixture of acetone/Tween/DMSO, then diluted with water to obtain the desired active material concentration. Barley plants (Express variety), sown on a 50/50 peat soil-pozzolana substrate in starter cups and grown at 12° C., are treated at the 1-leaf stage (10 cm tall) by spraying with the active ingredient prepared as described above. Plants, used as controls, are treated with an aqueous solution not containing the active material. After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity. Grading is carried out 12 days after the contamination, in comparison with the control plants.

Under these conditions, good (at least 70%) is observed at a dose of 500 ppm with the following compounds according to the invention: 605, 606, 824 and 948.

Example E

In Vivo Test on *Mycosphaerella graminicola* (Wheat Leaf Spot)

The active ingredients tested are prepared by homogenization in a mixture of acetone/tween/DMSO, then diluted with water to obtain the desired active material concentration. Wheat plants (Scipion variety), sown on a 50/50 peat soil-pozzolana substrate in starter cups and grown at 12° C., are treated at the 1-leaf stage (10 cm tall) by spraying with the aqueous suspension described above. Plants, used as controls, are treated with an aqueous solution not containing the active material. After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity. Grading (% of efficacy) is carried out 21 to 28 days after the contamination, in comparison with the control plants.

Under these conditions, good (at least 70%) or total protection is observed at a dose of 500 ppm with the following compounds according to the invention: 156, 158, 364, 435, 644, 645, 951, 1023 and 1032.

Example F

In Vivo Test on *Pyricularia grisea* (Rice Blast)

The active ingredients tested are prepared by homogenization in a mixture of acetone/Tween/DMSO, then diluted with water to obtain the desired active material concentration. Rice plants (Koshihikari variety), sown on a 50/50 peat soil-pozzolana substrate in starter cups and grown at 25° C., are treated at the 2-leaf stage (13-15 cm tall) by spraying with the active ingredient prepared as described above. Plants, used as controls, are treated with the mixture of acetone/Tween/DMSO/water not containing the active material. After 24 hours, the plants are contaminated by spraying them with an aqueous suspension of *Pyricularia* grisea spores (30,000 spores per ml). The spores are collected from a 17-day-old culture and are suspended in water containing 2.5 g/l of gelatine. The contaminated Rice plants are incubated for 72 hours at about 25° C. and at 100% relative humidity, and then for 3 days at 25° C. at 80% relative humidity during the day and 20% relative humidity during the night. Grading (% of efficacy) is carried out 6 days after the contamination, in comparison with the control plants.

Under these conditions, good (at least 70%) or total protection is observed at a dose of 500 ppm with the following compounds according to the invention: 174, 364, 659, 827 and 955.

Example G

*Phytophthora* Test (Tomato)/Preventive

Solvent: 49 parts by weight of N,N-Dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. One day after this treatment, the plants are inoculated with an aqueous spore suspension of *Phytophthora infestans*. The plants remain for one day in an incubation cabinet at approximately 22° C. and a relative atmospheric humidity of 100%. Then the plants are placed in an incubation cabinet at approximately 20° C. and a relative atmospheric humidity of 96%. The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 500 ppm of active ingredient: 5, 6, 15, 21, 22, 23, 24, 27, 32, 33, 34, 35, 36, 48, 52, 57, 58, 59, 60, 61, 63, 64, 65, 66, 72, 74, 79, 82, 85, 123, 124, 210, 212, 213, 214, 216, 217, 219, 221, 223, 232, 233, 234, 236, 239, 241, 242, 247, 252, 256, 259, 260, 263, 264, 266, 267, 268, 269, 270, 271, 275, 276, 279, 281, 284, 285, 287, 289, 291, 292, 294, 295, 297, 298, 299, 300, 301, 303, 304, 305, 306, 307, 309, 312, 313, 316, 317, 318, 321, 322, 324, 328, 329, 330, 332, 334, 341, 343, 348, 349, 356, 357, 360, 380, 388, 426, 471, 472, 473, 474, 476, 477, 487, 495, 496, 530, 531, 541, 543, 550, 551, 552, 553, 554, 559, 560, 561, 562, 571, 586, 593, 595, 619, 620, 687, 691, 696, 705, 706, 708, 714, 717, 720, 721, 722, 723, 724, 725, 728, 731, 734, 736, 737, 739, 741, 742, 746, 750, 751, 755, 760, 762, 763, 764, 768, 772, 774, 778, 793, 798, 799, 800, 803, 804, 805, 806, 811, 819, 821, 823, 826, 840, 842, 859, 870, 878, 880, 881, 892, 894, 898, 899, 903, 904, 905, 907, 908, 909, 913, 914, 914, 915, 916, 923, 924, 931, 931, 932, 933, 934, 938, 939, 940, 957, 958, 959, 960, 961, 970, 974, 976, 978, 980, 981, 986, 988, 989, 996, 997, 998, 1000, 1003, 1004, 1006, 1007, 1008, 1038, 1049, 1050, 1051, 1052, 1054, 1055, 1059, 1062, 1064, 1065, 1067, 1073, 1079, 1080, 1081, 1082, 1083, 1101, 1114, 1115, 1116, 1117, 1118, 1119, 1120, 1121, 1123, 1124, 1125, 1127, 1128, 1130, 1131, 1133, 1135, 1136, 1141, 1142, 1144, 1146, 1147, 1148, 1149, 1150, 1151, 1152, 1156, 1158, 1159, 1161, 1162, 1163, 1166, 1167, 1169, 1172, 1173, 1174, 1175, 1178, 1179, 1181, 1182, 1183, 1184, 1185, 1186, 1188, 1189, 1190, 1191, 1192, 1193, 1194, 1195, 1197, 1198, 1201, 1202, 1203, 1204, 1205, 1206, 1208, 1212, 1213, 1216, 1218, 1222, 1223, 1224, 1225, 1227, 1228, 1230, 1231, 1232, 1239, 1240, 1241, 1242, 1243, 1244, 1246, 1247, 1248, 1251, 1252, 1253, 1254, 1255, 1260, 1261, 1262, 1263, 1266, 1269, 1270, 1271, 1273, 1275, 1276, 1278, 1279, 1280, 1281, 1284, 1291, 1292, 1293, 1294, 1297, 1307, 1314, 1322, 1324, 1331, 1355, 1356, 1365, 1380, 1381, 1394, 1404, 1406, 1413, 1418, 1419, 1425, 1438, 1440, 1442, 1443, 1445, 1446, 1448, 1449, 1454, 1458, 1460, 1462, 1464, 1466, 1467, 1467, 1468, 1471, 1471, 1489, 1491, 1504, 1513, 1520, 1532, 1536, 1539, 1545, 1546, 1547, 1549, 1551, 1563, 1564, 1566, 1584, 1590, 1593, 1599, 1600, 1606, 1607, 1608, 1611, 1612, 1616, 1618, 1620, 1629, 1632, 1633, 1633, 1634, 1634, 1635, 1635, 1636, 1637, 1638, 1639, 1640, 1641, 1642, 1644, 1645, 1646, 1647, 1652, 1657, 1664, 1673, 1676, 1677, 1679, 1681, 1682, 1683, 1684, 1685, 1686, 1687, 1688, 1689.

Example H

*Alternaria* Test (Tomato)/Preventive

Solvent: 49 parts by weight of N,N-Dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. One day after this treatment, the plants are inoculated with an aqueous spore suspension of *Alternaria solani*. The plants remain for one day in an incubation cabinet at approximately 22° C. and a relative atmospheric humidity of 100%. Then the plants are placed in an incubation cabinet at approximately 20° C. and a relative atmospheric humidity of 96%. The test is evaluated 7 days after the inoculation. 0% means an efficacy which corresponds to that of the untreated control while an efficacy of 100% means that no disease is observed.

In this test the following compounds according to the invention showed efficacy of 70% or even higher at a concentration of 500 ppm of active ingredient: 28, 121, 296, 385, 992.

Example I

*Leptosphaeria* Test (Wheat)/Preventive

Solvent: 49 parts by weight of N,N-Dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration. To test for preventive activity, young plants are sprayed with a preparation of active compound at the stated rate of application. One day after this treatment, the plants are inoculated with an aqueous spore suspension of *Leptosphaeria nodorum*. The plants remain for 48 hours in an incubation cabinet at 22° C. and a relative atmospheric humidity of 100%. Then the plants are placed in a greenhouse at a temperature of approximately 22° C. and a relative atmospheric humidity of approximately 90%. The test is evaluated 7-9 days after the inoculation. 0% means an efficacy which corresponds to that of the untreated control, while an efficacy of 100% means that no disease is observed.

In this test the following compounds according to the invention showed efficacy of 70% or even higher at a concentration of 500 ppm of active ingredient: 284, 286, 296, 1054, 1067.

Example J

*Puccinia* Test (Wheat)/Preventive

Solvent: 49 parts by weight of N,N-Dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. One day after this treatment, the plants are inoculated with an aqueous spore suspension of *Puccinia recondita*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%. The test is evaluated 7-9 days after the inoculation. 0% means an efficacy which corresponds to that of the untreated control while an efficacy of 100% means that no disease is observed.

In this test the following compounds according to the invention showed efficacy of 70% or even higher at a concentration of 500 ppm of active ingredient: 69, 70, 73, 272, 273, 296, 302, 545, 546, 589, 591, 597, 843, 992, 993.

Example K

In Vivo Test on *Peronospora parasitica* (Crucifer Downy Mildew)

The active ingredients tested are prepared by homogenization in a mixture of acetone/Tween/DMSO, then diluted with water to obtain the desired active material concentration.

Cabbage plants (Eminence variety) in starter cups, sown on a 50/50 peat soil-pozzolana substrate and grown at 18-20° C., are treated at the cotyledon stage by spraying with the aqueous suspension described above. Plants, used as controls, are treated with an aqueous solution not containing the active material. After 24 hours, the plants are contaminated by spraying them with an aqueous suspension of *Peronospora parasitica* spores (50 000 spores per ml). The spores are collected from infected plant. The contaminated cabbage plants are incubated for 5 days at 20° C., under a humid atmosphere. Grading is carried out 5 days after the contamination, in comparison with the control plants.

Under these conditions, good (at least 70%) or total protection is observed at a dose of 500 ppm with the following compounds: 17, 21, 24, 85, 88, 89, 93, 96, 100, 101, 103, 104, 105, 112, 116, 117, 128, 130, 133, 135, 138, 139, 140, 141, 142, 143, 144, 145, 146, 148, 149, 152, 153, 154, 155, 156, 157, 158, 160, 161, 163, 167, 169, 172, 174, 180, 181, 182, 183, 186, 187, 188, 189, 190, 191, 193, 194, 195, 196, 199, 203, 204, 245, 334, 341, 343, 410, 427, 430, 433, 440, 442, 443, 444, 448, 450, 452, 453, 454, 455, 456, 610, 611, 612, 614, 615, 628, 633, 635, 636, 637, 639, 641, 642, 644, 645, 646, 647, 648, 650, 653, 655, 656, 657, 658, 659, 660, 661, 663, 669, 671, 673, 674, 675, 676, 678, 679, 680, 683, 684, 685, 686, 743, 767, 769, 770, 771, 772, 773, 780, 784, 792, 817, 824, 833, 834, 835, 853, 854, 855, 863, 864, 868, 872, 881, 882, 884, 886, 918, 921, 922, 925, 931, 941, 942, 945, 949, 950, 951, 952, 953, 954, 955, 1016, 1020, 1024, 1026, 1029, 1030, 1031, 1107 and 1109.

Example L

*Boophilus microplus*—Test Injection)

Solvent: dimethyl sulfoxide

To produce a suitable preparation of active compound, 10 mg of active compound are dissolved in 0.5 ml solvent, and the concentrate is diluted with solvent to the desired concentration. Five adult engorged female ticks (*Boophilus microplus*) are injected with 1 µl compound solution into the abdomen. Ticks are transferred into replica plates and incubated in a climate chamber for a period of time. Egg deposition of fertile eggs is monitored. After 7 days, mortality in % is determined. 100% means that all eggs are infertile; 0% means that all eggs are fertile.

In this test for example, the following compounds from the preparation examples showed good activity of 100% at an application rate of 20 µg/animal: 239

Example M

*Phaedon cochleariae*—Test; (PHAECO Spray Application)

Solvent: 78.0 parts by weight of acetone
1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. Chinese cabbage (*Brassica pekinesis*) leaf-disks are sprayed with a preparation of the active ingredient of the desired concentration. Once dry, the leaf disks are infested with mustard beetle larvae (*Phaedon cochleariae*). After 7 days mortality in % is determined. 100% means that all beetle larvae have been killed and 0% means that none of the beetle larvae have been killed.

In this test for example, the following compounds from the preparation examples showed good activity of 83% at an application rate of 500 g/ha: 40, 1028

In this test for example, the following compounds from the preparation examples showed good activity of 100% at an application rate of 500 g/ha: 957, 979, 1475, 1591.

Example N

*Myzus persicae*—Test; (MYZUPE Spray Application)

Solvent: 78.0 parts by weight acetone
1.5 parts by weight dimethylformamide
Emulsifier: 0.5 parts by weight alkylarylpolyglycolether To produce a suitable preparation of active compound, 1 part by weight of active compound is mixed with the stated amount of solvent and emulsifier, and the concentrate is diluted with emulsifier-containing water to the desired concentration. Chinese cabbage (*Brassica pekinesis*) leaf-disks infected with all instars of the green peach aphid (*Myzus persicae*), are sprayed with a preparation of the active ingredient at the desired concentration. After 6 days mortality in % is determined. 100% means that all aphids have been killed; 0% means that none of the aphids have been killed.

In this test for example, the following compounds from the preparation examples showed good activity of 90% at an application rate of 500 g/ha: 597

In this test for example, the following compounds from the preparation examples showed good activity of 100% at an application rate of 500 g/ha: 62, 600, 1244

The invention claimed is:

1. An aminopropenoate of formula (I)

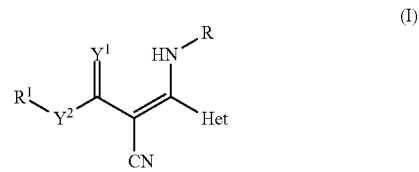

in which

R represents one of the following groups $R^A$, $R^B$ or $R^C$

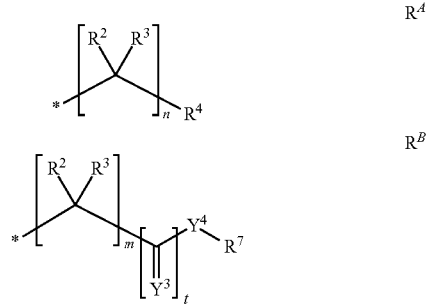

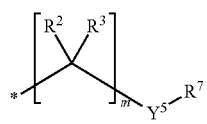
R<sup>C</sup> n represents 0, 1, 2, 3 or 4,
m represents 1, 2, 3 or 4,
t represents 0 or 1,
Y$^1$ represents S, O or NR$^5$,
Y$^2$ represents O, S or NR$^6$,
Y$^3$ represents S, O or NR$^8$,
Y$^4$ represents a bond or O, S or NR$^9$,
Y$^5$ represents SO or SO$_2$,
in case that Y$^2$ represents NR$^6$, then R$^6$ and R$^1$ together with the nitrogen atom to which they are linked may form a 5- to 7-membered, saturated or unsaturated, carbo- or heterocycle comprising up to 3 heteroatoms, which cycle may also include one of the groups C(═O) and C(═S),
in case that Y$^4$ represents NR$^9$, then R$^9$ and R$^7$ together with the nitrogen atom to which they are linked may form a 5- to 7-membered, saturated or unsaturated, carbo- or heterocycle comprising up to 3 heteroatoms, which cycle may also include one of the groups C(═O) and C(═S),
R$^1$ represents hydrogen, C$_1$-C$_8$-alkyl, C$_3$-C$_8$-cycloalkyl, C$_1$-C$_8$-halogenoalkyl comprising up to 9 halogen atoms which can be the same or different, C$_2$-C$_8$-alkenyl, C$_2$-C$_8$-alkynyl, C$_3$-C$_8$-cycloalkyl-C$_1$-C$_8$-alkyl, C$_2$-C$_8$-alkenyl-C$_1$-C$_8$-alkyl, C$_2$-C$_8$-alkynyl-C$_1$-C$_8$-alkyl, C$_1$-C$_8$-halogeno-C$_3$-C$_8$-cycloalkyl comprising up to 9 halogen atoms which can be the same or different, C$_3$-C$_8$-cycloalkenyl, C$_1$-C$_8$-alkoxy-C$_1$-C$_8$-alkyl, C$_3$-C$_8$-cycloalkoxy-C$_1$-C$_8$-alkyl, C$_1$-C$_8$-halogenoalkoxy-C$_1$-C$_8$-alkyl comprising up to 9 halogen atoms which can be the same or different, C$_1$-C$_8$-alkylsulfanyl-C$_1$-C$_8$-alkyl, C$_1$-C$_8$-alkylamino-C$_1$-C$_8$-alkyl, C$_1$-C$_8$-halogenoalkylamino-C$_1$-C$_8$-alkyl comprising up to 9 halogen atoms which can be the same or different, C$_3$-C$_8$-cycloalkylamino-C$_1$-C$_8$-alkyl, C$_1$-C$_8$-trialkylsilyl, C$_1$-C$_8$-trialkylsilyl-C$_1$-C$_8$-alkyl, benzotriazolyl, aryl-C$_3$-C$_8$-cycloalkyl which can be substituted by up to 5 groups Q;
and, provided that when Y$^2$ does not represent NH, R$^1$ can also represent aryl which can be substituted by up to 5 groups Q, or aryl-C$_1$-C$_8$-alkyl which can be substituted by up to 5 groups Q;
Het represents one of the heterocycles Het 48 to Het 50:

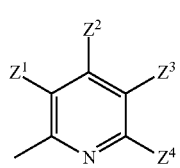
Het 48

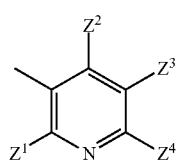
Het 49

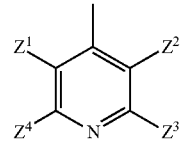
Het 50

R$^2$ and R$^3$, which can be the same or different, independently of one another represent hydrogen, halogen, CN, NH$_2$, NO$_2$, C$_1$-C$_8$-alkyl, C$_1$-C$_8$-hydroxyalkyl, C$_3$-C$_8$-cycloalkyl, C$_3$-C$_8$-halogenocycloalkyl comprising up to 9 halogen atoms which can be the same or different, C$_1$-C$_8$-halogenoalkyl comprising up to 9 halogen atoms which can be the same or different, C$_3$-C$_8$-cycloalkyl-C$_1$-C$_8$-alkyl, C$_2$-C$_8$-alkenyl, C$_2$-C$_8$-halogenoalkenyl comprising up to 9 halogen atoms which can be the same or different, C$_2$-C$_8$-alkynyl, C$_2$-C$_8$-alkenyl-C$_1$-C$_8$-alkyl, C$_2$-C$_8$-alkynyl-C$_1$-C$_8$-alkyl, C$_3$-C$_8$-halogeno-cycloalkyl comprising up to 9 halogen atoms which can be the same or different, C$_3$-C$_8$-cycloalkenyl, C$_1$-C$_8$-alkoxy-C$_1$-C$_8$-alkyl, C$_1$-C$_8$-alkoxy-C$_2$-C$_8$-alkenyl, C$_1$-C$_8$-alkoxy-C$_1$-C$_8$-alkynyl, C$_3$-C$_8$-cycloalkoxy-C$_1$-C$_8$-alkyl, C$_1$-C$_8$-halogenoalkoxy-C$_1$-C$_8$-alkyl comprising up to 9 halogen atoms which can be the same or different, C$_1$-C$_8$-alkylsulfanyl-C$_1$-C$_8$-alkyl, C$_1$-C$_8$alkylsulfinyl-C$_1$-C$_8$-alkyl, C$_1$-C$_8$-alkylsulfonyl-C$_1$-C$_8$-alkyl, amino-C$_1$-C$_8$-alkyl, C$_1$-C$_8$-alkylamino-C$_1$-C$_8$-alkyl, di-(C$_1$-C$_8$-alkyl)amino-C$_1$-C$_8$-alkyl, C$_1$-C$_8$-halogenoalkylamino-C$_1$-C$_8$-alkyl comprising up to 9 halogen atoms which can be the same or different, C$_3$-C$_8$-cycloalkylamino-C$_1$-C$_8$-alkyl, C$_1$-C$_8$-trialkylsilyl-C$_1$-C$_8$-alkyl, C$_1$-C$_8$-trialkylsilyl, phenyl which can be substituted by up to 5 groups Q, or phenyl-C$_2$-C$_4$-alkynyl, which can be substituted in the phenyl moiety by up to 5 groups Q, R$^2$ and R$^3$ also together with the carbon atom to which they are linked can form a C$_3$-C$_7$-cycloalkyl, which may be substituted by 1 to 4 identical or different substituents selected from halogen, OH, C$_1$-C$_4$-alkyl, C$_1$-C$_4$-halogenoalkyl, C$_1$-C$_4$-alkoxy, alkylthio or phenyl, or can form a C$_5$-C$_{10}$-bicycloalkyl, a 2,3-dihydro-1H-indene-1-yl or a decahydronaphthalenyl, R$^4$ represents aryl or a heterocycle E 1 to E 144:

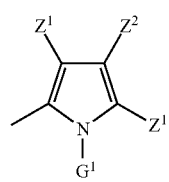
E 1

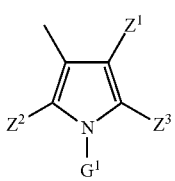
E 2

| | | |
|---|---|---|
| E 3 | 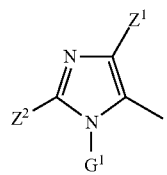 | E 13 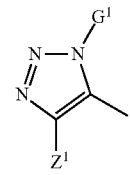 |
| E 4 | 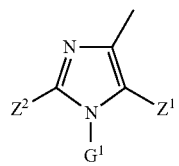 | E 14 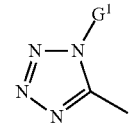 |
| E 5 | 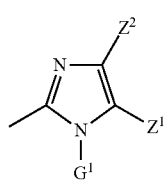 | E 15 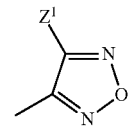 |
| E 6 | 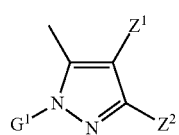 | E 16 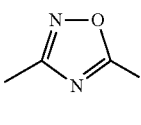 |
| E 7 | 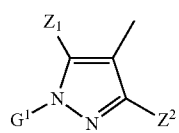 | E 17 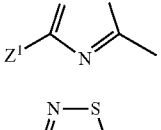 |
| E 8 | 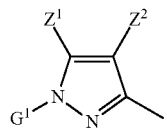 | E 18 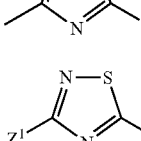 |
| E 9 | 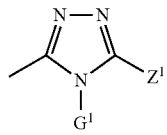 | E 19 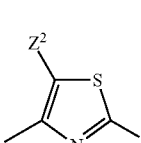 |
| E 10 | 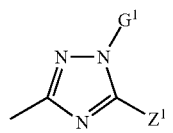 | E 20 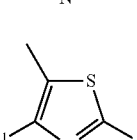 |
| E 11 | 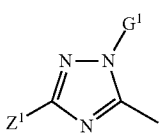 | E 21 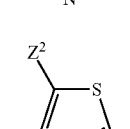 |
| E 12 | 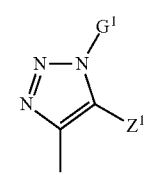 | E 22 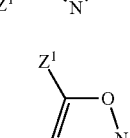 |
| | | E 23 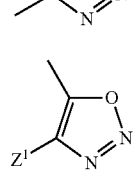 |
| | | E 24 |

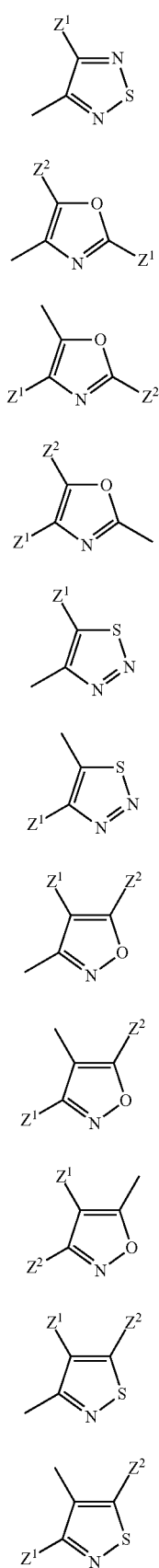
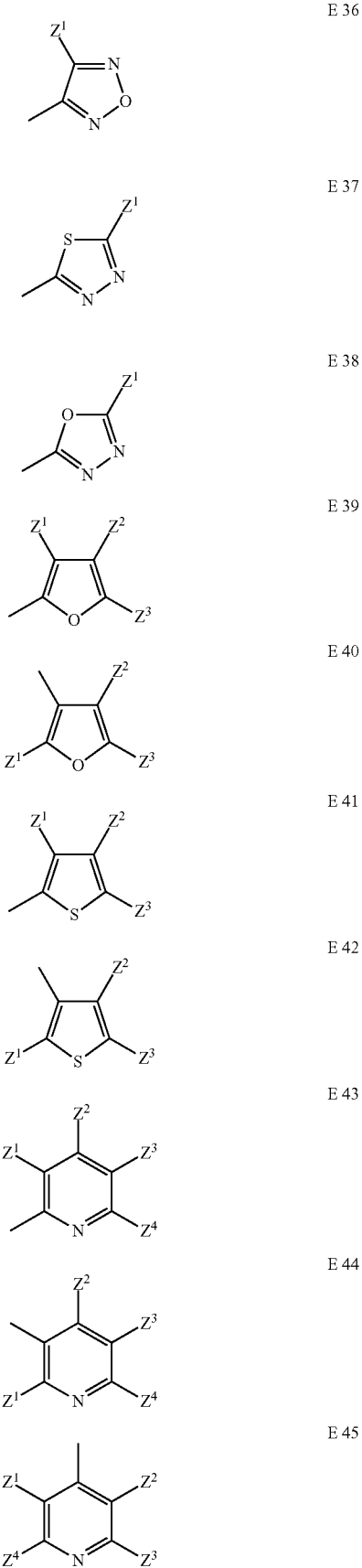

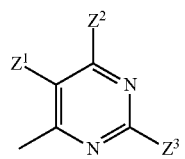 E 46
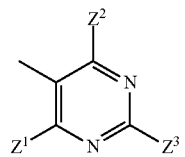 E 47
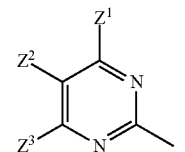 E 48
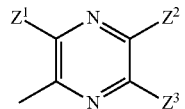 E 49
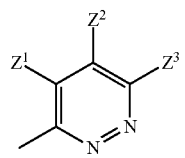 E 50
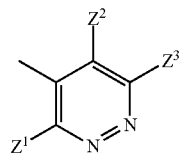 E 51
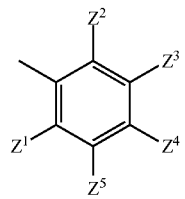 E 52
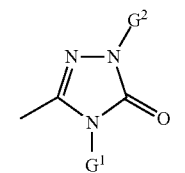 E 53
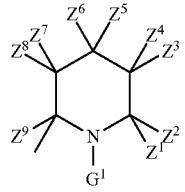 E 54
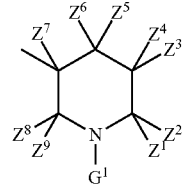 E 55
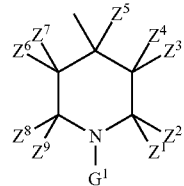 E 56
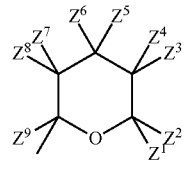 E 57
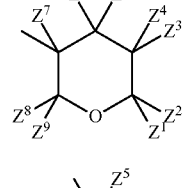 E 58
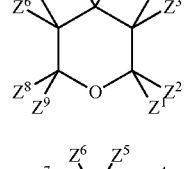 E 59
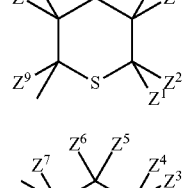 E 60
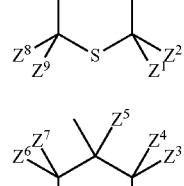 E 61
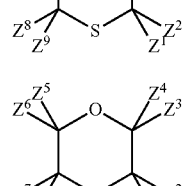 E 62
E 63

169
-continued
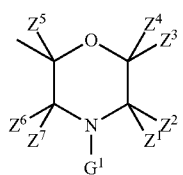
E 64
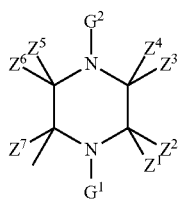
E 65
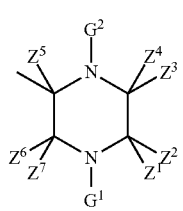
E 66
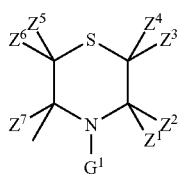
E 67
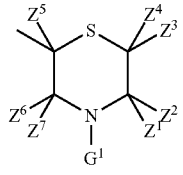
E 68
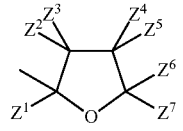
E 69
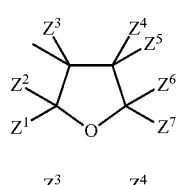
E 70
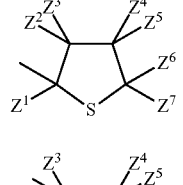
E 71
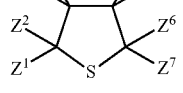
E 72
170
-continued
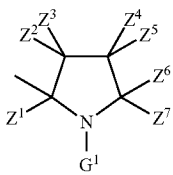
E 73
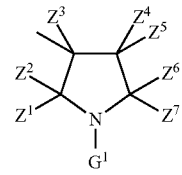
E 74
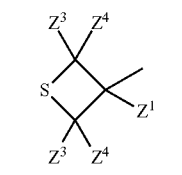
E 75
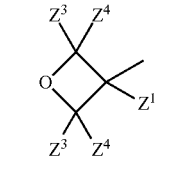
E 76
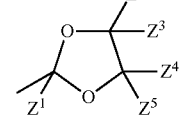
E 77
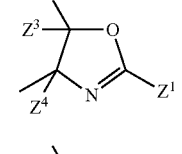
E 78
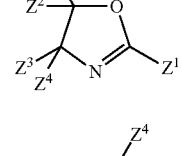
E 79
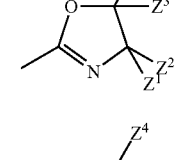
E 80
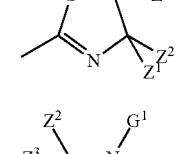
E 81
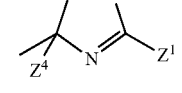
E 82

| | | |
|---|---|---|
| E 83 | 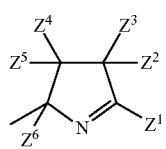 | |
| E 84 | 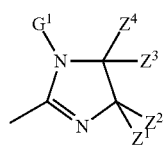 | |
| E 85 | 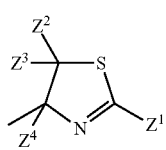 | |
| E 86 | 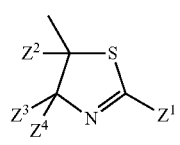 | |
| E 87 | 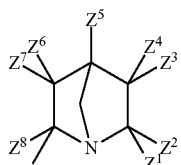 | |
| E 88 | 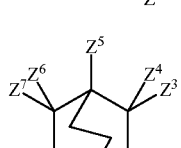 | |
| E 89 | 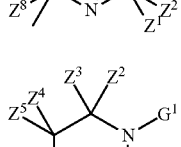 | |
| E 90 | 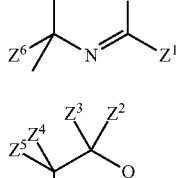 | |
| E 83 | 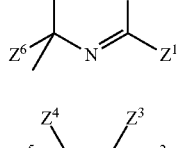 | |
| E 84 | 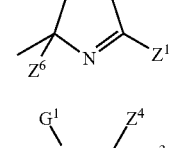 | |
| | | |
|---|---|---|
| E 85 | 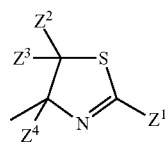 | |
| E 86 | 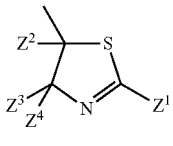 | |
| E 87 | 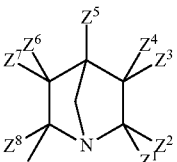 | |
| E 88 | 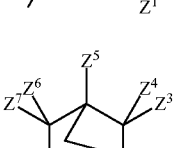 | |
| E 89 | 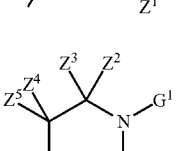 | |
| E 90 | 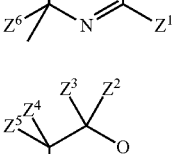 | |
| E 91 | 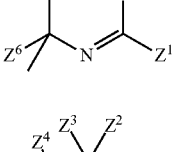 | |
| E 92 | 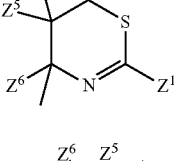 | |
| E 93 | 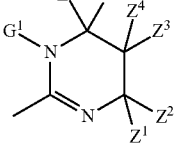 | |

-continued
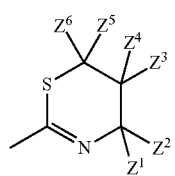 E94
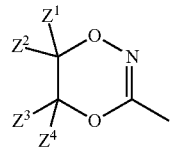 E95
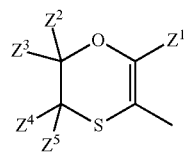 E96
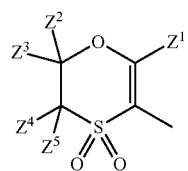 E97
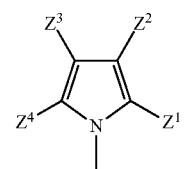 E98
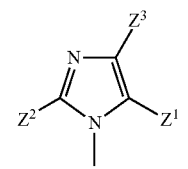 E99
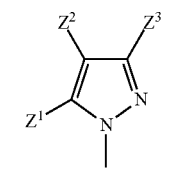 E100
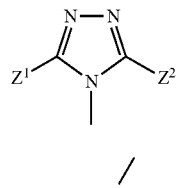 E101
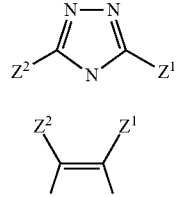 E102
-continued
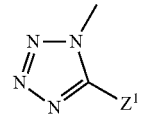 E104
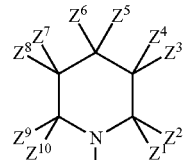 E105
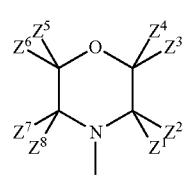 E106
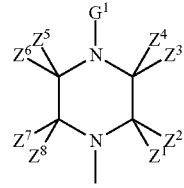 E107
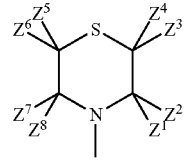 E108
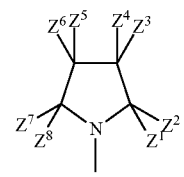 E109
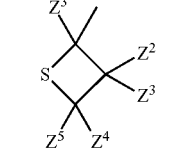 E110
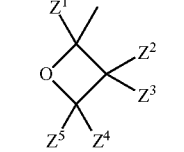 E111
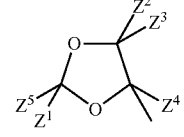 E112
E103

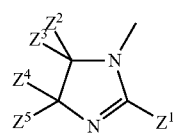 E 113
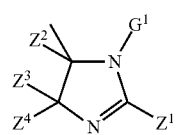 E 114
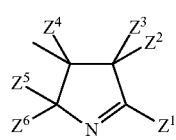 E 115
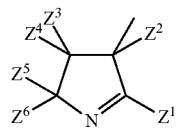 E 116
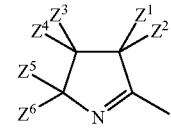 E 117
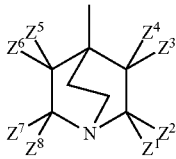 E 118
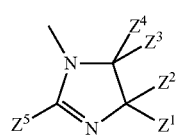 E 119
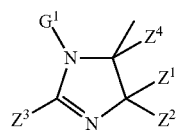 E 120
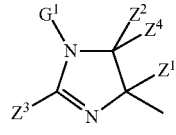 E 121
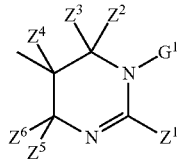 E 122
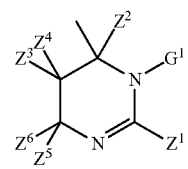 E 123
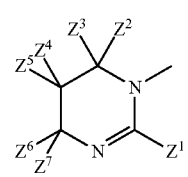 E 124
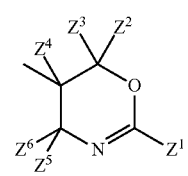 E 125
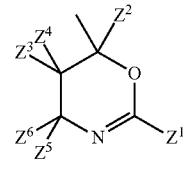 E 126
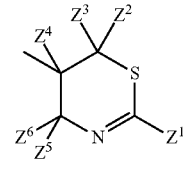 E 127
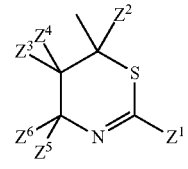 E 128
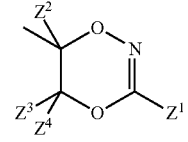 E 129
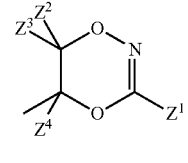 E 130
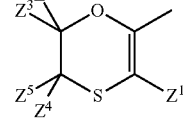 E 131

R[4] also represents hydrogen or halogen when n represents 1, 2, 3 or 4,

R[5] represents hydrogen, OH, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, aryl which can be substituted by up to 5 groups Q, aryl-$C_1$-$C_8$-alkyl which can be substituted by up to 5 groups Q, or aryl-$C_3$-$C_8$-cycloalkyl which can be substituted by up to 5 groups Q;

R[6] represents hydrogen, OH, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, $C_1$-$C_8$-alkoxy, $C_3$-$C_8$-cycloalkoxy, $C_1$-$C_8$-halogenoalkoxy comprising up to 9 halogen atoms which can be the same or different, $C_3$-$C_8$-cycloalkyl-$C_1$-$C_8$-alkoxy, $C_2$-$C_8$-alkenyl-$C_1$-$C_8$-alkoxy, $C_2$-$C_8$-alkynyl-$C_1$-$C_8$-alkoxy, $C_1$-$C_8$-halogeno-$C_3$-$C_8$-cycloalkoxy comprising up to 9 halogen atoms which can be the same or different, $C_3$-$C_8$-cycloalkenyloxy, $C_1$-$C_8$-alkoxy-$C_1$-$C_8$-alkoxy, $C_3$-$C_8$-cycloalkoxy-$C_1$-$C_8$-alkoxy, $C_1$-$C_8$-halogenoalkoxy-$C_1$-$C_8$-alkoxy comprising up to 9 halogen atoms which can be the same or different, $C_1$-$C_8$-alkylsulfanyl-$C_1$-$C_8$-alkoxy, $C_1$-$C_8$-alkylamino-$C_1$-$C_8$-alkoxy, $C_1$-$C_8$-halogenoalkylamino-$C_1$-$C_8$-alkoxy comprising up to 9 halogen atoms which can be the same or different, $C_3$-$C_8$-cycloalkylamino-$C_1$-$C_8$-alkoxy, $C_1$-$C_8$-trialkylsilyl-$C_1$-$C_8$-alkoxy, aryloxy which can be substituted by up to 5 groups Q, benzyloxy which can be substituted by up to 5 groups Q, $C_1$-$C_8$-alkylamino, ($C_1$-$C_8$-alkyl)carbonylamino, $C_3$-$C_8$-cycloalkylamino, $C_1$-$C_8$-halogenoalkylamino comprising up to 9 halogen atoms which can be the same or different, $C_3$-$C_8$-cycloalkyl-$C_1$-$C_8$-alkylamino, $C_2$-$C_8$-alkenyl-$C_1$-$C_8$-alkylamino, $C_2$-$C_8$-alkynyl-$C_1$-$C_8$-alkylamino, halogeno-$C_3$-$C_8$-cycloalkylamino comprising up to 9 halogen atoms which can be the same or different, arylamino which can be substituted by up to 5 groups Q, benzylamino which can be substituted by up to 5 groups Q, or aryl-$C_3$-$C_8$-cycloalkyl which can be substituted by up to 5 groups Q;

$R^7$ represents hydrogen, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl, $C_2$-$C_8$-alkynyl, $C_2$-$C_8$-alkenyl-$C_1$-$C_8$-alkyl, $C_2$-$C_8$-alkynyl-$C_1$-$C_8$-alkyl, halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl or naphthyl, each of which can be substituted by up to 5 groups Q, benzyl which can be substituted by up to 5 groups Q, or phenyl-$C_1$-$C_2$-alkylimino, $R^7$ also represents CN, if R is $R^B$, t is 0 and $Y^4$ is a bond, $R^8$ represents hydrogen, OH, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_1$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl which can be substituted by up to 5 groups Q, benzyl which can be substituted by up to 5 groups Q; $C_1$-$C_8$-alkoxy, $C_3$-$C_8$-cycloalkoxy, $C_1$-$C_8$-halogenoalkoxy comprising up to 9 halogen atoms which can be the same or different, $C_3$-$C_8$-cycloalkyl-$C_1$-$C_8$-alkoxy, $C_2$-$C_8$-alkenyl-$C_1$-$C_8$-alkoxy, $C_2$-$C_8$-alkynyl-$C_1$-$C_8$-alkoxy, $C_1$-$C_8$-halogeno-$C_3$-$C_8$-cycloalkoxy comprising up to 9 halogen atoms which can be the same or different, $C_3$-$C_8$-cycloalkenyloxy, $C_1$-$C_8$-alkoxy-$C_1$-$C_8$-alkoxy, $C_3$-$C_8$-cycloalkoxy-$C_1$-$C_8$-alkoxy, $C_1$-$C_8$-halogenoalkoxy-$C_1$-$C_8$-alkoxy comprising up to 9 halogen atoms which can be the same or different, $C_1$-$C_8$-alkylsulfanyl-$C_1$-$C_8$-alkoxy, $C_1$-$C_8$-alkylamino-$C_1$-$C_8$-alkoxy, $C_1$-$C_8$-halogenoalkylamino-$C_1$-$C_8$-alkoxy comprising up to 9 halogen atoms which can be the same or different, $C_3$-$C_8$-cycloalkylamino-$C_1$-$C_8$-alkoxy, $C_1$-$C_8$-trialkylsilyl-$C_1$-$C_8$-alkoxy, aryloxy which can be substituted by up to 5 groups Q, or benzyloxy which can be substituted by up to 5 groups Q;

$R^9$ represents hydrogen, OH, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_3$-$C_8$-halogenocycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl which can be substituted by up to 5 groups Q, benzyl which can be substituted by up to 5 groups Q; $C_1$-$C_8$-alkoxy, $C_3$-$C_8$-cycloalkoxy, $C_1$-$C_8$-halogenoalkoxy comprising up to 9 halogen atoms which can be the same or different, $C_3$-$C_8$-cycloalkyl-$C_1$-$C_8$-alkoxy, $C_2$-$C_8$-alkenyl-$C_1$-$C_8$-alkoxy, $C_2$-$C_8$-alkynyl-$C_1$-$C_8$-alkoxy, halogeno-$C_3$-$C_8$-cycloalkoxy comprising up to 9 halogen atoms which can be the same or different, $C_3$-$C_8$-cycloalkenyloxy, $C_1$-$C_8$-alkoxy-$C_1$-$C_8$-alkoxy, $C_3$-$C_8$-cycloalkoxy-$C_1$-$C_8$-alkoxy, $C_1$-$C_8$-halogenoalkoxy-$C_1$-$C_8$-alkoxy comprising up to 9 halogen atoms which can be the same or different, $C_1$-$C_8$-alkylsulfanyl-$C_1$-$C_8$-alkoxy, $C_1$-$C_8$-alkylamino-$C_1$-$C_8$-alkoxy, $C_1$-$C_8$-halogenoalkylamino-$C_1$-$C_8$-alkoxy comprising up to 9 halogen atoms which can be the same or different, $C_3$-$C_8$-cycloalkylamino-$C_1$-$C_8$-alkoxy, $C_1$-$C_8$-trialkylsilyl-$C_1$-$C_8$-alkoxy, phenyloxy which can be substituted by up to 5 groups Q, or benzyloxy which can be substituted by up to 5 groups Q, Q which can be the same or different, independently represents halogen, CN, $NO_2$, $C_1$-$C_8$-alkyl, $C_1$-$C_8$-alkoxy, $C_1$-$C_8$-alkylsulfanyl, $C_1$-$C_8$-halogenoalkyl comprising up to 9 halogen atoms which can be the same or different, $C_1$-$C_8$-halogenoalkoxy comprising up to 9 halogen atoms which can be the same or different, tri($C_1$-$C_8$)alkylsilyl or tri($C_1$-$C_8$)alkylsilyl-$C_1$-$C_8$-alkyl, or two vicinal substituents Q may be —$OCH_2O$—, —$OCF_2O$—, —$O(CH_2)_2O$—, —$O(CF_2)_2O$— or —N=CH—S—, $Z^1$, $Z^2$, $Z^3$, $Z^4$ $Z^5$, $Z^6$, $Z^7$, $Z^8$, $Z^9$, $Z^{10}$ and $Z^{11}$, which can be the same or different, independently of one another represent hydrogen, halogen, $NO_2$, CN, OH, SH, $NH_2$, $SF_5$, $C_1$-$C_8$-alkyl, $C_1$-$C_8$-halogenoalkyl comprising up to 9 halogen atoms which can be the same or different and optionally in addition one hydroxy group, $C_1$-$C_8$-alkylamino, di-$C_1$-$C_8$-alkylamino, $C_1$-$C_8$-alkoxy, $C_1$-$C_8$-halogenoalkoxy comprising up to 9 halogen atoms which can be the same or different, $C_1$-$C_8$-alkoxy-$C_1$-$C_8$-alkyl, $C_1$-$C_8$-alkylsulfanyl, $C_1$-$C_8$-halogenoalkylsulfanyl comprising up to 9 halogen atoms which can be the same or different, $C_2$-$C_8$-alkenyl, $C_2$-$C_8$-halogenoalkenyl comprising up to 9 halogen atoms which can be the same or different, $C_2$-$C_8$-alkynyl, $C_2$-$C_8$-halogenoalkynyl comprising up to 9 halogen atoms which can be the same or different, $C_2$-$C_8$-alkenyloxy, $C_2$-$C_8$-halogenoalkenyloxy comprising up to 9 halogen atoms which can be the same or different, $C_2$-$C_8$-alkynyloxy, $C_2$-$C_8$-halogenoalkynyloxy comprising up to 9 halogen atoms which can be the same or different, $C_2$-$C_8$-alkenylsulfanyl, $C_2$-$C_8$-alkynylsulfanyl, $C_3$-$C_7$-cycloalkyl, $C_3$-$C_7$-cycloalkyl-$C_1$-$C_8$-alkyl, $C_3$-$C_7$-halogenocyclo-alkyl comprising up to 9 halogen atoms which can be the same or different, formyl, formyloxy, formylamino, carbamoyl, N-hydroxycarbamoyl, (hydroxyimino)-$C_1$-$C_8$-alkyl, $C_1$-$C_8$-alkylcarbonyl, $C_1$-$C_8$-halogenoalkylcarbonyl comprising up to 9 halogen atoms which can be the same or different, $(C_3-C_7$-cycloalkyl)carbonyl, $C_1-C_8$-alkylcarbamoyl, di-$C_1-C_8$-alkylcarbamoyl, N—$C_1-C_8$-alkoxycarbamoyl, $C_1-C_8$-alkoxycarbamoyl, N—$C_1-C_8$-alkyl-$C_1-C_8$-alkoxycarbamoyl, $C_1-C_8$-alkoxycarbonyl, $C_1-C_8$-halogenoalkoxy-carbonyl comprising up to 9 halogen atoms which can be the same or different, $C_1-C_8$-alkylaminocarbonyl, di-($C_1-C_8$-alkyl)aminocarbonyl, $C_1-C_8$-alkylcarbonyloxy, $C_1-C_8$-halogenoalkylcarbonyloxy comprising up to 9 halogen atoms which can be the same or different, $C_1-C_8$-alkylcarbonylamino, $C_1-C_8$-halogenoalkylcarbonylamino comprising up to 9 halogen atoms which can be the same or different, $C_1-C_8$-alkylaminocarbonyloxy, di-($C_1-C_8$-alkyl)aminocarbonyloxy, $C_1-C_8$-alkoxycarbonyloxy, $C_1-C_8$-alkylsulphinyl, $C_1-C_8$-halogenoalkylsulphinyl comprising up to 9 halogen atoms which can be the same or different, $C_1-C_8$-alkylsulphonyl, $C_1-C_8$-halogenoalkylsulphonyl comprising up to 9 halogen atoms which can be the same or different, $C_1-C_8$-alkoxyimino, ($C_1-C_8$-alkylimino)-$C_1-C_8$-alkyl, ($C_1-C_8$ alkoxyimino)-$C_1-C_8$-alkyl, ($C_1-C_8$-alkenyloxyimino)-$C_1-C_8$-alkyl, ($C_2-C_8$-alkynyloxyimino)-$C_1-C_8$-alkyl, a (benzyloxyimino)-$C_1-C_8$-alkyl, tri-($C_1-C_8$-alkyl)silyl, tri($C_1-C_8$-alkyl)silyl-$C_1-C_8$-alkyl, benzyloxy which can be substituted by up to 5 groups Q, benzylsulfanyl which can be substituted by up to 5 groups Q, benzylamino which can be substituted by up to 5 groups Q, phenyl which can be substituted by up to 5 groups Q, naphthyl which can be substituted by up to 6 groups Q, phenoxy which can be substituted by up to 5 groups Q, phenylamino which can be substituted by up to 5 groups Q, phenylsulfanyl which can be substituted by up to 5 groups Q, or phenylmethylene which can be substituted by up to 5 groups Q, or two vicinal substituents Z together with the consecutive carbon atoms to which they are linked form a 5- or 6-membered, saturated or unsaturated, carbo- or heterocycle comprising up to 3 heteroatoms, which can be substituted by up to four groups Q which can be the same or different and the other substituents Z as defined above, or two geminal substituents Z together with the carbon atom to which they are linked can also be fused to represent C(=O); C(=S), or $C_3-C_9$-cycloalkyl;

$G^1$ and $G^2$ which can be the same or different, independently of one another represent hydrogen, CN, OH, $NH_2$, $C_1-C_8$-alkyl, $C_1-C_8$-halogenoalkyl comprising up to 9 halogen atoms which can be the same or different, $C_1-C_8$-alkylamino, di-$C_1-C_8$-alkylamino, $C_1-C_8$-alkoxy, $C_1-C_8$-halogenoalkoxy comprising up to 9 halogen atoms which can be the same or different, $C_1-C_8$-alkoxy-$C_1-C_8$-alkyl, $C_2-C_8$-alkenyl, $C_2-C_8$-halogenoalkenyl comprising up to 9 halogen atoms which can be the same or different, $C_2-C_8$-alkynyl, $C_2-C_8$-halogenoalkynyl comprising up to 9 halogen atoms which can be the same or different, $C_2-C_8$-alkenyloxy, $C_2-C_8$-halogenoalkenyloxy comprising up to 9 halogen atoms which can be the same or different, $C_2-C_8$-alkynyloxy, $C_2-C_8$-halogenoalkynyloxy comprising up to 9 halogen atoms which can be the same or different, $C_3-C_7$-cycloalkyl, $C_3-C_7$-cycloalkyl-$C_1-C_8$-alkyl, $C_1-C_7$-halogenocycloalkyl comprising up to 9 halogen atoms which can be the same or different, formyl, carbamoyl, (hydroxyimino)-$C_1-C_8$-alkyl, $C_1-C_8$-alkylcarbonyl, $C_1-C_8$-halogenoalkylcarbonyl comprising up to 9 halogen atoms which can be the same or different, $C_1-C_8$-alkylcarbamoyl, $C_1-C_8$-alkoxycarbonyl, $C_1-C_8$-halogenoalkoxycarbonyl comprising up to 9 halogen atoms which can be the same or different, $C_1-C_8$-alkylaminocarbonyl, di-$C_1-C_8$-alkylaminocarbonyl, $C_1-C_8$-alkylsulphonyl, $C_1-C_8$-halogenoalkylsulphonyl comprising up to 9 halogen atoms which can be the same or different, ($C_1-C_8$-alkoxyimino)-$C_1-C_8$-alkyl, ($C_1-C_8$-alkenyloxyimino)-$C_1-C_8$-alkyl, ($C_2-C_8$-alkynyloxyimino)-$C_1-C_8$-alkyl, (benzyloxyimino)-$C_1-C_8$-alkyl, tri($C_1-C_8$-alkyl)silyl, tri($C_1-C_8$-alkyl)silyl-$C_1-C_8$-alkyl, benzyloxy which can be substituted by up to 5 groups Q, benzylamino which can be substituted by up to 5 groups Q, phenyl which can be substituted by up to 5 groups Q; naphthyl which can be substituted by up to 6 groups Q, phenoxy which can be substituted by up to 5 groups Q, phenylamino which can be substituted by up to 5 groups Q, or phenylmethylene which can be substituted by up to 5 groups Q, provided that when n represents 1 then $R^2$, $R^3$ and $R^4$ do not represent simultaneously a hydrogen atom, or a salt, N-oxide, metallic complex, metalloidic complex or an optically active or geometric isomer thereof.

2. A composition, comprising at least one aminopropenoate of the formula (I) according to claim 1, and one or more extenders, surfactants, or combinations thereof.

3. A method for controlling fungi or bacteria, comprising applying at least one aminopropenoate of the formula (I) according to claim 1 to the fungi or bacteria, their habitat, or combinations thereof.

4. A process for preparing a composition comprising mixing at least one aminopropenoate of the formula (I) according to claim 1 with one or more extenders, surfactants, or combinations thereof.

5. A method for controlling fungi or bacteria on a transgenic plant, comprising applying at least one aminopropenoate of the formula (I) according to claim 1 to the transgenic plant, its seed, its habitat, or combinations thereof.

6. The aminopropenoate of the formula (I) according to claim 1, wherein R represents $R^A$.

7. The aminopropenoate of the formula (I) according to claim 1, wherein R represents $R^B$.

8. The aminopropenoate of the formula (I) according to claim 6, wherein n represents 0, 1 or 2.

9. The aminopropenoate of the formula (I) according to claim 1, wherein m represents 1 or 2.

10. The aminopropenoate of the formula (I) according to claim 1, wherein $Y^1$ is S or O.

11. The aminopropenoate of the formula (I) according to claim 1, wherein $Y^2$ represents O or $NR^6$, wherein $R^6$ represents hydrogen, $C_1-C_8$-alkyl, $C_3-C_8$-cycloalkyl, $C_1-C_8$-halogenoalkyl comprising up to 9 halogen atoms which can be the same or different, $C_3-C_8$-cycloalkyl-$C_1-C_8$-alkyl, $C_2-C_8$-alkenyl-$C_1-C_8$-alkyl, $C_2-C_8$-alkynyl-$C_1-C_8$-alkyl, $C_1-C_8$-halogeno-$C_3-C_8$-cycloalkyl comprising up to 9 halogen atoms which can be the same or different, $C_3-C_8$-cycloalkenyl, $C_1-C_8$-alkoxy-$C_1-C_8$-alkyl, $C_3-C_8$-cycloalkoxy-$C_1-C_8$-alkyl, $C_1-C_8$-halogenoalkoxy-$C_1-C_8$-alkyl comprising up to 9 halogen atoms which can be the same or different, $C_1-C_8$-alkylsulfanyl-$C_1-C_8$-alkyl, $C_1-C_8$-alkylamino-$C_1-C_8$-alkyl, $C_1-C_8$-halogenoalkylamino-$C_1-C_8$-alkyl comprising up to 9 halogen atoms which can be the same or different, $C_3-C_8$-cycloalkylamino-$C_1-C_8$-alkyl, $C_1-C_8$-trialkylsilyl-$C_1-C_8$-alkyl, or $C_1-C_8$-alkoxy.

12. The aminopropenoate of the formula (I) according to claim 1, wherein $Y^3$ represents O or $NR^8$, wherein $R^8$ represents hydrogen, $C_1-C_8$-alkyl, $C_3-C_8$-cycloalkyl, $C_1-C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, $C_1$-$C_6$-alkoxy, $C_3$-$C_6$-cycloalkoxy, $C_1$-$C_6$-halogenoalkoxy comprising up to 9 halogen atoms which can be the same or different, $C_3$-$C_6$-cycloalkyl-$C_1$-$C_6$-alkoxy, $C_2$-$C_6$-alkenyl-$C_1$-$C_6$-alkoxy, $C_2$-$C_6$-alkynyl-$C_1$-$C_6$-alkoxy, $C_1$-$C_6$-halogeno-$C_3$-$C_6$-cycloalkoxy comprising up to 9 halogen atoms which can be the same or different, $C_3$-$C_6$-cycloalkenyloxy, $C_1$-$C_6$-alkoxy-$C_1$-$C_6$-alkoxy, $C_3$-$C_6$-cycloalkoxy-$C_1$-$C_6$-alkoxy, $C_1$-$C_6$-halogenoalkoxy-$C_1$-$C_6$-alkoxy comprising up to 9 halogen atoms which can be the same or different, $C_1$-$C_6$-alkylsulfanyl-$C_1$-$C_6$-alkoxy, $C_1$-$C_6$-alkylamino-$C_1$-$C_6$-alkoxy, $C_1$-$C_6$-halogenoalkylamino-$C_1$-$C_6$-alkoxy comprising up to 9 halogen atoms which can be the same or different, $C_3$-$C_6$-cycloalkylamino-$C_1$-$C_6$-alkoxy, $C_1$-$C_6$-trialkylsilyl-$C_1$-$C_6$-alkoxy, aryloxy which can be substituted by up to 5 groups Q, or benzyloxy which can be substituted by up to 5 groups Q.

13. The aminopropenoate of the formula (I) according to claim 1, wherein $Y^4$ represents a bond, O or $NR^9$, wherein $R^9$ represents hydrogen or $C_1$-$C_6$-alkyl.

14. The aminopropenoate of the formula (I) according to claim 1, wherein $R^1$ represents hydrogen, $C_1$-$C_6$-alkyl, $C_3$-$C_6$-cycloalkyl, $C_1$-$C_4$-halogenoalkyl comprising up to 9 halogen atoms which can be the same or different, $C_2$-$C_4$-alkenyl, $C_2$-$C_4$-alkynyl, or $C_1$-$C_4$-alkoxy-$C_1$-$C_4$-alkyl.

15. The aminopropenoate of the formula (I) according to claim 1, wherein $R^4$ is selected from E 1 to E 48, E 52 to E 56, E 63, E 64, E 69 to E 77, E 98 to E 100, E 105, E 106, E 109 to E 112, E 129 or E 130, and wherein $Z^1$, $Z^2$, $Z^3$, $Z^4$, $Z^5$, $Z^6$, $Z^7$, $Z^8$, $Z^9$, $Z^{10}$ and $Z^{11}$, which can be the same or different, independently of one another represent hydrogen, halogen, $NO_2$, CN, OH, SH, $NH_2$, methyl, ethyl, n-propyl, isopropyl, n-butyl, i-butyl, s-butyl, t-butyl, difluoromethyl, trifluoromethyl, fluoroethyl, difluoroethyl, methylamino, ethylamino, dimethylamino, diethylamino, methoxy, ethoxy, trifluoromethoxy, vinyl, allyl, ethinyl, propargyl, cyclopropyl, cyclohexyl, acetyl, $C_1$-$C_3$-halogenoalkylcarbonyl comprising up to 5 halogen atoms which can be the same or different, carboxyl, methoxycarbonyl, ethoxycarbonyl, $C_1$-$C_4$-alkylcarbonyloxy, $C_1$-$C_4$-alkylcarbonylamino, methylthio, ethylthio, trimethylsilyl, phenyl which can be substituted by up to 3 groups Q, or naphthyl which can be substituted by up to 6 groups Q, or two geminal substituents Z together with the carbon atom to which they are linked can be fused to represent C(=O).

16. The aminopropenoate of the formula (I) according to claim 1, wherein $R^5$ represents hydrogen, OH, $C_1$-$C_4$-alkyl, $C_3$-$C_6$-cycloalkyl, $C_1$-$C_2$-halogenoalkyl comprising up to 5 halogen atoms which can be the same or different, $C_3$-$C_6$-cycloalkyl-$C_1$-$C_2$-alkyl, $C_2$-$C_4$-alkenyl-$C_1$-$C_4$-alkyl, $C_2$-$C_4$-alkynyl-$C_1$-$C_4$-alkyl, halogeno-$C_3$-$C_6$-cycloalkyl comprising up to 9 halogen atoms which can be the same or different, cyclohexenyl, alkyl, $C_3$-$C_6$-cycloalkoxy-$C_1$-$C_4$-alkyl, $C_1$-$C_4$-halogenoalkoxy-$C_1$-$C_4$-alkyl comprising up to 9 halogen atoms which can be the same or different, $C_1$-$C_4$-alkylsulfanyl-$C_1$-$C_4$-alkyl, $C_1$-$C_4$-alkylamino-$C_1$-$C_4$-alkyl, $C_1$-$C_4$-halogenoalkylamino-$C_1$-$C_4$-alkyl comprising up to 9 halogen atoms which can be the same or different, $C_1$-$C_4$-trialkylsilyl-$C_1$-$C_4$-alkyl, phenyl or naphthyl, each of which can be substituted by up to 5 groups Q, benzyl which can be substituted by up to 5 groups Q.

17. The aminopropenoate of the formula (I) according to claim 1, wherein $R^2$ and $R^3$, which can be the same or different, independently of one another represent hydrogen, halogen, CN, $NH_2$, $C_1$-$C_6$-alkyl, $C_1$-$C_6$-hydroxyalkyl, $C_1$-$C_6$-cycloalkyl, $C_3$-$C_6$-halogenocycloalkyl comprising up to 9 halogen atoms which can be the same or different, $C_1$-$C_6$-halogenoalkyl comprising up to 9 halogen atoms which can be the same or different, $C_3$-$C_6$-cycloalkyl-$C_1$-$C_6$-alkyl, $C_2$-$C_6$-alkenyl, $C_2$-$C_6$-alkynyl, $C_2$-$C_6$-alkenyl-$C_1$-$C_6$-alkyl, $C_2$-$C_6$-alkynyl-$C_1$-$C_6$-alkyl, $C_3$-$C_6$-halogenocycloalkyl comprising up to 9 halogen atoms which can be the same or different, $C_1$-$C_6$-alkoxy-$C_1$-$C_6$-alkyl, $C_3$-$C_6$-cycloalkoxy-$C_1$-$C_6$-alkyl, $C_1$-$C_6$-halogenoalkoxy-$C_1$-$C_6$-alkyl comprising up to 9 halogen atoms which can be the same or different, $C_1$-$C_6$-alkylsulfanyl-$C_1$-$C_6$-alkyl, $C_1$-$C_6$-alkylamino-$C_1$-$C_6$-alkyl, $C_1$-$C_6$-halogenoalkylamino-$C_1$-$C_6$-alkyl comprising up to 9 halogen atoms which can be the same or different, or $R_2$ and $R_3$ together with the carbon atom to which they are linked can form a $C_3$-$C_7$ cycloalkyl.

18. An aminopropenoate of the formula (I) according to 1, wherein $R^7$ represents hydrogen, CN, $C_3$-$C_6$-cycloalkyl, $C_1$-$C_6$-halogenoalkyl comprising up to 9 halogen atoms which can be the same or different, $C_3$-$C_6$-cycloalkyl-$C_1$-$C_6$-alkyl, $C_2$-$C_6$-alkenyl, $C_2$-$C_6$-alkynyl, halogeno-$C_3$-$C_6$-cycloalkyl comprising up to 9 halogen atoms which can be the same or different, $C_3$-$C_6$-cycloalkenyl, $C_1$-$C_6$-alkoxy-$C_1$-$C_6$-alkyl, $C_1$-$C_6$-halogenoalkoxy-$C_1$-$C_6$-alkyl comprising up to 9 halogen atoms which can be the same or different, $C_1$-$C_6$-alkylsulfanyl-$C_1$-$C_6$-alkyl, $C_1$-$C_6$-alkyl, phenyl or naphthyl, each of which can be substituted by up to 5 groups Q, benzyl which can be substituted by up to 5 groups Q, or phenyl-$C_1$-$C_2$-alkylimino.

19. The aminopropenoate of the formula (I) according to claim 1, wherein R represents $R^B$, wherein t represents 0, $Y^3$ represents O, $Y^4$ represents $NR^9$, and $R^9$ represents hydrogen, $C_1$-$C_8$-alkyl, $C_3$-$C_8$-cycloalkyl, $C_1$-$C_8$-halogenoalkyl comprising up to 9 halogen atoms which can be the same or different, $C_3$-$C_8$-cycloalkyl-$C_1$-$C_8$-alkyl, $C_2$-$C_8$-alkenyl-$C_1$-$C_8$-alkyl, $C_2$-$C_8$-alkynyl-$C_1$-$C_8$-alkyl, $C_1$-$C_8$-halogeno-$C_3$-$C_8$-cycloalkyl comprising up to 9 halogen atoms which can be the same or different, $C_3$-$C_8$-cycloalkenyl, $C_1$-$C_8$-alkoxy-$C_1$-$C_8$-alkyl, $C_3$-$C_8$-cycloalkoxy-$C_1$-$C_8$-alkyl, $C_1$-$C_8$-halogenoalkoxy-$C_1$-$C_8$-alkyl comprising up to 9 halogen atoms which can be the same or different, $C_1$-$C_8$-alkylsulfanyl-$C_1$-$C_8$-alkyl, $C_1$-$C_8$-alkylamino-$C_1$-$C_8$-alkyl, $C_1$-$C_8$-halogenoalkylamino-$C_1$-$C_8$-alkyl comprising up to 9 halogen atoms which can be the same or different, $C_3$-$C_8$-cycloalkylamino-$C_1$-$C_8$-alkyl, $C_1$-$C_8$-trialkylsilyl-$C_1$-$C_8$-alkyl, phenyl which can be substituted by up to 5 groups Q, benzyl which can be substituted by up to 5 groups Q.

20. The aminopropenoate of the formula (I) according to claim 1, wherein Q which can be the same or different, independently represents halogen, CN, $NO_2$, $C_1$-$C_6$-alkoxy, $C_1$-$C_6$-alkylsulfanyl, $C_1$-$C_6$-halogenoalkyl comprising up to 9 halogen atoms which can be the same or different, $C_1$-$C_6$-halogenoalkoxy comprising up to 9 halogen atoms which can be the same or different, tri($C_1$-$C_6$)alkylsilyl or tri($C_1$-$C_6$)alkylsilyl-$C_1$-$C_6$-alkyl.

* * * * *